US010603196B2

(12) United States Patent
Mayberry et al.

(10) Patent No.: US 10,603,196 B2
(45) Date of Patent: Mar. 31, 2020

(54) FENESTRATED PROSTHESIS

(71) Applicants: Endologix, Inc., Irvine, CA (US); The Cleveland Clinic Foundation, Cleveland, OH (US)

(72) Inventors: Kevin Mayberry, Mission Viejo, CA (US); Daniel Clair, Shaker Heights, OH (US); Craig Welk, Tracy, CA (US); Stefan G. Schreck, Fallbrook, CA (US)

(73) Assignee: Endologix, Inc., Irvine, CA (US)

( * ) Notice: Subject to any disclaimer, the term of this patent is extended or adjusted under 35 U.S.C. 154(b) by 0 days.

(21) Appl. No.: 14/581,675

(22) Filed: Dec. 23, 2014

(65) Prior Publication Data
US 2015/0173923 A1 Jun. 25, 2015

Related U.S. Application Data

(63) Continuation of application No. 12/769,581, filed on Apr. 28, 2010, now Pat. No. 8,945,202.
(Continued)

(51) Int. Cl.
*A61F 2/954* (2013.01)
*A61F 2/966* (2013.01)
(Continued)

(52) U.S. Cl.
CPC .............. *A61F 2/954* (2013.01); *A61F 2/07* (2013.01); *A61F 2/856* (2013.01); *A61F 2/89* (2013.01);
(Continued)

(58) Field of Classification Search
CPC .......... A61F 2/954; A61F 2/966; A61F 2/856; A61F 2/07; A61F 2002/065; A61F 2002/67; A61F 2002/9511
(Continued)

(56) References Cited

U.S. PATENT DOCUMENTS 2,127,903 A  8/1938  Bowen
2,437,542 A  5/1944  Krippendorf
(Continued)

FOREIGN PATENT DOCUMENTS

CA  2220141  11/1996
CA  2133530  1/1999
(Continued)

OTHER PUBLICATIONS

US 6,413,270 B1, 07/2002, Thornton et al. (withdrawn)
(Continued)

*Primary Examiner* — Kathleen S Holwerda
(74) *Attorney, Agent, or Firm* — Foley & Lardner LLP

(57) ABSTRACT

Some embodiments of the present disclosure are directed to endoluminal prostheses having one or more reinforced fenestrations therein. The one or more reinforced fenestrations can have improved sealing capabilities with respect to branch grafts deployed within the fenestrations, improved tear resistance and expandability, and improved pull-out resistance for branch grafts. In some embodiments, the endoluminal prosthesis can have a main graft body defining a flow lumen therethrough, a first opening passing through a wall of the main graft body, and a first support member supported by the main graft body and overlapping an edge of the first opening, the first support member being configured to at least increase the tear resistance of the main graft body adjacent to the first opening. The support member can be stitched or otherwise attached to the main graft adjacent to the fenestration.

16 Claims, 59 Drawing Sheets

Related U.S. Application Data

(60) Provisional application No. 61/231,898, filed on Aug. 6, 2009, provisional application No. 61/228,048, filed on Jul. 23, 2009, provisional application No. 61/173,485, filed on Apr. 28, 2009.

(51) Int. Cl.
| | | |
|---|---|---|
| *A61F 2/89* | (2013.01) | |
| *A61F 2/90* | (2013.01) | |
| *A61F 2/07* | (2013.01) | |
| *A61F 2/856* | (2013.01) | |
| A61F 2/06 | (2013.01) | |
| A61F 2/95 | (2013.01) | |
| A61F 2/97 | (2013.01) | |

(52) U.S. Cl.
CPC ............... *A61F 2/90* (2013.01); *A61F 2/966* (2013.01); *A61F 2/97* (2013.01); *A61F 2002/061* (2013.01); *A61F 2002/065* (2013.01); *A61F 2002/067* (2013.01); *A61F 2002/075* (2013.01); *A61F 2002/9511* (2013.01); *A61F 2250/0039* (2013.01); *Y10T 29/49863* (2015.01)

(58) Field of Classification Search
USPC .............................. 623/1.11, 1.12, 1.13, 1.35
See application file for complete search history.

(56) References Cited

U.S. PATENT DOCUMENTS

| | | |
|---|---|---|
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,805,301 A | 4/1974 | Liebig |
| 4,362,156 A | 12/1982 | Feller, Jr. et al. |
| 4,473,067 A | 9/1984 | Schiff |
| 4,497,074 A | 2/1985 | Ray et al. |
| 4,501,263 A | 2/1985 | Harbuck |
| 4,503,568 A | 3/1985 | Madras |
| 4,512,338 A | 4/1985 | Balko et al. |
| 4,525,157 A | 6/1985 | Vaillancourt |
| 4,562,596 A | 1/1986 | Kornberg |
| 4,580,568 A | 4/1986 | Gianturco |
| 4,592,754 A | 6/1986 | Gupte et al. |
| 4,617,932 A | 10/1986 | Kornberg |
| 4,756,307 A | 7/1988 | Crownshield |
| 4,795,465 A | 1/1989 | Marten |
| 4,800,882 A | 1/1989 | Gianturco |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,981,478 A | 1/1991 | Evard et al. |
| 4,981,947 A | 1/1991 | Tomagou et al. |
| 4,994,069 A | 2/1991 | Ritchart et al. |
| 4,994,071 A | 2/1991 | MacGregor |
| 5,019,090 A | 5/1991 | Pinchuk |
| 5,035,706 A | 7/1991 | Giantureo et al. |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,116,349 A | 5/1992 | Aranyi |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,151,105 A | 9/1992 | Kwan-Gett |
| 5,156,619 A | 10/1992 | Ehrenfeld |
| 5,158,545 A | 10/1992 | Trudell et al. |
| 5,178,634 A | 1/1993 | Martinez |
| 5,197,976 A | 3/1993 | Herweck et al. |
| 5,201,757 A | 4/1993 | Heyn et al. |
| 5,211,658 A | 5/1993 | Clouse |
| 5,246,452 A | 9/1993 | Sinnott |
| 5,256,141 A | 10/1993 | Gancheff et al. |
| 5,275,622 A | 1/1994 | Lazarus et al. |
| 5,282,860 A | 1/1994 | Matsuno et al. |
| 5,282,478 A | 2/1994 | Fleischhaker et al. |
| 5,282,824 A | 2/1994 | Giantruco |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpiel |
| 5,330,500 A | 7/1994 | Song |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,387,235 A | 2/1995 | Chuter |
| 5,397,355 A | 3/1995 | Marin et al. |
| 5,403,341 A | 4/1995 | Solar |
| 5,405,377 A | 4/1995 | Cragg |
| 5,405,378 A | 4/1995 | Strecker |
| 5,414,664 A | 5/1995 | Lin et al. |
| 5,415,178 A | 5/1995 | Hsi et al. |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |
| 5,443,500 A | 8/1995 | Sigwart |
| 5,453,090 A | 9/1995 | Martinez et al. |
| 5,458,615 A | 10/1995 | Klemm et al. |
| 5,462,530 A | 10/1995 | Jang |
| 5,464,449 A | 11/1995 | Ryan et al. |
| 5,464,450 A | 11/1995 | Buscemi et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,523,092 A | 6/1996 | Hanson et al. |
| 5,545,211 A | 8/1996 | An et al. |
| 5,549,635 A | 8/1996 | Solar |
| 5,545,118 A | 9/1996 | Jang |
| 5,554,181 A | 9/1996 | Das |
| 5,562,697 A | 10/1996 | Christiansen |
| 5,562,724 A | 10/1996 | Vorwerk et al. |
| 5,562,726 A | 10/1996 | Chuter |
| 5,562,728 A | 10/1996 | Lazarus et al. |
| 5,571,169 A | 11/1996 | Plaia et al. |
| 5,571,172 A | 11/1996 | Chin |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,195 A | 1/1997 | Taheri et al. |
| 5,591,197 A | 1/1997 | Orth et al. |
| 5,591,198 A | 1/1997 | Boyle et al. |
| 5,591,226 A | 1/1997 | Trerotola et al. |
| 5,591,229 A | 1/1997 | Parodi |
| 5,591,230 A | 1/1997 | Horn et al. |
| 5,593,417 A | 1/1997 | Rhodes |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,786 A | 5/1997 | Banas et al. |

(56) References Cited

U.S. PATENT DOCUMENTS

| | | |
|---|---|---|
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,666,968 A | 9/1997 | Imran et al. |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,690,671 A | 11/1997 | McGurk et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,697,971 A | 12/1997 | Fischell et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,733,325 A | 3/1998 | Robinson et al. |
| 5,746,776 A | 5/1998 | Smith et al. |
| 5,749,880 A | 5/1998 | Banas et al. |
| 5,755,735 A | 5/1998 | Richter et al. |
| 5,755,770 A | 5/1998 | Ravenscroft |
| 5,755,771 A | 5/1998 | Penn et al. |
| 5,755,777 A | 5/1998 | Chuter |
| 5,765,682 A | 6/1998 | Bley et al. |
| 5,766,203 A | 6/1998 | Imran et al. |
| 5,769,885 A | 6/1998 | Quiachon et al. |
| 5,769,887 A | 6/1998 | Brown et al. |
| 5,782,855 A | 7/1998 | Lau et al. |
| 5,782,909 A | 7/1998 | Quiachon et al. |
| 5,800,456 A | 9/1998 | Maeda et al. |
| 5,800,508 A | 9/1998 | Goicoechea et al. |
| 5,800,514 A * | 9/1998 | Nunez .................. A61F 2/06 139/384 R |
| 5,800,526 A | 9/1998 | Anderson et al. |
| 5,810,836 A | 9/1998 | Hussein et al. |
| 5,817,100 A | 10/1998 | Igaki |
| 5,823,198 A | 10/1998 | Jones et al. |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,855,600 A | 1/1999 | Alt |
| 5,860,998 A | 1/1999 | Robinson et al. |
| 5,867,432 A | 2/1999 | Toda |
| 5,868,783 A | 2/1999 | Tower |
| 5,871,536 A | 2/1999 | Lazarus |
| 5,873,906 A | 2/1999 | Lau et al. |
| 5,879,321 A | 3/1999 | Hill |
| 5,879,366 A | 3/1999 | Shau et al. |
| 5,891,193 A | 4/1999 | Robinson et al. |
| 5,893,868 A | 4/1999 | Hanson et al. |
| 5,893,887 A | 4/1999 | Jayaraman |
| 5,902,334 A | 5/1999 | Dwyer et al. |
| 5,906,640 A | 5/1999 | Penn et al. |
| 5,906,641 A | 5/1999 | Thompson et al. |
| 5,916,263 A | 6/1999 | Goicocehea et al. |
| 5,919,225 A | 7/1999 | Lau et al. |
| 5,925,075 A | 7/1999 | Myers et al. |
| 5,928,248 A | 7/1999 | Acker |
| 5,928,279 A | 7/1999 | Shannon et al. |
| 5,935,161 A | 8/1999 | Robinson et al. |
| 5,938,696 A | 8/1999 | Goicoechea et al. |
| 5,948,017 A | 9/1999 | Taheri |
| 5,948,018 A | 9/1999 | Dereume et al. |
| 5,957,929 A | 9/1999 | Brenneman |
| 5,957,973 A | 9/1999 | Quiachon et al. |
| 5,961,546 A | 10/1999 | Robinson et al. |
| 5,961,548 A | 10/1999 | Shmulewitz |
| 5,980,514 A | 11/1999 | Kupiecki et al. |
| 5,984,929 A | 11/1999 | Bashiri et al. |
| 5,984,955 A | 11/1999 | Wisselink |
| 5,989,242 A | 11/1999 | Saadat et al. |
| 5,993,489 A | 11/1999 | Lewis et al. |
| 6,001,125 A | 12/1999 | Golds et al. |
| 6,004,347 A | 12/1999 | McNamara et al. |
| 6,004,348 A | 12/1999 | Banas et al. |
| 6,017,363 A | 1/2000 | Hojeibane |
| 6,027,508 A | 2/2000 | Ren et al. |
| 6,027,520 A | 2/2000 | Tsugita et al. |
| 6,027,779 A | 2/2000 | Campbell et al. |
| 6,027,811 A | 2/2000 | Campbell et al. |
| 6,030,415 A | 2/2000 | Chuter |
| 6,033,434 A | 3/2000 | Borghi |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,059,824 A | 5/2000 | Taheri |
| 6,063,092 A | 5/2000 | Shin |
| 6,063,113 A | 5/2000 | Kavteladze et al. |
| 6,068,654 A | 5/2000 | Berg et al. |
| 6,070,589 A | 6/2000 | Keith et al. |
| 6,074,398 A | 6/2000 | Leschinsky |
| 6,077,296 A | 6/2000 | Shokoohi et al. |

(56) References Cited

U.S. PATENT DOCUMENTS

| | | | |
|---|---|---|---|
| 6,077,297 A | 6/2000 | Robinson et al. |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,027 A | 8/2000 | Layne |
| 6,106,548 A | 8/2000 | Reubin et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,136,006 A | 10/2000 | Johnson et al. |
| 6,143,002 A | 11/2000 | Vietmeier |
| 6,143,016 A | 11/2000 | Bleam et al. |
| 6,146,389 A | 11/2000 | Geitz |
| 6,146,415 A | 11/2000 | Fitz |
| 6,149,681 A | 11/2000 | Houser et al. |
| 6,152,944 A | 11/2000 | Holman et al. |
| 6,156,063 A | 12/2000 | Douglas |
| 6,162,237 A | 12/2000 | Chan |
| 6,165,195 A | 12/2000 | Wilson et al. |
| 6,165,214 A | 12/2000 | Lazarus |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,015 B1 | 2/2001 | Brenneman |
| 6,187,033 B1 | 2/2001 | Schmitt et al. |
| 6,187,036 B1 | 2/2001 | Shaolian et al. |
| 6,192,944 B1 | 2/2001 | Greenhalgh |
| 6,193,726 B1 | 2/2001 | Vanney |
| 6,193,745 B1 | 2/2001 | Fogarty et al. |
| 6,197,049 B1 | 3/2001 | Shaolian et al. |
| 6,203,735 B1 | 3/2001 | Edwin et al. |
| 6,210,429 B1 | 4/2001 | Vardi et al. |
| 6,221,090 B1 | 4/2001 | Wilson |
| 6,221,098 B1 | 4/2001 | Wilson |
| 6,221,102 B1 | 4/2001 | Baker et al. |
| 6,224,609 B1 | 5/2001 | Ressemann et al. |
| 6,224,627 B1 | 5/2001 | Armstrong et al. |
| 6,231,563 B1 | 5/2001 | White et al. |
| 6,235,051 B1 | 5/2001 | Murphy |
| 6,254,609 B1 | 7/2001 | Vrba et al. |
| 6,254,628 B1 | 7/2001 | Wallace et al. |
| 6,261,316 B1 | 7/2001 | Shaolian et al. |
| 6,264,682 B1 | 7/2001 | Wilson et al. |
| 6,273,909 B1 | 8/2001 | Kugler et al. |
| 6,280,465 B1 | 8/2001 | Cryer |
| 6,280,466 B1 | 8/2001 | Kugler et al. |
| 6,280,467 B1 | 8/2001 | Leonhardt |
| 6,283,991 B1 | 9/2001 | Cox et al. |
| 6,287,329 B1 | 9/2001 | Duerig et al. |
| 6,296,622 B1 | 10/2001 | Kurz et al. |
| 6,312,406 B1 | 11/2001 | Jayaraman |
| 6,325,826 B1 | 12/2001 | Vardi et al. |
| 6,331,184 B1 | 12/2001 | Abrams |
| 6,331,190 B1 | 12/2001 | Shokoohi et al. |
| 6,334,867 B1 | 1/2002 | Anson |
| 6,344,056 B1 | 2/2002 | Dehdashtian |
| 6,346,118 B1 | 2/2002 | Baker et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,554 B2 | 3/2002 | De Paulis |
| 6,352,561 B1 | 3/2002 | Leopold et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,557 B1 | 3/2002 | Gittings et al. |
| 6,361,559 B1 | 3/2002 | Houser et al. |
| 6,361,637 B2 | 3/2002 | Martin et al. |
| 6,383,213 B2 | 5/2002 | Wilson et al. |
| 6,387,120 B2 | 5/2002 | Wilson et al. |
| 6,395,017 B1 | 5/2002 | Dwyer et al. |
| 6,395,018 B1 * | 5/2002 | Castaneda ............... A61F 2/07 623/1.13 |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,542 B1 | 7/2002 | Marcade et al. |
| 6,425,765 B1 | 7/2002 | Irwin, III |
| 6,428,565 B1 | 8/2002 | Wisselink |
| 6,428,567 B2 | 8/2002 | Wilson et al. |
| 6,432,130 B1 | 8/2002 | Hanson |
| 6,432,131 B1 | 8/2002 | Ravenscroft |
| 6,432,134 B1 | 8/2002 | Anson et al. |
| 6,436,135 B1 | 8/2002 | Goldfarb |
| 6,440,161 B1 | 8/2002 | Madrid et al. |
| 6,447,540 B1 | 9/2002 | Fontaine et al. |
| 6,458,152 B1 | 10/2002 | Khosravi et al. |
| 6,464,721 B1 | 10/2002 | Marcade et al. |
| 6,475,166 B1 | 11/2002 | Escano |
| 6,475,170 B1 | 11/2002 | Doron et al. |
| 6,482,211 B1 | 11/2002 | Choi |
| 6,485,513 B1 | 11/2002 | Fan |
| 6,491,719 B1 | 12/2002 | Fogrty et al. |
| 6,500,182 B2 | 12/2002 | Foster |
| 6,500,202 B1 | 12/2002 | Shaolian et al. |
| 6,508,833 B2 | 1/2003 | Pavcnick et al. |
| 6,508,835 B1 | 1/2003 | Shaolian et al. |
| 6,508,836 B2 | 1/2003 | Wilson et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,558,396 B1 | 5/2003 | Inoue |
| 6,562,063 B1 | 5/2003 | Euteneurer et al. |
| 6,565,596 B1 | 5/2003 | White et al. |
| 6,565,597 B1 | 5/2003 | Fearnot et al. |
| RE38,146 E | 6/2003 | Palmaz et al. |
| 6,572,645 B2 | 6/2003 | Leonhardt |
| 6,576,005 B1 | 6/2003 | Geitz |
| 6,576,009 B2 | 6/2003 | Ryan et al. |
| 6,579,308 B1 | 6/2003 | Jansen et al. |
| 6,579,312 B2 | 6/2003 | Wilson et al. |
| 6,582,394 B1 | 6/2003 | Reiss et al. |
| 6,582,460 B1 | 6/2003 | Cryer |
| 6,585,758 B1 | 7/2003 | Chouinard et al. |
| 6,592,548 B2 | 7/2003 | Jayaraman |
| 6,592,614 B2 | 7/2003 | Lenker et al. |
| 6,592,615 B1 | 7/2003 | Marcade et al. |
| 6,599,315 B2 | 7/2003 | Wilson |
| 6,607,552 B1 | 8/2003 | Hanson |
| 6,613,073 B1 | 9/2003 | White et al. |
| 6,616,675 B1 | 9/2003 | Evard et al. |
| 6,645,242 B1 | 11/2003 | Quinn |
| 6,652,567 B1 | 11/2003 | Deaton |
| 6,652,579 B1 | 11/2003 | Cox et al. |
| 6,656,213 B2 | 12/2003 | Solem |
| 6,660,033 B1 | 12/2003 | Marcade et al. |
| 6,663,665 B2 | 12/2003 | Shaolian et al. |
| 6,669,718 B2 | 12/2003 | Besselink |
| 6,692,483 B2 | 2/2004 | Vardi et al. |
| 6,695,875 B2 | 2/2004 | Stelter et al. |
| 6,702,843 B1 | 3/2004 | Brown et al. |
| 6,706,062 B2 | 3/2004 | Vardi et al. |
| 6,723,116 B2 | 4/2004 | Taheri |
| 6,733,523 B2 | 5/2004 | Shaolian et al. |
| 6,740,101 B2 | 5/2004 | Houser et al. |
| 6,761,733 B2 | 7/2004 | Chobotov et al. |
| 6,767,359 B2 | 7/2004 | Weadcock |
| 6,773,457 B2 | 8/2004 | Ivancev et al. |
| 6,790,224 B2 | 9/2004 | Gerberding |
| 6,793,671 B2 | 9/2004 | Wall |

(56) References Cited

U.S. PATENT DOCUMENTS

| | | |
|---|---|---|
| 6,800,065 B2 | 10/2004 | Duane et al. |
| 6,802,859 B1 | 10/2004 | Pazienza et al. |
| 6,811,566 B1 | 11/2004 | Penn et al. |
| 6,814,752 B1 | 11/2004 | Chuter |
| 6,818,014 B2 | 11/2004 | Brown et al. |
| 6,821,292 B2 | 11/2004 | Pazienza et al. |
| 6,827,706 B2 | 12/2004 | Parodi |
| 6,827,726 B2 | 12/2004 | Parodi |
| 6,833,003 B2 | 12/2004 | Jones et al. |
| 6,835,203 B1 | 12/2004 | Vardi et al. |
| 6,840,950 B2 | 1/2005 | Stanford et al. |
| 6,858,038 B2 | 2/2005 | Heuser |
| 6,875,229 B2 | 4/2005 | Wilson et al. |
| 6,887,249 B1 | 5/2005 | Houser et al. |
| 6,887,251 B1 | 5/2005 | Suval |
| 6,889,026 B2 | 5/2005 | Schlageter et al. |
| 6,896,699 B2 | 5/2005 | Wilson et al. |
| 6,899,727 B2 | 5/2005 | Armstrong et al. |
| 6,899,728 B1 | 5/2005 | Phillips et al. |
| 6,905,505 B2 | 6/2005 | Nash et al. |
| 6,908,477 B2 | 6/2005 | McGuckin, Jr. et al. |
| 6,918,925 B2 | 7/2005 | Tehrani |
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,368 B2 | 9/2005 | Simso |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,948,017 B2 | 9/2005 | Carpenter et al. |
| 6,953,475 B2 | 10/2005 | Shaolian et al. |
| 6,955,679 B1 | 10/2005 | Hendricksen et al. |
| 6,955,688 B2 | 10/2005 | Wilson et al. |
| 6,960,217 B2 | 11/2005 | Bolduc |
| 6,962,602 B2 | 11/2005 | Vardi et al. |
| 6,974,471 B2 | 12/2005 | Van Schie et al. |
| 6,981,982 B2 | 1/2006 | Armstrong et al. |
| 6,984,244 B2 | 1/2006 | Perez et al. |
| 6,989,024 B2 | 1/2006 | Hebert et al. |
| 6,989,026 B2 | 1/2006 | Richter et al. |
| 6,994,721 B2 | 2/2006 | Israel |
| 6,994,722 B2 | 2/2006 | DiCarlo |
| 7,004,926 B2 | 2/2006 | Navia et al. |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,494 B2 | 4/2006 | Soun et al. |
| 7,029,496 B2 | 4/2006 | Rakos et al. |
| 7,074,235 B1 * | 7/2006 | Roy .................. A61F 2/06 606/108 |
| 7,074,236 B2 | 7/2006 | Rabkin et al. |
| 7,105,015 B2 | 9/2006 | Goshgarian |
| 7,105,017 B2 | 9/2006 | Kerr |
| 7,105,020 B2 | 9/2006 | Greenberg et al. |
| 7,118,593 B2 | 10/2006 | Davidson et al. |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,131,991 B2 | 11/2006 | Zarins et al. |
| 7,144,422 B1 | 12/2006 | Rao |
| 7,160,318 B2 | 1/2007 | Greenberg et al. |
| 7,162,302 B2 | 1/2007 | Wang et al. |
| 7,163,715 B1 | 1/2007 | Kramer |
| 7,175,651 B2 | 2/2007 | Kerr |
| 7,175,652 B2 | 2/2007 | Cook et al. |
| 7,175,657 B2 | 2/2007 | Khan et al. |
| 7,189,256 B2 | 3/2007 | Smith |
| 7,189,257 B2 | 3/2007 | Schmitt |
| 7,195,648 B2 | 3/2007 | Jones et al. |
| 7,201,770 B2 | 4/2007 | Johnson et al. |
| 7,220,274 B1 | 5/2007 | Quinn |
| 7,220,275 B2 | 5/2007 | Davidson et al. |
| 7,229,472 B2 | 6/2007 | DePalma et al. |
| 7,232,449 B2 | 6/2007 | Sharkawy et al. |
| 7,235,095 B2 | 6/2007 | Haverkost et al. |
| 7,237,552 B2 | 7/2007 | Khera et al. |
| 7,241,300 B2 | 7/2007 | Sharkawy et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,285,130 B2 | 10/2007 | Austin |
| 7,294,145 B2 | 11/2007 | Ward |
| 7,300,460 B2 | 11/2007 | Levine et al. |
| 7,306,623 B2 | 12/2007 | Watson |
| 7,309,351 B2 | 12/2007 | Escamilla et al. |
| 7,314,481 B2 | 1/2008 | Karpiel |
| 7,314,483 B2 | 1/2008 | Landau et al. |
| 7,320,703 B2 | 1/2008 | DiMatteo et al. |
| 7,341,598 B2 | 3/2008 | Davidson et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,402,168 B2 | 7/2008 | Acosta et al. |
| 7,402,171 B2 | 7/2008 | Osborne et al. |
| 7,407,509 B2 | 8/2008 | Greenberg et al. |
| 7,413,573 B2 | 8/2008 | Hartley et al. |
| 7,425,219 B2 | 9/2008 | Quadri |
| 7,435,253 B1 | 10/2008 | Hartley et al. |
| 7,438,721 B2 | 10/2008 | Doig et al. |
| 7,491,230 B2 | 2/2009 | Holman et al. |
| 7,491,232 B2 | 2/2009 | Bolduc et al. |
| 7,520,890 B2 | 4/2009 | Phillips |
| 7,520,895 B2 | 4/2009 | Douglas et al. |
| 7,527,636 B2 | 5/2009 | Dunfee et al. |
| 7,537,606 B2 | 5/2009 | Hartley et al. |
| 7,553,324 B2 | 6/2009 | Andreas et al. |
| 7,572,289 B2 | 8/2009 | Sisken et al. |
| 7,575,590 B2 | 8/2009 | Watson |
| 7,578,841 B2 | 8/2009 | Yadin et al. |
| 7,582,111 B2 | 9/2009 | Krolik et al. |
| 7,591,832 B2 | 9/2009 | Eversull et al. |
| 7,591,843 B1 | 9/2009 | Escano et al. |
| 7,611,529 B2 | 11/2009 | Greenberg et al. |
| 7,615,072 B2 | 11/2009 | Rust et al. |
| 7,618,398 B2 | 11/2009 | Holman et al. |
| 7,632,299 B2 | 12/2009 | Weber |
| 7,635,383 B2 | 12/2009 | Gumm |
| 7,637,932 B2 | 12/2009 | Bolduc et al. |
| 7,641,684 B2 | 1/2010 | Hilaire et al. |
| 7,645,298 B2 | 1/2010 | Hartley et al. |
| 7,651,519 B2 | 1/2010 | Dittman |
| 7,670,369 B2 | 3/2010 | Shaeffer et al. |
| 7,674,284 B2 | 3/2010 | Melsheimer |
| 7,678,141 B2 | 3/2010 | Greenan et al. |
| 7,691,135 B2 | 4/2010 | Shaolian et al. |
| 7,695,508 B2 | 4/2010 | Van Der Leest et al. |
| 7,699,885 B2 | 4/2010 | Leonhardt et al. |
| 7,708,771 B2 | 5/2010 | Chuter et al. |
| 7,722,657 B2 | 5/2010 | Hartley |
| 7,753,951 B2 | 7/2010 | Shaked et al. |
| 7,758,633 B2 | 7/2010 | Nazzaro |
| 7,766,961 B2 | 8/2010 | Patel et al. |
| 7,771,465 B2 | 8/2010 | Zukowski |
| 7,785,340 B2 | 8/2010 | Heidner et al. |
| 7,785,361 B2 | 8/2010 | Nikolchev et al. |
| 7,806,917 B2 | 10/2010 | Xiao |
| 7,815,601 B2 | 10/2010 | Jordan et al. |
| 7,815,661 B2 | 10/2010 | Mirizzi et al. |
| 7,828,837 B2 | 11/2010 | Khoury |
| 7,833,259 B2 | 11/2010 | Boatman |
| 7,867,270 B2 | 1/2011 | Hartley et al. |
| 7,879,081 B2 | 2/2011 | DeMatteo et al. |
| 7,892,275 B2 | 2/2011 | Hartley et al. |
| 7,909,873 B2 | 3/2011 | Tan-Malecki et al. |
| 7,914,572 B2 | 3/2011 | Hartley et al. |
| 8,034,100 B2 | 10/2011 | Shaolian et al. |
| 8,118,856 B2 | 2/2012 | Schreck et al. |
| 8,152,830 B2 | 4/2012 | Gumm |

(56) References Cited

U.S. PATENT DOCUMENTS

| | | |
|---|---|---|
| 8,216,295 B2 | 7/2012 | Benjamin et al. |
| 8,221,494 B2 | 7/2012 | Schreck et al. |
| 8,236,040 B2 | 8/2012 | Mayberry et al. |
| 8,343,204 B2 | 1/2013 | Osborne |
| 8,357,192 B2 | 1/2013 | Mayberry et al. |
| 8,491,646 B2 | 7/2013 | Schreck |
| 8,523,931 B2 | 9/2013 | Mayberry et al. |
| 8,672,989 B2 | 3/2014 | Schreck et al. |
| 8,764,812 B2 | 7/2014 | Mayberry et al. |
| 8,808,350 B2 | 8/2014 | Schreck et al. |
| 8,828,074 B2 | 9/2014 | Xiao et al. |
| 8,845,708 B2 * | 9/2014 | Hartley ............... A61F 2/954 623/1.11 |
| 8,945,202 B2 | 2/2015 | Mayberry et al. |
| 9,149,381 B2 | 10/2015 | Schreck et al. |
| 2001/0003161 A1 | 6/2001 | Vardi et al. |
| 2001/0014823 A1 | 8/2001 | Ressemann |
| 2001/0016767 A1 | 8/2001 | Wilson et al. |
| 2001/0027338 A1 | 10/2001 | Greenberg |
| 2001/0037142 A1 | 11/2001 | Stelter et al. |
| 2001/0039445 A1 | 11/2001 | Hall et al. |
| 2002/0042650 A1 | 4/2002 | Vardi et al. |
| 2002/0049412 A1 | 4/2002 | Madrid et al. |
| 2002/0052648 A1 | 5/2002 | McGuckin et al. |
| 2002/0058986 A1 | 5/2002 | Landau et al. |
| 2002/0123786 A1 | 9/2002 | Gittings et al. |
| 2002/0138088 A1 | 9/2002 | Nash et al. |
| 2002/0143383 A1 | 10/2002 | Parodi |
| 2002/0147491 A1 | 10/2002 | Khan et al. |
| 2002/0156516 A1 | 10/2002 | Vardi et al. |
| 2002/0156518 A1 * | 10/2002 | Tehrani ............... A61F 2/07 623/1.11 |
| 2002/0173835 A1 | 11/2002 | Bourang et al. |
| 2002/0193872 A1 | 12/2002 | Trout, III et al. |
| 2002/0198585 A1 | 12/2002 | Wisselink |
| 2003/0004560 A1 | 1/2003 | Chobotov et al. |
| 2003/0028233 A1 | 2/2003 | Vardi et al. |
| 2003/0083678 A1 | 5/2003 | Herweck et al. |
| 2003/0097169 A1 | 5/2003 | Brucker et al. |
| 2003/0167083 A1 | 9/2003 | Lashinski et al. |
| 2003/0176910 A1 | 9/2003 | Vrba et al. |
| 2003/0236565 A1 | 12/2003 | DiMatteo et al. |
| 2003/0236566 A1 | 12/2003 | Heuser |
| 2004/0049204 A1 | 3/2004 | Harari et al. |
| 2004/0049257 A1 | 3/2004 | Kaspersen et al. |
| 2004/0073288 A1 | 4/2004 | Kerr |
| 2004/0093058 A1 | 5/2004 | Cottone et al. |
| 2004/0098084 A1 | 5/2004 | Hartley et al. |
| 2004/0098096 A1 | 5/2004 | Eton |
| 2004/0106972 A1 | 6/2004 | Deaton |
| 2004/0127975 A1 | 7/2004 | Levine et al. |
| 2004/0143312 A1 | 7/2004 | Samson et al. |
| 2004/0176832 A1 | 9/2004 | Hartley et al. |
| 2004/0193254 A1 | 9/2004 | Greenberg et al. |
| 2004/0215327 A1 | 10/2004 | Doig et al. |
| 2004/0230287 A1 * | 11/2004 | Hartley ............... A61F 2/07 623/1.12 |
| 2004/0236403 A1 | 11/2004 | Leonhardt et al. |
| 2005/0015135 A1 | 1/2005 | Shanley |
| 2005/0033403 A1 | 2/2005 | Ward et al. |
| 2005/0033405 A1 | 2/2005 | Solovay |
| 2005/0038494 A1 | 2/2005 | Eidenschink |
| 2005/0049672 A1 | 3/2005 | Murphy |
| 2005/0058327 A1 | 3/2005 | Pieper |
| 2005/0059923 A1 | 3/2005 | Gamboa |
| 2005/0059994 A1 | 3/2005 | Walak et al. |
| 2005/0060025 A1 | 3/2005 | Mackiewicz et al. |
| 2005/0060026 A1 | 3/2005 | Gamboa |
| 2005/0080476 A1 | 4/2005 | Gunderson et al. |
| 2005/0085891 A1 | 4/2005 | Goto et al. |
| 2005/0102018 A1 * | 5/2005 | Carpenter ............... A61F 2/07 623/1.11 |
| 2005/0113693 A1 | 5/2005 | Smith et al. |
| 2005/0113853 A1 | 5/2005 | Noriega et al. |
| 2005/0113905 A1 | 5/2005 | Greenberg et al. |
| 2005/0119719 A1 | 6/2005 | Wallace et al. |
| 2005/0119731 A1 | 6/2005 | Brucker et al. |
| 2005/0121120 A1 | 6/2005 | Van Dijk et al. |
| 2005/0131517 A1 | 6/2005 | Hartley et al. |
| 2005/0131518 A1 | 6/2005 | Hartley et al. |
| 2005/0131519 A1 | 6/2005 | Hartley |
| 2005/0131526 A1 | 6/2005 | Wong |
| 2005/0149166 A1 * | 7/2005 | Schaeffer ............... A61F 2/07 623/1.13 |
| 2005/0154444 A1 * | 7/2005 | Quadri ............... A61F 2/07 623/1.13 |
| 2005/0159803 A1 | 7/2005 | Lad et al. |
| 2005/0165470 A1 | 7/2005 | Weber |
| 2005/0165480 A1 | 7/2005 | Jordan et al. |
| 2005/0171597 A1 | 8/2005 | Boatman et al. |
| 2005/0171598 A1 | 8/2005 | Schaeffer |
| 2005/0177221 A1 | 8/2005 | Mustapha |
| 2005/0215327 A1 | 9/2005 | Weisel et al. |
| 2005/0216043 A1 | 9/2005 | Blatter et al. |
| 2005/0222668 A1 | 10/2005 | Schaeffer et al. |
| 2005/0228480 A1 | 10/2005 | Douglas et al. |
| 2005/0228488 A1 | 10/2005 | Nazzaro |
| 2005/0240153 A1 | 10/2005 | Opie |
| 2005/0240258 A1 | 10/2005 | Bolduc et al. |
| 2005/0240260 A1 | 10/2005 | Bolduc |
| 2005/0273150 A1 | 12/2005 | Howell et al. |
| 2005/0288772 A1 | 12/2005 | Douglas |
| 2006/0004433 A1 * | 1/2006 | Greenberg ............... A61F 2/07 623/1.11 |
| 2006/0020320 A1 | 1/2006 | Shaolian et al. |
| 2006/0036315 A1 | 2/2006 | Yadin et al. |
| 2006/0058864 A1 | 3/2006 | Schaeffer et al. |
| 2006/0089704 A1 | 4/2006 | Douglas |
| 2006/0142704 A1 | 6/2006 | Lentz |
| 2006/0142838 A1 | 6/2006 | Molaei et al. |
| 2006/0149350 A1 | 7/2006 | Patel et al. |
| 2006/0155358 A1 | 7/2006 | LaDuca et al. |
| 2006/0155363 A1 | 7/2006 | LaDuca et al. |
| 2006/0155366 A1 * | 7/2006 | LaDuca ............... A61F 2/2418 623/1.23 |
| 2006/0161241 A1 * | 7/2006 | Barbut ............... A61F 2/013 623/1.15 |
| 2006/0161244 A1 | 7/2006 | Sequin |
| 2006/0173525 A1 | 8/2006 | Behl et al. |
| 2006/0178726 A1 | 8/2006 | Myles |
| 2006/0217794 A1 | 9/2006 | Ruiz et al. |
| 2006/0224232 A1 | 10/2006 | Chobotov |
| 2006/0229669 A1 | 10/2006 | Mirizzi et al. |
| 2006/0229699 A1 | 10/2006 | Tehrani et al. |
| 2006/0229707 A1 | 10/2006 | Khoury |
| 2006/0233990 A1 | 10/2006 | Humphrey et al. |
| 2006/0233991 A1 | 10/2006 | Humphrey et al. |
| 2006/0247760 A1 * | 11/2006 | Ganesan ............... A61F 2/07 623/1.16 |
| 2006/0247761 A1 | 11/2006 | Greenberg et al. |
| 2006/0259063 A1 | 11/2006 | Bates et al. |
| 2006/0271163 A1 | 11/2006 | Shokoohi et al. |
| 2006/0271164 A1 | 11/2006 | Shaolian et al. |
| 2007/0010867 A1 | 1/2007 | Carter et al. |
| 2007/0016280 A1 | 1/2007 | Yacoby et al. |
| 2007/0021828 A1 | 1/2007 | Krolik et al. |
| 2007/0027522 A1 | 2/2007 | Chang et al. |
| 2007/0027526 A1 | 2/2007 | Demetriades et al. |
| 2007/0043425 A1 | 2/2007 | Hartley et al. |
| 2007/0050016 A1 | 3/2007 | Gregorich et al. |
| 2007/0055350 A1 | 3/2007 | Erickson et al. |
| 2007/0055360 A1 | 3/2007 | Hanson et al. |
| 2007/0055362 A1 | 3/2007 | Brown et al. |
| 2007/0067019 A1 | 3/2007 | Miller et al. |
| 2007/0067023 A1 | 3/2007 | Kveen et al. |
| 2007/0073376 A1 | 3/2007 | Krolik et al. |
| 2007/0073388 A1 | 3/2007 | Krolik et al. |
| 2007/0088424 A1 | 4/2007 | Greenberg et al. |
| 2007/0112420 A1 | 5/2007 | LaDuca |
| 2007/0118208 A1 | 5/2007 | Kerr |
| 2007/0123805 A1 | 5/2007 | Shireman et al. |
| 2007/0142896 A1 | 6/2007 | Anderson et al. |
| 2007/0150051 A1 | 6/2007 | De La Menardiere et al. |
| 2007/0167955 A1 | 7/2007 | De La Menardiere et al. |

(56) References Cited

U.S. PATENT DOCUMENTS

| | | |
|---|---|---|
| 2007/0168019 A1 | 7/2007 | Amplatz et al. |
| 2007/0173921 A1 | 7/2007 | Wholey et al. |
| 2007/0179592 A1 | 8/2007 | Schaeffer |
| 2007/0198076 A1 | 8/2007 | Hebert et al. |
| 2007/0203571 A1 | 8/2007 | Kaplan et al. |
| 2007/0213804 A1 | 9/2007 | Schaeffer et al. |
| 2007/0219620 A1 | 9/2007 | Eells et al. |
| 2007/0219621 A1 | 9/2007 | Hartley et al. |
| 2007/0225796 A1 | 9/2007 | Yadin et al. |
| 2007/0225797 A1 | 9/2007 | Krivoruhko |
| 2007/0225798 A1 | 9/2007 | Gregorich |
| 2007/0233220 A1* | 10/2007 | Greenan ............ A61F 2/07 623/1.11 |
| 2007/0233229 A1* | 10/2007 | Berra ............ A61F 2/07 623/1.13 |
| 2007/0244540 A1 | 10/2007 | Pryor |
| 2007/0244542 A1 | 10/2007 | Greenan et al. |
| 2007/0244547 A1 | 10/2007 | Greenan |
| 2007/0248640 A1 | 10/2007 | Karabey et al. |
| 2007/0250084 A1 | 10/2007 | Sharkway et al. |
| 2007/0250152 A1 | 10/2007 | Xiao et al. |
| 2007/0260302 A1 | 11/2007 | Igaki |
| 2007/0260304 A1 | 11/2007 | Gregorich et al. |
| 2007/0149166 A1 | 12/2007 | Schaeffer et al. |
| 2007/0293940 A1 | 12/2007 | Schaeffer et al. |
| 2007/0299494 A1 | 12/2007 | Zukowski |
| 2007/0299495 A1 | 12/2007 | Zukowski et al. |
| 2007/0299497 A1 | 12/2007 | Shaolian et al. |
| 2007/0299499 A1* | 12/2007 | Hartley ............ A61F 2/962 623/1.11 |
| 2007/0299501 A1 | 12/2007 | Herbert et al. |
| 2008/0009932 A1 | 1/2008 | Ta et al. |
| 2008/0009933 A1 | 1/2008 | Ta et al. |
| 2008/0009937 A1 | 1/2008 | Kipperman |
| 2008/0015681 A1 | 1/2008 | Wilson |
| 2008/0033525 A1 | 2/2008 | Shaked et al. |
| 2008/0046066 A1 | 2/2008 | Jenson et al. |
| 2008/0058918 A1 | 3/2008 | Watson |
| 2008/0065197 A1 | 3/2008 | Meyer et al. |
| 2008/0071343 A1 | 3/2008 | Mayberry et al. |
| 2008/0086191 A1 | 4/2008 | Valencia et al. |
| 2008/0109065 A1 | 5/2008 | Bowe |
| 2008/0114444 A1 | 5/2008 | Yu |
| 2008/0114446 A1 | 5/2008 | Hartley et al. |
| 2008/0133000 A1 | 6/2008 | Molony |
| 2008/0167704 A1 | 7/2008 | Wright et al. |
| 2008/0172119 A1 | 7/2008 | Yamasaki et al. |
| 2008/0172122 A1 | 7/2008 | Mayberry et al. |
| 2008/0188921 A1 | 8/2008 | Yamasaki |
| 2008/0208319 A1 | 8/2008 | Rabkin et al. |
| 2008/0255652 A1 | 10/2008 | Thomas et al. |
| 2008/0262595 A1 | 10/2008 | Chu et al. |
| 2008/0262596 A1 | 10/2008 | Xiao |
| 2008/0269866 A1 | 10/2008 | Hamer et al. |
| 2008/0269867 A1 | 10/2008 | Johnson |
| 2008/0275542 A1 | 11/2008 | LaDuca et al. |
| 2008/0281399 A1 | 11/2008 | Hartley et al. |
| 2008/0294237 A1 | 11/2008 | Chu |
| 2009/0005847 A1 | 1/2009 | Adams |
| 2009/0012602 A1 | 1/2009 | Quadri |
| 2009/0043373 A1 | 2/2009 | De La Menardiere et al. |
| 2009/0043377 A1 | 2/2009 | Greenberg et al. |
| 2009/0048663 A1* | 2/2009 | Greenberg ............ A61F 2/07 623/1.35 |
| 2009/0069880 A1 | 3/2009 | Vonderwalde et al. |
| 2009/0088791 A1 | 4/2009 | Drasler et al. |
| 2009/0099649 A1 | 4/2009 | Chobotov et al. |
| 2009/0109065 A1 | 4/2009 | Pinheiro |
| 2009/0132024 A1 | 5/2009 | Berkhoff |
| 2009/0155337 A1 | 6/2009 | Schreck et al. |
| 2009/0164001 A1 | 6/2009 | Biggs et al. |
| 2009/0216315 A1 | 8/2009 | Schreck et al. |
| 2009/0240316 A1 | 9/2009 | Bruszewski |
| 2009/0254170 A1 | 10/2009 | Hartley et al. |
| 2009/0259290 A1 | 10/2009 | Bruszewski et al. |
| 2009/0259296 A1 | 10/2009 | McIff et al. |
| 2009/0259298 A1 | 10/2009 | Mayberry et al. |
| 2009/0264985 A1 | 10/2009 | Bruszewski |
| 2009/0287145 A1 | 11/2009 | Cragg et al. |
| 2010/0004730 A1 | 1/2010 | Benjamin et al. |
| 2010/0063575 A1 | 3/2010 | Shalev et al. |
| 2010/0063576 A1 | 3/2010 | Schaeffer et al. |
| 2010/0094390 A1 | 4/2010 | Goldmann et al. |
| 2010/0179636 A1 | 7/2010 | Mayberry et al. |
| 2010/0179638 A1 | 7/2010 | Shaolian et al. |
| 2010/0261662 A1 | 10/2010 | Schreck et al. |
| 2011/0015718 A1 | 1/2011 | Schreck |
| 2011/0022153 A1 | 1/2011 | Schreck et al. |
| 2011/0054586 A1 | 3/2011 | Mayberry et al. |
| 2011/0054587 A1 | 3/2011 | Mayberry et al. |
| 2011/0224772 A1 | 9/2011 | Mayberry et al. |
| 2011/0230947 A1* | 9/2011 | Hartley ............ A61F 2/95 623/1.11 |
| 2011/0288627 A1 | 11/2011 | Hartley et al. |
| 2012/0109279 A1 | 5/2012 | Mayberry |
| 2014/0249615 A1 | 9/2014 | Schreck |
| 2014/0350658 A1 | 11/2014 | Benary et al. |
| 2015/0366688 A1 | 12/2015 | Schreck |
| 2017/0128246 A1 | 5/2017 | Mayberry |
| 2017/0266025 A1 | 9/2017 | Schreck |

FOREIGN PATENT DOCUMENTS

| | | |
|---|---|---|
| DE | 295 21 548 U1 | 2/1995 |
| DE | 295 21 776 U1 | 2/1995 |
| DE | 100 17 147 | 10/2001 |
| EP | 0 458 568 B1 | 5/1991 |
| EP | 0 177 330 B1 | 6/1991 |
| EP | 0 282 175 B1 | 11/1991 |
| EP | 0 323 176 B1 | 3/1994 |
| EP | 0 596 145 | 5/1994 |
| EP | 0 621 015 B1 | 10/1994 |
| EP | 0 659 389 | 6/1995 |
| EP | 0 688 545 B1 | 12/1995 |
| EP | 0 689 806 B1 | 1/1996 |
| EP | 0 712 614 B1 | 5/1996 |
| EP | 0 732 088 B1 | 9/1996 |
| EP | 0 740 928 B1 | 11/1996 |
| EP | 0 747 020 B1 | 12/1996 |
| EP | 0 732 089 | 2/1997 |
| EP | 0 732 089 B1 | 2/1997 |
| EP | 0 775 470 B1 | 5/1997 |
| EP | 0 782 841 B1 | 7/1997 |
| EP | 0 783 873 B1 | 7/1997 |
| EP | 0 783 874 B1 | 7/1997 |
| EP | 0 880 948 B1 | 5/1998 |
| EP | 0 880 938 B1 | 12/1998 |
| EP | 0 904 745 A2 | 3/1999 |
| EP | 0 974 314 B1 | 1/2000 |
| EP | 0 732 088 | 4/2000 |
| EP | 1 433 438 A2 | 6/2004 |
| EP | 1 470 797 | 10/2004 |
| EP | 0 935 374 | 1/2005 |
| EP | 0 935 374 B1 | 12/2007 |
| EP | 1 935 374 B1 | 6/2008 |
| EP | 1935374 | 6/2008 |
| EP | 2 429 452 | 3/2012 |
| EP | 2 635 241 | 9/2013 |
| ES | 1 038 606 | 7/1998 |
| JP | 04-25755 | 1/1992 |
| JP | 08-336597 | 12/1996 |
| JP | 9-511160 | 11/1997 |
| JP | 2000-500047 | 1/2000 |
| JP | 2004-528862 | 9/2004 |
| JP | 2007-236472 | 9/2007 |
| JP | 5629871 | 10/2014 |
| WO | WO 93/13825 | 7/1993 |
| WO | WO 94/24961 | 11/1994 |
| WO | WO 95/21592 | 8/1995 |
| WO | WO 96/34580 | 11/1996 |
| WO | WO 96/39999 | 12/1996 |
| WO | WO 96/41589 | 12/1996 |
| WO | WO 97/10757 | 3/1997 |
| WO | WO 97/10777 | 3/1997 |

(56) References Cited

FOREIGN PATENT DOCUMENTS

| | | |
|---|---|---|
| WO | WO 97/14375 | 4/1997 |
| WO | WO 97/19652 | 6/1997 |
| WO | WO 97/26936 | 7/1997 |
| WO | WO 97/033532 | 9/1997 |
| WO | WO 97/045072 | 12/1997 |
| WO | WO 98/02100 | 1/1998 |
| WO | WO 98/11846 | 3/1998 |
| WO | WO 98/27894 | 7/1998 |
| WO | WO 98/27895 | 7/1998 |
| WO | WO 98/53761 | 12/1998 |
| WO | WO 99/13808 | 3/1999 |
| WO | WO 99/029262 | 6/1999 |
| WO | WO 99/44536 | 9/1999 |
| WO | WO 99/47077 | 9/1999 |
| WO | WO 99/53865 | 10/1999 |
| WO | WO 99/58084 | 11/1999 |
| WO | WO 00/33769 | 6/2000 |
| WO | WO 00/53251 | 9/2000 |
| WO | WO 00/74595 | 12/2000 |
| WO | WO 01/03762 | 1/2001 |
| WO | WO 01/26707 | 4/2001 |
| WO | WO 2001/067993 | 9/2001 |
| WO | WO 02/39888 | 5/2002 |
| WO | WO 03/094796 | 11/2003 |
| WO | WO 04/047885 | 6/2004 |
| WO | WO 2004/089249 | 10/2004 |
| WO | WO 04/105693 A2 | 12/2004 |
| WO | WO 04/105693 A3 | 12/2004 |
| WO | WO 05/037076 | 4/2005 |
| WO | WO 05/037141 | 4/2005 |
| WO | WO 05/041810 | 5/2005 |
| WO | WO 06/028925 | 3/2006 |
| WO | WO 2006/036690 A1 | 4/2006 |
| WO | WO 06/047708 | 5/2006 |
| WO | WO 07/027830 | 3/2007 |
| WO | WO 08/034106 | 3/2008 |
| WO | WO 08/083767 | 7/2008 |
| WO | WO 08/086084 | 7/2008 |
| WO | WO 09/000546 | 12/2008 |
| WO | WO 09/105699 | 8/2009 |
| WO | WO 10/127040 | 11/2010 |
| WO | WO 12/061526 | 5/2012 |

OTHER PUBLICATIONS

U.S. Appl. No. 7,316,661, dated Jan. 2008, Zadno-Azizi (withdrawn).

International Search Report and Written Opinion for International Application No. PCT/US2010/032843, dated Jul. 29, 2010 in 17 pages.

* cited by examiner

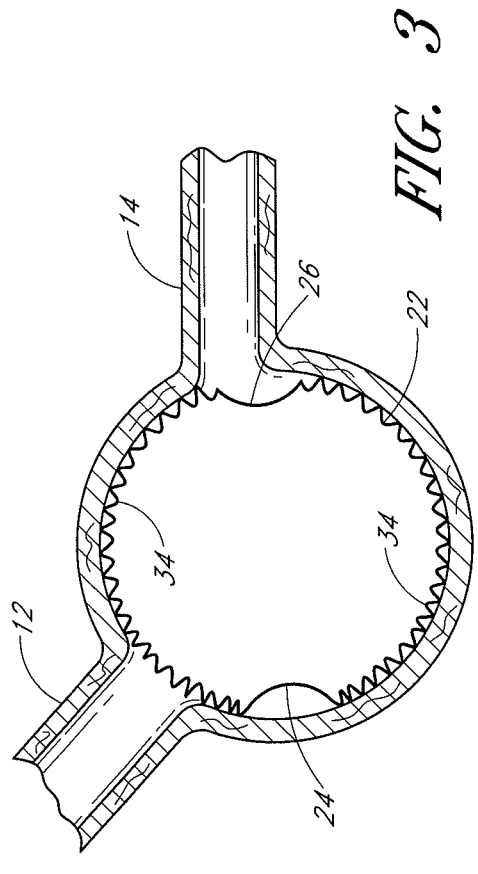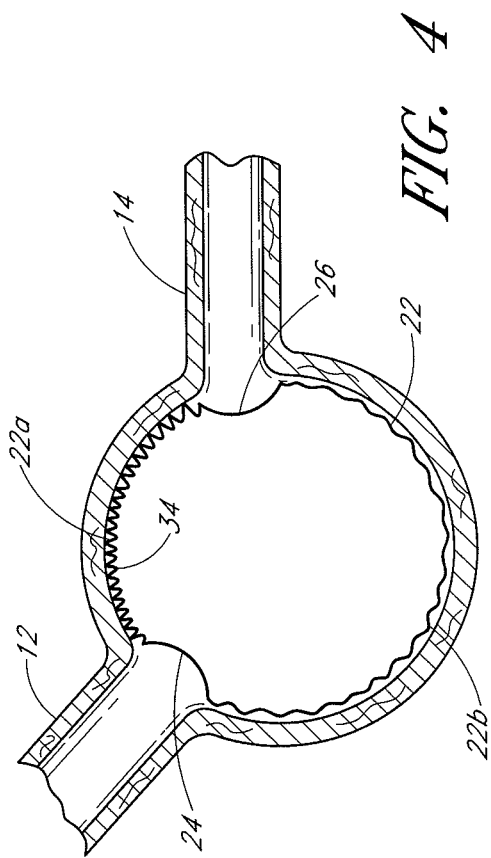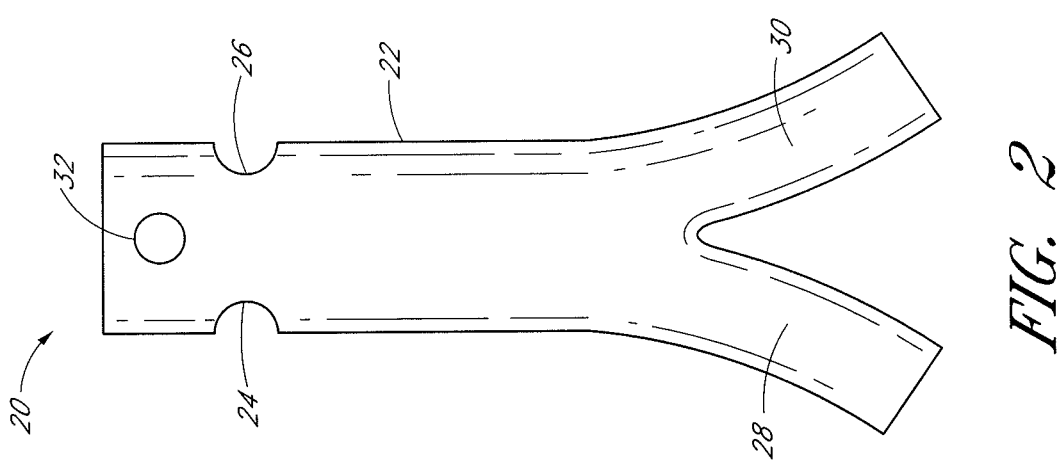

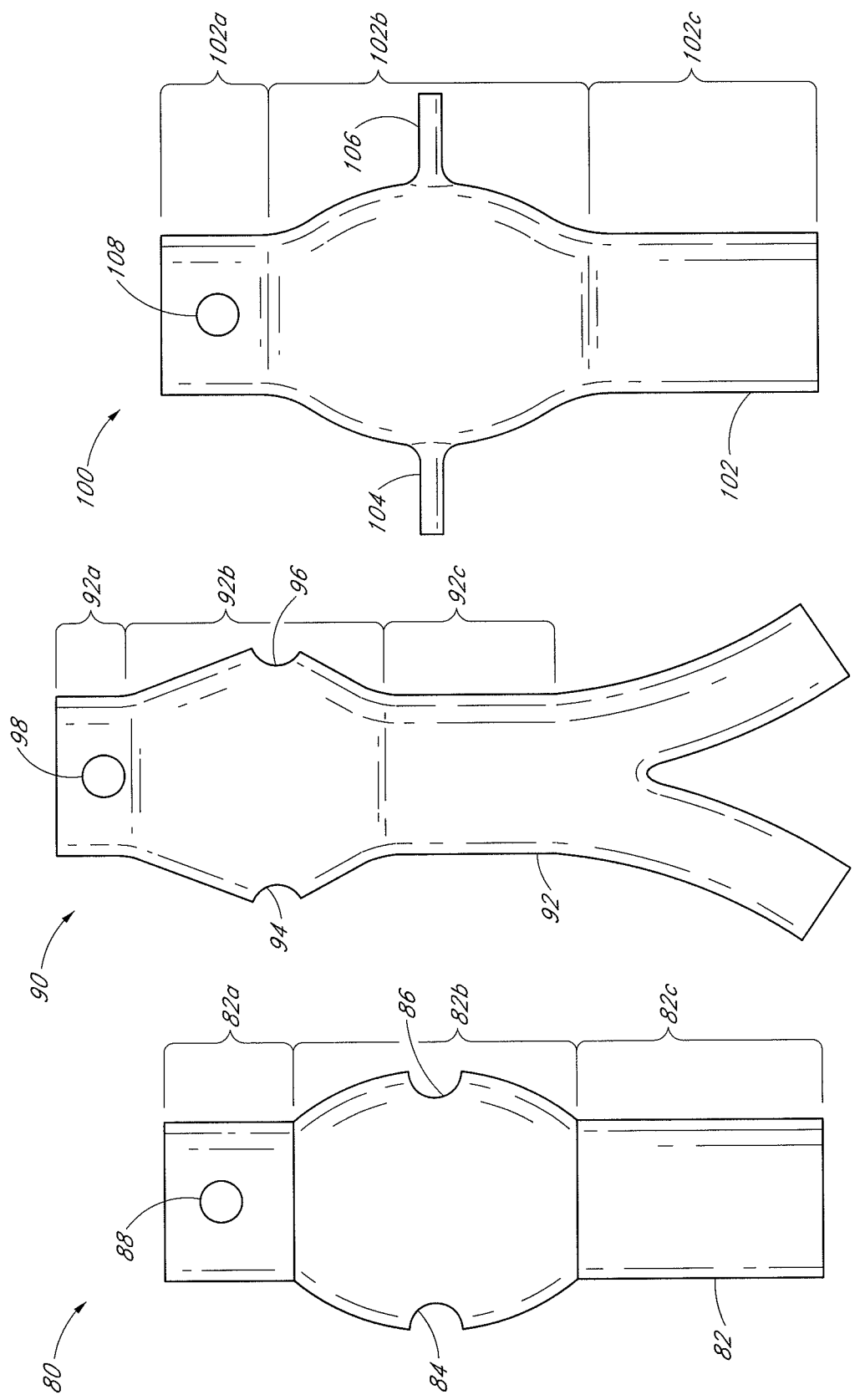

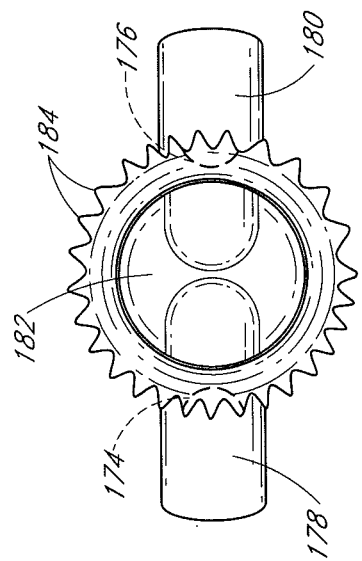
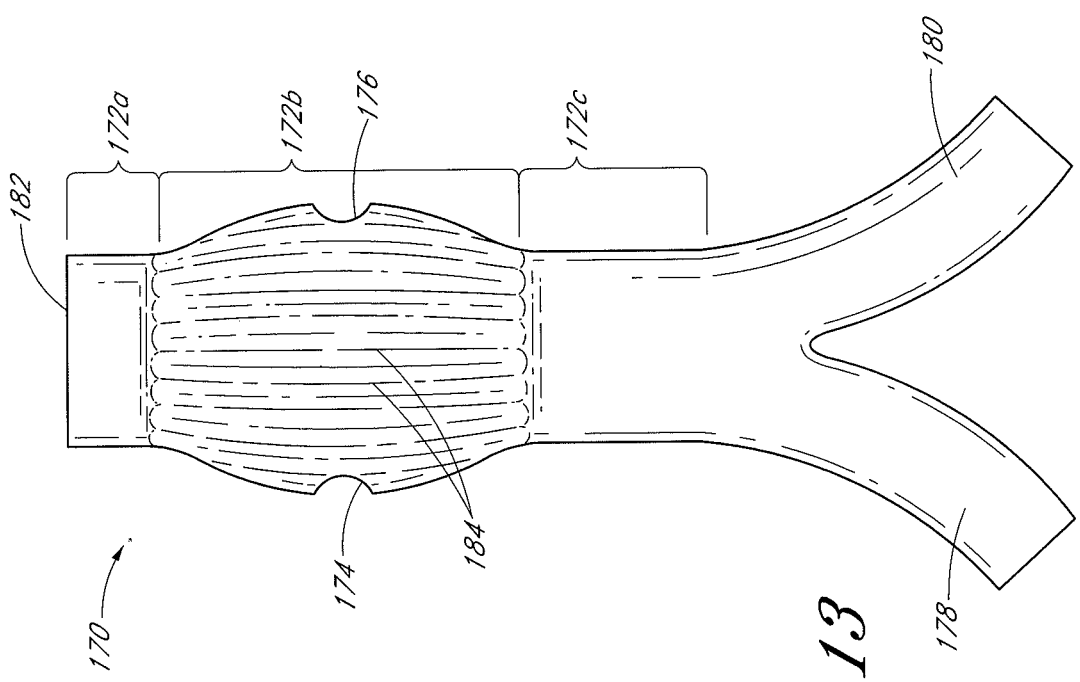
FIG. 14
FIG. 13

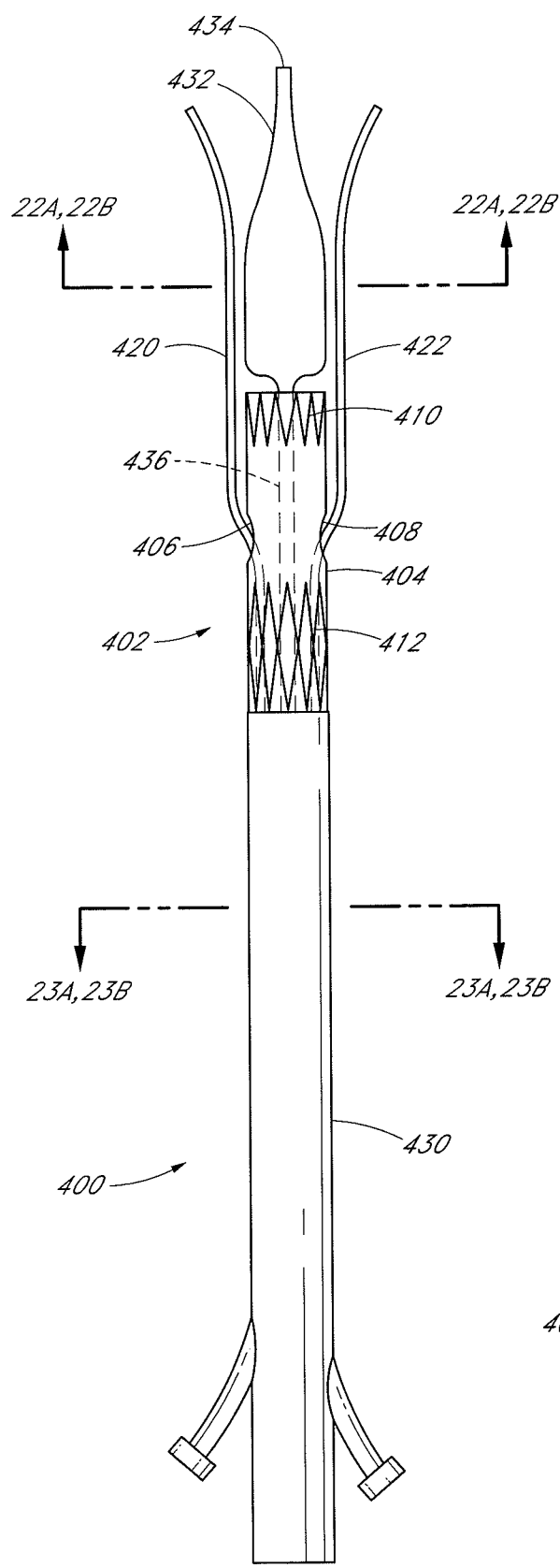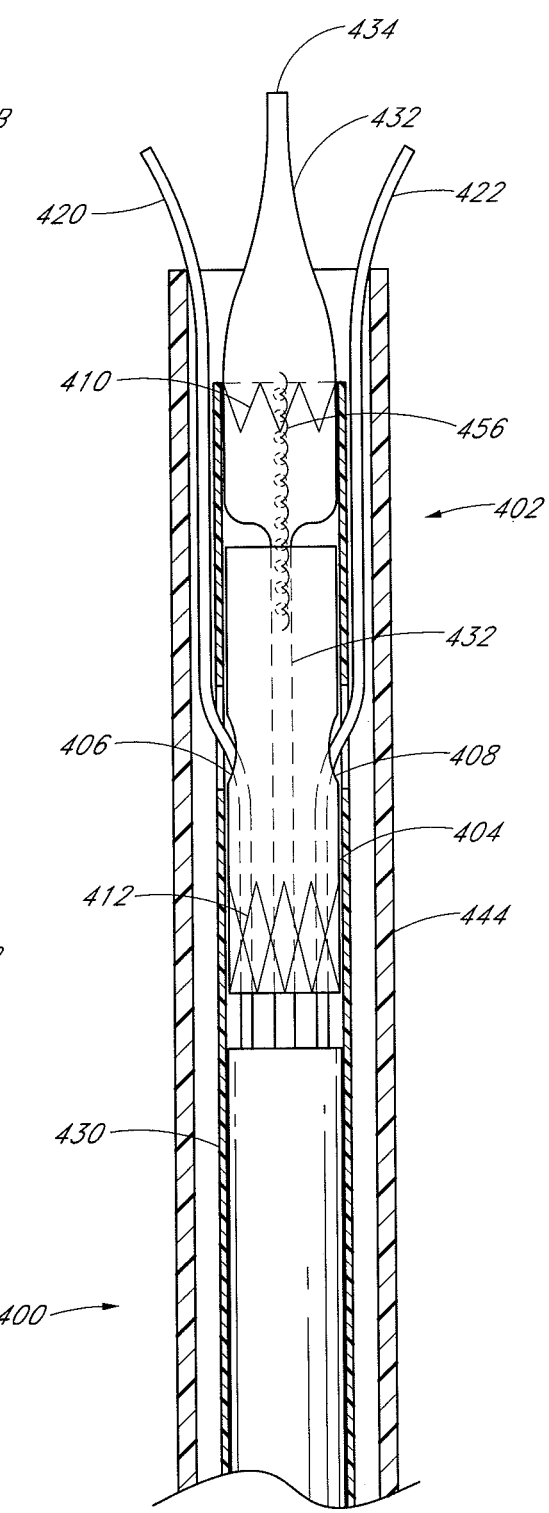
FIG. 20
FIG. 21

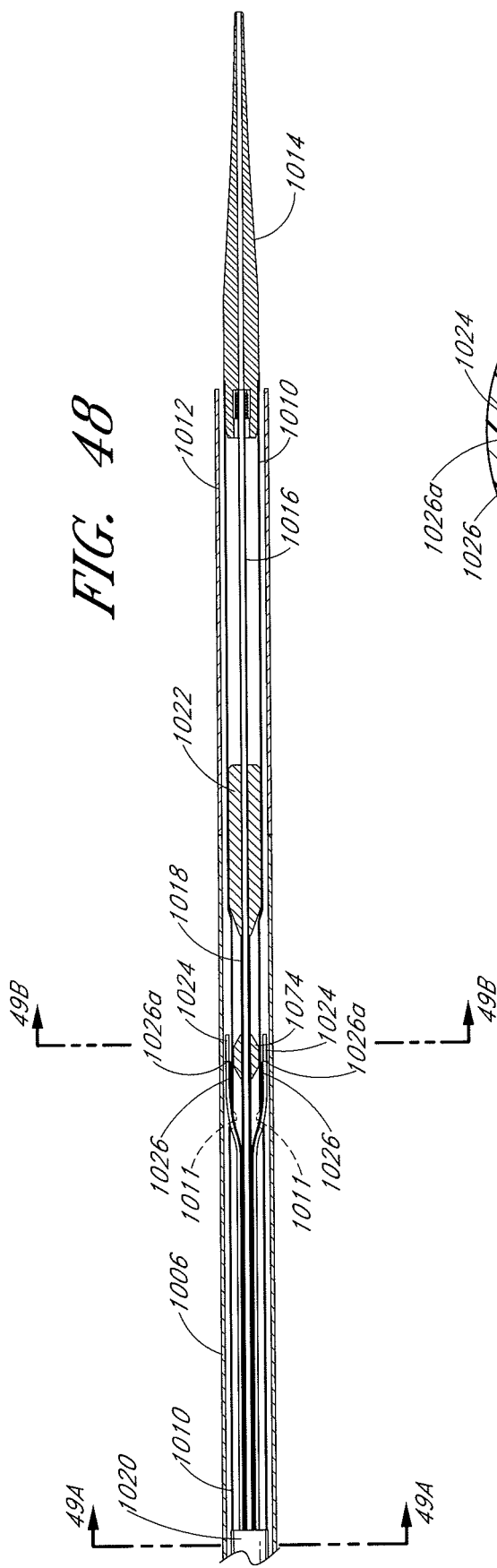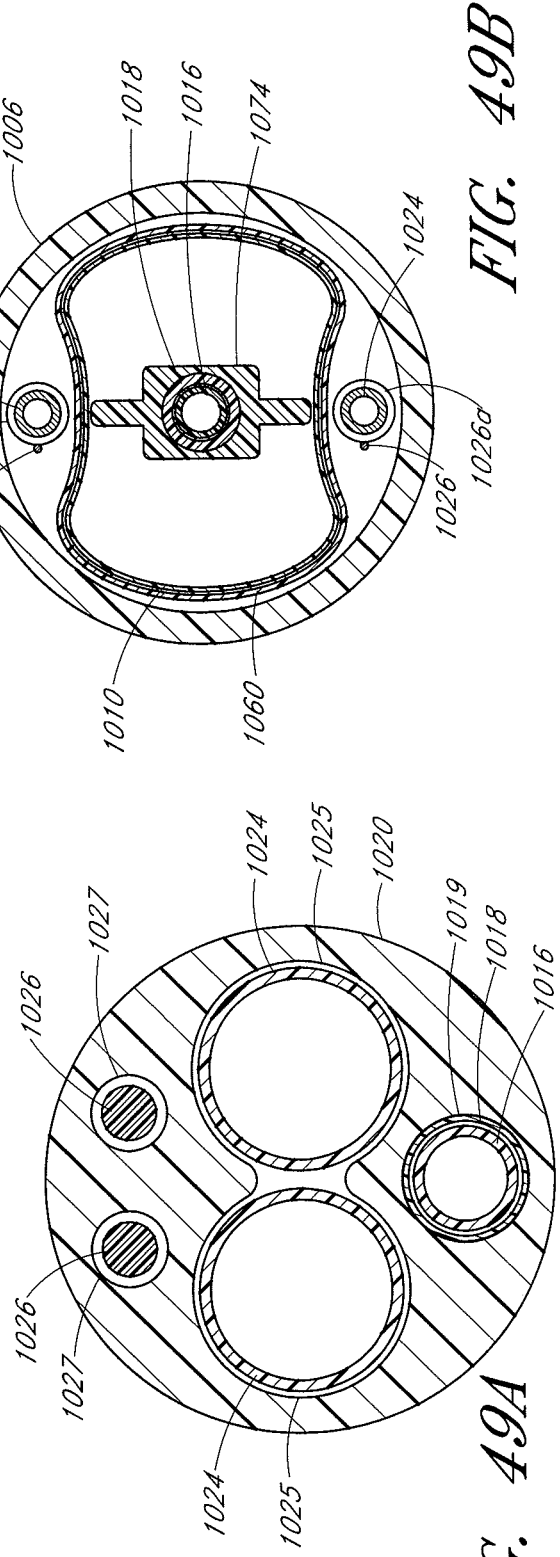

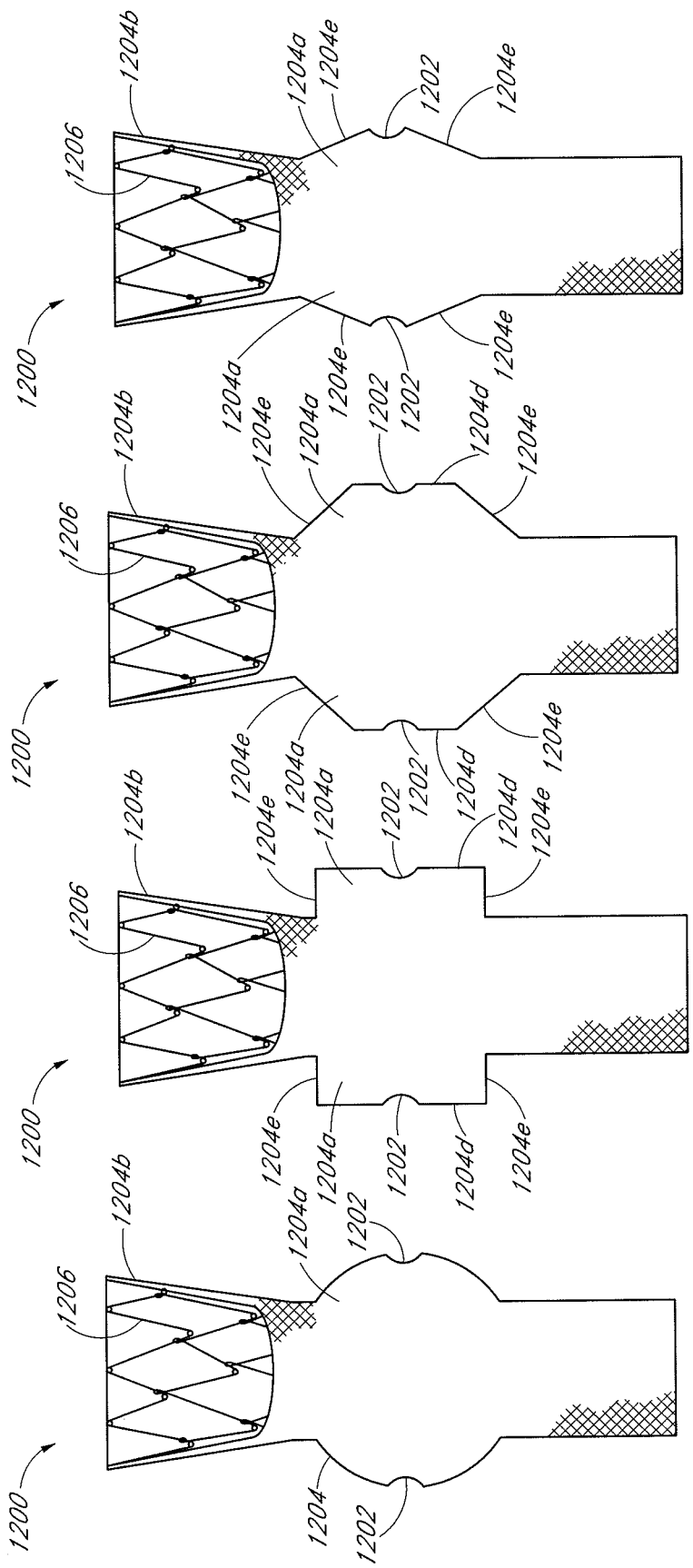

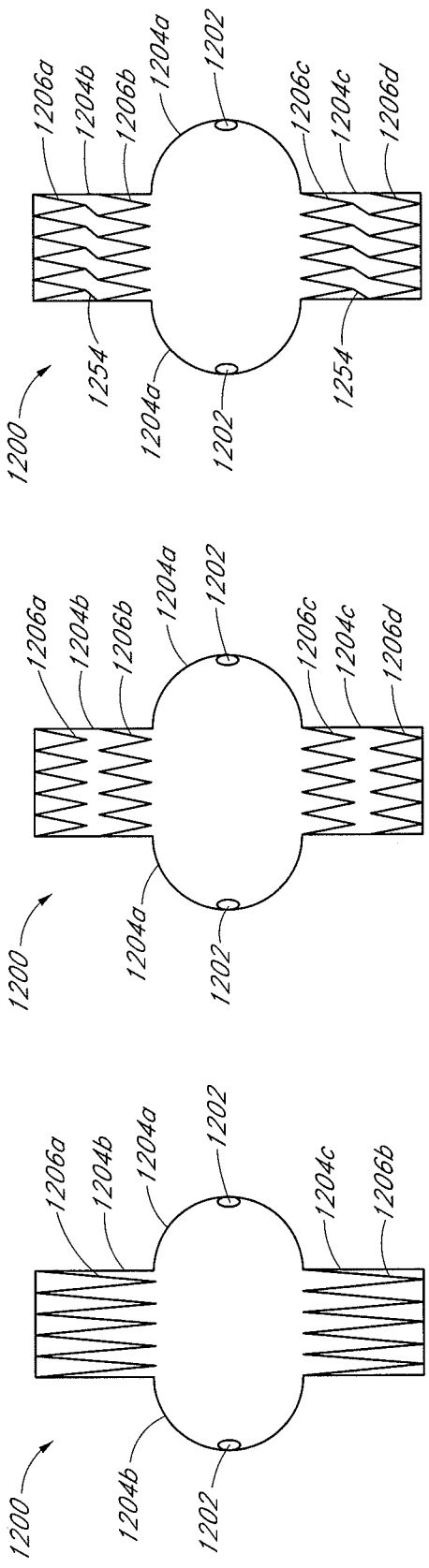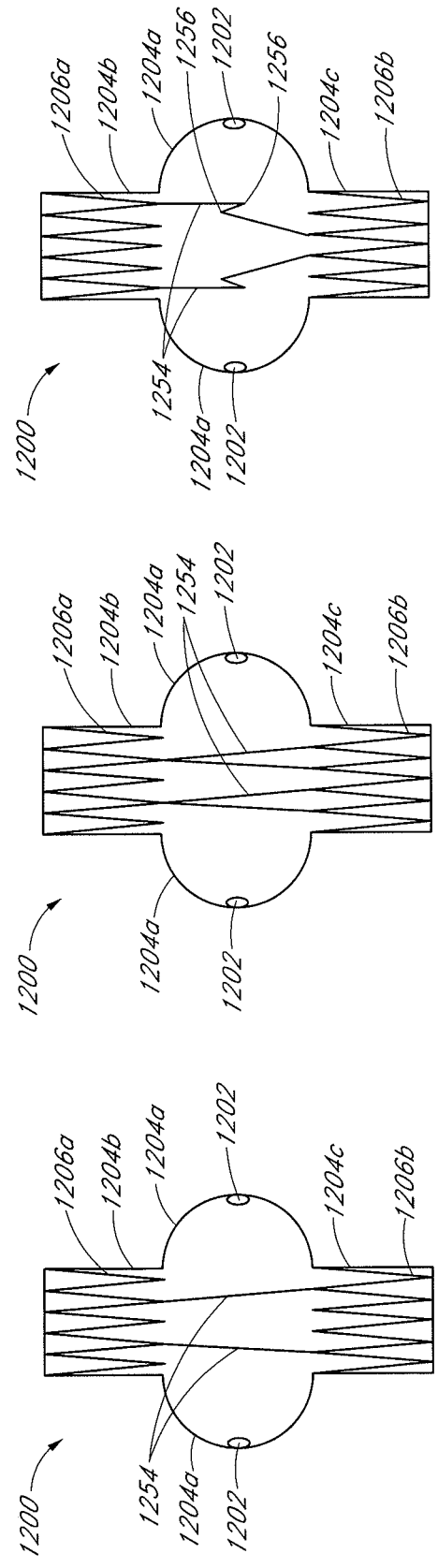
FIG. 75 FIG. 76 FIG. 77
FIG. 78 FIG. 79 FIG. 80

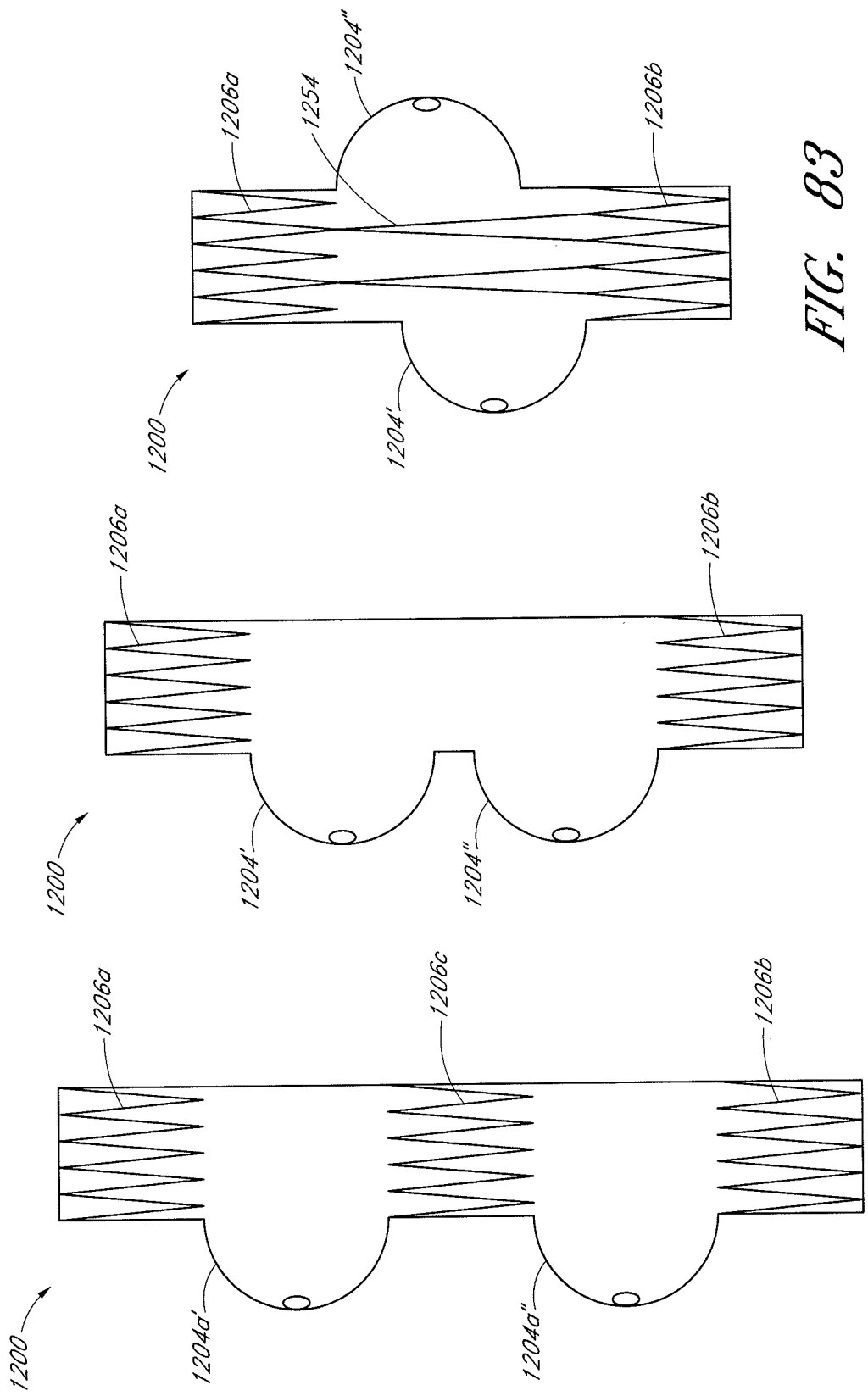

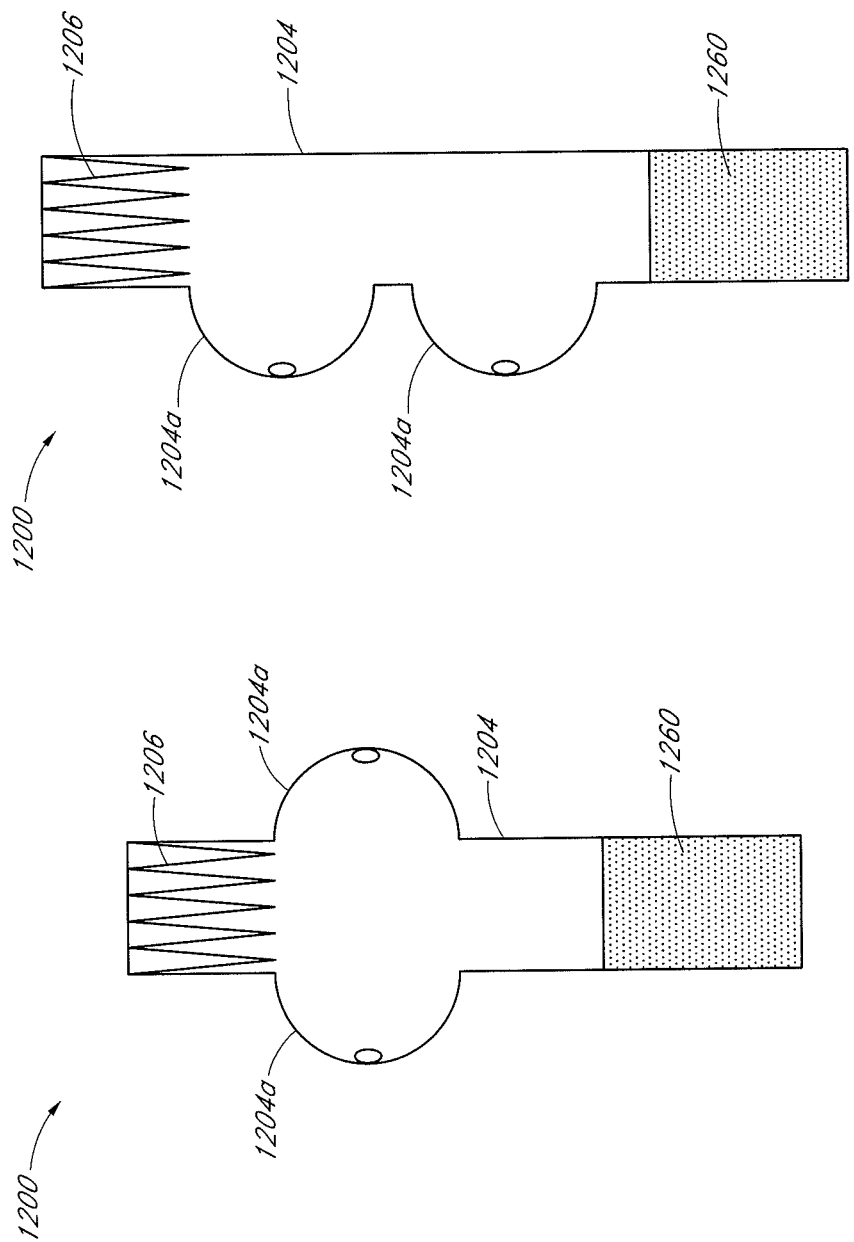

Axial Movement

If the fenestrations are evaluated in a triangle, the movement in the axial direction can be calculated.

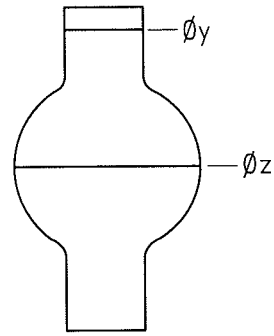

x = native vessel diameter
y = graft proximal diameter
z = diameter of enlarged graft portion

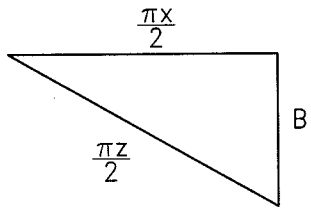

$\frac{1}{2}$ perimeter of enlarged portion = $\frac{\pi z}{2}$ $\frac{1}{2}$ perimeter of native vessel = $\frac{\pi x}{2}$ Movement = B $$B^2 + \left(\frac{\pi x}{2}\right)^2 = \left(\frac{\pi z}{2}\right)^2$$

$$B = \sqrt{\left(\frac{\pi x}{2}\right)^2 - \left(\frac{\pi z}{2}\right)^2}$$

Example:

$$B = \sqrt{\left(\frac{\pi 36}{2}\right)^2 - \left(\frac{\pi 26}{2}\right)^2}$$

Angular Movement
x = native vessel diameter
y = graft proximal diameter
z = diameter of enlarged graft portion
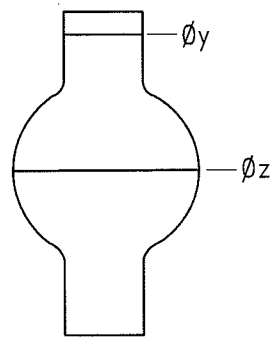
$\frac{1}{2}$ perimeter of enlarged portion = $\frac{\pi z}{2}$
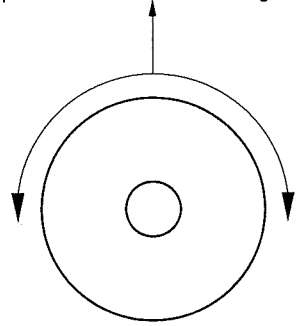
Maximum angular movement = $\dfrac{\frac{\pi z}{2}}{\pi x} \cdot 360° - 180°$
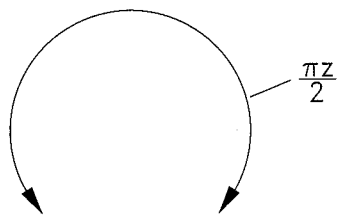
Example:
    x = 26mm
    z = 36mm
$$\dfrac{\frac{\pi(36)}{2}}{\pi(26)} \cdot 360° - 180° = 69°$$
*FIG. 87*

FENESTRATED PROSTHESIS

PRIORITY INFORMATION AND INCORPORATION BY REFERENCE

This application is a continuation of U.S. application Ser. No. 12/769,581, filed Apr. 28, 2010, which claims priority benefit under 35 U.S.C. § 119(e) of Provisional Application 61/173,485 filed Apr. 28, 2009, Provisional Application 61/228,048 filed Jul. 23, 2009, and Provisional Application 61/231,898 filed Aug. 6, 2009, which applications are hereby incorporated by reference as if fully set forth herein. Additionally, U.S. patent application Ser. No. 12/496,446, filed on Jul. 1, 2009 (entitled "CATHETER SYSTEM AND METHODS OF USING SAME"), U.S. patent application Ser. No. 12/390,346, filed on Feb. 20, 2009 (entitled "DESIGN AND METHOD OF PLACEMENT OF A GRAFT OR GRAFT SYSTEM"), U.S. patent application Ser. No. 12/101,863, filed on Apr. 11, 2008 (entitled "BIFURCATED GRAFT DEPLOYMENT SYSTEMS AND METHODS"), U.S. Pat. No. 6,077,296, filed on Mar. 4, 1998 (entitled "ENDOLUMINAL VASCULAR PROSTHESIS"), U.S. Pat. No. 6,953,475, filed on Sep. 30, 2003 (entitled "BIFURCATION GRAFT DEPLOYMENT CATHETER"), and U.S. Pat. No. 7,520,895, filed on Apr. 8, 2002 (entitled "SELF EXPANDING BIFURCATED ENDOVASCULAR PROSTHESIS") are also hereby incorporated by reference in their entireties as if fully set forth herein.

BACKGROUND OF THE DISCLOSURE

Technical Field

The present invention relates to endoluminal vascular prostheses and methods of deploying such prostheses, and, in one application, to endoluminal vascular prostheses for use in the treatment of vessels with branches.

Description of the Related Art

An abdominal aortic aneurysm is a sac caused by an abnormal dilation of the wall of the aorta, a major artery of the body, as it passes through the abdomen. The abdomen is that portion of the body that lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of polyester, urethane, Dacron®, Teflon®, or other suitable material.

To perform the surgical procedure requires exposure of the aorta through an abdominal incision which can extend from the rib cage to the pubis. The aorta must typically be closed both above and below the aneurysm, so that the aneurysm can then be opened and the thrombus, or blood clot, and arteriosclerotic debris removed. Small arterial branches from the back wall of the aorta are tied off. The Dacron® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. Since the graft must typically be secured, or sutured, to the remaining portion of the aorta, it is many times difficult to perform the suturing step because the thrombosis present on the remaining portion of the aorta, and that remaining portion of the aorta wall may be friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft in the endoluminal position (within the lumen of the artery). By this method, the graft is attached to the internal surface of an arterial wall by means of attachment devices (expandable stents), typically one above the aneurysm and a second stent below the aneurysm.

Stents can permit fixation of a graft to the internal surface of an arterial wall without sewing or an open surgical procedure. Expansion of radially expandable stents is conventionally accomplished by dilating a balloon at the distal end of a balloon catheter. In U.S. Pat. No. 4,776,337, for example, Palmaz describes a balloon-expandable stent for endovascular treatments. Also known are self-expanding stents, such as described in U.S. Pat. No. 4,655,771 to Wallsten.

In certain conditions, the diseased region of the blood vessels can extend across branch vessels. The blood flow into these branch vessels is critical for the perfusion of the peripheral regions of the body and vital organs. Many arteries branch off the aorta. For example, the carotid arteries supply blood into the brain, the renal arteries supply blood into the kidneys, the superior mesenteric artery ("SMA") supplies the pancreas, the hypogastric arteries supply blood to the reproductive organs, and the subclavian arteries supply blood to the arms. When the aorta is diseased, the branch vessels may also be affected. Thoracic aortic aneurysms may involve the subclavian and carotid arteries, abdominal aneurysms may involve the SMA, renal and hypogastric arteries. Aortic dissections may involve all branch vessels mentioned above. When this occurs, it may be detrimental to implant a conventional tubular graft in this location of the aorta or the blood vessel, since such a graft may obstruct the flow of blood from the aorta into the branches.

Grafts and graft systems are typically used to treat aneurysms in the aorta or in other blood vessels. These grafts can be positioned within the aorta or other blood vessels at the location of an aneurysm and, generally speaking, can provide a synthetic vessel wall that channels the flow of blood through the diseased portion of the blood vessel. As such, the grafts are typically fluid impermeable so that no blood can flow through the walls of the graft. Rather, the blood is channeled through the central passageway defined by the graft.

Thus, there is a need to place endoluminal prostheses in the aorta without obstructing critical branch vessels. The embodiments of the endoluminal prostheses disclosed herein provide a solution to the problems described above.

SUMMARY OF SOME EXEMPLIFYING EMBODIMENTS

Some embodiments of the endoluminal prostheses disclosed (directly and/or by incorporation by reference) herein pertain to designs and methods of placement of a branch graft or branch graft system having lateral openings in the main graft. The main graft can be positioned within the main blood vessel such as the aorta so that the lateral openings (also referred to herein as fenestrations) can be aligned with the branch blood vessels, to allow blood to flow through the openings in the main graft and into the branch vessels. Because the axial and angular position of the branch blood vessels can vary from one patient's anatomy to the next, the embodiments of the graft systems disclosed herein can allow a surgeon to adjust the position of the fenestrations so as to align the fenestrations with the branch vessels so that blood flow through the branch vessels is not obstructed by the main graft.

The branch graft system can comprise a tubular expandable main body and at least one fenestration or at least one branch graft at any desired location. The main graft body and/or the branch graft can be made from an expandable material, such as but not limited to ePTFE. In some embodiments, the main graft can have two fenestrations or branch grafts formed therein at generally diametrically opposed locations or at positions that are offset from the diametrically opposed positions. Depending on the particular patient's anatomy, other cut-outs, scallops, or fenestrations, such as but not limited to a fenestration for the superior mesenteric artery ("SMA"), can be formed in the main graft depending on the patient's anatomy and position of the graft.

Some embodiments of the main graft body can have a tubular shape and can have a diameter that can be significantly larger than the diameter of the target vessel into which the graft is intended to be deployed. As will be described in greater detail below, the oversized diameter of the main graft can provide excess or slack graft material in the main graft to allow the fenestrations to each be moved in a plurality of axial and/or angular directions so that the fenestrations can be aligned with the branch arteries.

In some embodiments, one or more branch grafts can be supported by the main graft body adjacent to the one or more openings that can be formed in the main graft body. The diameter of each branch graft can be sufficiently small so as to allow each branch graft to be manipulated into the desired vascular position by moving the branch graft over a guidewire. The branch graft can be expanded to the diameter of the branch vessel by mechanical means, which can be a dilation balloon.

Some embodiments are directed to endoluminal prostheses, comprising a first stent portion and a second stent portion, a main graft body comprising a first portion, a second portion, and a third portion, the second portion having a cross-sectional size that is significantly larger than a cross-sectional size of the first portion or the third portion, and also significantly larger than a cross-sectional size of the target vessel, and one or more openings formed in the second portion of the main graft body. In some embodiments, the first portion of the main graft body can be attached to the first stent portion and the third portion of the main graft body can be attached to the second stent portion. Further, prosthesis can be configured such that the second portion of the main graft body is not directly attached to the first stent portion, the second stent portion, or any other internal support structure, or so that the second portion has a minimal number of attachment points thereto.

Some embodiments are directed to endoluminal prostheses, comprising a main graft body comprising a first portion, a second portion, and a third portion, the second portion having a cross-sectional size that is significantly larger than a cross-sectional size of the first portion or the third portion, and also significantly larger than a cross-sectional size of the target vessel, and one or more openings formed in the second portion of the main graft body. In some embodiments, the first portion of the main graft body can be radially supported by a first support member and the third portion of the main graft body can be radially supported by a second support member. In some embodiments, the second portion of the main graft body can be free of radial support from a stent or other support member.

Some embodiments are directed to endoluminal prostheses, comprising a main graft body comprising a first portion, a second portion, and a third portion, a support member positioned within the main graft body, the support member having a first support portion, a second support portion, and a third support portion, and one or more openings formed in the second portion of the main graft body. In some embodiments, the first portion of the main graft body can be attached to the first support portion of the support member at a first number of attachment points, the second portion of the main graft body can be attached to the second support portion of the support member at a second number of attachment points, and the third portion of the main graft body can be attached to the third support portion of the support member at a third number of attachment points. Without limitation, the third number of attachment points can be less than the first number of attachment points and the third number of attachment points. In some embodiments, the entirety of the second portion can have a cross-sectional size that is significantly larger than a cross-sectional size of the first portion or the third portion, and also significantly larger than a cross-sectional size of the target vessel.

Some embodiments or arrangements are directed to methods for deploying an endoluminal prosthesis, comprising advancing a catheter supporting the endoluminal prosthesis therein through a patient's vasculature to a target vessel location, advancing one or more catheters through one or more fenestrations formed in the main graft body and into one or more branch vessels in the patient's vasculature, at least partially expanding at least the second portion of the main graft body, and substantially aligning the one or more fenestrations formed within the second portion of the main graft body with the one or more branch vessels by moving the one or more fenestrations in a circumferential and/or axial direction toward the ostium of the one or more branch vessels. In some embodiments or arrangements, the prosthesis can have a main graft body comprising a first portion, a second portion, and a third portion. Further, in some embodiments or arrangements, the second portion of the main graft body can have a cross-sectional size that is significantly larger than a cross-sectional size of the first portion and the third portion, and also significantly larger than a cross-sectional size of the target vessel.

Some embodiments or arrangements are directed to methods for deploying a graft in a patient's blood vessel having at least a first branch blood vessel, comprising advancing a delivery catheter into a blood vessel, the delivery catheter supporting a fenestrated prosthesis comprising a main graft body therein, and exposing at least one branch sheath. The branch sheath can be positioned within the delivery catheter so as to extend from a main lumen of the prosthesis through a first opening formed through a wall of the prosthesis. Some embodiments can further comprise advancing an angiographic catheter into the branch sheath and cannulating a first target branch vessel before expanding the main graft body of the prosthesis.

Some embodiments or arrangements are directed to methods for deploying a fenestrated prosthesis in a patient's blood vessel having at least a first branch blood vessel, comprising advancing a delivery catheter into a blood vessel, exposing at least one guide sheath, the guide sheath being positioned within the delivery catheter so as to extend from a main lumen of the prosthesis through a first opening formed through a wall of the prosthesis, and advancing an angiographic catheter through the guide sheath and cannulating a first target branch vessel before completely removing the second restraint. In some embodiments, the delivery catheter can support the fenestrated prosthesis having a main graft body and at least one fenestration extending through the main graft body, a first restraint restraining a proximal portion of the prosthesis, and a second restraint restraining a distal portion of the prosthesis, the distal portion of the prosthesis being closer to a proximal portion of the delivery catheter than the proximal portion of the prosthesis.

Some embodiments or arrangements are directed to methods for deploying a fenestrated prosthesis in a patient's blood vessel having at least a first branch blood vessel, comprising advancing a delivery catheter into a blood vessel, exposing at least one guide sheath, the guide sheath being positioned within the delivery catheter so as to extend from a main lumen of the prosthesis through a first opening formed through a wall of the prosthesis, and advancing the guide sheath into a first target branch vessel before completely removing the second restraint. In some embodiments, the delivery catheter can support the fenestrated prosthesis, and the fenestrated prosthesis can have a main graft body and at least one fenestration therein, a first restraint restraining a proximal portion of the prosthesis, and a second restraint restraining a distal portion of the prosthesis, the distal portion of the prosthesis being closer to a proximal portion of the delivery catheter than the proximal portion of the prosthesis, Some embodiments or arrangements are directed to delivery systems for deploying an endoluminal prosthesis, comprising a first restraint configured to restrain a portion of the prosthesis, a second restraint configured to restrain a second portion of the prosthesis, a first opening through a wall of the prosthesis, a first guide sheath extending from a proximal end of the delivery system into a main lumen of the endoluminal prosthesis and through the first opening in the wall of the prosthesis, a first stent configured to support the first portion of the endoluminal prosthesis, and a second stent configured to support the second portion of the endoluminal prosthesis, wherein the guide sheath is moveable before removing the first and second restraints. The first opening can be positioned between the first and second portions.

Some embodiments or arrangements are directed to endoluminal prostheses comprising a main graft body defining a flow lumen therethrough, a first opening passing through a wall of the main graft body, and a first support member supported by the main graft body and overlapping an edge of the first opening, the first support member being configured to increase the tear resistance of the main graft body adjacent to the first opening.

Some embodiments or arrangements are directed to methods for forming an endoluminal prosthesis having at least one reinforced fenestration in a main portion thereof, comprising forming a graft body having a tubular main body portion, forming a first opening through a wall of the main body portion, the first opening having a first state in which the first opening is substantially unstretched and a second state in which the first opening is stretched so that a size of the first opening increases, advancing a tubular member partially through the first opening, and fastening a first end portion and a second end portion of the tubular member to the wall of the main body portion adjacent to the first opening so that the tubular member completely overlaps an edge of the first opening.

In any of the embodiments disclosed (directly or by incorporation by reference) herein, main graft body, branch grafts, or any other component of the endoluminal prostheses or deployment systems disclosed herein can have at least one radiopaque suture or marker attached thereto to assist with the placement of such components.

BRIEF DESCRIPTION OF THE DRAWINGS

FIG. 2 is a side view of the endoluminal prosthesis illustrated in FIG. 1.

FIG. 3 is a cross-sectional view of the embodiment of the endoluminal prosthesis deployed in the patient's anatomy, taken through line 3-3 in FIG. 1, before the fenestrations have been aligned with the respective branch vessels.

FIG. 4 is a cross-sectional view of the embodiment of the endoluminal prosthesis deployed in the patient's anatomy, taken through line 3-3 in FIG. 1, after the fenestrations have been aligned with the respective branch vessels.

FIGS. 6-12 are side views of additional embodiments of endoluminal prostheses.

FIG. 13 is a side view of another embodiment of an endoluminal prosthesis.

FIG. 14 is a top view of the embodiment of the endoluminal prosthesis shown in FIG. 14.

FIG. 20 is a side view of another embodiment of a delivery catheter that can be used to deploy at least some of the embodiments of the endoluminal prostheses disclosed herein, showing the endoluminal prosthesis being loaded within a delivery catheter.

FIG. 21 is an enlarged side view of a portion of the embodiment of a delivery catheter illustrated in FIG. 20, showing the endoluminal prosthesis loaded within a delivery catheter.

FIG. 48 is a section view of a portion of the embodiment of the delivery catheter shown in FIG. 43, defined by curve 48-48 shown in FIG. 43A.

FIG. 49A is a section view of the embodiment of the delivery catheter shown in FIG. 43, defined by the line 49A-49A shown in FIG. 48.

FIG. 49B is a section view of the embodiment of the delivery catheter shown in FIG. 43, defined by the line 49B-49B shown in FIG. 48.

FIGS. 71-85 are side views of additional embodiments of prostheses having or more enlarged portions and one or more fenestrations therein.

FIG. 86 illustrates calculations regarding the theoretical axial adjustability of at least some embodiments of the grafts disclosed herein.

FIG. 87 illustrates calculations regarding the theoretical angular or radial adjustability of at least some embodiments of the grafts disclosed herein.

DETAILED DESCRIPTION OF SOME EXEMPLIFYING EMBODIMENTS

Figure 1:
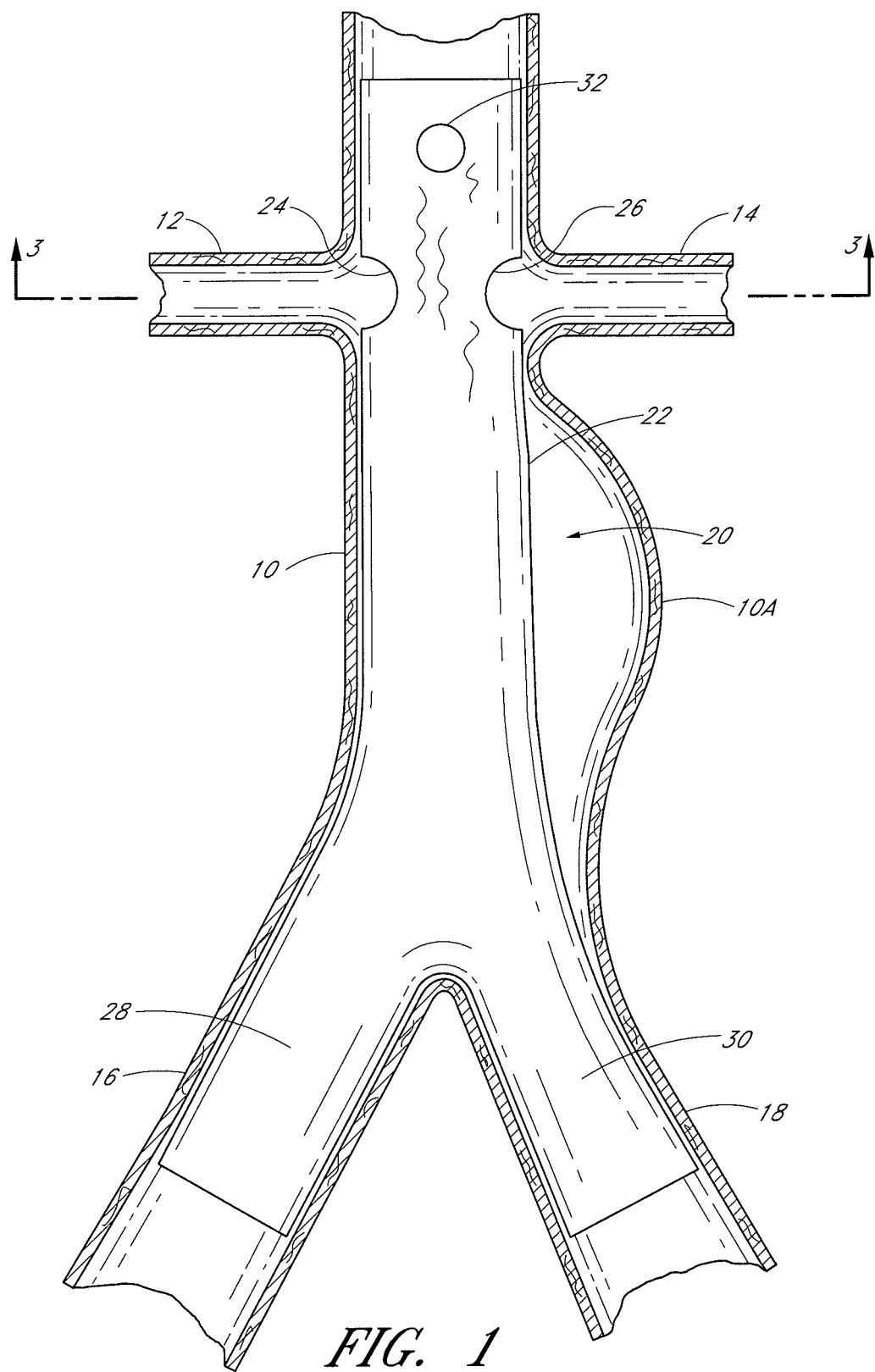
FIG. 1 is a partial section view of a patient's vasculature illustrating an embodiment of an endoluminal prosthesis deployed in the desired position within the patient's vasculature.

The following detailed description is now directed to certain specific embodiments of the disclosure. In this description, reference is made to the drawings wherein like parts are designated with like numerals throughout the description and the drawings.

Some embodiments described herein are directed to systems, methods, and apparatuses to treat lesions, aneurysms, or other defects in the aorta, including, but not limited to, the thoracic, ascending, and abdominal aorta, to name a few. However, the systems, methods, and apparatuses may have application to other vessels or areas of the body, or to other fields, and such additional applications are intended to form a part of this disclosure. For example, it will be appreciated that the systems, methods, and apparatuses may have application to the treatment of blood vessels in animals. In short, the embodiments and/or aspects of the endoluminal prosthesis systems, methods, and apparatuses described herein can be applied to other parts of the body or may have other applications apart from the treatment of the thoracic, ascending, and abdominal aorta. And, while specific embodiments may be described herein with regard to particular portions of the aorta, it is to be understood that the embodiments described can be adapted for use in other portions of the aorta or other portions of the body and are not limited to the aortic portions described.

As will be described, any of the graft embodiments disclosed herein can be configured to have excess or slack graft material in at least a portion thereof relative to the stent or support member which supports the graft. In some embodiments, without limitation, the excess or slack material can result from either an enlarged diametric portion of the graft, excess length of the graft material relative to a stent or other support structure, or a combination of both the enlarged diametric portion of the graft and excess length of the graft material. For example, without limitation, the excess graft material can form a bulge or other enlargement in the graft in the approximate location of one or more fenestrations formed through the graft material. The excess or slack material along the circumference of the graft (for example, without limitation, in the enlarged portion of the graft) can allow for circumferential and/or axial movement of the graft material and, hence, can allow for circumferential and/or axial movement of the one or more fenestrations, relative to the stent and the ostium of the patient's branch vessels. Therefore, in some embodiments, the diameter of the graft at and/or adjacent to the location of one or more fenestrations through the graft material can be larger than the local diameter of the target vessel. Similarly, in some embodiments, the diameter of the graft at and/or adjacent to the location of one or more fenestrations can be larger than the diameter of the non-enlarged portion of the graft material.

For example, any of the embodiments disclosed herein can be configured such that the graft has an enlarged or excess slack portion at or adjacent to the location of the fenestrations, wherein such enlarged or excess slack portion is free of attachment points or has only a minimal number of attachment points to the stent or support structure radially adjacent to the enlarged or excess slack portion. In some embodiments, this can result in both freedom of circumferential and axial movement of the fenestrations, thereby improving the positional adjustability of the fenestrations. In some embodiments, the enlarged or excess slack portions of the graft can be radially unsupported by the stent or support member, or can be supported by a stent or support member or by connectors connecting support members positioned axially adjacent to the enlarged or excess slack portion. Accordingly, any of the graft embodiments described herein can be configured to have excess circumferential or longitudinal material at any portion of the graft to increase the positional adjustability of one or more fenestrations formed in the graft.

Further, any of the graft embodiments disclosed herein, including those with diametrically enlarged portions, can have excess graft material in an axial direction. The excess or slack material along the length of the graft can increase the circumferential and/or axial movement of the graft material adjacent to the one or more fenestrations formed in the graft material. Accordingly, in some embodiments, the length of the graft material between the proximal and distal attachment points to the stent can be longer than that of the stent between the proximal and distal attachment points. Or, in some embodiments, the graft material in a mid portion of the graft, including on either side of the enlarged portion, can have an increased length relative to the stent adjacent to such graft portion.

As can be seen in the table of measurement data below, the relative position of a patient's left and right renal arteries, a patient's superior mesenteric artery ("SMA"), and a patient's celiac artery can vary widely. For this reason, the adjustability of one or more fenestrations within the graft material can greatly improve the positional ease and accuracy of the fenestrations relative to the patient's branch arteries during deployment of the graft.

| Measurement Description | Average | Minimum | Maximum |
| --- | --- | --- | --- |
| Distance from right renal to SMA | 14.0 mm | −8.9 mm | 42.9 mm |
| Distance from left renal to SMA | 16.9 mm | −8.0 mm | 47.0 mm |
| Distance from celiac to SMA | −10.6 mm | −36.0 mm | 23.6 mm |
| Angle from right renal to SMA | 72.3 degrees | 32.1 degrees | 115.9 degrees |
| Angle from left renal to SMA | 79.0 degrees | 30.9 degrees | 118.4 degrees |
| Angle between left and right renal arteries | 151.3 degrees | | |

FIG. 1 is a partial section view of a patient's vasculature illustrating an embodiment of an endoluminal prosthesis deployed in the desired position within the patient's vasculature. Although the prostheses disclosed herein can be adapted for deployment in any suitable vessels in the body, some embodiments are described as being deployed in particular vessels or vascular regions within a patient's body. However, the particular prostheses illustrated are not limited to deployment in only one particular vessel or vascular region. In some embodiments, the embodiments shown can be adapted for deployment in other suitable vessels within a patient's body, including the aorta, thoracic artery, renal arteries, iliac arteries, etc.

As an example, with reference to FIG. 1, an embodiment of an endoluminal prosthesis is shown deployed in a patient's aorta 10. An anuerysmic sac 10A is also shown. For reference, also illustrated are a patient's first and second renal arteries 12, 14, respectively, and a patient's ipsilateral and contralateral iliac arteries 16, 18, respectively. FIG. 2 is a side view of the endoluminal prosthesis 20 illustrated in FIG. 1. The embodiment of the endoluminal prosthesis 20 illustrated in FIGS. 1 and 2 can have a main graft body 22, a first fenestration 24, and a second fenestration 26. In some embodiments, as in the illustrated embodiment, the main graft can be a bifurcated graft having a first bifurcated branch 28 and a second bifurcated branch 30 for placement in the ipsilateral and contralateral iliac arteries.

In some embodiments, the main graft body 22 can have a generally cylindrical, tubular shape. The endoluminal prosthesis 20 can be formed from any suitable material, such as, but not limited to, ePTFE. Some embodiments of the endoluminal prosthesis 20 can be formed from an expandable material. The endoluminal prosthesis 20 can be formed such that the main graft body 22 can be significantly larger than the target vessel into which the main graft body 22 is to be deployed. As illustrated in FIG. 1, the target vessel can be the aortic artery, and the endoluminal prosthesis can be deployed so as to span across an aneurysm in the abdominal aortic.

In any of the graft embodiments disclosed herein, the diameter of the graft body (such as without limitation the main graft body 22) or an enlarged portion of any embodiment of a graft body disclosed herein can be approximately 30% larger than the diameter of the target vessel or the diameter of the non-enlarged portion of the graft body. In some embodiments, the diameter of the graft body (such as without limitation the main graft body 22) or an enlarged portion of any embodiment of a graft body disclosed herein can be less than approximately 20%, or from approximately 20% to approximately 50% or more, or from approximately 25% to approximately 40% larger than the target vessel or the diameter of the non-enlarged portion of the graft body, or to or from any values within these ranges.

Further, in any of the graft embodiments disclosed herein, at least a portion of the graft material adjacent to the one or more fenestrations or openings can be free to translate in a circumferential or axial direction relative to the stent that the graft is supported by. For example, without limitation, particular portions such as the end portions of the graft material can be sutured or otherwise fastened to the stent, while a mid portion of the graft having one or more fenestrations therethrough can be unattached to the stent so that such mid portion can be free to translate relative to the stent and, hence, permit the adjustability of the fenestrations relative to the stent. In this configuration, the fenestrations can be adjusted to align with the ostium of the patient's branch vessels.

As one non-limiting example, the diameter of the main graft body 22 configured for placement in an approximately 26 mm vessel can be approximately 34 mm. Therefore, in some embodiments, the diameter of the main graft body 22 can be approximately 8 mm larger than the diameter of the target vessel. In some embodiments, the diameter of the main graft body 22 can be between approximately 2 mm and approximately 14 mm, or between approximately 4 mm and approximately 12 mm, or between approximately 6 mm and approximately 10 mm larger than the diameter of the target vessel, or to or from any values within these ranges.

The oversized diameter of the main graft body 22 can provide excess or slack graft material in the main graft body 22 such that the fenestrations 24, 26 can each be moved in an axial or angular direction to align the fenestrations 24, 26 with the branch vessels arteries, as will be described in greater detail below.

As described above, two or more fenestrations can be formed in the main graft body 22 at any desired location. With reference to FIG. 2, the two fenestrations 24, 26 can be formed at generally diametrically opposed locations. However, any number of fenestrations can be formed in the main graft body 22 at any desired locations. Additionally, scallops or cutouts can be formed in the distal end portion or at any suitable location in the main graft body 22, the scallops or cutouts being configured to prevent obstruction of other arteries branching off of the main vessel into which the main graft body 22 is to be deployed. For example, in some embodiments, an additional fenestration 32 can be formed in a distal portion of the main graft body 22. The fenestration 32 can be formed so as to align with a patient's SMA FIG. 3 is a cross-sectional view of the embodiment of the endoluminal prosthesis 20 deployed in the patient's anatomy, taken through line 3-3 in FIG. 1, before the fenestrations 24, 26 have been aligned with the respective branch vessels, for example renal arteries 12, 14. With reference to FIG. 3, the main graft body 22 (which can be oversized) has been deployed in the target vessel. In some embodiments, after the main graft body 22 has been deployed in the target vessel, because the main graft body 22 can have a larger diameter than the vessel diameter, folds, wrinkles, or other undulations (collectively referred to as folds) 34 can form in the main graft body 22 about the circumference of the main graft body 22. The folds 34 can form in the main graft body 22 as a result of the fact that there can be excess or slack material in the main graft body 22 after the main graft body 22 has been deployed in the target vessel.

In some embodiments, at least a portion of the main graft body 22 can have undulations, folds, bends, corrugations, or other similar features in the axial direction therein when the main graft body 22 is in a relaxed state (i.e., before the graft has been deployed). In some embodiments, a middle portion of the graft can have undulations, folds, bends, corrugations or other similar features while the distal or upstream portion defines a smooth contour FIG. 4 is a cross-sectional view of the embodiment of the endoluminal prosthesis 20 deployed in the patient's anatomy, taken through line 3-3 in FIG. 1, after the fenestrations 24, 26 have been aligned with the respective branch vessels. With reference to FIG. 4, the oversized main graft body 22 can be aligned with the patient's anatomy by moving fenestration 24 to align the fenestration 24 with the respective branch vessel and by moving the fenestration 26 to align the fenestration 26 with the other respective branch vessel. For example, the fenestration 24 can be drawn closer to the fenestration 26, thereby gathering slack material or folds 34 in a first portion 22a of the main graft body 22 and partially or fully removing the slack material or folds from a second portion 22b of the main graft body 22.

After the main graft body 22 has been positioned within the patient's anatomy such that the fenestrations 24, 26 have been aligned with the respective branch vessels, a covered stent, a bare wire stent, or any other suitable stent or anchoring device can be deployed within the main graft to secure the graft in the desired location (not illustrated). In some embodiments, a bare metal stent deployed within the main graft body 22 can compress the folds 34 that are formed in the main graft body 22, if any, against the wall of the vessel and secure the main graft body 22 and the fenestrations 24, 26 in the desired locations.

Alternatively, a supra renal stent can be deployed at a distal or upper portion of the main graft body to secure the distal or upper portion of the main graft body in the desired location within the patient's vasculature, and one or more axial springs 40 can be anchored to the main graft body to provide axial or column strength to the main graft body. The springs 40 can have a helical shape, as illustrated, and can have any suitable size, length, pitch, or diameter. However, such helical shape is not required. In some embodiments, the springs 40 can have any suitable shape, including a straight, flat, round, or non-round shape. The springs 40 can be formed from any suitable biocompatible material, such as without limitation stainless steel, Nitinol, or suitable metalic or polymeric materials.

Figure 5:
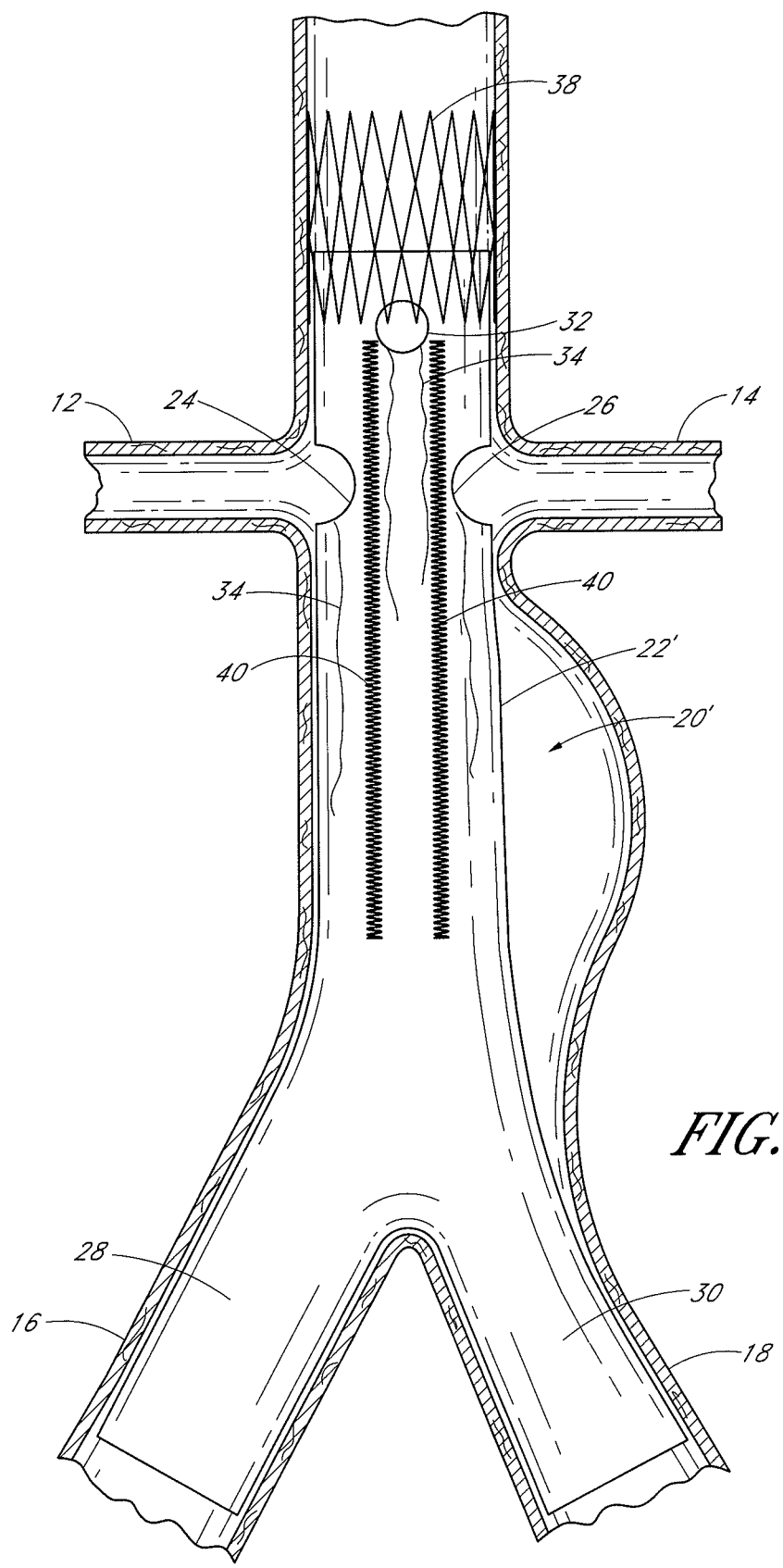
FIG. 5 is a partial section view of a patient's vasculature illustrating another embodiment of an endoluminal prosthesis deployed in the desired position within the patient's vasculature.

FIG. 5 is a partial section view of a patient's vasculature illustrating another embodiment of an endoluminal prosthesis 20' deployed in the desired position within the patient's vasculature wherein the main graft body 22' can have a supra renal stent 38 deployed within the upper or distal end portion of the main graft body 22' and one or more axial springs 40 secured to the main graft body 22'. The springs 40 can be secured to the main graft body 22' using any suitable fasteners or method, such as without limitation, sutures or adhesive.

Figure 6:
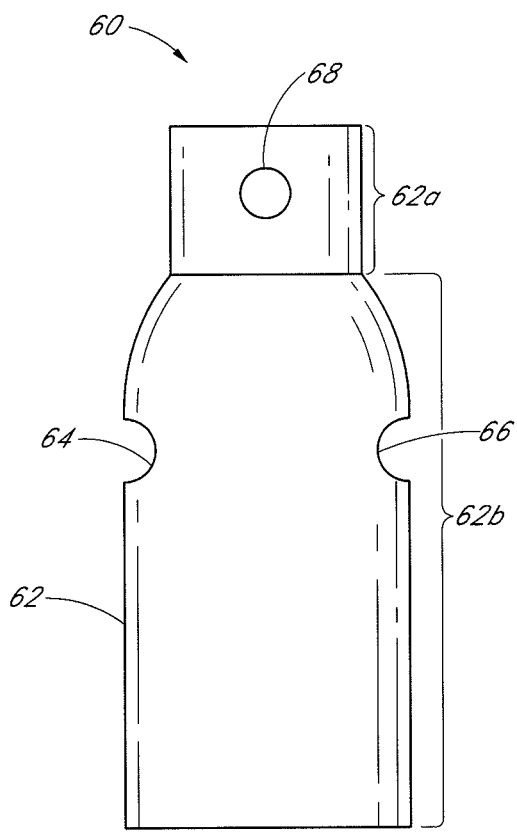

In some embodiments, any of the embodiments of the endoluminal prostheses disclosed herein can be formed such that one or more portions of the main graft body have an enlarged diameter, while one or more other portions of the main graft body can have a reduced diameter as compared to the enlarged diameter. For example, with reference to FIG. 6, which is a side view of another embodiment of an endoluminal prosthesis 60, the endoluminal prosthesis 60 can have a main graft body 62 and fenestrations 64, 66 formed therein. In some embodiments, an additional fenestration 68 can be formed in the main graft body 62 to accommodate blood flow to the SMA or otherwise. With reference to FIG. 6, a first or upper portion 62*a* of the main graft body 62 can have a first diameter while a second or lower portion 62*b* can have a second diameter. In some embodiments, as in the illustrated embodiment, the first portion 62*a* can have a smaller diameter than the second portion 62*b* of the main graft body 62. Accordingly, to accommodate adjustability of the fenestrations 64, 66, the fenestrations 64, 66 can be formed in the second or enlarged portion 62*b* of the main graft body 62.

The first portion 62*a* can have any diameter suitable for the size of the target vessel. Additionally, the second portion 62*b* can have an enlarged diameter within any of the ranges described above with respect to the main graft body 22. For example, without limitation, the endoluminal prosthesis 60 can be configured for deployment in a 26 mm target vessel, wherein the first portion 62*a* can have an approximately 28 mm or any other suitable diameter, and the second portion 62*b* can have an approximately 34 mm or any other suitable enlarged diameter so as to allow for the adjustability of the fenestrations 64, 66. As illustrated in FIG. 6, the diameter of the main graft body 62 in the second portion 62*b* can transition from the diameter of the first portion 62*a* to the diameter of the remainder of the second portion 62*b*.

Figure 7:
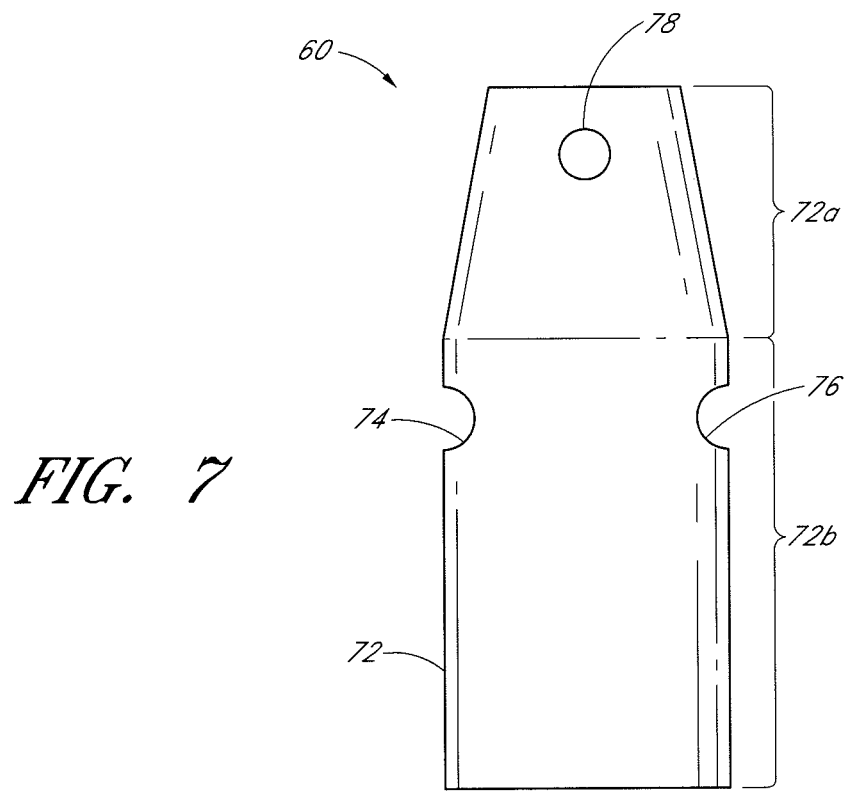

FIG. 7 is a side view of another embodiment of an endoluminal prosthesis 70 having a main graft body 72 and fenestrations 74, 76 formed therein. In some embodiments, an additional fenestration or cutout 78 can be formed in the main graft body 72 to accommodate blood flow to the SMA or otherwise. With reference to FIG. 7, a first or upper portion 72*a* of the main graft body 72 can be tapered from a first to a second diameter, while a second or lower portion 72*b* can have a second diameter. In some embodiments, as in the illustrated embodiment, the first portion 72*a* can have a smaller diameter than the second portion 72*b* of the main graft body 72. Accordingly, to accommodate adjustability of the fenestrations 74, 76, the fenestrations 74, 76 can be formed in the second or enlarged portion 72*b* of the main graft body 72.

The first portion 72*a* can have any suitable first diameter for the size of the target vessel. Additionally, the second portion 72*b* can have an enlarged diameter within any of the ranges described above. For example, without limitation, the endoluminal prosthesis 70 can be configured for deployment in a 26 mm target vessel, wherein the first portion 72*a* can have an approximately 28 mm first diameter that tapers outwardly to an approximately 34 mm second diameter, and the second portion 72*b* can have an approximately 34 mm diameter so as to allow for the adjustability of the fenestrations 74, 76.

FIG. 8 is a side view of another embodiment of an endoluminal prosthesis 80 having a main graft body 82 and fenestrations 84, 86 formed therein. In some embodiments, an additional fenestration 88 can be formed in the main graft body 82 to accommodate blood flow to the SMA or otherwise. With reference to FIG. 8, a first or upper portion 82*a* of the main graft body 82 can have a first diameter, a second or middle portion 82*b* can have a second diameter, and a third or lower portion 82*c* can have a third diameter. In some embodiments, as in the illustrated embodiment, the first portion 82*a* can have a smaller diameter than the second portion 82*b* of the main graft body 82. Additionally, the third portion 82*c* can have a smaller diameter than the second portion 82*b* of the main graft body 82. In some embodiments, the third portion 82*c* can have the same diameter as compared to the first portion 82*a*. Accordingly, to accommodate adjustability of the fenestrations 84, 86, the fenestrations 84, 86 can be formed in the second or enlarged portion 82*b* of the main graft body 82. The second portion 82*b* can have a generally curved surface, or can define a generally cylindrical surface that conically or curvedly tapers to the diameter of the first and third portions 82*a*, 82*c*.

The first portion 82*a* can have any suitable first diameter for the size of the target vessel. Additionally, as mentioned, the second portion 82*b* can have an enlarged diameter within any of the ranges described above. For example, without limitation, the endoluminal prosthesis 80 can be configured for deployment in a 26 mm target vessel, wherein the first portion 82*a* can have an approximately 28 mm diameter, the second portion 82*b* can have an approximately 34 mm diameter so as to allow for the adjustability of the fenestrations 84, 86, and the third portion 82*c* can have an approximately 28 mm diameter.

Please note that any of the endoluminal prostheses disclosed or described herein can be bifurcated or non-bifurcated, and can be formed from any suitable material, such as but not limited to ePTFE. Additionally, any of the deployment procedures described herein or any other suitable deployment procedures currently known or later developed that are suitable for such endoluminal prostheses can be used to deploy any of the endoluminal prostheses described herein. Further, any of the endoluminal prostheses can be secured to the target vessel wall using covered stents, bare metal stents, supra renal stents, springs, anchors, or any other suitable medical device or fasteners. For example, without limitation, with reference to FIG. 9, which is a side view of another embodiment of an endoluminal prosthesis 90, the endoluminal prosthesis 90 can be a bifurcated prosthesis. As illustrated therein, the main graft body 92 can have three portions 92*a*, 92*b*, 92*c* of varying diameters.

Further, in any of the graft embodiments disclosed herein, at least a portion of the graft material adjacent to the one or more fenestrations or openings, such as the graft material in the enlarged section 92*b*, can be free to translate in a circumferential or axial direction relative to the stent that the graft is supported by. For example, without limitation, particular portions of the graft material, such as the end portions of the graft material, can be sutured or otherwise fastened to the stent, while a mid or enlarged portion of the graft having one or more fenestrations therethrough can be unattached to the stent so that such portion can be free to translate relative to the stent. This configuration can improve the adjustability of the graft material and, hence, the fenestrations, relative to the stent, permitting the fenestrations to be adjusted to align with the ostium of the patient's branch vessels.

Additionally, as mentioned above, any of the embodiments of the endoluminal prostheses disclosed herein (which is meant throughout this specification to include the embodiments incorporated herein by reference) can be formed with a branch graft adjacent to one or more of the openings or fenestrations formed in the main graft body. For example, with reference to FIG. 10, which is a side view of another embodiment of an endoluminal prosthesis 100, the endoluminal prosthesis 100 can have a main graft body 102 and branch grafts 104, 106 supported by the main graft body 102. In some embodiments, an additional fenestration 108 can be formed in the main graft body 102 to accommodate blood flow to the SMA or otherwise. Alternatively, an additional branch graft (not illustrated) can be supported by the main graft body 102 to accommodate the blood flow to the SMA With reference to FIG. 10, a first or upper portion 102a of the main graft body 102 can have a first diameter, a second or middle portion 102b can have a second diameter, and a third or lower portion 102c can have a third diameter. The main graft body 102 can have any suitable shape, including any of the shapes disclosed elsewhere herein. In some embodiments, as in the illustrated embodiment, the first portion 102a can have a smaller diameter than the second portion 102b of the main graft body 102. Additionally, the third portion 102c can have a smaller diameter than the second portion 102b of the main graft body 102. In some embodiments, the third portion 102c can have the same diameter as compared to the first portion 102a. Accordingly, to accommodate adjustability of the branch grafts 104, 106, the branch grafts 104, 106 can be supported by the second or enlarged portion 102b of the main graft body 102.

The first portion 102a can have any suitable first diameter for the size of the target vessel. Additionally, as mentioned, the second portion 102b can have an enlarged diameter within any of the ranges described above. For example, without limitation, the endoluminal prosthesis 100 can be configured for deployment in a 26 mm target vessel, wherein the first portion 102a can have an approximately 28 mm diameter, the second portion 102b can have an approximately 34 mm diameter so as to allow for the adjustability of the fenestrations 104, 106, and the third portion 102c can have an approximately 28 mm diameter.

In some embodiments, the branch grafts 104, 106 can be integrally formed with the main graft body 12. Alternatively, the branch graft portions 104, 106 can be formed separately and later attached, adhered, sutured, or otherwise fastened or supported by the main graft body 102. In some embodiments, the main graft body 102 can have fenestrations or openings in place of the branch grafts 104, 106.

Additionally, as mentioned above, any of the embodiments of the endoluminal prostheses disclosed herein can be formed with a branch graft adjacent to one or more of the openings or fenestrations formed in the main graft body. For example, with reference to FIG. 10, which is a side view of another embodiment of an endoluminal prosthesis 100, the endoluminal prosthesis 100 In some embodiments, an additional fenestration 108 can be formed in the main graft body 102 to accommodate blood flow to the SMA or otherwise. Alternatively, an additional branch graft (not illustrated) can be supported by the main graft body 102 to accommodate the blood flow to the SMA With reference to FIG. 10, a first or upper portion 102a of the main graft body 102 can have a first diameter, a second or middle portion 102b can have a second diameter, and a third or lower portion 102c can have a third diameter. The main graft body 102 can have any suitable shape, including any of the shapes disclosed elsewhere herein. In some embodiments, as in the illustrated embodiment, the first portion 102a can have a smaller diameter than the second portion 102b of the main graft body 102. Additionally, the third portion 102c can have a smaller diameter than the second portion 102b of the main graft body 102. In some embodiments, the third portion 102c can have the same diameter as compared to the first portion 102a. Accordingly, to accommodate adjustability of the branch grafts 104, 106, the branch grafts 104, 106 can be supported by the second or enlarged portion 102b of the main graft body 102.

The first portion 102a can have any suitable first diameter for the size of the target vessel. Additionally, as mentioned, the second portion 102b can have an enlarged diameter within any of the ranges described above. For example, without limitation, the endoluminal prosthesis 100 can be configured for deployment in a 26 mm target vessel, wherein the first portion 102a can have an approximately 28 mm diameter, the second portion 102b can have an approximately 34 mm diameter so as to allow for the adjustability of the fenestrations 104, 106, and the third portion 102c can have an approximately 28 mm diameter.

In some embodiments, the branch grafts 104, 106 can be integrally formed with the main graft body 12. Alternatively, the branch graft portions 104, 106 can be formed separately and later attached, adhered, sutured, or otherwise fastened or supported by the main graft body 102.

Figure 11:
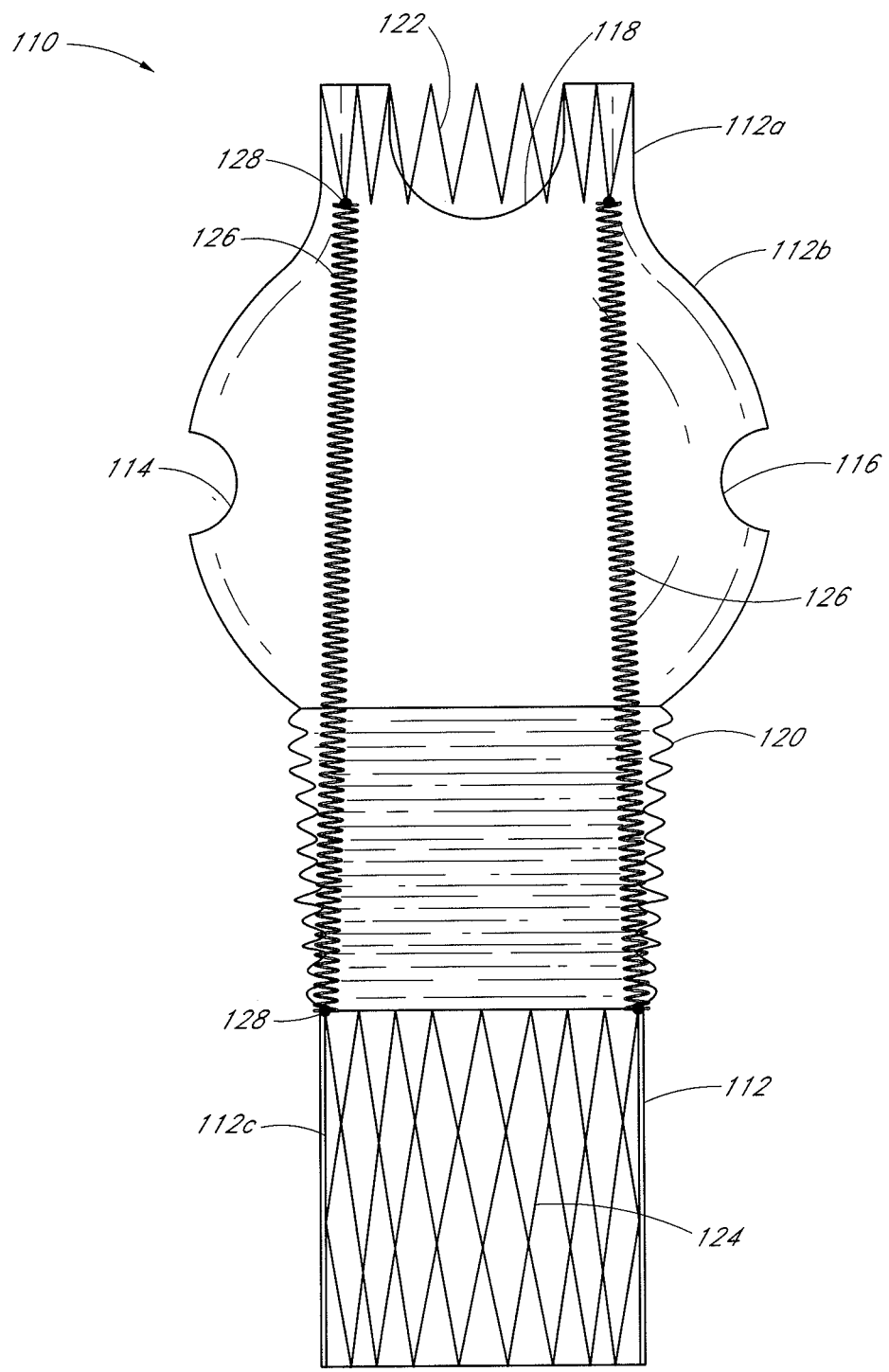

FIG. 11 is a side view of another embodiment of an endoluminal prosthesis 110. As with any of the embodiments of the endoluminal prostheses disclosed herein, any of the features of the endoluminal prosthesis 110 can be combined with any of the features of any other embodiment or combination of embodiments of the endoluminal prostheses disclosed herein. Additionally, endoluminal prosthesis 110 can have any of the features, components, or other details of any of the other embodiments of the endoluminal prostheses disclosed (directly or by incorporation by reference) herein. As illustrated in FIG. 11, the endoluminal prosthesis 110 can have a main graft body 112, fenestrations 114, 116 formed in the main graft body 112, and an opening or cutout 118 formed in the distal end portion of the main graft body 112 to accommodate blood flow to the SMA or otherwise. In some embodiments, branch grafts can be positioned within the fenestrations 114, 116, or can be sewn, adhered, or otherwise attached to the main graft body 112 adjacent to the fenestrations 114, 116.

In some embodiments, the main graft body 112 can have three portions 112a, 112b, 112c of varying diameters. However, in some embodiments, the diameter of the three portions 112a, 112b, 112c of the main graft body 112 can be approximately the same. As illustrated in FIG. 11, the first portion 112a can have any diameter suitable for the size of the target vessel. Additionally, the second portion 112b can have an enlarged diameter within any of the ranges described above with respect to the main graft body 22. For example, without limitation, the endoluminal prosthesis 110 can be configured for deployment in a 26 mm target vessel, wherein the first portion 112a can have an approximately 28 mm or any other suitable diameter, and the second portion 112b can have an approximately 34 mm or any other suitable enlarged diameter so as to allow for the adjustability of the fenestrations 114, 116. The diameter of the third portion 112c can be similar to the diameter of the first portion 112a, or can be any suitable diameter.

Additionally, in some embodiments, the main graft body 112 be sized and configured so as to have excess length or material 120 in the graft material. For example, as illustrated in FIG. 11, the main graft body 112 can be sized and configured so as to have excess material 120 below the enlarged second portion 112b. In some embodiments, the main graft body 112 can be configured so that the excess material 120 is positioned above the enlarged second portion 112b, or so that excess material 120 is positioned both above and below the enlarged second portion 112b to allow for greater axial and/or radial adjustability of the fenestrations 114, 116. The excess material positioned above and/or below the enlarged portion or, if no enlarged portion, above and/or below the fenestrated portion, can permit a greater amount of adjustability of the fenestrations or branch grafts. Any of the embodiments of grafts disclosed herein can have excess material positioned above and/or below the enlarged or fenestrated portion of the graft, or at any suitable position on the graft to increase the adjustability of the fenestrations or branch grafts.

In some embodiments, the excess material 120 can be approximately 20% of the unstretched length of the main graft body 112. In some embodiments, the excess material 120 can be from approximately 10% or less to approximately 30% or more of the unstretched length of the main graft body 112. For example, in some embodiments, the total excess length of the graft can be approximately 2 cm. In some embodiments, the total excess length of the graft can be between approximately 1 cm and approximately 3 cm such that a main graft body 112 having an unstretched length of approximately 10 cm can have from approximately 11 cm or less to approximately 13 cm or more of graft material positioned thereon.

In some embodiments, the endoluminal prosthesis 110 can have a supra visceral stent or stent segment 122 deployed within the first or distal end portion 112a of the main graft body 112, a stent segment 124 deployed within the third or proximal end portion 112c of the main graft body 112, and one or more axial springs 126 extending between the supra renal stent segment 122 and the stent segment 124. In some embodiments, the springs 126 can be substantially rigid so as to axially position the stent segment 122 at a fixed position relative to the stent segment 124. The springs 126 can be attached to the stent segments 124, 126 at connection points 128.

The endoluminal prosthesis 110 can be configured such that the main graft body 112 is secured to the stent segments 122, 124 only at the end portions of the main graft body 112. In some embodiments, the endoluminal prosthesis 110 can be configured such that the main graft body 112 is secured to the stent segments 122, 124 at the end portions of the main graft body 112 and also at one or more intermediate positions, such as at positions adjacent to one or more of the connection points 128.

In some embodiments (not illustrated), the endoluminal prosthesis 110 can be configured to be a bifurcated prosthesis, having one or more branch portions extending below the stent 124. In such embodiments, the main graft body 112 can extend below the stent 124 so as to comprise the branch graft portions. Alternatively, bifurcation branch graft portions can be formed separately and stitched or otherwise attached to the main graft body 112. Further, in some embodiments, bifurcation branch stents can be pre-positioned within or otherwise deployed within the branch grafts.

Figure 12:
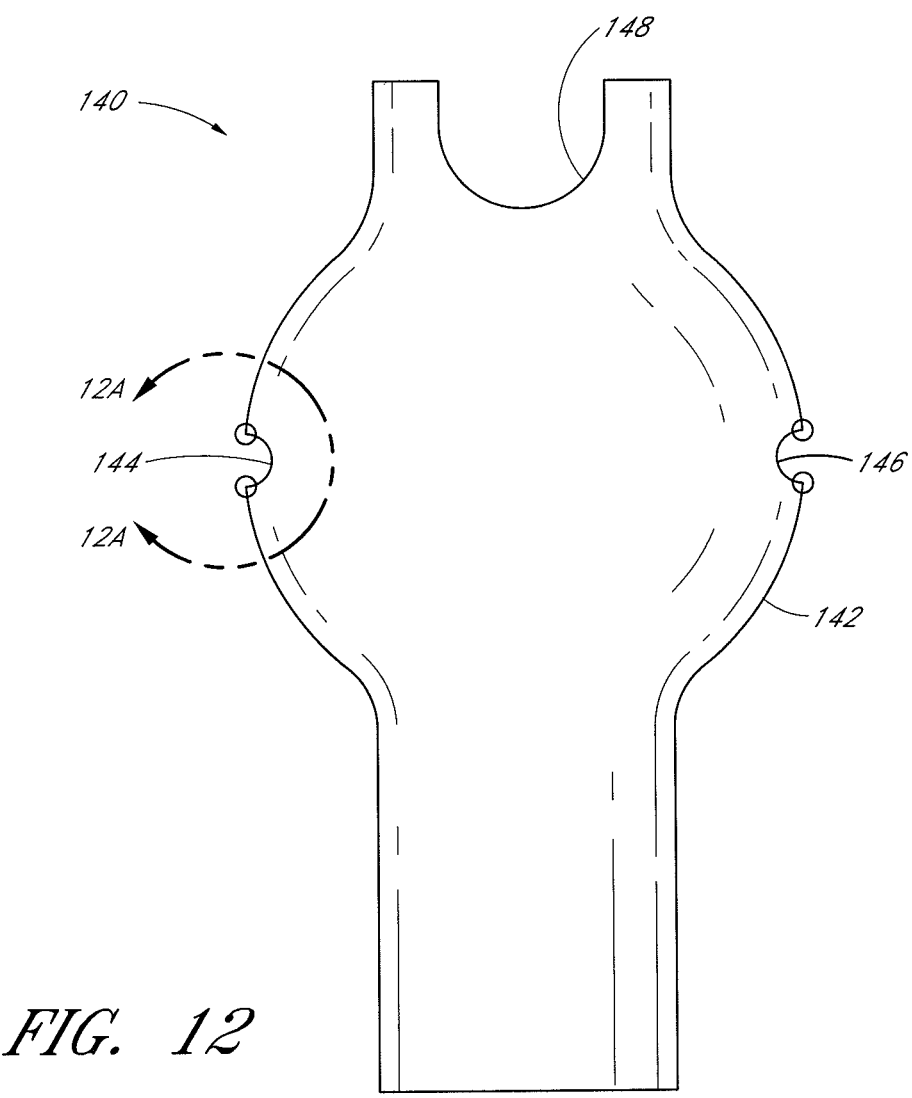
Figure 12A:
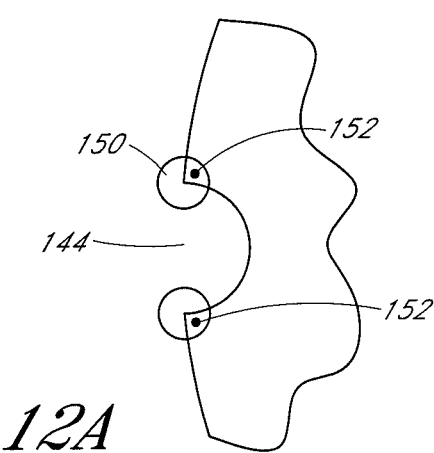
FIG. 12A is an enlarged side view of the embodiment of the endoluminal prosthesis illustrated in FIG. 12, defined by curve 12A-12A in FIG. 12.

FIG. 12 is a side view of another embodiment of an endoluminal prosthesis 140. FIG. 12A is an enlarged side view of the embodiment of the endoluminal prosthesis 140 defined by curve 12A-12A in FIG. 12. As with any of the embodiments of the endoluminal prostheses disclosed (directly or by incorporation by reference) herein, any of the features of the endoluminal prosthesis 140 can be combined with any of the features of any other embodiment or combination of embodiments of the endoluminal prostheses disclosed (directly or by incorporation by reference) herein. As such, endoluminal prosthesis 140 can have any of the features, components, or other details of any of the other embodiments of the endoluminal prostheses disclosed herein. As illustrated in FIG. 12, the endoluminal prosthesis 140 can have a main graft body 142, fenestrations 144, 146 formed in the main graft body 142, and an opening or cutout 148 formed in the distal end portion of the main graft body 142 to accommodate blood flow to the SMA or otherwise. In some embodiments, branch grafts can be positioned within the fenestrations 144, 146, or can be sewn, adhered, or otherwise attached to the main graft body 112 adjacent to the fenestrations 144, 146.

In some embodiments, the diameter of the fenestrations 144, 146 or any other fenestrations disclosed herein can be from approximately 1 mm to approximately 10 mm or more, or from approximately 3 mm to approximately 8 mm, or from approximately 4 mm to approximately 6 mm. The fenestrations 144, 146 can be positioned at any desired or suitable axial or radial position in the main graft body 142 based on a patient's anatomy. In some embodiments, as illustrated in FIG. 12, the fenestrations 144, 146 can be circumscribed with a supportive graft material 150 (also referred to herein as a fenestration border) to increase the strength of the graft material adjacent to the fenestrations 144, 146. In some embodiments, the fenestration border 150 can increase the strength of the graft material adjacent to the fenestrations 144, 146 so that the fenestrations 144, 146 can withstand expansion pressures of up to approximately 15 atm or more.

In some embodiments, the fenestration border 150 can be a generally cylindrically shaped tube of graft material such as PTFE, ePTFE, or any other suitable material that is formed around the fenestration. For example, with reference to FIGS. 12 and 12A, the tube of graft material can be slit longitudinally along the length thereof and positioned over the edge of the fenestrations 144, 146. The fenestration border 150 can be bonded, sutured, or otherwise attached to or supported by the main graft body 142 adjacent to the fenestrations 144, 146. In some embodiments, the fenestration border 150 can be a ring of polyurethane or urethane that can be bonded, sutured, or otherwise attached to or supported by the main graft body 142 adjacent to the fenestrations 144, 146. The polyurethane or urethane can allow for radial expansion of the fenestration by a balloon expander or other suitable expander. In some embodiments, the polyurethane or urethane rings (or rings made from any other suitable material) can be positioned between two or more sheets or layers of graft material (such as, but not limited to, ePTFE) having the polyurethane or urethane bonded thereto. The sheets or layers can be positioned relative to one another with the polyurethane or urethane surfaces facing each other so that the polyurethane or urethane is sandwiched between the sheets or layers of the graft material.

In some embodiments, as in the illustrated embodiment, a radiopaque material (that can be non-rigid or spring-like) can be embedded in or supported within the fenestration border 150. The radiopaque marker can be formed from platinum iridium, which can be in the form of a spring, or any other suitable metallic material known to the industry.

FIG. 13 is a side view of another embodiment of an endoluminal prosthesis 170. FIG. 14 is a top view of the embodiment of the endoluminal prosthesis 170 shown in FIG. 13. The embodiment of the endoluminal prosthesis 170 illustrated in FIGS. 13 and 14 can have a main graft body 172, a first fenestration 174, and a second fenestration 176. In some embodiments, as in the illustrated embodiment, the main graft body 172 can be bifurcated, having a first bifurcated branch 178 and a second bifurcated branch 180 for placement in the ipsilateral and contralateral iliac arteries and a lumen 182 through the main graft body 172 in communication with the openings in the first and second bifurcated branches 178, 180. Additionally, in some embodiments, the endoluminal prosthesis 170 can have any of the components, features, dimensions, materials, or other details of any of the other embodiments of endoluminal prostheses disclosed or incorporated by reference herein, or any other suitable features of endoluminal prostheses known in the field.

The endoluminal prosthesis 170 can be formed from any suitable material, such as, but not limited to, ePTFE. In some embodiments, the endoluminal prosthesis 170 can be formed from an expandable material. The endoluminal prosthesis 170 can be formed such that at least a portion of the main graft body 172 can be significantly larger than the target vessel into which the main graft body 172 is to be deployed. With reference to FIG. 13, the endoluminal prosthesis 170 can be bifurcated and can be deployed so as to span across an aneurysm in the abdominal aortic. In some embodiments, at least a portion of the main graft body 172 can have a diameter that can be approximately 30% larger than the diameter of the target vessel. In some embodiments, at least a portion of the main graft body 172 can have a diameter that can be from approximately 20% or less to approximately 50% or more, or from approximately 25% to approximately 40% larger than the target vessel, or to or from any values within these ranges.

As one non-limiting example, the main graft body 172 configured for placement in an approximately 28 mm vessel can have at least a portion thereof that has a diameter of approximately 34 mm. Therefore, in some embodiments, the diameter of at least a portion of the main graft body 172 can be approximately 8 mm larger than the diameter of the target vessel. In some embodiments, the diameter of at least a portion of the main graft body 172 can be between approximately 2 mm and approximately 14 mm, or between approximately 4 mm and approximately 12 mm, or between approximately 6 mm and approximately 10 mm larger than the diameter of the target vessel, or to or from any values within these ranges.

For example, with reference to FIG. 13, the main graft body 172 can have a first portion 172a, a second or middle portion 172b, and a third or lower portion 172c. In some embodiments, the first portion 172a can have a generally cylindrical shape defined by a first diameter. In some embodiments, the second portion 172b can have a generally spherical shape defined by a second, enlarged diameter. The third portion 172c can have a generally cylindrical shape defined by a third diameter. The third diameter can be approximately the same as the first diameter, or can be larger or smaller than the first diameter. In some embodiments, the second portion 172b can have approximately the same cross-sectional diameter as compared to the first portion 172a, the second portion 172b having corrugations 184 formed therein, as described below, to allow for the adjustability of the fenestrations 174, 176 or branch grafts (not illustrated).

As discussed above, the oversized diameter of the main graft body 172 can provide excess or slack graft material in the main graft body 172 such that the fenestrations 174, 176 can each be moved in an axial or angular direction to align the fenestrations 174, 176 with the branch vessels arteries. In some embodiments, branch grafts (not illustrated) can be integrally formed with the main graft body 172, or can be formed separately and later attached, adhered, sutured, or otherwise fastened or supported by the main graft body 172.

As described above, two or more fenestrations 174, 176 can be formed in the main graft body 172 at any desired location. With reference to FIG. 13, the two fenestrations 174, 176 can be formed at generally diametrically opposed locations. However, any number of fenestrations can be formed in the main graft body 172 at any desired locations. Additionally, scallops or cutouts can be formed in the distal end portion or at any suitable location in the main graft body 172, the scallops or cutouts being configured to prevent obstruction of other arteries branching off of the main vessel into which the main graft body 172 is to be deployed. For example, in some embodiments, an additional fenestration can be formed in a distal portion of the main graft body 172 so as to align with a patient's SMA.

In some embodiments, as in the illustrated embodiment, the fenestrations 174, 176 can be formed in the second portion 172b of the main graft body 172. In some embodiments, the surface of the second portion 172b of the main graft body 172 can have waves, undulations, folds, corrugations, or other similar features 184 (collectively referred to as corrugations) pre-formed therein. The corrugations 184 can be formed in an axial direction, as illustrated in FIGS. 13 and 14, or can be formed in a lateral direction or at any other suitable angular orientation. Additionally, the corrugations 184 can have a linear shape, as illustrated, or can have a curved or any other suitable shape, such as is illustrated in FIGS. 15 and 16.

Figure 16:
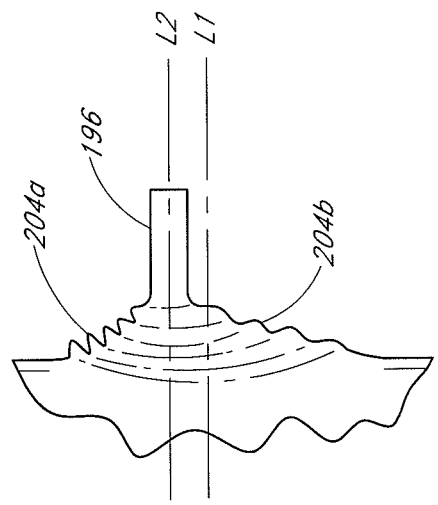
FIG. 16 is an enlargement of a portion of the embodiment of an endoluminal prosthesis shown in FIG. 15, defined by curve 16-16, illustrating the adjustability of a branch graft.
Figure 15:
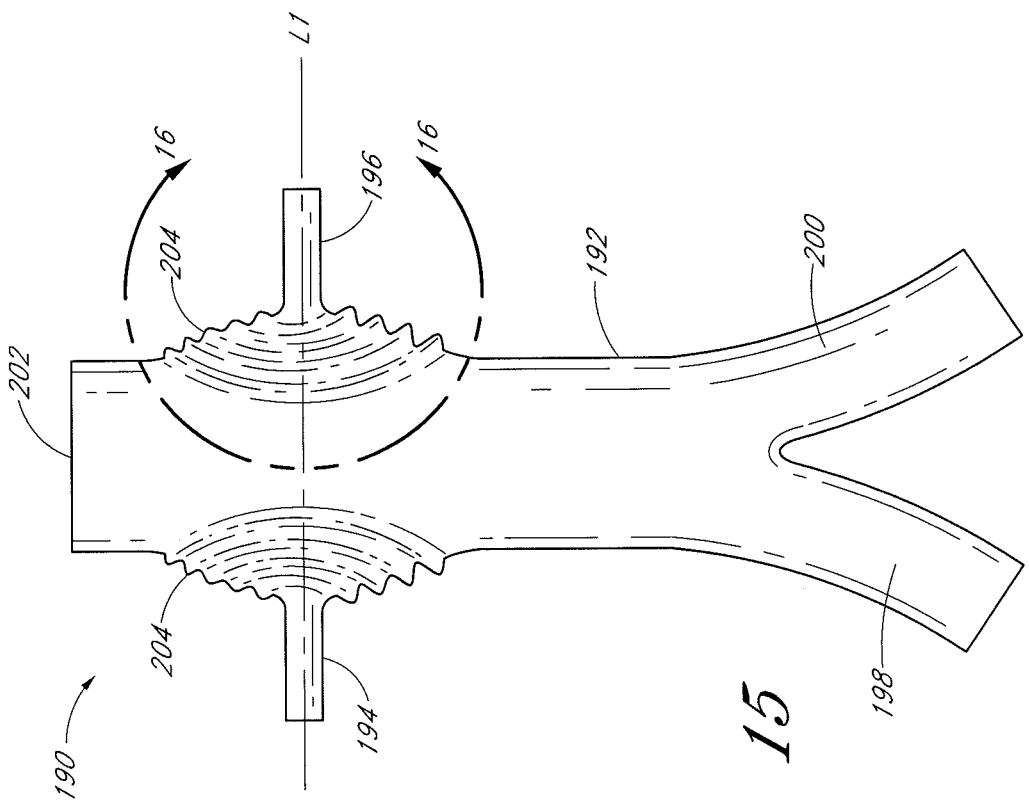
FIG. 15 is a side view of another embodiment of an endoluminal prosthesis.

FIG. 15 is a side view of another embodiment of an endoluminal prosthesis 190, and FIG. 16 is an enlargement of a portion of the embodiment of an endoluminal prosthesis 190 shown in FIG. 15, defined by curve 16-16, illustrating the adjustability of a branch graft. With reference to FIGS. 15 and 16, the embodiment of the endoluminal prosthesis 190 illustrated therein can have a main graft body 192, a first branch graft 194, and a second branch graft 196. In some embodiments, as in the illustrated embodiment, the main graft body 192 can be bifurcated, having a first bifurcated branch 198 and a second bifurcated branch 200 for placement in the ipsilateral and contralateral iliac arteries and a lumen 202 through the main graft body 192 in communication with the openings in the first and second bifurcated branches 198, 180.

Additionally, in some embodiments, the endoluminal prosthesis 190 can have any of the components, features, dimensions, materials, or other details of any of the other embodiments of endoluminal prostheses disclosed or incorporated by reference herein, or any other suitable features of endoluminal prostheses known in the field. For example, without limitation, in some embodiments, the main graft body 192 can be formed without the branch grafts 194, 196 so that fenestrations are to be aligned with the branch vessels. Further, any suitable number of branch grafts or fenestrations can be formed on the main graft body 192.

With reference to FIGS. 15 and 16, the corrugations 204 formed in the main graft body 192 can be curved. In some embodiments, the corrugations 204 can be generally curved in shape and can be formed about the axial centerline of each of the branch grafts 194, 196. With reference to FIG. 15, line L1 represents the axial centerline of each of the branch grafts 194, 196 when the branch grafts 194, 196 are in a relaxed state. In some embodiments, the corrugations 204 can define a generally circular shape. As described with respect to endoluminal prosthesis 170 described above, the corrugations 204 can be configured to allow the branch grafts 194, 196 to move in an axial or angular direction to align the branch grafts 194, 196 with the branch vessels arteries.

As mentioned, FIG. 16 is an enlargement of a portion of the endoluminal prosthesis 190 shown in FIG. 15, illustrating the adjustability of a branch graft 196. For example, the branch graft 196 can be adjusted from the position defined by line L1 (which represents the axial centerline of the branch graft 196 in the relaxed state) to the position defined by line L2 (which represents the axial centerline of the branch graft 196 in the adjusted state). As the branch graft is adjusted from the positioned defined by line L1 to the position defined by line L2, the portions of the corrugations 204a above the line L2 gather or become closer together, while the portions of the corrugations 204b below the line L2 stretch or move further apart from one another, thus allowing the branch graft 196 to be adjusted upwardly without deforming or stretching other portions of the main graft body 192. Lines L1 and L2 are meant to describe the adjustment of the branch grafts 194, 196 in any suitable axial or angular direction and are not meant to be limited by the example or examples provided herein. Further, lines L1 and L2 need not be parallel lines, since angular orientation of the branch grafts 194, 196 relative to the main graft body 192 can be adjustable also.

In the illustrated embodiment, the branch grafts 194, 196 can be approximately aligned so that the axial centerline of the branch graft 194 is approximately collinear with the axial centerline of the branch graft 196. In some embodiments, the branch grafts 194, 196 can be positioned on the main graft body 192 so that the axial centerline of the branch graft 194 is not aligned or collinear with the axial centerline of the branch graft 196.

In some of the embodiments disclosed herein, one or more stents can be pre-positioned within the branch grafts before the endoluminal prosthesis has been deployed in the target location. For example, in some embodiments, the one or more stents can be balloon expandable, self-expandable, or other suitable stents that can be positioned within the branch grafts before the endoluminal prosthesis is loaded into a delivery catheter. For example, with reference to FIG. 17, which is a side view of another embodiment of an endoluminal prosthesis 300, the endoluminal prosthesis 300 can have a main graft body 302 and branch grafts 304, 306 supported by the main graft body 302. In some embodiments, an additional fenestration can be formed in the main graft body 302 to accommodate blood flow to the SMA or otherwise. Alternatively, a branch graft (not illustrated) can be supported by the main graft body 302 to accommodate the blood flow to the SMA The endoluminal prosthesis 300 illustrated in FIG. 17 can have any of the same features as compared to the embodiment of the endoluminal prosthesis 100 illustrated in FIG. 10 and described above or any of the embodiments of the endoluminal prostheses disclosed (directly or by incorporation by reference) herein. As with the endoluminal prosthesis 100 illustrated in FIG. 10 above, to accommodate positional adjustability of the branch grafts 304, 306, the branch grafts 304, 306 can be supported by the second or enlarged portion 302b of the main graft body 302.

In some embodiments, the branch grafts 304, 306 can be integrally formed with the main graft body 302. Alternatively, the branch graft portions 304, 306 can be formed separately and later attached, adhered, sutured, or otherwise fastened or supported by the main graft body 302. Additionally, before the endoluminal prostheses 300 is loaded into a delivery catheter, first and second guidewires 310, 312 can be advanced through the branch grafts 304, 306, respectively. In some embodiments, the guidewires 310, 312 can be hollow so that they can be passed or advanced over guidewires that are pre-wired in the patient's vasculature to guide the endoluminal prostheses 300 to the target location. Advancing the guidewires 310, 312 over the pre-wired guidewires can also facilitate the alignment of each of the branch grafts 304, 306 with each of the branch vessels in the patient's vasculature.

In some embodiments, the guidewires 310, 312 can be made from a plastic extrusion or metal braids. For example, in some embodiments, the hollow guidewires 310, 312 can be made from braided Nitinol wire. In some embodiments, the outer diameter of the guidewires 310, 312 can be approximately 0.035 in and the lumen of the guidewire can be approximately 0.016 in to accommodate a second 0.014 in guidewire. In some embodiments, the guidewires 310, 312 can be configured to pass over a 0.018 in or any other suitable guidewire. As mentioned above, in some embodiments, the guidewires 310, 312 can support balloons on the distal ends of the guidewires 310, 312. The balloons can be inflated in the branch vessel to deploy expandable stents within the branch grafts 304, 306.

Figure 17:
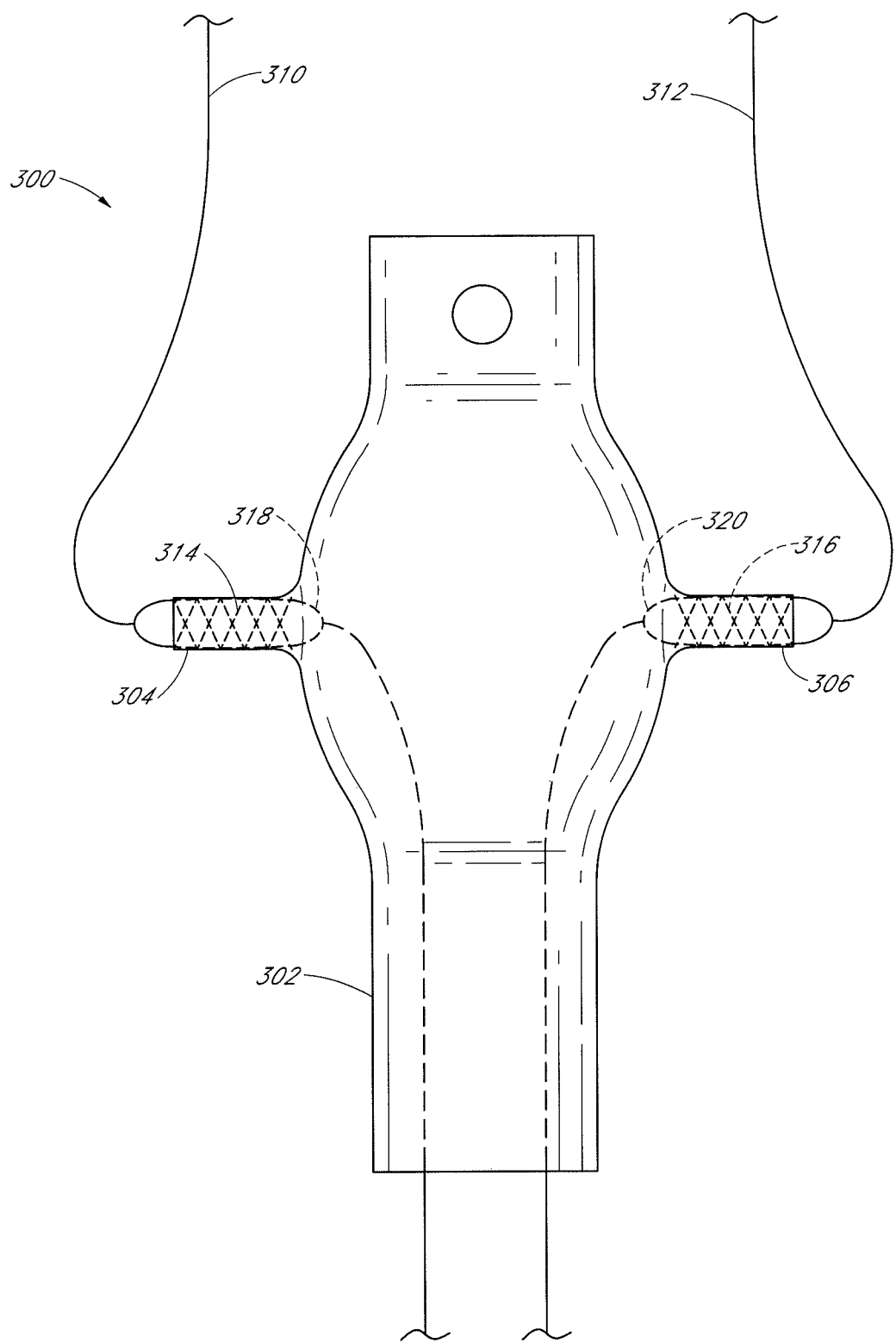
FIG. 17 is a side view of another embodiment of an endoluminal prosthesis with guidewires advanced through each of the branch grafts.

Additionally, as illustrated in FIG. 17, stents 314, 316 can be positioned within each of the branch grafts 304, 306, respectively, before the endoluminal prosthesis 300 is loaded into the delivery catheter. In some embodiments, each of the stents 314, 316 can be a bare metal stent or a covered stent (i.e., covered with a tubular shaped graft material). Additionally, in some embodiments, the stents 314, 316 can be self expanding or can be balloon expandable. In the illustrated embodiment, each of the stents 314, 316 can be supported by an expansion balloon 318, 320, respectively, positioned within each of the branch grafts 304, 306. Accordingly, each of the guidewires 310, 312 can be configured to allow for the inflation and expansion of the expansion balloons 318, 320. For example, the guidewires 310, 312 can have a first lumen that can be advanced over a pre-wired guidewire and a second inflation lumen configured to communicate a positive pressure to each of the expansion balloons 318, 320.

In some embodiments, the endoluminal prostheses 300 can be loaded into a delivery catheter so that each of the guidewires 310, 312 protrudes out from the inside of an outer sleeve of the delivery catheter so that each of the guidewires 310, 312 can be advanced over the pre-wired guidewires positioned within the patient's vasculature. Thus, during deployment, in some embodiments, each of the stents 314, 316 can be expanded and hence deployed within each of the branch grafts 304, 306 after each of the branch grafts 304, 306 has been aligned and positioned within the respective branch vessels. In some embodiments, each of the stents 314, 316 can be expanded and hence deployed within each of the branch grafts 304, 306 before the main graft body 302 has been secured in the main target vessel.

In some embodiments, the stents 314, 316 and the expansion balloons 318, 320 can be supported within the branch grafts 304, 306, respectively, so that the stents 314, 316 and the expansion balloons 318, 320 are axially secured to each of the branch grafts 304, 306. In this arrangement, advancing the guidewires 310, 312 and, accordingly, the stents 314, 316 and the expansion balloons 318, 320, into the respective branch vessels after the endoluminal prosthesis 300 has been at least partially released from the deployment catheter, can allow the branch grafts 304, 306 to be aligned with and advanced into the target branch vessels.

Additionally, in some embodiments, covered or uncovered stents can be pre-positioned in the main graft body of a fenestrated endoluminal prosthesis so as to be partially advanced through each of the fenestrations before the endoluminal prosthesis is loaded into the delivery catheter. The stents can be secured to or otherwise configured to engage each of the fenestrations such that, as the stents are advanced along the pre-wired guidewires into the respective branch vessels, the fenestrations can be aligned with the respective branch vessels. In some embodiments, the stents can have flanged portions or be partially expanded so as to engage the fenestrations such that advancing the stents into the respective branch vessels can align the fenestrations with the respective branch vessels. Additionally, in some embodiments, the guidewires themselves can be configured to engage each of the fenestrations such that, as the deployment guidewires are advanced along the pre-wired guidewires into the respective branch vessels, the fenestrations can be aligned with the respective branch vessels without the use of stents for alignment.

However, the pre-positioning of the stents 314, 316 and the balloons 318, 320 in the endoluminal prostheses 300 described above is not required. In some embodiments, one or more stents can be advanced through the patient's vasculature and into the branch grafts 304, 306 after the endoluminal prostheses 300 has been positioned within the target vessel in the patient's vasculature. For example, one or more stents can be advanced through the patient's vasculature into the branch grafts 304, 306 after the branch grafts 304, 306 have been positioned within the target branch vessels and after the main graft body 302 has been secured within the main target vessel.

Additionally, any of the features, components, or details of any of the graft, stents, or other apparatuses disclosed in U.S. patent application Ser. No. 12/496,446, filed on Jul. 1, 2009, entitled CATHETER SYSTEM AND METHODS OF USING SAME, U.S. patent application Ser. No. 12/390,346, filed on Feb. 20, 2009, entitled DESIGN AND METHOD OF PLACEMENT OF A GRAFT OR GRAFT SYSTEM, and U.S. patent application Ser. No. 12/101,863, filed on Apr. 11, 2008, entitled BIFURCATED GRAFT DEPLOYMENT SYSTEMS AND METHODS can be used, with or without modification, in place of or in combination with any of the features or details of any of the grafts, stents, prostheses, or other components or apparatuses disclosed herein. Similarly, any of the features, components, or details of the delivery apparatuses and deployment methods disclosed in U.S. patent application Ser. Nos. 12/496,446, 12/390,346, and 12/101,863, can be used, with or without modification, to deploy any of grafts, stents, or other apparatuses disclosed herein, or in combination with any of the components or features of the deployment systems disclosed herein. The complete disclosures of U.S. patent application Ser. Nos. 12/496,446, 12/390,346, and 12/101,863 are hereby incorporated by reference as if set forth fully herein.

Figure 18:
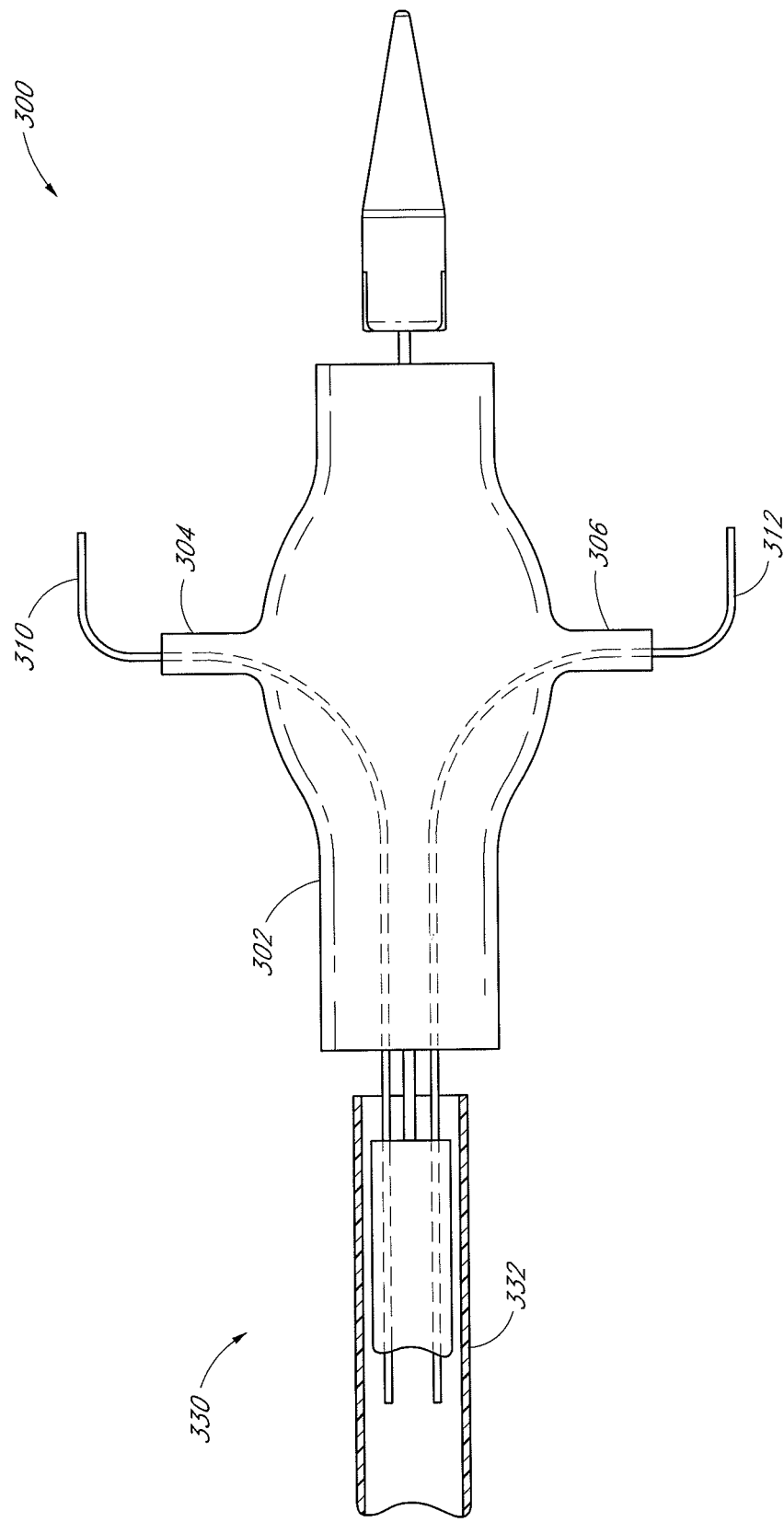
FIG. 18 is a side view of the embodiment of the endoluminal prosthesis shown in FIG. 17 with guidewires advanced through each of the branch grafts, showing the endoluminal prosthesis being loaded within a delivery catheter.

FIG. 18 is a side view of the endoluminal prosthesis 300 with guidewires 310, 312 advanced through each of the branch grafts 304, 306, showing the endoluminal prostheses 300 being loaded within a delivery catheter 330. The outer sheath 332 illustrated in FIG. 18 is sectioned for clarity. With reference to FIG. 18, the collapsed endoluminal prosthesis 300 can be supported within the outer sheath 332 of the delivery catheter 330 in the space between the catheter shaft 334 and the catheter tip 336. In some embodiments, the hollow guidewires 310, 312 can slide through openings or lumens in the catheter shaft 86. Alternatively, in some embodiments, the hollow guidewires 310, 312 can be fixed to the catheter shaft 334.

Figure 19:
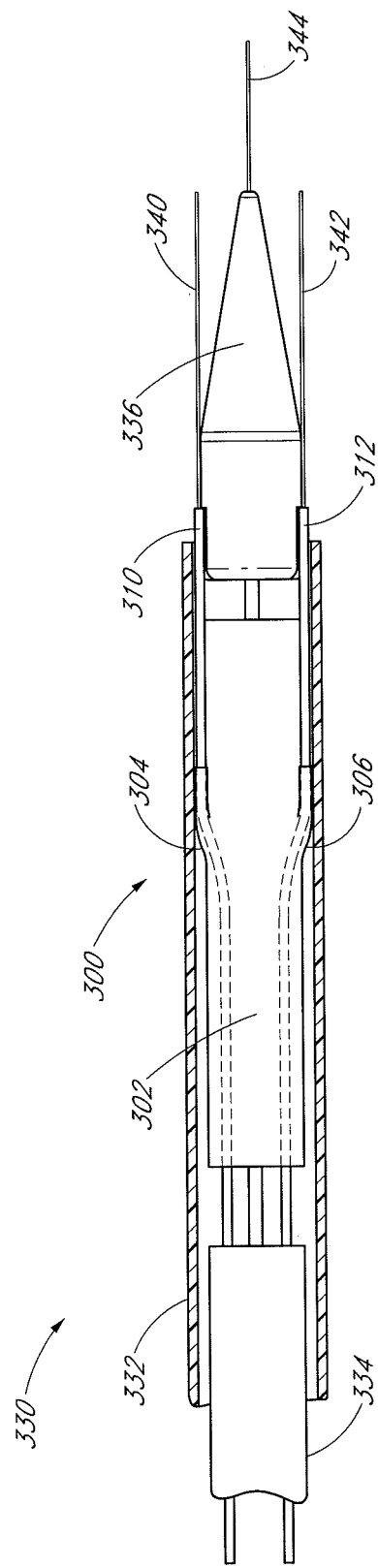
FIG. 19 is a side view of the embodiment of the endoluminal prosthesis shown in FIG. 17 with guidewires advanced through each of the branch grafts, showing the endoluminal prosthesis fully loaded within a delivery catheter and being advanced along guidewires pre-wired in the patient's vasculature.

FIG. 19 is a side view of the endoluminal prostheses 300 with guidewires 310, 312 advanced through each of the branch grafts 304, 306, showing the endoluminal prostheses 300 fully loaded within a delivery catheter 330 and being advanced along guidewires pre-wired in the patient's vasculature. The outer sheath 332 illustrated in FIG. 19 is sectioned for clarity. With reference to FIG. 19, as discussed above, the hollow guidewires 310, 312 can be advanced through the branch grafts 304, 306, respectively, of the endoluminal prosthesis 300. The endoluminal prosthesis 300 can then be compressed and loaded within the delivery catheter 330, as is illustrated in FIG. 19. For example, in this configuration, the endoluminal prosthesis 300 can be retained in the delivery catheter 330 by the outer sheath 332. Retraction of the outer sheath 332 can deploy the endoluminal prosthesis 300. With the outer sheath 332 retracted, the endoluminal prosthesis 300 can expand either by self-expansion, balloon expansion, or by any other suitable method or mechanism.

The hollow guidewires 310, 312 can pass through the outer sheath 332 from the proximal end of the delivery catheter 330 (i.e., the end of the delivery catheter 330 located outside of the patient) to the distal end of the delivery catheter 330. Each of the hollow guidewires 310, 312 can be configured to receive or allow the insertion of a 0.014 in guidewire, a 0.018 in guidewire, a 0.035 in guidewire, or any diameter guidewire therethrough deemed suitable for the design. In this configuration, the hollow guidewires 310, 312 can pass over guidewires 340, 342 that can be pre-wired in the target vessels.

As can be seen in FIGS. 18 and 19, in some embodiments, the catheter 330 can have at least three lumens through at least a portion of the catheter 330. Each of the three lumens can be configured to receive a guidewire. Having three lumens through at least a portion of the catheter 330 can prevent twisting of the guidewires so as to ensure proper deployment of the endoluminal prostheses 300 or any other endoluminal prostheses disclosed (directly or by incorporation by reference) herein. The catheter 330 can be configured to receive the pre-wired guidewire 344 through a lumen formed in the approximate center of the catheter. The lumen can pass through the catheter tip 336 and the catheter shaft 334.

The guidewires 340, 342 can each be pre-wired through the patient's vasculature to pass into each of the target branch vessels branching from the target main vessel. The guidewire 344 can be passed through the target main vessel. As described above, once the endoluminal prosthesis 300 has been advanced to the target location along the guidewires 340, 342, 344 within the patient's vasculature, retracting the outer sheath 332 of the catheter 330 and can cause the endoluminal prosthesis 300 to be deployed at the target location such that each of the branch grafts 304, 306 can be advanced into each of the branch vessels. After the branch grafts 300, 306 are positioned within the target branch vessels, each of the stents 304, 306 can be expanded in the branch vessels to secure the branch grafts 304, 306 in the branch vessels. A stent or other suitable device can be deployed within the main graft body 302 to secure the main graft body 302 within the main vessel.

In some embodiments, one or more of the pre-wired guidewires 340, 342 described above can be configured to be insertable into a branch vessel and to be biased such that an end portion of the guidewire 340, 342 remains in the branch vessel. During manipulation of the guidewires and/or deployment catheter, it sometimes becomes difficult to maintain the position of the distal portion of the guidewires in the branch vessels. Biasing the end portion of the guidewire 340, 342 to remain in the branch vessel can thus improve any of the deployment procedures described herein. Additional details regarding such guidewires is set forth below.

FIG. 20 is a side view of another embodiment of a delivery catheter 400 that can be used to deploy at least some of the embodiments of the endoluminal prostheses disclosed herein, showing an embodiment of an endoluminal prosthesis 402 being loaded within a delivery catheter 400. FIG. 21 is an enlarged partial section view of a portion of the embodiment of a delivery catheter 400 illustrated in FIG. 20, showing the endoluminal prostheses 402 loaded within a delivery catheter 400. As illustrated in FIGS. 20 and 21, the endoluminal prosthesis 402 can be similar to the endoluminal prosthesis 80 described above, can be a bifurcated endoluminal prosthesis such as endoluminal prosthesis 90 described above, or can have any of the features, components, or other details of any of the other endoluminal prostheses disclosed herein, directly or by incorporation by reference. As with the endoluminal prostheses described herein, the main graft body 404 can be configured to accommodate positional adjustability of the fenestrations 406, 408. For example, without limitation, fenestrations 406, 408 can be formed within an enlarged portion of the main graft body 404.

With reference to FIGS. 20 and 21, the endoluminal prosthesis 302 can have a main graft body 404 having fenestrations 406, 408 formed therein, and one or more stent segments 410, 412 deployed within the main graft body 404. The stents 410, 412 can be bare metal, covered, self-expandable, balloon expandable, or any other suitable stents either disclosed (directly or by incorporation by reference) herein or otherwise known in the art or later developed. As illustrated in FIGS. 20 and 21, first and second guidewire sheaths 420, 422 can be advanced through the fenestrations 406, 408, respectively, before the endoluminal prosthesis 402 is loaded into a delivery catheter 400 or otherwise such that the first and second guidewire sheaths 420, 422 are advanced through the fenestrations 406, 408, respectively, when the endoluminal prostheses 402 is in the loaded state in the delivery catheter 400.

In some embodiments, the guidewire sheaths 420, 422 can be hollow so that they can be passed or advanced over pre-positioned guidewires that are pre-wired in the patient's vasculature to guide the endoluminal prostheses 402 to the target location. Advancing the guidewire sheaths 420, 422 over the pre-wired guidewires can also facilitate the alignment of each of the fenestrations 406, 408 with each of the branch vessels in the patient's vasculature.

In some embodiments, each of the guidewire sheaths 420, 422 can be made from the same material and have the same features, sizes, or other details of any other guidewire disclosed herein, including without limitation guidewires 310, 312 described above. Additionally, as with guidewires 310, 312, in some embodiments, the guidewire sheaths 420, 422 can support balloons on the distal ends of the guidewire sheaths 420, 422. The balloons can be inflated in the branch vessel to deploy expandable stents within or adjacent to the fenestrations 406, 408. In some embodiments (not illustrated), flared, flareable, bare metal, covered, self-expandable, balloon expandable, or any other suitable stents disclosed (directly or by incorporation by reference) herein, known in the field, or later developed can be positioned within each of the fenestrations 406, 408, respectively, before the endoluminal prosthesis 402 is loaded into the delivery catheter 400. The stents can be deployed following any suitable procedure, including without limitation the procedure described above with respect to the stents 314, 316.

In this configuration, the branch stents (not illustrated) can be secured to or otherwise configured to engage each of the fenestrations 406, 408 such that, as the stents are advanced along the pre-wired guidewires into the respective branch vessels, the fenestrations 406, 408 can be aligned with the respective branch vessels. In some embodiments, as mentioned, the stents can have flanged or flared portions or be partially expanded so as to engage the fenestrations 406, 408 such that advancing the stents into the respective branch vessels can align the fenestrations 406, 408 with the respective branch vessels. Additionally, in some embodiments, the guidewires themselves can be configured to engage each of the fenestrations 406, 408 such that, as the deployment guidewire sheaths 420, 422 are advanced along the pre-wired guidewires into the respective branch vessels, the fenestrations 406, 408 can be aligned with the respective branch vessels without the use of stents for alignment.

However, the pre-positioning of the stents and the balloons in the endoluminal prostheses 402 described above is not required. In some embodiments, one or more stents can be advanced through the patient's vasculature and into the fenestrations 406, 408 after the endoluminal prostheses 402 has been positioned within the target vessel in the patient's vasculature. For example, one or more stents can be advanced through the patient's vasculature into the fenestrations 406, 408 after the main graft body 404 has been positioned within the main target vessel or after the fenestrations 406, 408 have been positioned adjacent to the target branch vessels.

With reference to FIGS. 20 and 21, the delivery catheter 400 can have an outer sheath 430, a distal tip 432 having a lumen or opening 434 therethrough, and a central tube 436 that can secure the distal tip 432 to the delivery catheter 400. The opening 434 in the distal tip 432 can extend through the central tube 436 so that the delivery catheter 400 can be advanced over a pre-positioned guidewire. The outer sheath 430 can be axially moveable relative to the central tube 436 and the distal tip 432, so that the endoluminal prosthesis 402 can be exposed and deployed from the delivery catheter 400 by retracting the outer sheath 430 relative to the central tube 436 and the distal tip 432.

Figure 22A:
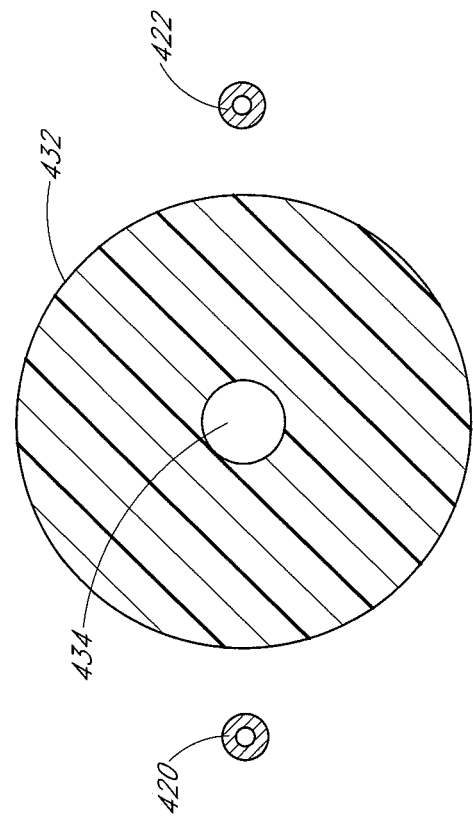
FIG. 22A is a section view of an embodiment of a distal tip that can be used with the embodiment of the delivery catheter that is illustrated in FIG. 20, taken through line 22A-22A in FIG. 20.

The distal tip 432 can be made from a soft material and/or otherwise be configured to be atraumatic to the patient's vasculature so as to minimize injury to the patient's vasculature during advancement of the delivery catheter 400 through the patient's vasculature. In some embodiments, the distal tip 432 can have a substantially circular cross-section along the length thereof, as illustrated in FIG. 22A, which is a section view of an embodiment of a distal tip 432, taken through line 22A-22A in FIG. 20. As illustrated, the distal tip 432 can be tapered along a portion of the length thereof.

Figure 22B:
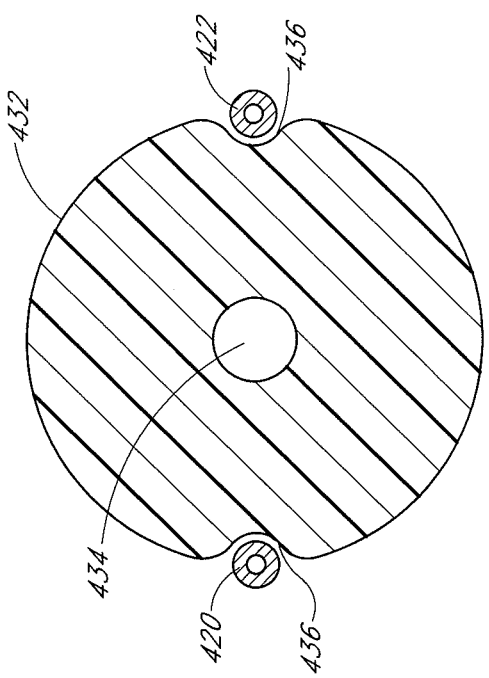
FIG. 22B is a section view of another embodiment of a distal tip that can be used with the embodiment of the delivery catheter that is illustrated in FIG. 20, taken through line 22B-22B in FIG. 20.

In some embodiments, the distal tip 432 can have a cross-section that is generally circular, as illustrated in FIG. 22A. In some embodiments, as illustrated in FIG. 22B, the distal tip 432' can have a non-circular cross-section. FIG. 22B is a section view of another embodiment of a distal tip 432' that can be used with the embodiment of the delivery catheter 400 that is illustrated in FIG. 20, taken through line 22B-22B in FIG. 20. For example, as illustrated, the distal tip 432' can have one or more channels 438 formed along a portion of the length of the distal tip 432'. The one or more channels 438 (two being shown) can each be configured to receive a guidewire sheath 420, 422 therein. For example, with reference to FIG. 22B, the two channels 438 can be configured to releasably receive each of the guidewire sheaths 420, 422 therein so as to reduce the cross-sectional profile of the delivery catheter 400 and to permit the outer sheath 430 to be advanced over the distal tip 432 with the guidewires positioned adjacent to the distal tip 432 and advancing beyond the distal tip 432 without obstruction from the guidewire sheaths 420, 422. For example, the channels 438 can be configured so that the outer sheath 430 can be advanced over and fit closely around the distal tip 432.

Figure 23A:
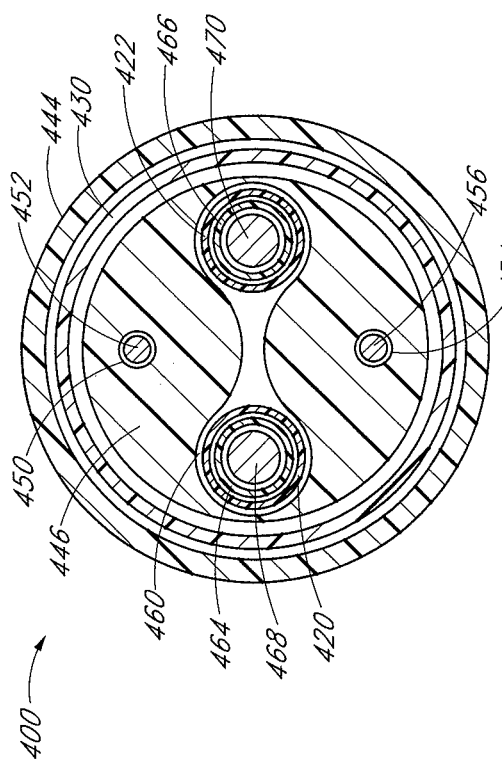
FIG. 23A is a section view of the embodiment of the delivery catheter shown in FIG. 20, taken through line 23A-23A in FIG. 20.
Figure 23B:
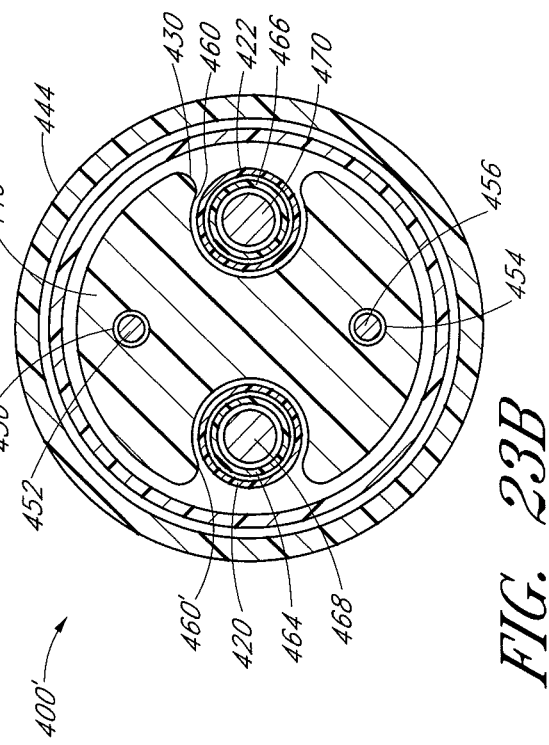
FIG. 23B is a section view of the embodiment of the delivery catheter shown in FIG. 20, taken through line 23B-23B in FIG. 20.

FIG. 23A is a section view of the embodiment of the delivery catheter 400 shown in FIG. 20, taken through line 23A-23A in FIG. 20. FIG. 23B is a section view of the embodiment of the delivery catheter 400 shown in FIG. 20, taken through line 23B-23B in FIG. 20. FIGS. 23A and 23B represent different embodiments of the delivery catheter 400. With reference to FIG. 23A, some embodiments of the delivery catheter 400 can have an outer sheath 430 that can be advanced through an introducer sheath 444 and an inner core 446 that can be axially advanced relative to the outer sheath 430. Some embodiments of the delivery catheter 400 can be configured so that the inner core 446 can be rotated relative to the outer sheath 430, or can be configured so that the inner core 446 can be rotationally linked to the outer sheath 430. Additionally, the inner core 446 can be configured to axially support the central tube 436 and, hence, the distal tip 432 so that, as the inner core 446 is advanced relative to the outer sheath 430, the central tube 436 and the distal tip 432 can be simultaneously advanced relative to the outer sheath 430.

Further, with reference to FIG. 23A, a lumen 450 can be formed axially through at least a portion of the inner core 446, the lumen 450 being configured to slideably receive a guidewire 452 therein. In some embodiments, the lumen 450 can be in communication with the opening 434 that can be formed through the distal tip 432 and the central tube 436 such that the opening 434 and the lumen 450 can slidingly receive a pre-positioned guidewire as the delivery catheter 400 is advanced over the guidewire. Similarly, a lumen 454 can be formed through at least a portion of the inner core 446 as illustrated in FIG. 23A, the lumen 454 being configured to slideably receive a guidewire, release wire, or other wire 456 therein.

In some embodiments, the endoluminal prosthesis 402 can be similar to or have any of the features of the endoluminal prostheses disclosed in U.S. patent application Ser. No. 12/101,863, filed on Apr. 11, 2008 (entitled "BIFURCATED GRAFT DEPLOYMENT SYSTEMS AND METHODS"), which is hereby incorporated by reference in its entirety as if fully set forth herein. In some embodiments, the release wire 456 can be or can be connected to the sheath release wire 166 used to deploy the main branch sheath 186 in U.S. patent application Ser. No. 12/101,863.

A lumen 460 having one or more lobes can be formed axially through at least a portion of the inner core 446. The lumen 460 can be configured to receive one or more guidewires or guidewire sheaths therein. In the illustrated embodiment, the lumen 460 can be configured to receive two guidewire sheaths therein, such as without limitation guidewire sheaths 420, 422. Additionally, in some embodiments, the guidewire sheaths 420, 422 each can be configured to receive a guidewire catheter therein, such as without limitation guidewire catheters 464, 466, respectively, having guidewires 468, 470 therein. In some embodiments, the guidewire sheaths 420, 422 can each be sized and configured to axially receive a renal, covered or bare metal stent therein so that a renal stent can be advanced through the guidewire sheaths 420, 422 and deployed in the renal branch arteries as described herein. In some embodiments, the renal stents (not illustrated) can be advanced over the guidewire catheters 464, 466 within the guidewire sheaths 420, 422.

In some embodiments, the hollow guidewire sheaths 420, 422 can slide within the lumen 460. Alternatively, in some embodiments, the hollow guidewire sheaths 420, 422 can be fixed to the inner core 446. The guidewire catheters 464, 466 can each be configured to receive a pre-positioned guidewire therein, so that the guidewire catheters 464, 466 can be advanced over pre-positioned guidewires routed into the renal arteries as the delivery catheter 400 is advanced over the pre-positioned guidewire 452.

Similarly, with reference to FIG. 23B, in some embodiments, the delivery catheter 400 can have an outer sheath 430 that can be advanced through an introducer sheath 444 and an inner core 446' that can be axially advanced relative to the outer sheath 430. In some embodiments, the delivery catheter 400 can be configured so that the inner core 446' can be rotated relative to the outer sheath 430, or can be configured so that the inner core 446' can be rotationally linked to the outer sheath 430. Additionally, the inner core 446' can be configured to axially support the central tube 436 and, hence, the distal tip 432 so that, as the inner core 446' is advanced relative to the outer sheath 430, the central tube 436 and the distal tip 432 can be simultaneously advanced relative to the outer sheath 430.

Further, with reference to FIG. 23B, a lumen 450 can be formed axially through at least a portion of the inner core 446', the lumen 450 being configured to slideably receive a guidewire 452 therein. In some embodiments, the lumen 450 can be in communication with the opening 434 that can be formed through the distal tip 432 and the central tube 436 such that the opening 434 and the lumen 450 can slidingly receive a pre-positioned guidewire as the delivery catheter 400 is advanced over the guidewire. Similarly, a lumen 454 can be formed through at least a portion of the inner core 446' as illustrated in FIG. 23B, the lumen 454 being configured to slideably receive a guidewire, release wire, or other wire 456 therein.

In some embodiments, one or more channels 460' can be formed axially on at least a portion of the inner core 446'. The channels 460' can each be configured to receive one or more guidewires or guidewire sheaths therein. In the illustrated embodiment, the channels 460' can be configured to receive two guidewire sheaths therein, such as without limitation guidewire sheaths 420, 422, configured as described above. The guidewire catheters 464, 466 can each be configured to receive a pre-positioned guidewire therein, so that the guidewire catheters 464, 466 can be advanced over pre-positioned guidewires routed into the renal arteries as the delivery catheter 400 is advanced over the pre-positioned guidewire 452.

Figure 24:
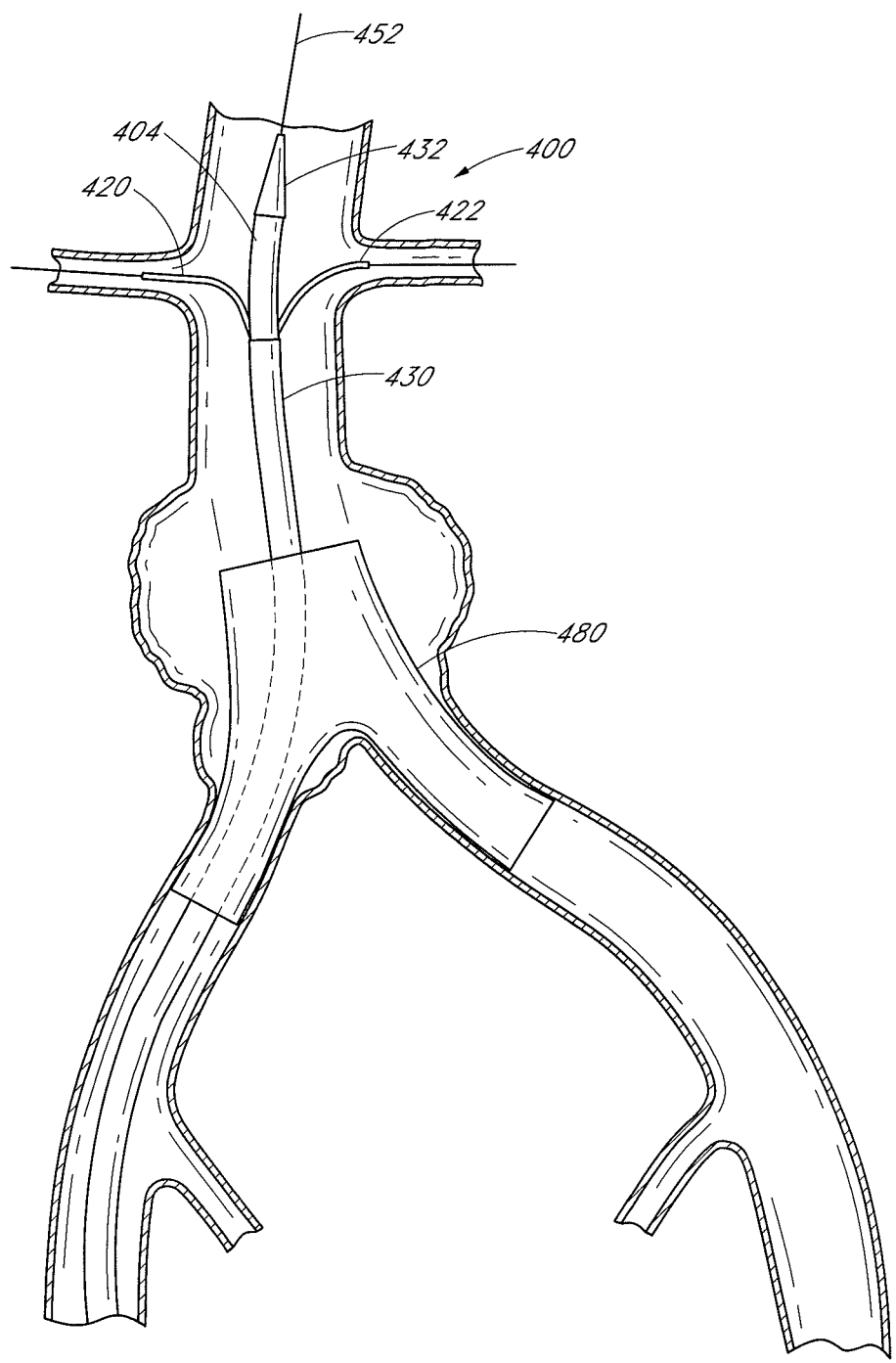
FIG. 24 is a side view of another embodiment of a delivery catheter showing a delivery catheter being advanced distally past a bifurcated graft and showing guidewires being advanced into the renal arteries.

With reference to FIGS. 24-28, some non-limiting examples of delivery methods for delivering some embodiments of the endoluminal prostheses disclosed herein to the abdominal aortic region will be described. FIG. 24 is a side view of an embodiment of a delivery catheter, such as without limitation delivery catheter 400 described above, showing a delivery catheter 400 being advanced distally past a bifurcated prosthesis 480 and showing guidewire sheaths 420, 422 being advanced into the renal arteries.

With reference to FIG. 24, after the bifurcated prosthesis 480 has been deployed in the abdominal aorta following any suitable methods for such deployment, including without limitation the deployment methods disclosed in U.S. patent application Ser. No. 12/390,346 or U.S. patent application Ser. No. 12/101,863, the delivery catheter 400 can then be advanced through the main body of the bifurcated prosthesis 480 into the abdominal aorta and renal artery region.

In some embodiments, the guidewire sheaths 420, 422 can be advanced along pre-positioned guidewires into the renal arteries. In some embodiments, as illustrated in FIG. 24, the outer sheath 430 can be partially retracted so that the guidewire sheaths 420, 422 can be advanced into the renal arteries as the distal tip 432 of the delivery catheter 400 is advanced past the renal arteries along guidewire 452. Thereafter, the pre-placement guidewires (if any) positioned within the guidewire sheaths 420, 422 and already advanced into the renal arteries can be removed.

Figure 25:
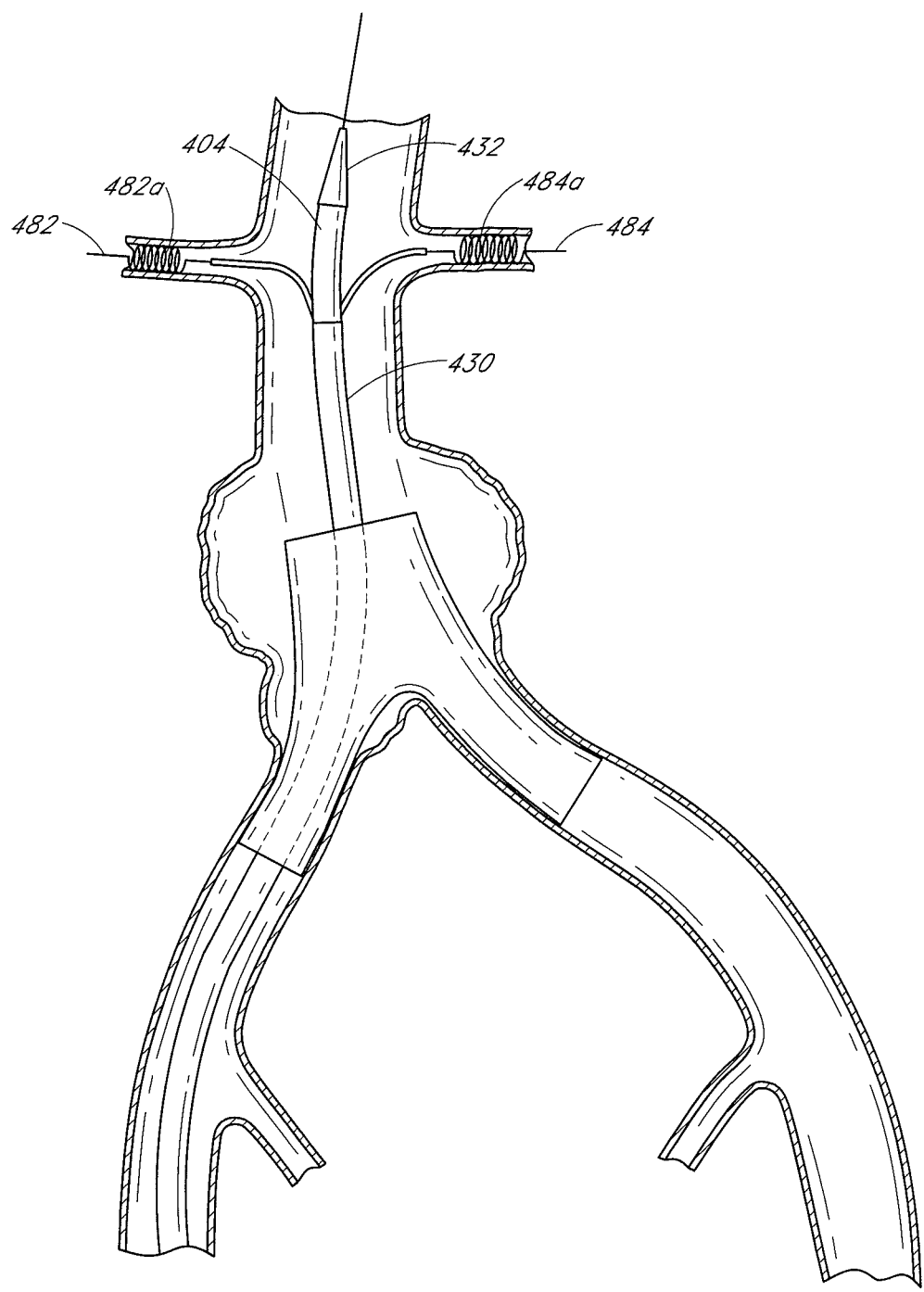
FIG. 25 is a side view of the embodiment of the delivery catheter shown in FIG. 24, showing biased guidewires being advanced into the renal arteries.

As illustrated in FIG. 25, which is a side view of the embodiment of the delivery catheter 400 shown in FIG. 24, biased guidewires 482, 484, which will be described in greater detail below, can be advanced through the guidewire sheaths 420, 422 and into the renal arteries. As will be described, the coiled distal end portions 482a, 484a of each of the biased guidewires 482, 484 can be configured to be insertable into a branch vessel and can be biased to remain in the branch vessel.

Figure 26:
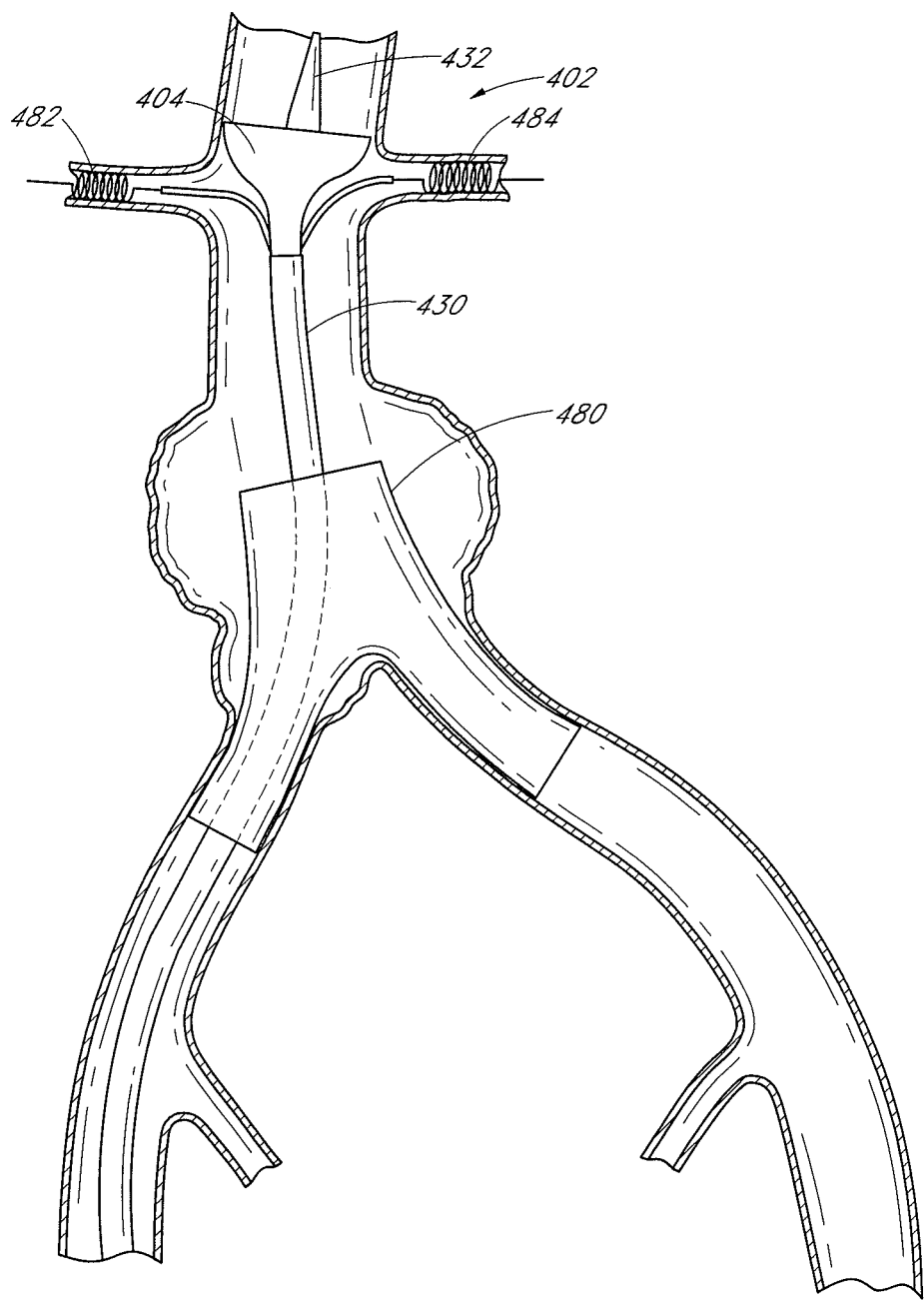
FIG. 26 is a side view of the embodiment of the delivery catheter shown in FIG. 24, showing the embodiment of the endoluminal prosthesis being deployed within the target vessel region.

FIG. 26 is a side view of the embodiment of the delivery catheter 400 shown in FIG. 24, showing the embodiment of the endoluminal prosthesis 402 being deployed within the target vessel region. In some embodiments, the endoluminal prosthesis 402 can be a fenestrated cuff. The endoluminal prosthesis 402 can be deployed by any suitable method, such as without limitation removing a restraining sheath or by any of the methods disclosed in U.S. patent application Ser. No. 12/390,346 or U.S. patent application Ser. No. 12/101,863, each of which are hereby incorporated by reference as if fully set forth herein.

For example, without limitation, the endoluminal prosthesis 402 can be deployed by removing a perforated sheath using a sheath release wire threaded through perforations in the sheath, such as is set forth in some embodiments of U.S. patent application Ser. No. 12/101,863, which application is fully incorporated herein by reference. Additionally, in some embodiments, the proximal end portion of the endoluminal prosthesis 402 can be deployed by distally advancing a sheath or other restraint so as to deploy the proximal end of the endoluminal prosthesis 402 (i.e., the end of the endoluminal prosthesis 402 that is furthest advanced into the vasculature or closest to the heart).

Figure 27:
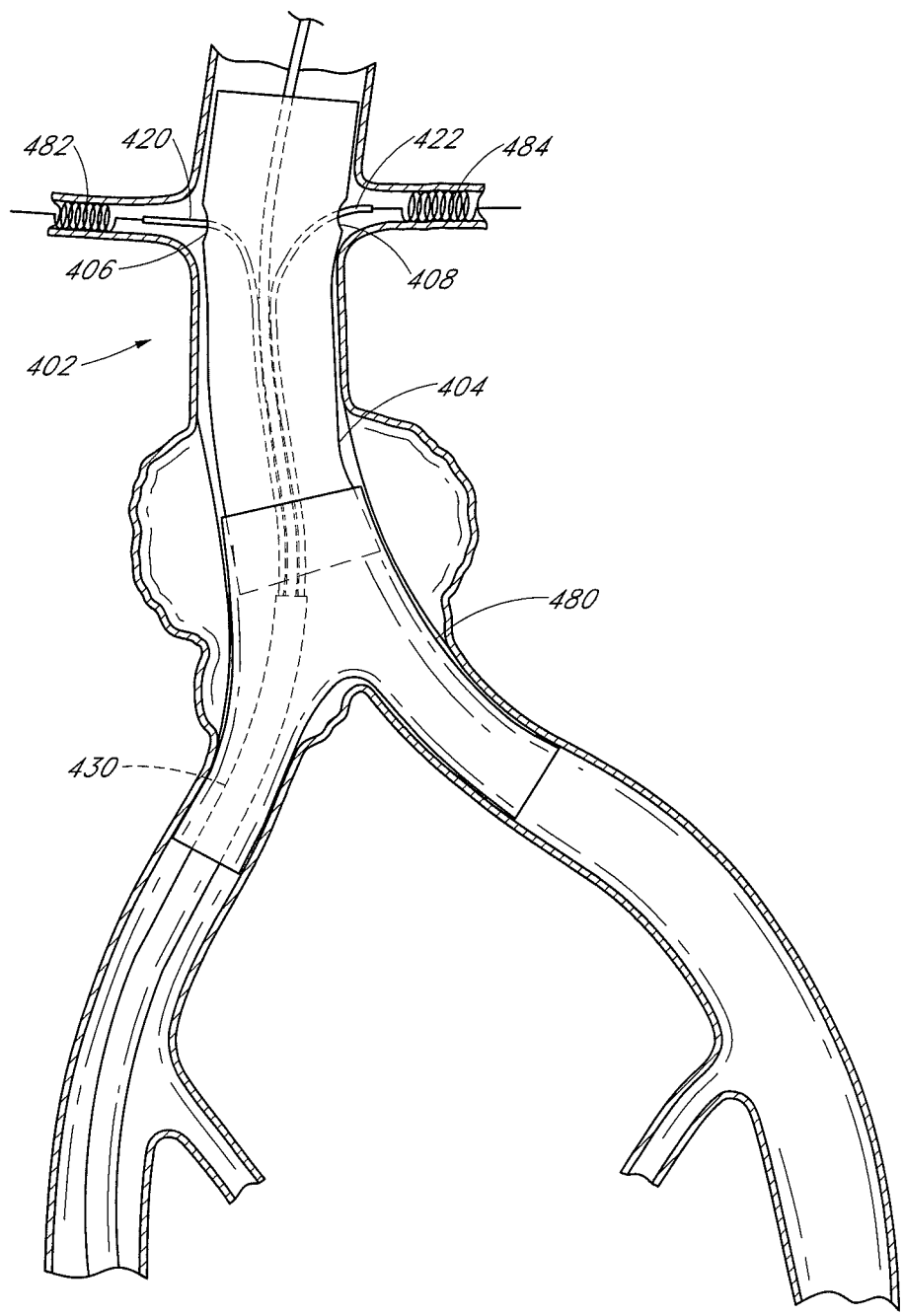
FIG. 27 is a side view of the embodiment of the delivery catheter shown in FIG. 24, showing the endoluminal prosthesis after the distal portion of the endoluminal prosthesis has been deployed within the bifurcated prosthesis.
Figure 28:
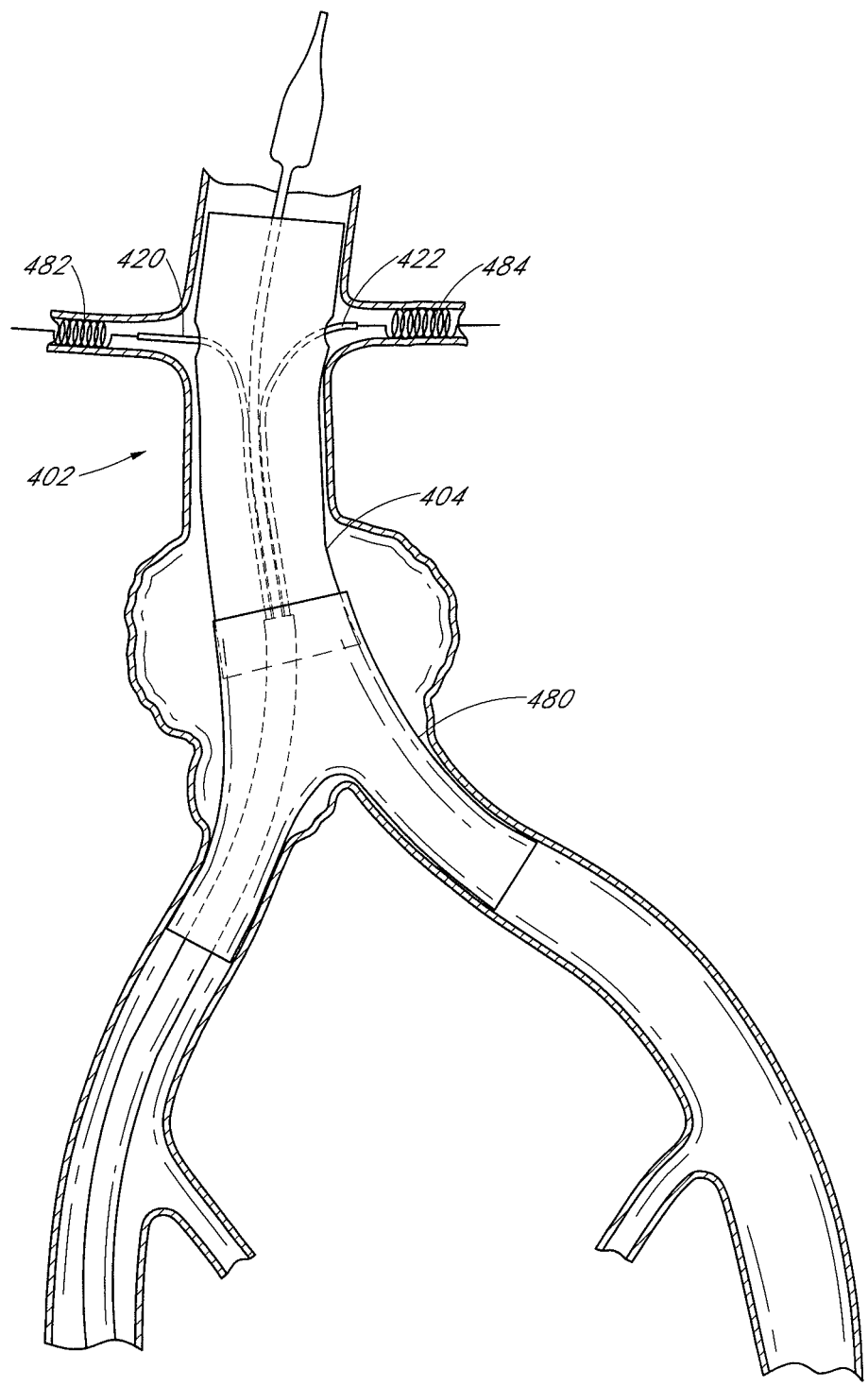
FIG. 28 is a side view of the embodiment of the delivery catheter shown in FIG. 24, showing the endoluminal prosthesis after the distal portion of the endoluminal prosthesis has been deployed within the bifurcated prosthesis.

The proximal end of the endoluminal prosthesis 402 can be deployed proximal to the desired visceral vessel (such as, without limitation, the SMA) and then axially retracted until the proximal portion of the endoluminal prosthesis 402 is positioned just below the target visceral vessel (e.g., without limitation, the SMA). The adjustable fenestrations 406, 408 can then be adjusted to be positioned adjacent to the respective renal arteries. Thereafter, the distal portion of the endoluminal prosthesis 402 (i.e., the portion of the endoluminal prosthesis 402 furthest away from the heart) can be deployed within the bifurcated prosthesis 480 by retracting the outer sheath 430, as is illustrated in FIG. 27. FIG. 27 is a side view of the embodiment of the delivery catheter 400 shown in FIG. 24, showing the endoluminal prosthesis 402 after the distal portion of the endoluminal prosthesis 402 has been deployed within the bifurcated prosthesis 480.

As further illustrated in FIG. 27, the inner core 446, distal tip 432, and central tube 436 can be axially retracted through the outer sheath 430 and removed from the target vessel region, leaving the guidewire sheaths 420, 422 positioned within the patient's renal arteries. In some embodiments, the delivery catheter 400 illustrated in FIG. 23B can be configured such that the inner core 446, distal tip 432, and central tube 436 can be axially retracted through the outer sheath 430 while leaving the guidewire sheaths 420, 422 positioned within the renal arteries. Thereafter, any suitable renal stents (such, as without limitation, stents 314, 316 described above) can be advanced through the guidewire sheaths 420, 422 and deployed within the renal arteries over the biased guidewires 482, 484 or other guidewires in the renal arteries. In some embodiments, with reference to FIG. 28, renal stents (such as without limitation stents 314, 316) can be advanced through the guidewire sheaths 420, 422 and deployed within the renal arteries over the biased guidewires 482, 484 or any other guidewires without removing the inner core 446, distal tip 432, and central tube 436.

Figure 29:
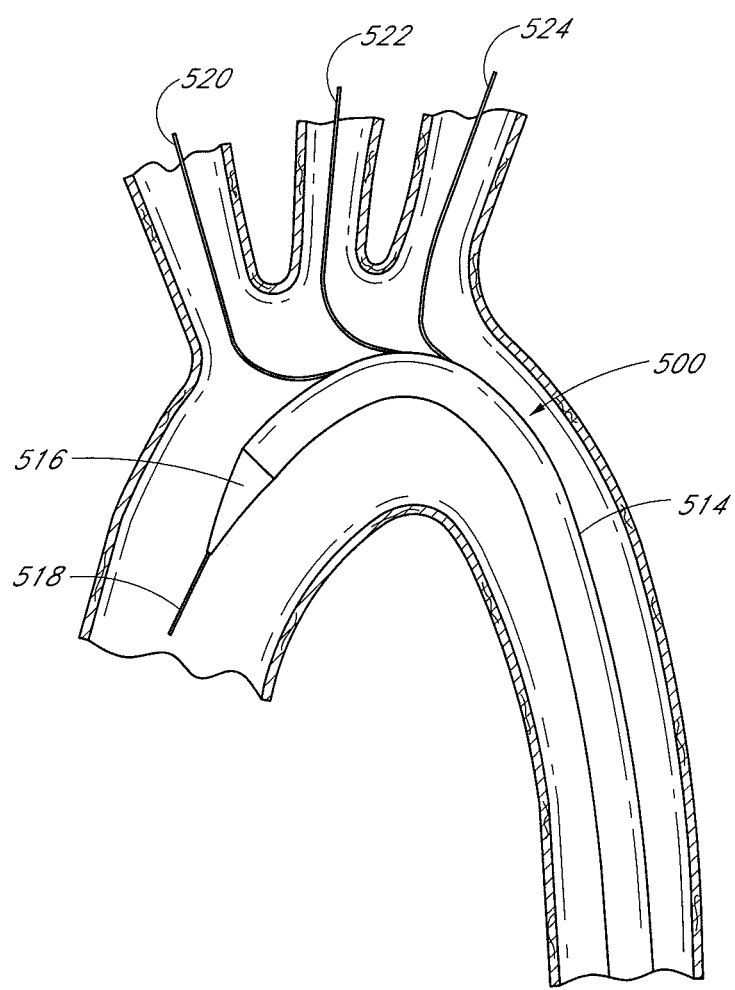
FIG. 29 is a side view of another embodiment of a delivery catheter showing a delivery catheter being advanced distally past renal arteries in the thoracic aorta region of a patient's vasculature.
Figure 30:
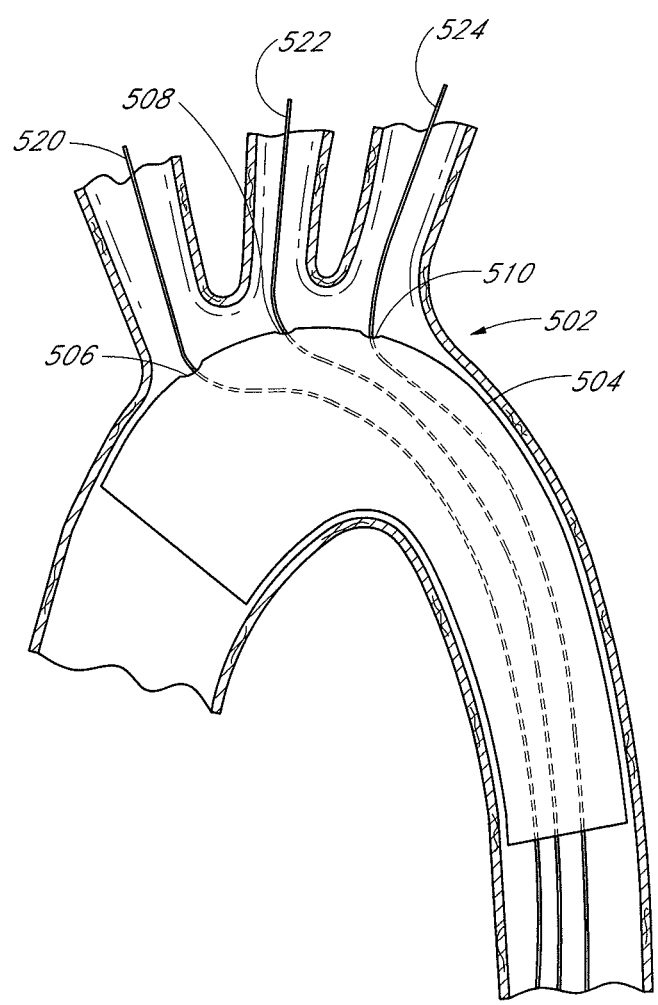
FIG. 30 is a side view of an endoluminal prosthesis that can be deployed using the embodiment of the delivery catheter shown in FIG. 29.

FIG. 29 is a side view of another embodiment of a delivery catheter 500 showing a delivery catheter 500 being advanced distally past branch arteries in the thoracic aorta region of a patient's vasculature. FIG. 30 is a side view of an endoluminal prosthesis 502 that can be deployed using the embodiment of the delivery catheter 500 shown in FIG. 29. In some embodiments, the endoluminal prosthesis 502 can have a main graft body 504 having multiple fenestrations 506, 508, 510 formed therein. The delivery catheter 500 can have an outer sheath 514 and a distal tip 516 configured to be advanced over a guidewire 518, as with the other embodiments of the delivery catheters disclosed herein.

The endoluminal prosthesis 502 and delivery catheter 500 can have any of the components, features, or other details of any of the other endoluminal prostheses or delivery catheters disclosed (directly or by incorporation by reference) herein. For example, in some embodiments, the endoluminal prosthesis 502 can have stents or stent segments deployed within the main graft body 504, springs, or other suitable structures deployed or supported within the main graft body 504. Additionally, in some embodiments, the main graft body 504 can have an enlarged diameter along at least a portion of the main graft body 504 and/or an additional graft material or length along at least a portion of the main graft body 504 to improve the adjustability of the fenestrations 506, 508, 510.

In some embodiments, the delivery catheter 500 and the endoluminal prosthesis 502 can be configured such that a guidewire sheath (such as without limitation guidewire sheaths 420) can be pre-positioned within the delivery catheter 500 and the endoluminal prosthesis 502, the guidewire sheaths (not illustrated in FIGS. 29, 30) advancing through each of the fenestrations 506, 508, 510. The distal tip 516 of the delivery catheter can be configured to have channels formed therein configured to receive the guidewire sheaths, similar to the distal tip 432' disclosed herein.

In some embodiments, the branch arteries can be pre-wired with guidewires 520, 522, 524 (which can be biased guidewires), similar to any of the pre-wiring techniques for the renal arteries disclosed herein, so that the delivery catheter 500 and the endoluminal prosthesis 502 having guidewire sheaths positioned therein can be advanced over the guidewires 520, 522, 524 to approximately align the fenestrations 506, 508, 510 as the endoluminal prosthesis 502 is being advanced into the target vessel region. Additionally, in some embodiments, the guidewire sheaths can be advanced into the branch arteries as the endoluminal prosthesis 502 is being deployed, similar to the deployment of the aortic grafts disclosed herein. Thereafter, any suitable branch stents (such as without limitation stents 314, 316) can be advanced through the guidewire sheaths (not illustrated) and deployed within the branch arteries over the guidewires 520, 522, 524.

Figure 31:
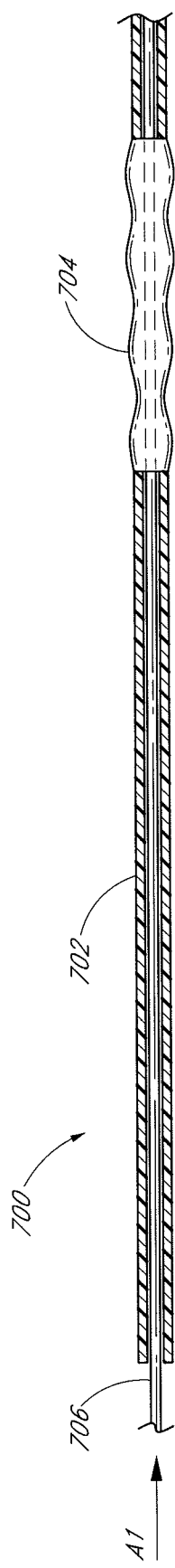
FIG. 31 is a section view of an embodiment of a guidewire, showing the guidewire in a collapsed configuration.
Figure 32:
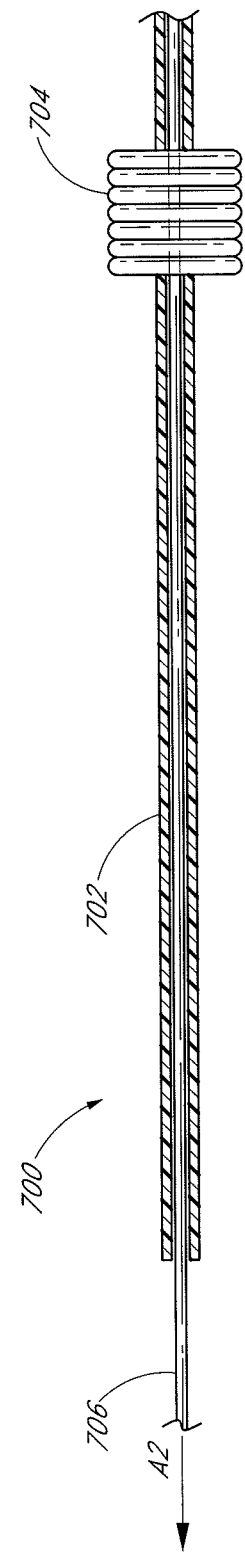
FIG. 32 is a section view of the embodiment of the guidewire shown in FIG. 31, showing the guidewire in an expanded configuration.

FIG. 31 is a section view of an embodiment of a guidewire 700, showing the guidewire 700 in the open or collapsed configuration. FIG. 32 is a section view of the embodiment of the guidewire 700 shown in FIG. 31, showing the guidewire 700 in the closed or expanded configuration. In some embodiments, without limitation, the guidewire 700 can be used in place of either of the guidewires 340, 342 shown in FIG. 19 and described above. Any of the guidewires disclosed herein can comprise a shape memory material, such as without limitation Nitinol.

In some embodiments, the guidewire 700 can have an outer guidewire sheath 702 having an expandable portion 704. Additionally, the guidewire 700 can have an inner guidewire core 706 slidably received within a lumen formed within the outer guidewire sheath 702. In some embodiments, the outer guidewire sheath 702 can be sized and configured such that the guidewires 310, 312 described above or any other guidewires or lumens can be advanced over the outside of the outer guidewire sheath 702, as described above.

With reference to FIG. 31, the expandable portion 704 can be configured such that, when the expandable portion 704 is axially collapsed, the diameter of the expandable portion 704 can increase and be configured such that, when the expandable portion 704 is axially extended, the diameter of the expandable portion 704 can decrease. For example, with reference to FIG. 31, as the inner guidewire core 706 is advanced relative to the outer guidewire sheath 702 in the direction represented by arrow A1 in FIG. 31, the expandable portion 704 can be axially extended, thus reducing the diameter of the expandable portion 704. In contrast, with reference to FIG. 32, as the inner guidewire core 706 is retracted relative to the outer guidewire sheath 702 in the direction represented by arrow A2 in FIG. 32, the collapsible portion can be axially compressed, thus increasing the diameter of the expandable portion 704. In some embodiments, the expandable portion 704 can have a bellows type, undulating, or corrugated outer surface.

In this arrangement, the guidewire 700 can be advanced through the patient's vasculature to the target branch vessel while the guidewire 700 is in the collapsed configuration (i.e., the configuration shown in FIG. 31). When the distal end portion of the guidewire 700 has reached the desired position within the branch vessel, the inner guidewire core 706 can then be retracted relative to the outer guidewire sheath 702 (i.e., retracted in direction A2 relative to the outer guidewire sheath 702) so that the diameter of the expandable portion 704 can be increased and expand radially against the inner surface of the branch vessel wall. In this arrangement, the expandable portion 704 can secure the distal end portion of the guidewire 700 in the desired branch vessel. The expandable portion 704 can be formed from a soft, atraumatic material to minimize the risk of any injury to the vessel wall.

Figure 33:
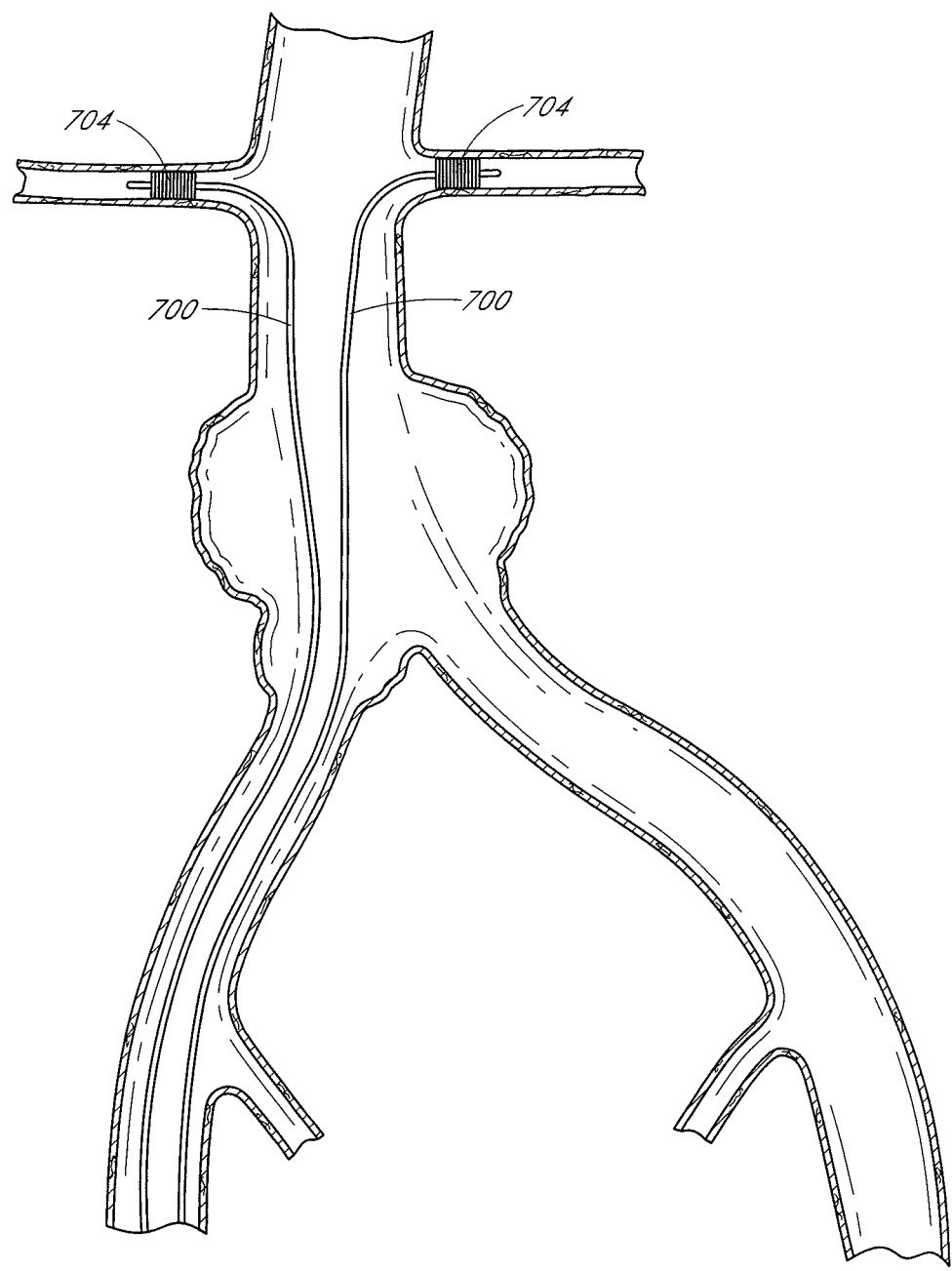
FIGS. 33 and 34 illustrate a pair of guidewires positioned within the patient's vasculature such that the distal end portions of the guidewires are secured within the patient's branch vessels.
Figure 34:
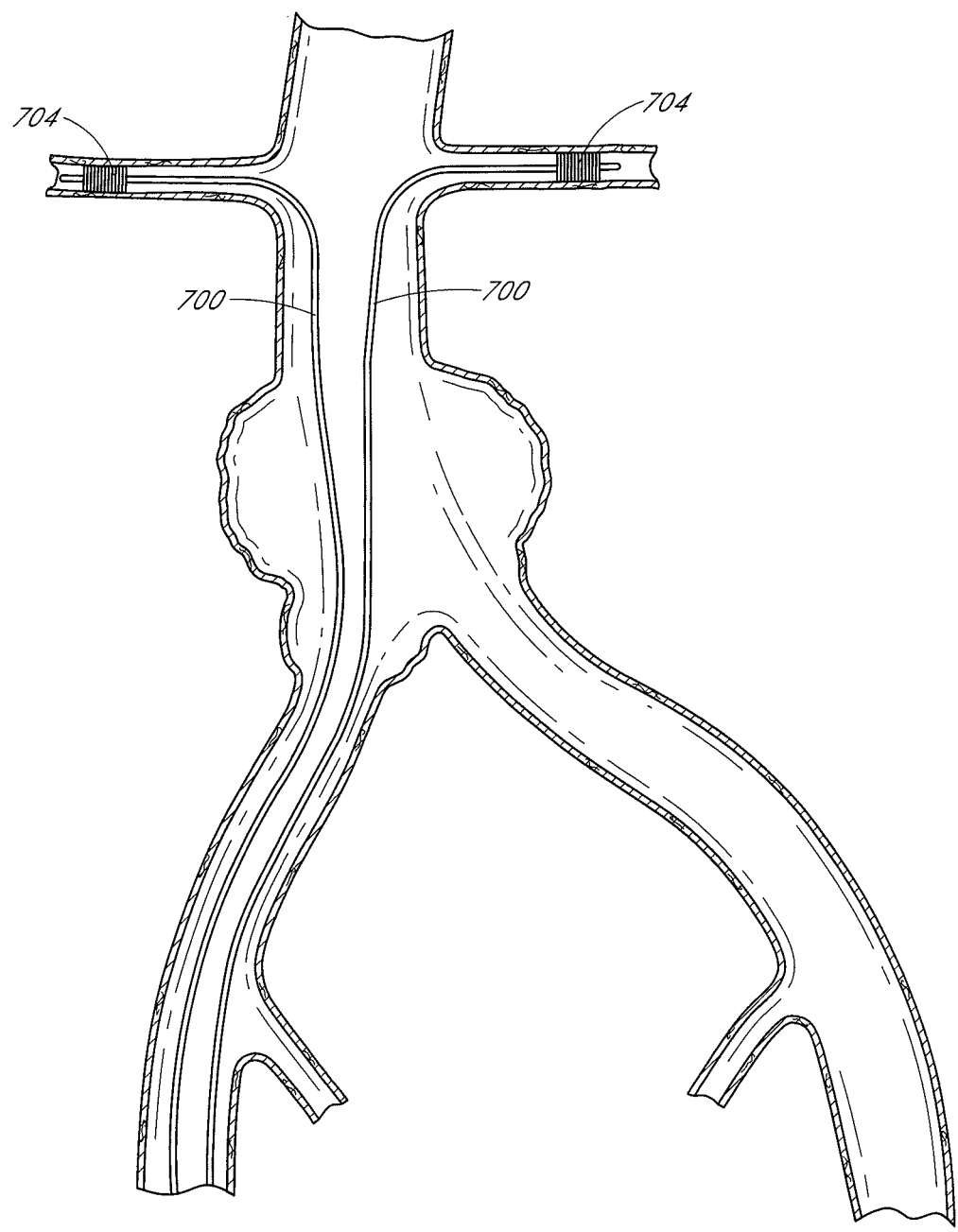

FIGS. 33 and 34 each illustrate a pair of guidewires 700 positioned within the patient's vasculature such that the distal end portions of the guidewires 700 can be secured at least partially within the patient's branch vessels. In some embodiments, the guidewires 700 can be positioned within the patient's vasculature such that a portion of the expandable portion 704 protrudes into the lumen of the main vessel, which a portion of the expandable portion 704 protrudes into the branch vessel. In FIG. 34, the distal end portion of the guidewires 700 have been advanced further as compared to the guidewires 700 shown in FIG. 33, to allow additional space for the deployment of branch grafts within the branch vessels. The expandable portion 704 can be formed from metal, plastic, or any other suitable material, and can have an expandable bellows configuration or can be formed from one or more braids of wire. Additionally, in some embodiments, the expandable portion 704 can be used to align the fenestrations or branch grafts with the branch vessels.

Once the guidewires 700 have been secured in the desired branch vessels, any of the deployment catheters described above can then be advanced over the guidewires 700. When the graft deployment procedure is complete and the guidewires 700 are no longer needed in the branch vessels, the guidewire core 706 can then be retracted relative to the outer sheath 702 of the guidewires 700 so that the guidewires 700 can be removed from the patient's vasculature. Alternatively, other securing mechanisms can be attached to the distal end portion of the guidewire, such as, without limitation, hooks, barbs, or other similar features, to removably secure one or more of the guidewires 700 within the vessel.

For example, in some embodiments, one of more of the guidewires disclosed herein (such as, without limitation, guidewires 700) can have a coiled distal end portion. The coiled distal end portion can be configured to be insertable into a branch vessel and can be biased to remain in the branch vessel. For example, in some embodiments, the size or diameter of the coils can be greater than the inside diameter of the branch vessel so as to bias the coiled portion to remain within the branch vessel when the proximal end of the guidewire is retracted. In this configuration, proximal retraction of the guidewire can cause a proximal end of the coil to unravel, allowing a portion of the coiled portion of the guidewire to be unraveled and retracted while the remaining portion of the coiled portion can remain within the branch vessel. This configuration can inhibit the distal end portion of the guidewire from being inadvertently removed from the branch vessel. To completely remove the coiled distal end portion from the branch vessel, the guidewire can be retracted until the entire coiled portion is unraveled and retracted. In some embodiments (not illustrated), the inner guidewire core 706 of the guidewire 700 can be configured such that, when the distal end of the inner guidewire core 706 is advanced beyond the distal end of the outer guidewire sheath 702, the distal end of the inner guidewire core 706 forms coils that expand against the inner vessel wall and secure the guidewire 700 to the branch vessel.

Figure 35:
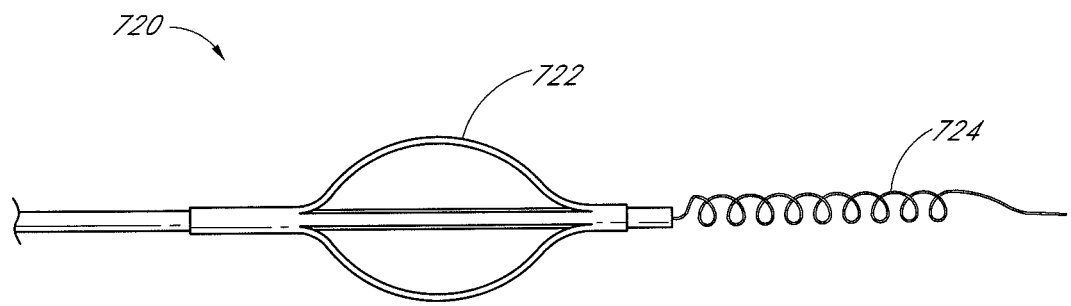
FIG. 35 is a side view of another embodiment of a guidewire, showing the guidewire in an expanded configuration.

FIG. 35 is a side view of another embodiment of an expandable guidewire 720, showing the guidewire 720 in an expanded configuration. The guidewire 720 can have expansion struts 722 that can expand when deployed in the renal or other branch arteries. In some embodiments, the guidewire 720 can be formed from a tube of Nitinol that can be perforated or cut so as to form a plurality of axial members or struts 722, and heat set so that the expansion struts 722 form a size that is larger than the desired vessel diameter. In some embodiments, the guidewire can have four or less, or six, or eight or more struts 722.

In some embodiments, the guidewire 720 can be advanced through a tubular guidewire sheath that terminates in the desired branch vessel location. As the expansion struts 722 exit the distal end of the tubular guidewire sheath, the expansion struts 722 can self-expand against the walls of the target vessel so as to bias the guidewire 720 in the desired location. Alternatively, a two-way guidewire (i.e., one having sufficient compressive and tensile strength) can be advanced through the hollow guidewire 720 so as to elongate and, hence, radially collapse the expansion struts 722. In some embodiments, the guidewire 722 can have a coiled end portion 724 to be more atraumatic.

Figure 36:
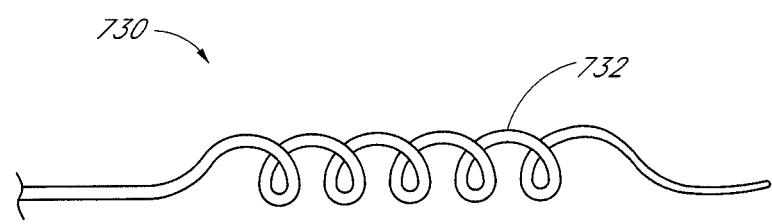
FIG. 36 is a side view of another embodiment of a guidewire, showing the guidewire in an expanded configuration.

FIG. 36 is a side view of another embodiment of a guidewire 730, showing the guidewire 730 in an expanded configuration. The guidewire 730 can have a coiled expansion portion 732 that can expand when deployed in the renal or other branch arteries. In some embodiments, the guidewire 730 can be formed from a tube of Nitinol that can be formed so as to define a coiled expansion portion, and heat set so that the coiled expansion portion 732 defines a diameter that is larger than the desired vessel diameter. The force from the coiled expansion portion 732 expanding against the vessel wall can provide a frictional force that inhibits the guidewire from being inadvertently removed from the target branch vessel. In some embodiments, the coiled expansion portion 732 can have two or more, or four or more coils.

In some embodiments, the guidewire 730 can be advanced through a tubular guidewire sheath that terminates in the desired branch vessel location. As the coiled expansion portion 732 exits the distal end of the tubular guidewire sheath, the coiled expansion portion 732 can self-expand against the walls of the target vessel so as to bias the guidewire 730 in the desired location. Alternatively, a two-way guidewire (i.e., one having sufficient compressive and tensile strength) can be advanced through the guidewire 730 so as to elongate and, hence, radially collapse the coiled expansion portion 732.

Figure 37:
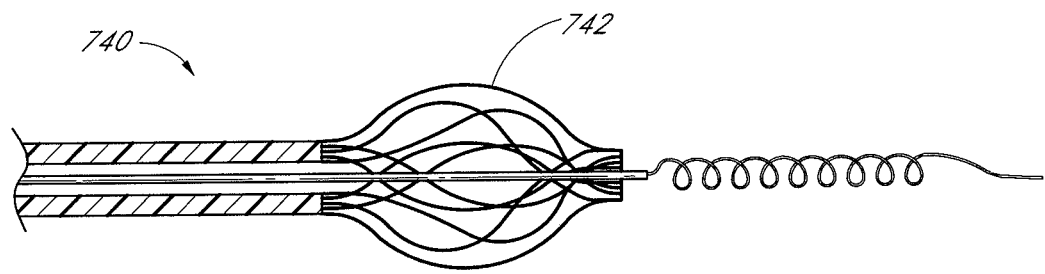
FIG. 37 is a section view of another embodiment of a guidewire, showing the guidewire in an expanded configuration.

FIG. 37 is a section view of another embodiment of a guidewire 740, showing the guidewire 740 in an expanded configuration. The guidewire 740 can have a braided or wire expansion portion 742 that can expand when deployed in the renal or other branch arteries. In some embodiments, the guidewire 740 can be formed from a tube of Nitinol that can be formed so as to define a coiled expansion portion, and heat set so that the braided or wire expansion portion 742 defines a diameter that is larger than the desired vessel diameter. The expansion portion 742 can be formed from between approximately five and ten or more wires each having a diameter between approximately 0.003 in or less and approximately 0.005 in or more. In some embodiments, the expansion portion 742 can be formed from between approximately three and twelve or more wires. The force from the expansion portion 742 expanding against the vessel wall can provide a frictional force that inhibits the guidewire from being inadvertently removed from the target branch vessel.

In some embodiments, the guidewire 740 can be advanced through a tubular guidewire sheath that terminates in the desired branch vessel location. As the expansion portion 742 exits the distal end of the tubular guidewire sheath, the expansion portion 742 can self-expand against the walls of the target vessel so as to bias the guidewire 740 in the desired location. Alternatively, a two-way guidewire (i.e., one having sufficient compressive and tensile strength) can be advanced through the guidewire 740 so as to elongate and, hence, radially collapse the expansion portion 742.

Figure 38:
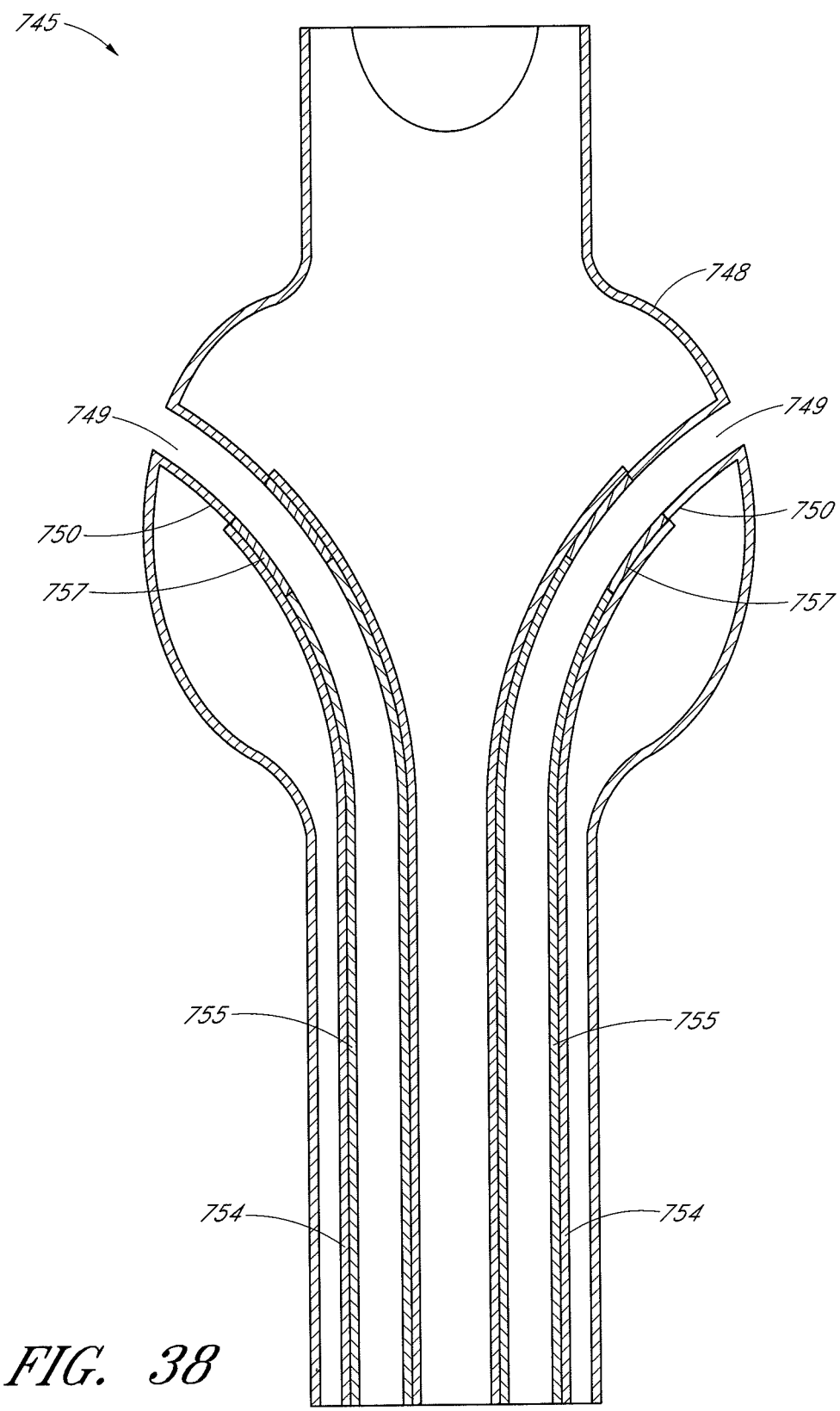
FIG. 38 is a side view of another embodiment of an endoluminal prosthesis, showing the branch grafts in an inverted position inside the main body of the prosthesis.
Figure 39:
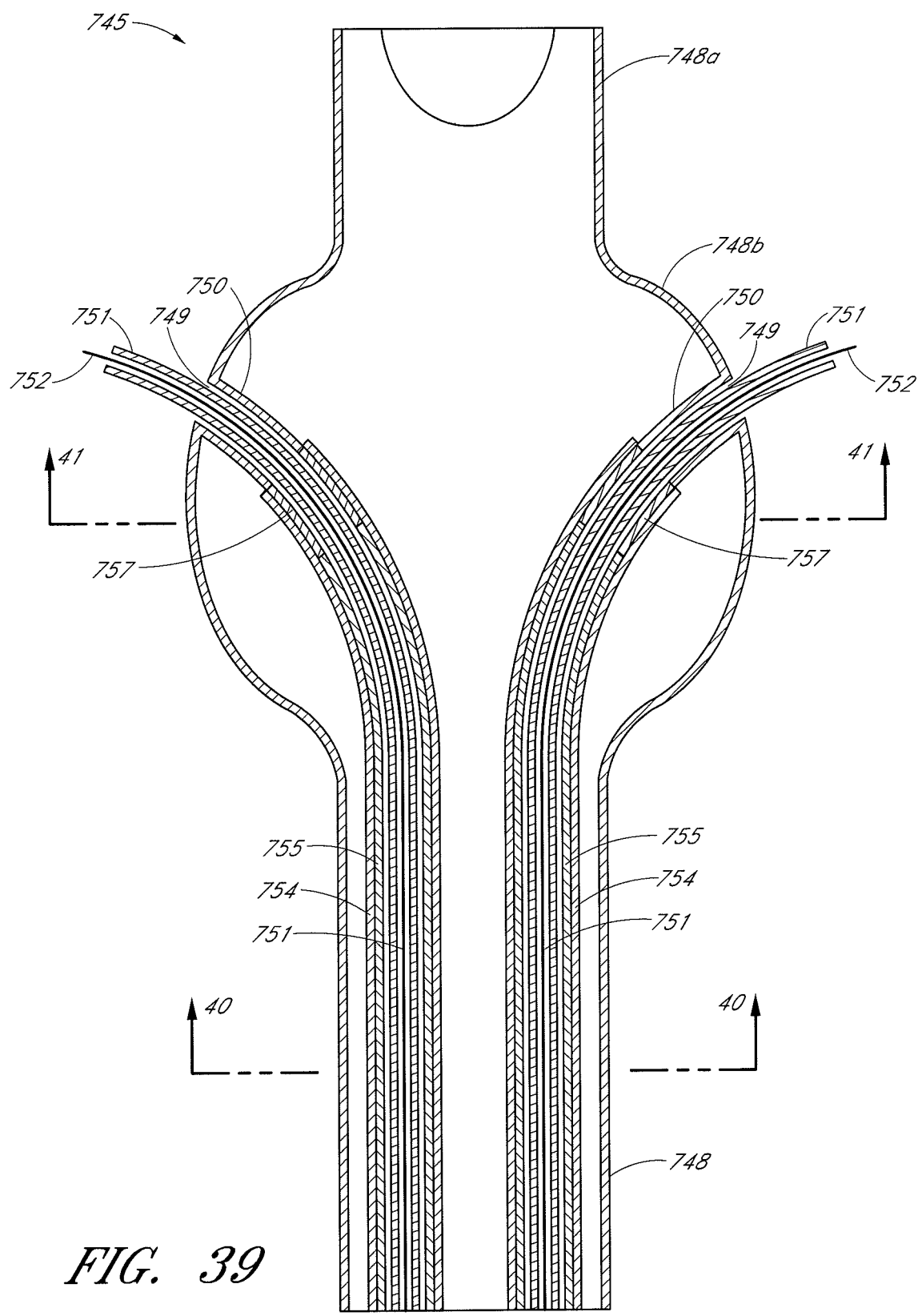
FIG. 39 is a side view of the embodiment of the prosthesis shown in FIG. 38, showing the branch grafts in an inverted position inside the prosthesis and showing an embodiment of an angiographic catheter being advanced through each of the inverted branch grafts and the fenestrations.

FIG. 38 is a side view of another embodiment of an endoluminal prosthesis 745, showing the branch grafts 750 in an inverted position inside the main body 748 of the prosthesis 745. FIG. 39 is a side view of the embodiment of the prosthesis 745 shown in FIG. 38, showing the branch grafts 750 in an inverted position inside the main body 748 of the prosthesis 745 and showing an embodiment of an angiographic catheter 751 being advanced through each of the inverted branch grafts 750 and the fenestrations 749. Some embodiments of the angiographic catheter 751 can be configured such that an end portion thereof is biased to have a curved disposition. In some embodiments, this can be accomplished by shortening the length of the wall of one side of the end portion of the angiographic catheter 751 as compared to the length of the wall of the other side of the angiographic catheter 751.

Some embodiments of the endoluminal prosthesis 745 can have a main graft body 748 having fenestrations or openings 749 therein and branch grafts 750 supported by the main graft body 748. Though not required, an additional fenestration can be formed in a first portion 748a of the main graft body 748 to accommodate blood flow to the SMA or otherwise. Alternatively, a branch graft (not illustrated) can be supported by the main graft body 748 to accommodate the blood flow to the SMA.

The endoluminal prosthesis 745 illustrated in FIG. 38 can have any of the same features, components, or other details as compared to any of the embodiments of the endoluminal prostheses disclosed (directly or by incorporation by reference) herein, including without limitation the embodiment of the endoluminal prosthesis 100 illustrated in FIG. 10 and described above. As with the endoluminal prosthesis 100 illustrated in FIG. 10 above, to accommodate positional adjustability of the branch grafts 750, the branch grafts 750 can be supported by the second or enlarged portion 748b of the main graft body 748.

In some embodiments, the branch grafts 750 can be integrally formed with the main graft body 748. Alternatively, the branch graft portions 750 can be formed separately and later attached, adhered, sutured, or otherwise fastened or supported by the main graft body 748. Additionally, in some embodiments, before the endoluminal prostheses 745 is loaded into a delivery catheter, angiographic catheters 751 or hollow guidewires can be advanced through the branch grafts 750 and fenestrations 749. As is illustrated, in some embodiments, the angiographic catheters 751 can define a lumen therethrough so that they can be passed or advanced over guidewires 752 that are pre-wired in the patient's vasculature to guide the endoluminal prostheses 745 to the target location. Advancing the angiographic catheters 751 over the pre-wired guidewires 752 can also facilitate the alignment of each of the branch grafts 750 with each of the branch vessels in the patient's vasculature.

As illustrated, in some embodiments, the branch grafts 750 can be inverted and positioned within the main body 748 of the prosthesis 745 during the initial steps of deployment of the prosthesis 745. In some embodiments of this configuration, the prosthesis 745 may be easier to advance to and deploy at the target vessel location when the branch grafts 750 are inverted and positioned within the main body 748 of the prosthesis 745. Additionally, in some embodiments, the prosthesis may be configured such that the branch grafts 750 can be advanced through the fenestrations 749 in the main body 748 of the prosthesis 745 and into the desired branch vessels after the main body 748 of the prosthesis 745 has been positioned in the target vessel location.

In some embodiments, one or more stents 757 can be deployed or expanded within the branch grafts 750 after the branch grafts have been advanced into the branch vessels. The stents 757, or any other stents disclosed (directly or by incorporation by reference) herein, can be balloon expandable, self-expandable, flared, flareable, or be of any other suitable configuration or material, and can be carried or supported within a guidewire catheter sheath 754. With reference to the figures, the prosthesis 745 can be configured such that the stents 757 are affixed to an end portion of the branch grafts 750 such that the branch grafts 750 can be inverted and advanced through the fenestrations 749 formed in the main graft body 748 and into the branch vessels by advancing the stents 757 distally through the guidewire catheter sheath 754. In some embodiments, the stents 757 can be advanced distally through the guidewire catheter sheath 754 by advancing a pusher catheter 755 that is radially supported but axially unrestrained within the guidewire catheter sheath 754.

Figure 40:
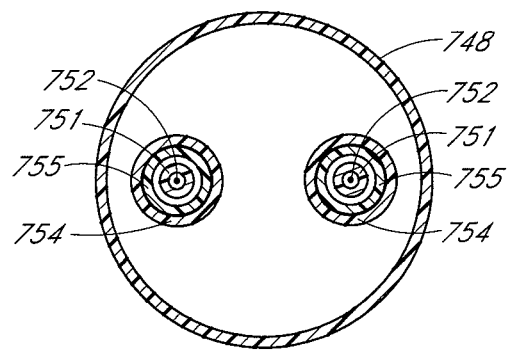
FIG. 40 is a section view of the embodiment of the prosthesis shown in FIG. 40, taken through line 40-40 in FIG. 39.

FIG. 40 is a section view of the embodiment of the prosthesis 745 shown in FIG. 38, taken through line 40-40 in FIG. 39. With reference to FIG. 40, the angiographic catheters 751 can be configured to be axially advanceable over the guidewires 752. Further, a pusher catheter 755 can be housed within each guidewire catheter sheath 754 so as to be axially advanceable over each angiographic catheter 751 and within the guidewire catheter sheath 754.

Figure 41:
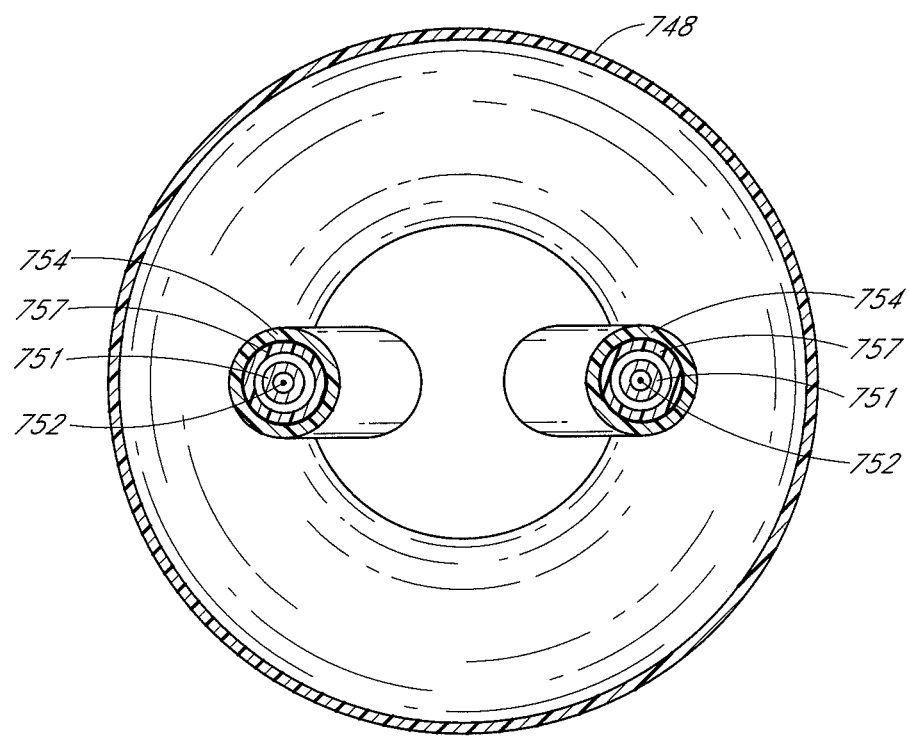
FIG. 41 is a section view of the embodiment of the prosthesis shown in FIG. 40, taken through line 41-41 in FIG. 39.
Figure 42:
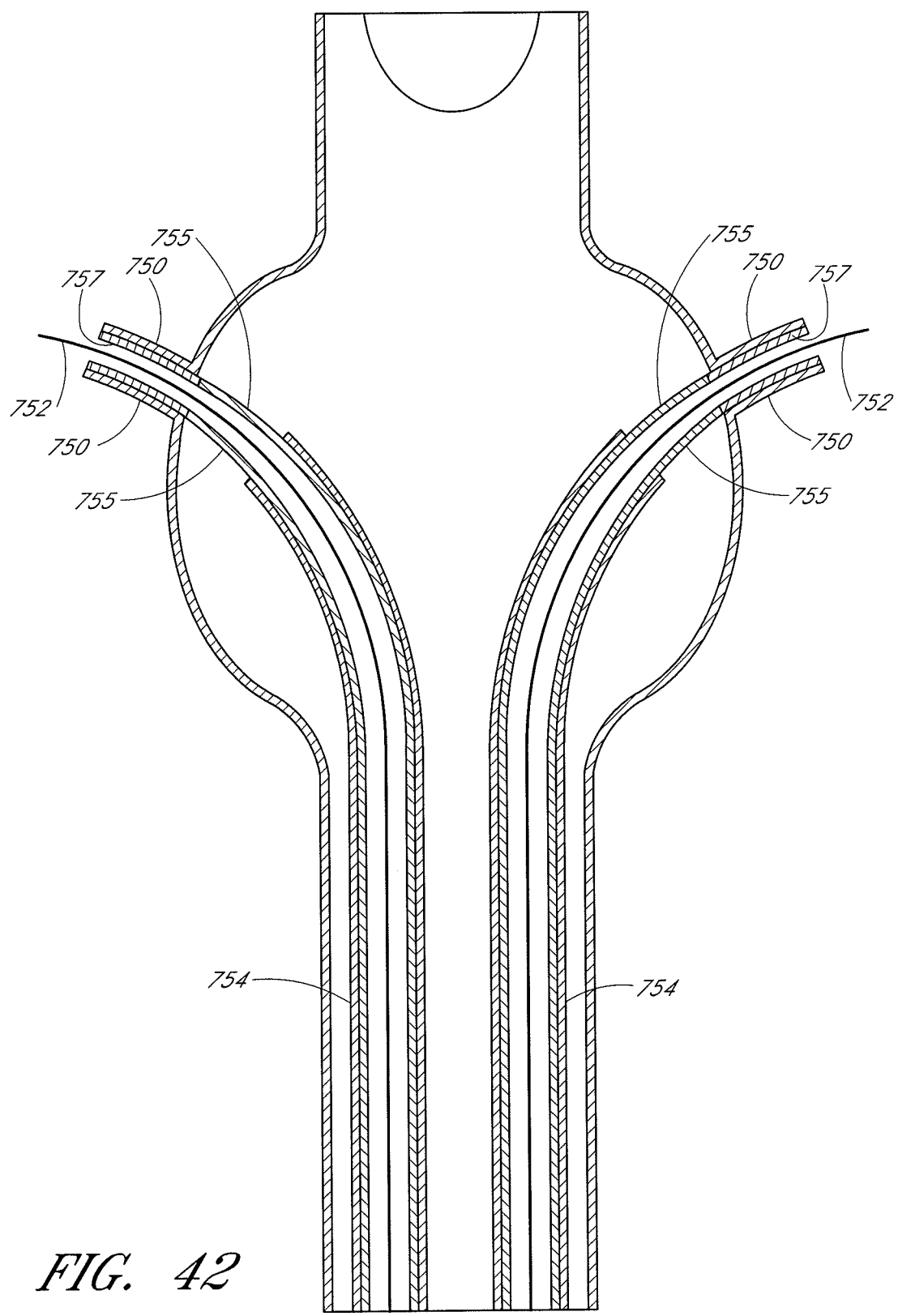
FIG. 42 is a section view of the embodiment of the prosthesis shown in FIG. 40, after the branch grafts have been advanced through the fenestrations in the main body of the embodiment of the prosthesis shown in FIG. 38.

FIG. 41 is a section view of the embodiment of the prosthesis 745 shown in FIG. 40, taken through line 41-41 in FIG. 39. With reference to FIG. 41, the angiographic catheter 751 can be configured to be axially advanceable over a guidewire 752. Further, the stents 757 can be housed within the guidewire catheter sheath 754 so as to be axially advanceable over the angiographic catheter 751 and within the guidewire catheter sheath 754. FIG. 42 is a section view of the embodiment of the prosthesis 745 shown in FIG. 38, after the branch grafts 750 have been advanced through the fenestrations 749 in the main body 748 of the embodiment of the prosthesis 745 shown in FIG. 38.

In some embodiments, the angiographic catheters 751 can be made from a plastic extrusion or metal braids. For example, in some embodiments, the hollow angiographic catheters 751 can be made from braided Nitinol wire. In some embodiments, the outer diameter of the angiographic catheters 751 can be approximately 0.035 in and the lumen of the guidewire can be approximately 0.016 in to accommodate a second 0.014 in guidewire. In some embodiments, the angiographic catheters 751 can be configured to pass over a 0.018 in or any other suitable guidewire. In some embodiments, the outer diameter of the angiographic catheters 751 can be approximately 5 Fr and the lumen of the guidewire can be approximately 0.040 in to accommodate a second 0.035 or 0.038 in guidewire. In some embodiments, the angiographic catheters 751 can be configured to pass over a 0.018 in or any other suitable guidewire. In some embodiments, the angiographic catheters 751 can be configured to support balloons on the distal ends of the angiographic catheters 751. The balloons can be inflated in the branch vessel to deploy expandable stents such as stents 757 within the branch grafts 750.

In some embodiments, each of the stents 757 can be a bare metal stent or a covered stent (i.e., covered with a tubular shaped graft material). Additionally, in some embodiments, the stents 757 can be self expanding or can be balloon expandable. Although not required, each branch graft 750 can be fixed at an end portion thereof to an end portion of each stent 757. In some embodiments, each of the stents 757 can be supported by or positioned over an expansion balloon positioned within each of the guidewire catheter sheaths 754. The balloons can be slideable within the guidewire catheter sheaths 754 so that the balloons can be advanced distally simultaneously with the stents 757. In some embodiments, the balloons can be slideable over the angiographic catheters 751 so that the balloons can be advanced over the angiographic catheters 751 as the stents 757 are advanced over the angiographic catheters 751. The balloons can be expanded to deploy the stents 757 once the stents 757 are positioned in the target location within the branch vessels.

Alternatively, in some embodiments, the angiographic catheters 751 can be retracted after the stents 757 are positioned in the target location within the branch vessels. Thereafter, one or more balloons supported by a guidewire catheter, balloon catheter, or other suitable catheter can be advanced over the guidewires 752 and into the branch vessels to expand or otherwise deploy the stents 757.

Accordingly, in some embodiments, the angiographic catheters 751 can be configured to allow for the inflation and expansion of expansion balloons so as to expand or deploy the branch stents 757. For example, the angiographic catheters 751 can have a first lumen that can be advanced over a pre-wired guidewire and a second inflation lumen configured to communicate a positive pressure to the expansion balloon or balloons.

In some embodiments, the endoluminal prostheses 745 can be loaded into a delivery catheter so that each of the angiographic catheters 751 protrudes out from the inside of the guidewire catheter sheath 754 so that each of the angiographic catheters 751 can be advanced over the pre-wired guidewires 752 positioned within the patient's vasculature. Thus, during deployment, in some embodiments, each of the stents 757 can be expanded and, hence, deployed within each of the branch grafts 750 after each of the branch grafts 750 has been advanced into the respective branch vessels. In some embodiments, each of the stents 757 can be expanded and, hence, deployed within each of the branch grafts 750 before the main graft body 748 has been secured in the main target vessel.

However, as mentioned, the pre-positioning of the stents 757 and/or the balloons in the endoluminal prostheses 745 described above is not required. In some embodiments, one or more stents can be advanced through the patient's vasculature and into the branch grafts 750 after the endoluminal prostheses 745 has been positioned within the target vessel in the patient's vasculature. For example, one or more stents can be advanced through the patient's vasculature into the branch grafts 750 after the branch grafts 750 have been inverted and advanced into the target branch vessels and after the main graft body 748 has been secured within the main target vessel.

In some embodiments, the hollow angiographic catheters 751 can pass through a distal end opening of an outer sheath of a deployment catheter, just as with the delivery catheter 330 described above. As mentioned, each of the hollow angiographic catheters 751 can be configured to receive or allow the insertion of a 0.014 in guidewire, a 0.018 in guidewire, a 0.035 in guidewire, or any diameter guidewire therethrough deemed suitable for the design. In some embodiments, the outer diameter of the angiographic catheters 751 can be approximately 5 Fr and the lumen of the guidewire can be approximately 0.040 in to accommodate a second 0.035 or 0.038 in guidewire. In some embodiments, the angiographic catheters 751 can be configured to pass over a 0.018 in or any other suitable guidewire. In this configuration, the hollow angiographic catheters 751 can pass over guidewires 752 that can be pre-wired in the target vessels so that the deployment catheter housing the prosthesis 745 can be advanced along the guidewires 752 pre-wired in the patient's vasculature, similar to any of the other embodiments of the deployment catheters disclosed or incorporated by reference herein or any other suitable catheter configurations known in the field.

In some embodiments, once the endoluminal prosthesis 745 has been advanced to the target location along the guidewires 752 within the patient's vasculature, the guidewire catheter sheaths 755 and the pusher catheters 755 can be advanced through each of the fenestrations 749 in the main body 748 of the prosthesis 745. Advancing the guidewire catheter sheaths 755 and the pusher catheters 755 through each of the fenestrations 749 in the main body 748 of the prosthesis 745 can cause each branch graft 750 to be advanced through the fenestrations 749 and to invert and slide over an end portion of each guidewire catheter sheath 755 and slide around an outside surface of each guidewire catheter sheath 755, so that each branch graft 750 can extend in the appropriate orientation in each of the branch vessels.

In this arrangement, an end portion of the guidewire catheter sheath 755 can be positioned within the branch graft 750 after the branch graft 750 has been advanced into the branch vessel as described above. Thereafter, in some embodiments, the pusher catheter 755 can be used to hold the stent 757 in the target location while the guidewire catheter sheath 755 is retracted. If the stent 757 is self-expandable, retracting the guidewire catheter sheath 755 will permit the stent 757 to self-expand radially outwardly, thereby securing the branch graft 750 in the target location. If the stent 757 is not self-expandable, the angiographic catheter 751, a balloon catheter, or other suitable instrument can be used to expand and deploy the stent 757 in the target location. Each of the branch grafts 750 can be deployed sequentially or simultaneously in this arrangement. A stent or other suitable device can be deployed within the main graft body 748 to secure the main graft body 748 within the main vessel.

As mentioned, although not required, each branch graft 750 can be fixed at an end portion thereof to an end portion of each stent 757. In some embodiments, an end portion of the branch graft 750 can be affixed to at least a proximal end portion of the respective stent 757 so that the branch graft 250 can substantially completely cover an inside and an outside surface of the stent 757 after the branch graft 750 has been inverted and advanced into the branch vessel.

Additionally, in some embodiments, one or more of the pre-wired guidewires 752 described above can be configured to be insertable into a branch vessel and to be biased such that an end portion of the guidewires 752 remains in the branch vessel, such as with any of the guidewires. In particular, one or more of the guidewires 752 can be configured to have the same features as, without limitation, any of guidewires 700, 720, 730, or 740 disclosed herein.

Figure 43A:
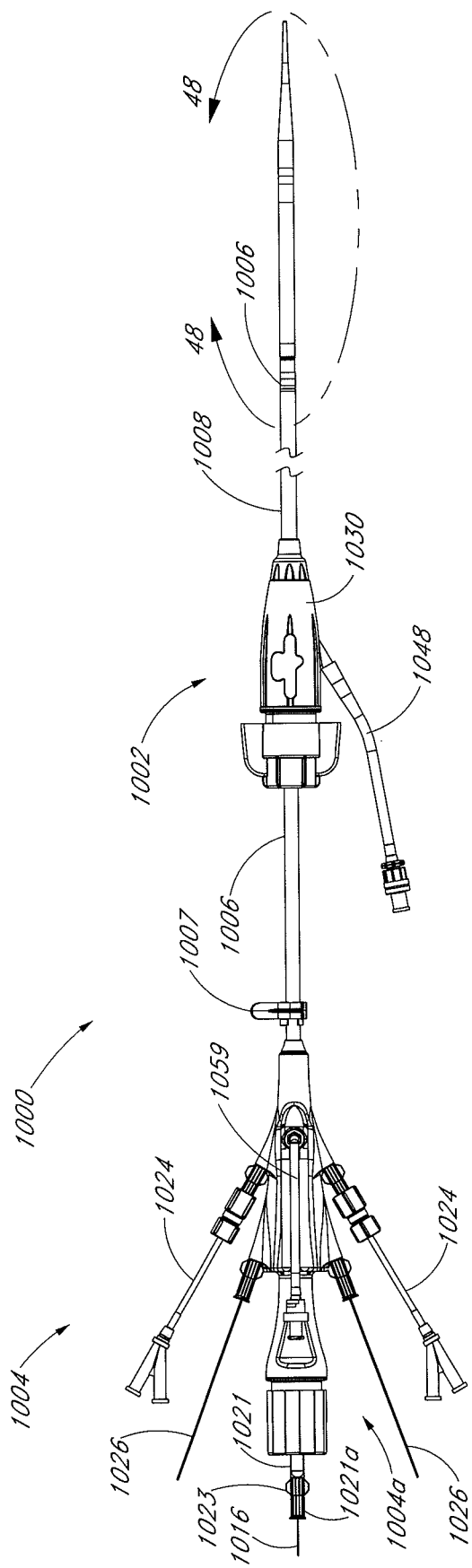
FIG. 43A is a side view of another embodiment of a catheter system comprising an embodiment of an introducer catheter and an embodiment of a delivery catheter.

FIG. 43A is a side view of another embodiment of a catheter system 1000 comprising an embodiment of an introducer catheter 1002 (also referred to as an introducer) and an embodiment of a delivery catheter 1004. The delivery catheter 1004 can be configured for the delivery of an endoluminal prosthesis, including without limitation any endoluminal prosthesis embodiment disclosed herein or any other suitable prosthesis, or for any other suitable use. Therefore, the embodiments of the catheters and introducers disclosed herein can be configured for any suitable purpose, including deployment of a stent graft system as described herein.

Figure 43B:
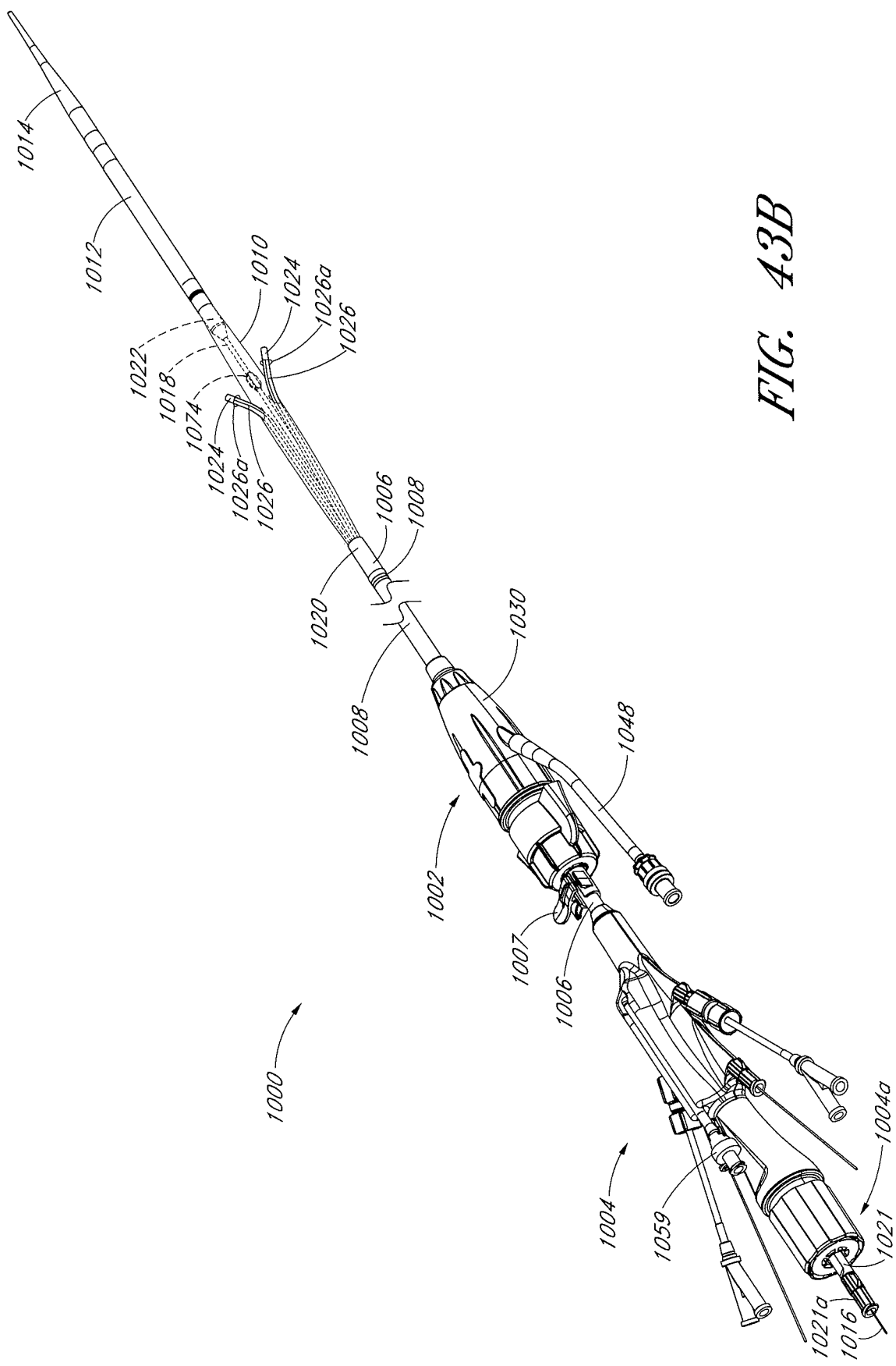
FIG. 43B is a perspective view of the embodiment of a catheter system illustrated in FIG. 43A, showing the outer sheath in a partially retracted position.

FIG. 43B is a perspective view of the embodiment of a catheter system 1000 illustrated in FIG. 43A, showing an outer sheath 1006 of the delivery catheter 1004 in a partially retracted position. With reference to FIGS. 43A and 43B, some embodiments of the outer sheath 1006 can be used to constrain at least a portion of a prosthesis 1010. In some embodiments, the prosthesis 1010 can have any of the same features, components, or other details of any of the other prosthesis embodiments disclosed herein, including without limitation the embodiments of the prosthesis 1200 described below. The prosthesis 1010 can have any number of stents or other support members, connectors, grafts, cuts, fenestrations, or other suitable components or features. As used herein, when referring to the prosthesis 1010, distal refers to the end of the prosthesis that is further from the patient's heart, and proximal refers to the end of the prosthesis that is closer to the patient's heart. As used herein with regard to the embodiments of the catheter system 1000, the term distal refers to the end of the catheter system that is further from the surgeon or medical practitioner using the catheter system, and the term proximal refers to the end of the catheter system that is closer to the surgeon or medical practitioner.

In some embodiments, as illustrated in FIG. 43, a distal sheath 1012 (also referred to herein as a first restraint or first restraining means) can be used to constrain a proximal portion of the stent graft 1010. The distal sheath 1012 can be supported by a distal tip 1014 of the catheter system 1000. In some embodiments, the distal tip 1014 can comprise an atraumatic material and design. As will be described in greater detail below, the distal tip 1014 and, hence, the distal sheath 1012 can be attached to an inner tube 1016 to control the position of the distal tip 1014 and the distal sheath 1012 relative to an inner core 1020 of the delivery catheter 1004. The inner core 1020 can be rotatable relative to the outer sheath 1006 so that a prosthesis supported by the delivery catheter 1004 can be rotated during deployment. The inner tube 1016 can be slidably positioned coaxially within a lumen in an outer tube 1018 that can connect a support member 1022 to the inner core 1020. In some embodiments, the outer tube 1018 can be connected to an opening or partial lumen 1019 in the inner core 1020 so as to be axially and rotationally fixed to the inner core 1020.

In this configuration, the catheter system 1000 can be configured such that advancing the inner tube 1016 relative to an inner core 1020 of the delivery catheter 1004 can cause the distal sheath 1012 to be advanced relative to the prosthesis 1010, causing the proximal portion of the prosthesis 1010 to be deployed. The prosthesis 1010 (or any other prosthesis disclosed herein) can be at least partially self-expanding such that, as the tubular distal sheath 1012 is advanced relative to the prosthesis 1010, a proximal portion of the prosthesis 1010 expands against a vessel wall. In some embodiments, only some segments or portions of the prosthesis 1010 such as, without limitation, portions of the prosthesis axially adjacent to englarged graft portions of the prosthesis, can be configured to be self-expanding.

The inner core 1020 can be slideably received within the outer sheath 1006 of the delivery catheter 1004. In some embodiments, as in the illustrated embodiment, the outer sheath 1006 of the delivery catheter 1004 can be longer than an introducer sheath 1008 of the introducer catheter 1002. Further, a clip 1007 can be supported by the outer sheath 1006 to limit the range of axial movement of the outer sheath 1006 relative to the introducer catheter 1002.

In some embodiments, although not required, a core assembly 1021 can be connected to a proximal end portion of the inner core 1020, the core assembly 1021 having a reduced cross-sectional profile so as to permit one or more sheath members, push catheters, or other tubular or other components to pass through the main body of the delivery catheter 1004 and be advanced into one or more lumen within the inner core 1020. In some embodiments, the inner core 1020 can be configured to accommodate the insertion of such sheath members, push catheters, or other tubular components into the lumen of the inner core 1020.

In the illustrated embodiment, a proximal end portion of the core assembly 1021 can comprise a handle member 1023 that is positioned outside a proximal end portion of the delivery catheter 1004 so as to be accessible by a user. The handle member 1023 can be configured to permit a user to axially or rotationally adjust the position of the inner core 1020 relative to the outer sheath 1006.

As discussed above, the inner core 1020, or components axially connected to the inner core 1020 such as the core assembly 1021, can extend proximally past the proximal end portion 1004a of the delivery catheter system 1004 so that a user can adjust and/or change the axial and/or radial position of the inner core 1020 and, hence, the prosthesis 1010, relative to the outer sheath 1006. Similarly, the inner tube 1016 can extend proximally past the proximal end portion 1004a of the delivery catheter 1004 and a proximal end portion 1021a of the core assembly 1021 so that a user can adjust and change the position of the inner tube 1016 relative to the inner core 1020.

In the partially retracted position of the outer sheath 1006 illustrated in FIG. 43B, at least a portion of the prosthesis 1010 supported by the catheter system 1000 can be exposed and, potentially, deployed. In some embodiments, a distal portion of the prosthesis 1010 can be exposed and deployed by retracting the outer sheath 1006 relative to the inner core 1020 or distally advancing the inner core 1020 relative to the outer sheath 1006, causing at least a portion of the distal portion of the prosthesis 1010 to self-expand. As will be described, some embodiments of the prosthesis 1010 can be configured to have radially self-expanding support members therein along only a portion or portions of the prosthesis 1010. For example, without limitation, some embodiments of a graft of the prosthesis 1010 can be radially unsupported at or adjacent to fenestrations formed in the graft. Alternatively, in some embodiments, at least the distal portion of the prosthesis 1010 can be constrained within a sheath, such as a peelable sheath. Embodiments of the sheath will be described in greater detail below.

The delivery catheter 1004 can also have one or more branch or guide sheaths 1024 supported thereby. In some embodiments, the delivery catheter 1004 can have three or more branch sheaths 1024. Such a configuration can be used for deploying branch stents into one or more branch vessels in the thoracic aorta. Each of the one or more branch sheaths 1024 can be configured to be slideably supported within one or more lumen 1025 formed in the inner core 1020 so that each of the one or more branch sheaths 1024 can be axially advanced or retracted relative to the inner core 1020. Further, some embodiments of the delivery catheter 1004 can be configured such that the branch sheaths 1024 can be rotationally adjusted or twisted relative to the inner core 1020. In some embodiments, each branch sheath 1024 can be positioned within the delivery catheter 1004 such that, in the loaded configuration wherein a prosthesis 1010 is supported within the delivery catheter 1004, each branch sheath 1024 is pre-positioned so as to be advanced through a fenestration or branch graft of the prosthesis 1010. Each branch sheath 1024 can be positioned within the delivery catheter 1004 such that a distal end portion of each branch sheath 1024 projects past an end portion of the inner core 1020 and is constrained within the outer sheath 1006. As illustrated in FIGS. 43A-43B, in this configuration, the distal end portion of each branch sheath 1024 can be exposed by retracting the outer sheath 1006 relative to the inner core 1020 and/or the branch sheaths 1024.

Additionally, with reference to FIG. 43B, in some embodiments, although not required, the delivery catheter 1004 can have one or more push catheters 1026 supported thereby. In some embodiments, the one or more push catheters 1026 can be slideably received within one or more lumen 1027 formed in the inner core 1020. In some embodiments, the one or more push catheters 1026 can each have an end portion 1026a that can be sized and configured to surround an outer surface of each of the branch sheaths 1024. The end portion 1026a of each push catheter 1026 can have, without limitation, an open or closed annular or circular shape and can be of sufficient size and stiffness to permit a user to engage a fenestration or branch graft formed in or supported by a main body of the prosthesis 1010. For example, as will be described in greater detail below, after the main body of the prosthesis 1010 has been released from the outer sheath 1006 and any other radial restraints, a user can independently or collectively axially advance the push catheter 1026 over the branch sheaths 1024 such that the end portion 1026a of each push catheter 1026 engages the fenestration or branch graft of the prosthesis 1010 and pushes the fenestration or branch graft toward an ostium of the target branch vessel of the patient's vasculature.

Accordingly, in this configuration, at least a portion of each of the one or more push catheters 1026 can be configured to be slideably supported within a lumen formed in the inner core 1020 so that each of the one or more push catheters 1026 can be axially advanced relative to the inner core 1020. Further, some embodiments of the delivery catheter 1004 can be configured such that the push catheters 1026 can be axially or rotationally adjusted or twisted relative to the inner core 1020, for increased maneuverability of the push catheters 1026.

In some embodiments, each push catheter 1026 can be positioned within the delivery catheter 1004 such that, in the loaded configuration wherein a prosthesis 1010 is supported within the delivery catheter 1004, each push catheter 1026 is pre-positioned so that the end portion 1026a of each push catheter 1026 is positioned distal to the end portion of the inner core 1020. In some embodiments, in the loaded configuration, each push catheter 1026 can be positioned such that the end portion 1026a of each push catheter 1026 is located within the main lumen of the main body of the prosthesis 1010. As mentioned, in some embodiments, one or more of the branch sheaths 1024 can have a loop, protrusion, snare, or other similar feature supported thereby, or otherwise be configured to enable the sheath 1024 to engage a fenestration or branch graft to advance the fenestration or branch graft toward the ostium of the target branch vessel by advancing the branch sheath 1024.

The branch sheaths 1024 and push catheters 1026 can have any suitable size and can be made from any suitable material. For example, without limitation, the branch sheaths 1024 can have an approximately 6.5 French diameter, or from an approximately 5 Fr diameter or less to an approximately 8 Fr diameter or more, or to or from any values within this range. The push catheters 1026 can be formed from stainless steel, Nitinol, or any other suitable metallic or non-metallic material, and can have a thickness suitable to prevent the push catheters 1026 from buckling when axially advanced against a portion of the prosthesis 1010. For example, without limitation, the push catheters 1026 can have an approximately 1 Fr diameter, or between approximately a 1 Fr and approximately a 4 Fr diameter. Further, some embodiments of the push catheter or catheters can be formed from a 0.035 in guidewire or otherwise have a 0.035 in diameter.

Additionally, as will be described below in greater detail, the catheter system 1000 can be configured such that the distal sheath 1012 can be advanced relative to the inner core 1020 and the prosthesis 1010, to expose a proximal portion of the prosthesis 1010. In particular, in some embodiments, advancing the distal sheath 1012 can be accomplished by advancing the inner tube 1016 connected to the distal tip 1014 and the distal sheath 1012, so that the distal sheath 1012 releases the proximal portion of the prosthesis 1010. Other details regarding the distal sheath 1012 or methods of using the distal sheath can be found in U.S. Pat. No. 6,953,475, which application is incorporated by reference as if fully set forth herein.

Figure 44:
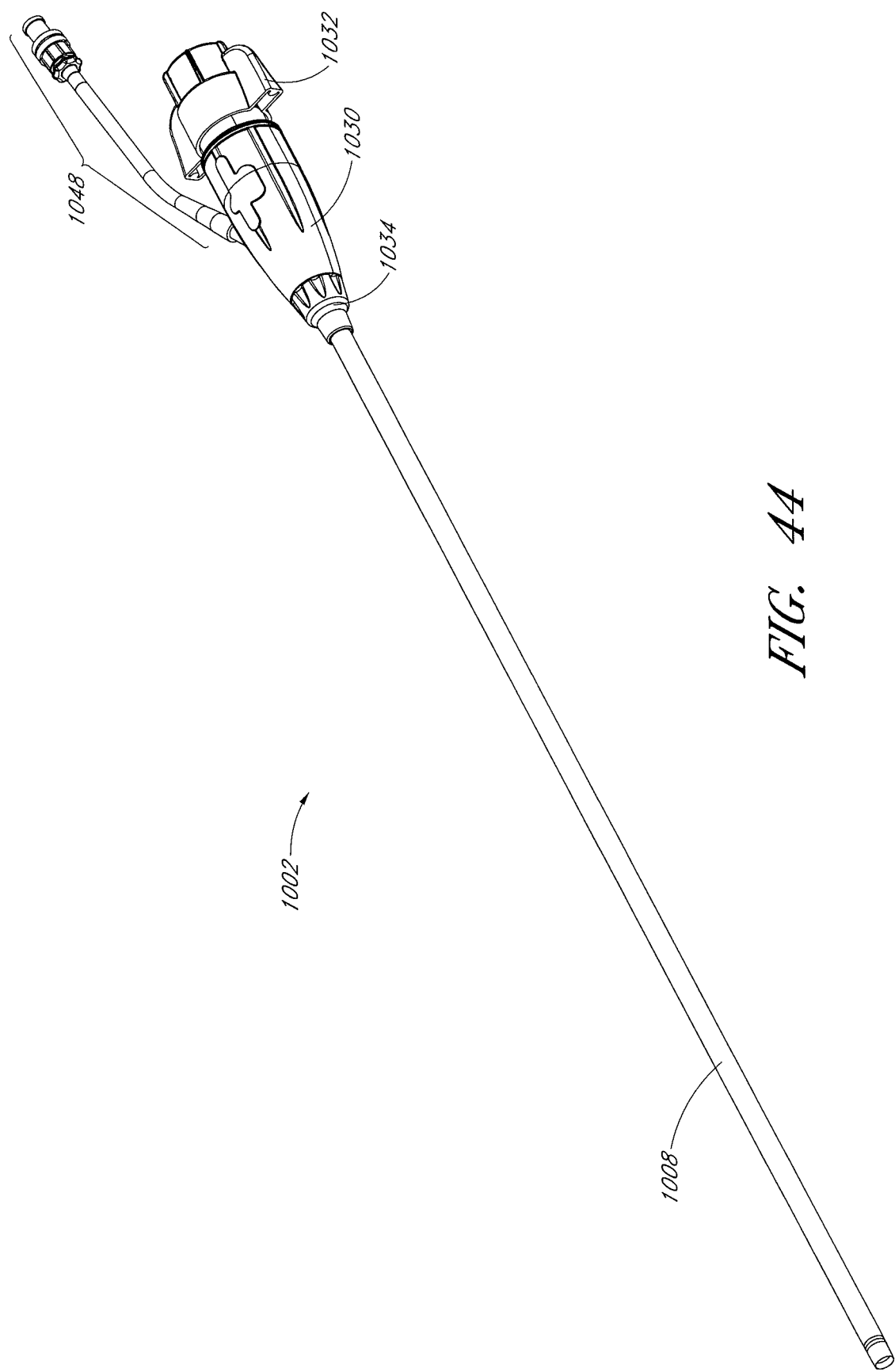
FIG. 44 is a perspective view of the embodiment of the introducer catheter shown in FIG. 43.
Figure 45:
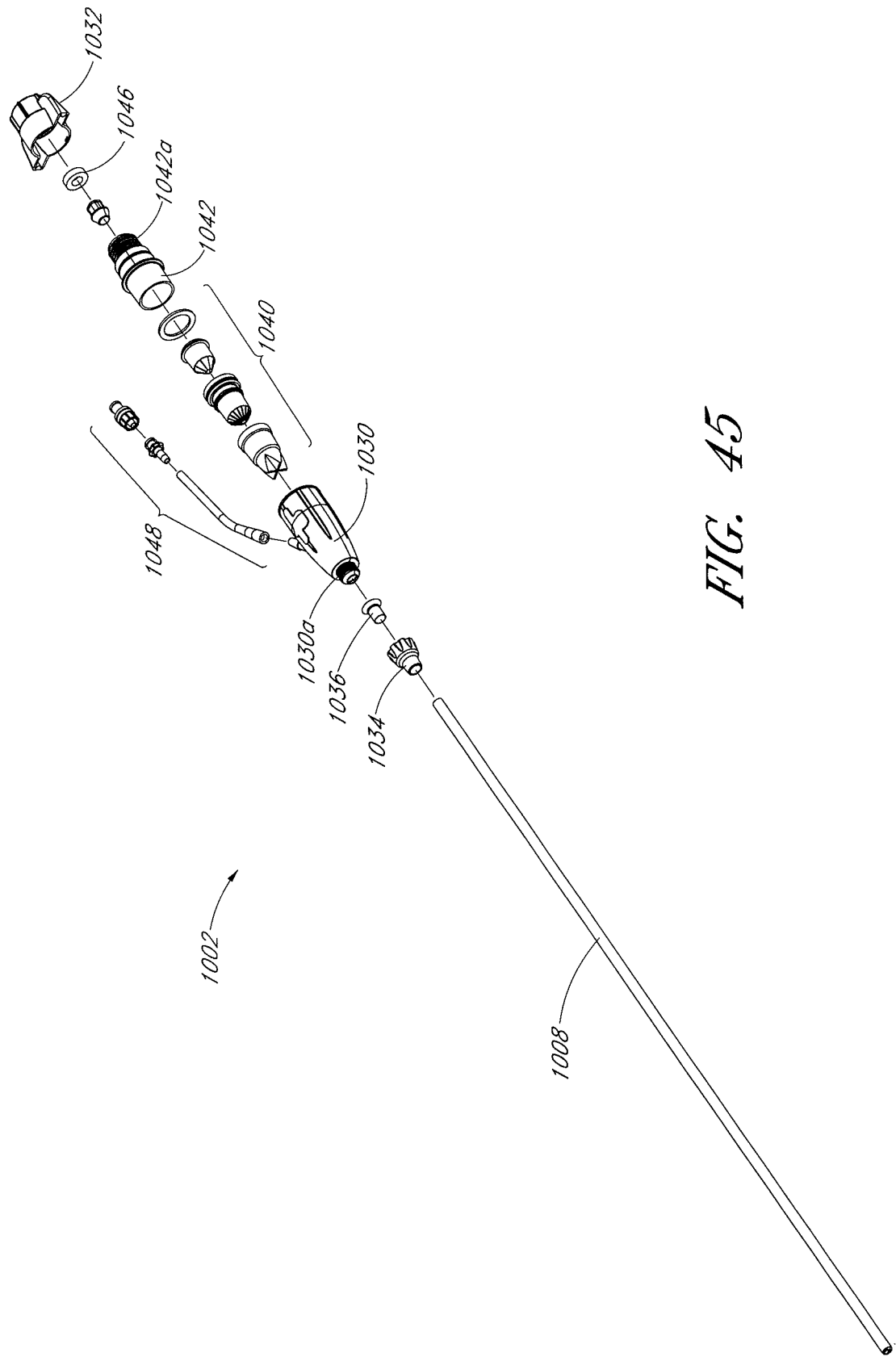
FIG. 45 is an exploded view of the embodiment of the introducer catheter shown in FIG. 43.

FIGS. 44 and 45 are a perspective view and an exploded view, respectively, of the embodiment of the introducer catheter 1002 shown in FIG. 43. In some embodiments, the introducer catheter 1002 can have any of the features or components of any of the embodiments disclosed in U.S. patent application Ser. No. 12/496,446, which disclosure is hereby incorporated by reference as if set forth herein. With reference to FIGS. 44-45, in some embodiments, the introducer 1002 can have a main body 1030, a threadably engageable hub portion 1032, a threaded cap 1034 configured to threadably engage with a threaded distal end portion 1030a of the main body 1030 so as to secure the outer sheath 1006 to the main body 1030. The outer sheath 1006 can have a flanged end portion 1036 secured thereto or integrally formed therewith. The main body 1030 can support a seal assembly 1040 therein to seal around the inner core 1020 of the delivery catheter 1004 and/or other components of the catheter system 1000. A threaded end member 1042 having a threaded proximal end portion 1042a can be supported by the main body 1030. An annular seal member 1046 can be supported by the main body 1030 of the introducer catheter 1002. The introducer catheter 1002 can be configured such that the seal member 1046 can be adjusted to provide an additional seal around the inner core 1020 of the delivery catheter 1004 by threadedly engaging the hub portion 1032. The seal assembly 1040 and seal member 1046 can have any of the details, features, or components of any of the embodiments of the introducer catheter described in U.S. patent application Ser. No. 12/496,446, which application is incorporated by reference as if fully set forth herein.

In some embodiments, a tube assembly 1048 can be supported by the main body 1030 of the introducer catheter 1002 so as to provide an orifice or access port into the main body 1030. The tube assembly 1048 can be used to flush the introducer catheter 1002 with saline or other suitable substances at any stage, such as but not limited to prior to the advancement of an endoluminal prosthesis through the introducer catheter 1002 and/or delivery catheter 1004, or prior to other procedures for which another type of delivery catheter may be used. The tube assembly 1048 can support any suitable medical connector and/or valve on the distal end thereof.

Figure 46:
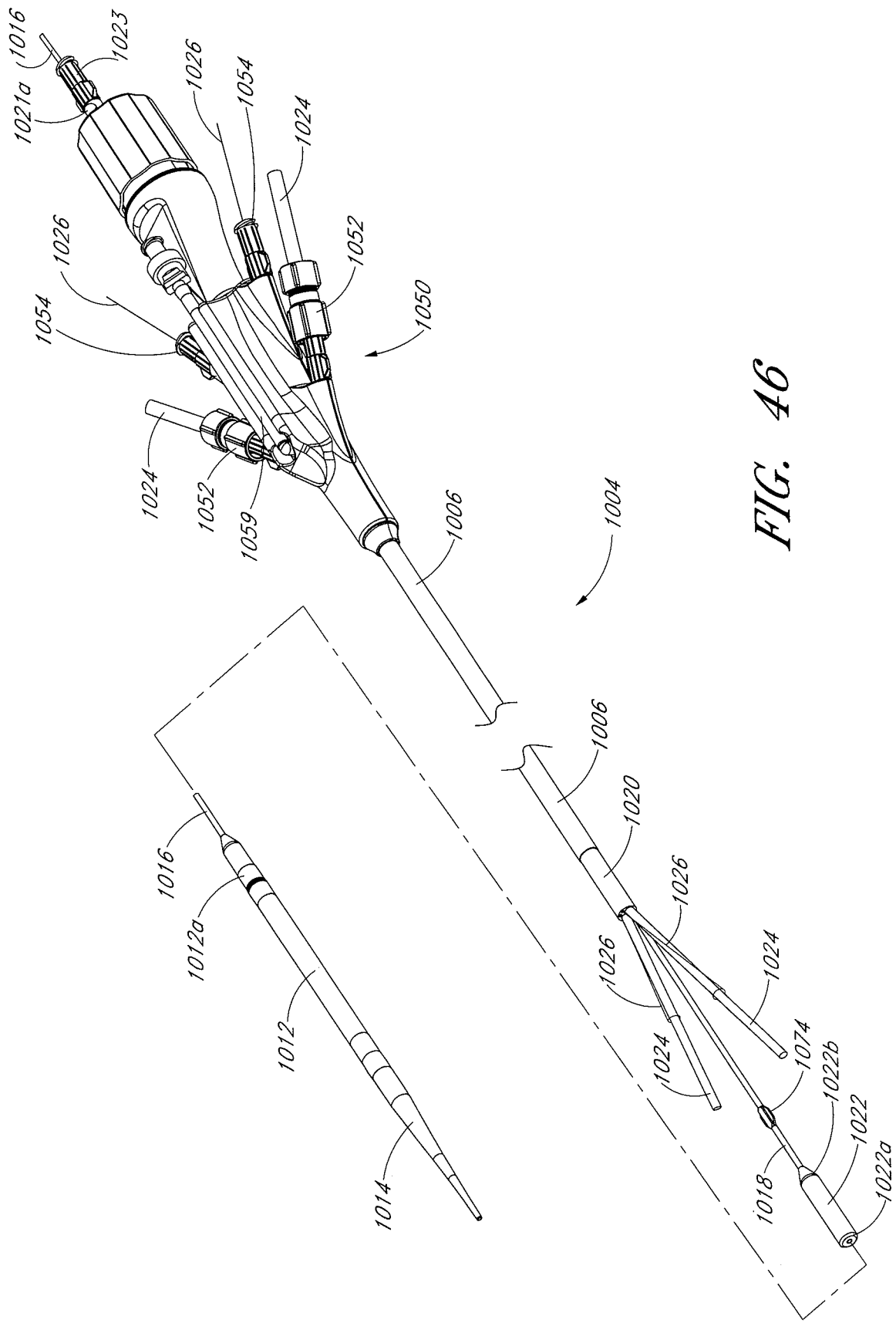
FIG. 46 is a perspective view of the embodiment of the delivery catheter shown in FIG. 43.
Figure 47:
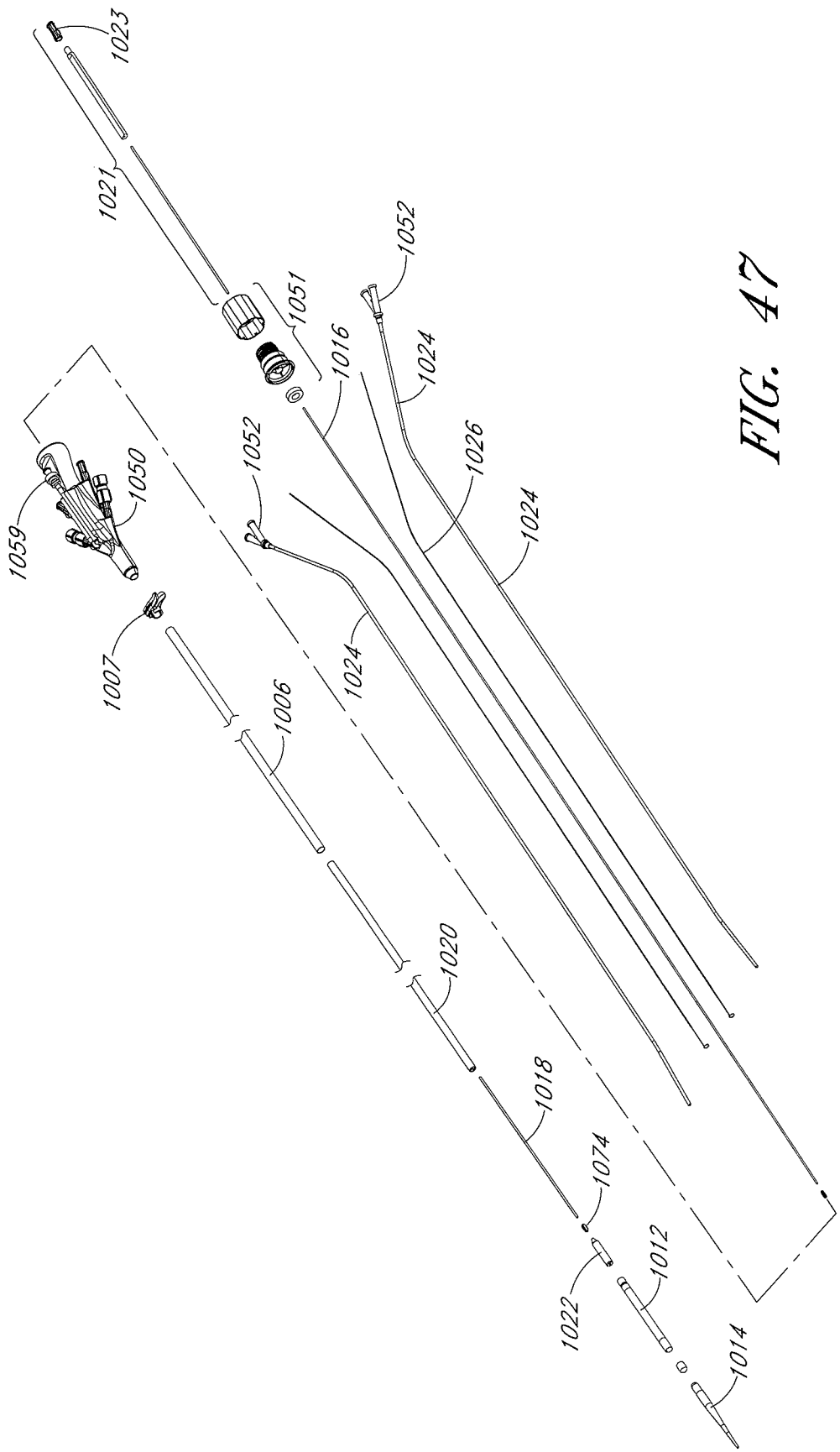
FIG. 47 is an exploded view of the embodiment of the delivery catheter shown in FIG. 43.

FIGS. 46 and 47 are a perspective view and an exploded view, respectively of the embodiment of the delivery catheter 1004 shown in FIG. 43. FIG. 48 is a section view of a portion of the embodiment of the delivery catheter 1004 shown in FIG. 43, defined by curve 48-48 shown in FIG. 43A. FIG. 49A is a section view of the embodiment of the delivery catheter 1004 shown in FIG. 43, defined by the line 49A-49A shown in FIG. 48. FIG. 49B is a section view of the embodiment of the delivery catheter 1004 shown in FIG. 43, defined by the line 49B-49B shown in FIG. 48.

As shown therein, some embodiments of the delivery catheter 1004 can have a main body 1050 that can support the inner core 1020 and/or core assembly 1021, one or more access ports 1052 for the one or more branch sheaths 1024, and one or more access ports 1054 for the one or more push catheters 1026. The access ports 1052, 1054 can be configured to sealingly tighten around the branch sheaths 1024 or the push catheters 1026, and to constrict around the branch sheaths 1024 or the push catheters 1026 so as to substantially axially secure the branch sheaths 1024 or the push catheters 1026. A sealable cap assembly 1051 can be threadingly engaged with the main body 1050 of the delivery catheter 1004. The cap assembly 1051 can be configured such that, when a user tightens the cap assembly 1051 relative to the main body 1050 of the delivery catheter 1004, the core assembly 1021 and/or inner core 1020 will be axially and/or rotational secured to the main body 1050 of the delivery catheter 1004.

In some embodiments, a tube assembly 1059 can be supported by the main body 1050 of the delivery catheter 1004 so as to provide an orifice or access port into the main body 1050. The tube assembly 1059 can be used to flush the delivery catheter 1004 with saline or other suitable substances. The tube assembly 1059 can support any suitable medical connector and/or valve on the distal end thereof.

As mentioned above, the support member 1022 can be connected to a distal end portion of the outer tube 1018 so as to be axially engaged by the outer tube 1018. Some embodiments of the support member 1022 can have a substantially cylindrical shape and can be sized to fit within the inner lumen of a main body of the prosthesis 1010 when the prosthesis 1010 is in a constrained configuration. As will be described, in the loaded configuration, the prosthesis 1010 can be positioned over the support member 1022 so that a proximal portion of a main body of the prosthesis 1010 is positioned distally of the support member 1022 and so that a distal portion of a main body of the prosthesis 1010 is positioned proximally of the support member 1022. In this configuration, a proximal end portion 1012a of the distal sheath 1012 can be positioned over a distal portion 1022a of the support member 1022, and a distal end portion 1006a of the outer sheath 1006 over a proximal portion 1022b of the support member 1022.

In some embodiments, one or more tab members 1074 can be supported by the outer tube 1018. The one or more tab members 1074 can be configured to increase the rotational engagement of the constrained prosthesis 1010 relative to the outer tube 1018 so that the constrained prosthesis 1010 can be rotated with greater accuracy during deployment. Some embodiments of the one or more tab members 1074 can have a generally flat, plate-like shape, such as is illustrated in FIG. 46. The one or more tab members 1074 can be formed from a suitable polymeric or metallic material. Some embodiments of the one or more tab members 1074 can comprise one or more radiopaque features or be formed from a radiopaque material to improve the visibility and alignability of the delivery catheter 1004 under fluoroscopy during deployment of the prosthesis 1010.

In some embodiments, the one or more tab members 1074 can be similar to any of the embodiments of the torsion tab (such as without limitation, the embodiment of the torsion tab 196) disclosed in U.S. patent application Ser. No. 12/101,863, which disclosure is incorporated by reference as if fully set forth herein. In some embodiments, the one or more tab members 1074 can be integrally formed with the outer tube 1018, or secured thereto such as by thermal bonding, adhesive bonding, and/or any of a variety of other securing techniques known in the art.

As is illustrated, the main body portion of the prosthesis 1010 can be constrained by a peelable sheath or by the outer sheath 1006 such that the prosthesis 1010 is engaged with the one or more tab members 1074. In some embodiments, the one or more tabs 1074 can engage a stent or other portion of an endoskeleton of the prosthesis 1010, or, in some embodiments, can engage the material of the graft 1204 surrounding the tab member 1074 so that the prosthesis 1010 can substantially rotate with the inner core 1020 of the deployment catheter 1004.

Figure 50:
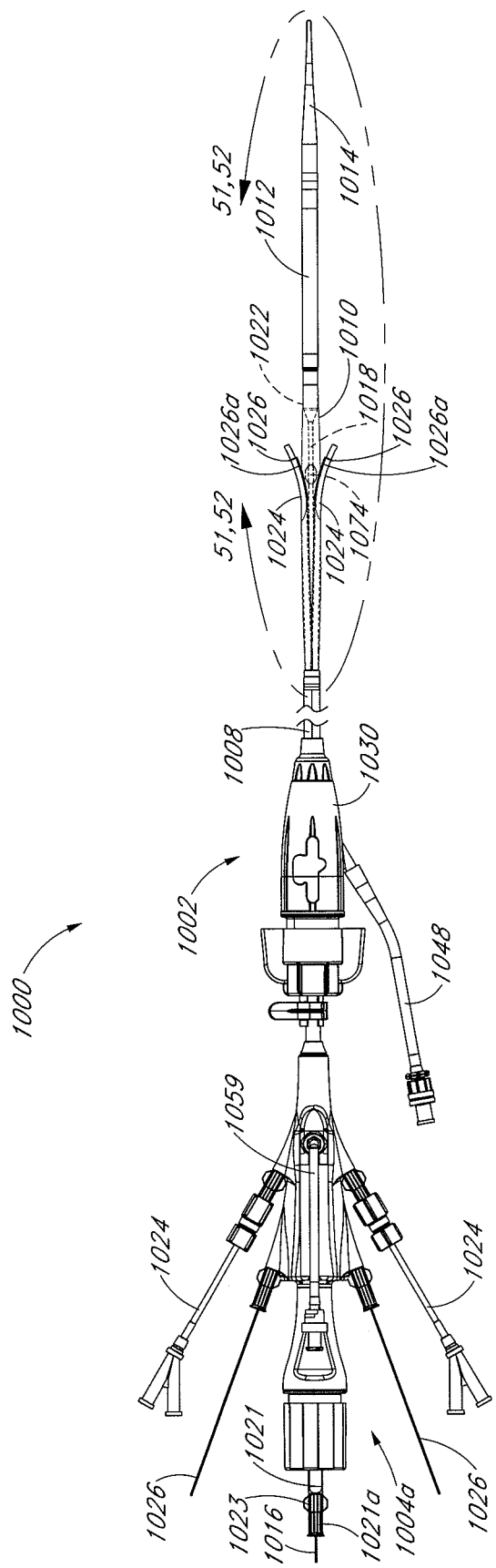
FIG. 50 is a side view of the embodiment of the catheter system shown in FIG. 43, showing the outer sheath in a partially retracted position.
Figure 51:
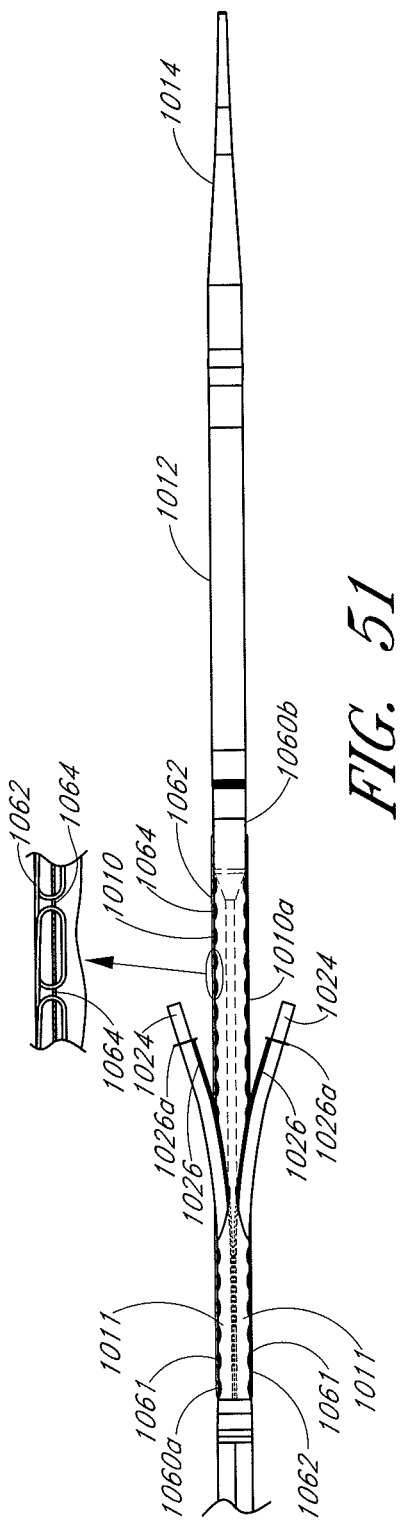
FIG. 51 is an enlarged side view of the embodiment of the catheter system shown in FIG. 43, defined by curve 51-51 shown in FIG. 50, showing the outer sheath in a partially retracted position.

FIG. 50 is a side view of the embodiment of the catheter system 1000 shown in FIG. 43, showing the outer sheath 1006 in a partially retracted position, similar to the configuration shown in FIG. 43B. FIG. 51 is an enlarged side view of the embodiment of the catheter system shown in FIG. 43, defined by curve 51-51 of FIG. 50, showing the outer sheath 1006 in a partially retracted position.

With reference to FIG. 51, in some embodiments, the mid portion of the prosthesis 1010 adjacent to the one or more fenestrations 1011 and/or the distal portion 1010*a* of the prosthesis can be constrained within a peelable sheath 1060. The peelable sheath 1060 can have a release wire 1062 threadably advanced through a plurality of openings 1064 formed along at least a portion of the sheath 1060. In some embodiments, the peelable sheath 1060, release wire 1062, and openings 1064 can have any of the same features, materials, or other details of the similar components disclosed in U.S. patent application Ser. No. 12/101,863, which application is incorporated by reference as if fully set forth herein. In some embodiments, the release wire 1062 can be slideably received within a lumen in the inner core 1020 so that a user can retract the release wire 1062 by grasping and retracting a proximal portion of the release wire 1062 positioned outside the patient's body.

However, in some embodiments (not illustrated), the mid portion of the prosthesis 1010 adjacent to the one or more fenestrations 1011 and/or the distal portion 1010*a* of the prosthesis can be constrained within one or more tubular sheaths, such as the outer sheath 1006 (also referred to herein as a second restraint or second restraining means) and/or distal sheath 1012 such that additional restraining means such as the sheath 1060 are not required. Therefore, any of the embodiments disclosed herein having the optional sheath 1060 should be understood to be configurable to not use the sheath 1060 to restrain one or more portions of the prosthesis 1010. In some embodiments, the prosthesis 1010 can be configured such that the mid portion of the prosthesis 1010 adjacent to the one or more fenestrations 1011 is not radially supported by a stent, connectors, struts, or any other similar structure such that, when the outer sheath 1006 is partially retracted, the mid portion of the prosthesis does not self-expand.

In some embodiments, the prosthesis 1010 can have one or more openings 1011 formed therein. For example and without limitation, the fenestrations or openings 1011 can be formed in the prosthesis 1010 at diametrically opposing positions. As will be described in greater detail below, in some embodiments, one or more of the openings 1011 can be formed in the prosthesis 1010 at a position that is angularly offset from the diametrically opposing position. Similarly, in some embodiments, when used, the sheath 1060 can have one or more openings 1061 formed therein, the openings 1061 being positioned adjacent to the similar number of openings 1011 formed in the prosthesis. Some embodiments of the catheter system 1000 can be configured such that the sheaths 1024 are advanced through the openings 1011 formed in the prosthesis 1010 and the openings 1061 formed in the sheath 1060, when the prosthesis 1010 is loaded within the catheter system 1000.

With reference to FIG. 49B, due to the non-uniform design of the stent within the graft material, in some embodiments, the prosthesis 1010 can be efficiently packed within the outer sheath 1006 so as to surround the sheaths 1024 and efficiently fill the space within the outer sheath 1006. In this configuration, for example, the prosthesis 1010 can be loaded within the outer sheath 1006 so that the sheaths 1024 are advanced between many of the struts, bends, loops, and other features that the stent can comprise, thereby permitting the sheaths 1024 sufficient space to be loaded within the outer sheath 1006 so that the lumen of the sheaths 1024 are not compressed or collapsed in the loaded state. Additionally, the graft can be formed from a bi-directionally expanded, layered PTFE material have thin walls to further increase the space efficiency of the prosthesis 1010.

In some embodiments, as illustrated in FIG. 51, where used, the peelable sheath 1060 can have one or more release wires 1062 (two being shown) advanced through openings or perforations 1064 formed in the sheath 1060 along two sides of the sheath 1060. The release wires 1062 can be configured to tear the sheath 1060 along two lines of perforations 1064 and/or scores formed along two sides of the sheath 1060, so that the sheath 1060 can be removed from the prosthesis 1010 while the sheaths 1024 are advanced through the fenestrations 1011, 1061, respectively, in the prosthesis 1010 and sheath 1060. In this configuration, each of the two release wires 1062 can be secured to a proximal end portion 1060*a* of the sheath 1060, so that both halves of the sheath 1060 can be retracted through the outer sheath 1006.

Figure 52:
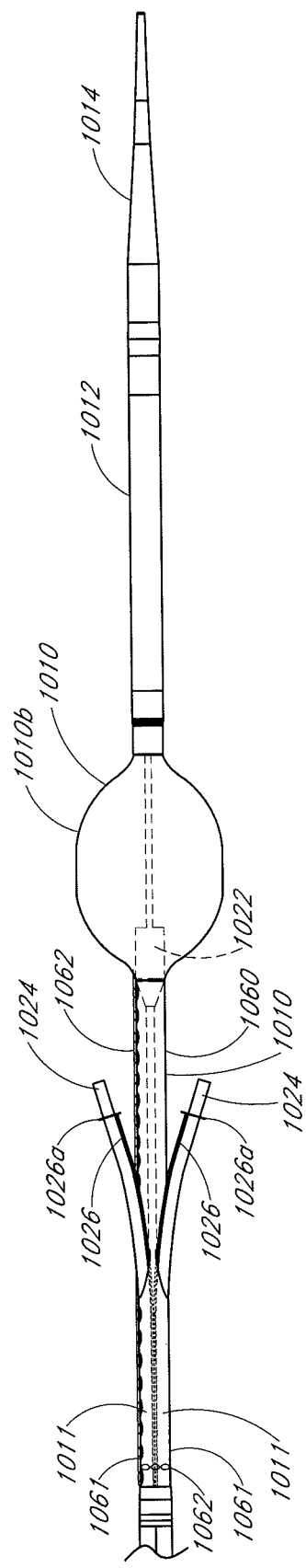
FIG. 52 is an enlarged side view of the embodiment of the catheter system shown in FIG. 43, defined by curve 52-52 shown in FIG. 50, showing the outer sheath in a partially retracted position and the proximal sheath in a partially advanced position.

However, as illustrated in FIG. 52, some embodiments of the catheter system 1000 can be configured to only have one release wire 1062 threadedly advanced through the sheath 1060. FIG. 52 is an enlarged side view of the embodiment of the catheter system 1000 shown in FIG. 43, defined by curve 52-52 shown in FIG. 50, showing the outer sheath 1006 in a partially retracted position and the distal sheath 1012 in a partially advanced position.

In some embodiments, the perforations 1064 formed in the sheath 1060 can be arranged along an axial line along the length of the portion of the sheath 1060 from the fenestrations 1061 to the distal end of the sheath 1060, and also arranged to split the sheath 1060 between the two fenestrations 1061 formed in the sheath 1060. In some embodiments, as illustrated in FIG. 52, the perforations 1064 formed in the sheath 1060 arranged along the length of the sheath 1060 can be positioned to tear the sheath 1060 from one of the fenestrations 1061 to the distal end 1060*b* of the sheath 1060, and also to circumferentially tear the sheath 1060 between the fenestrations 1061.

As mentioned above, with reference to FIG. 52, some embodiments of the catheter system 1000 can be configured such that a proximal portion 1010*b* of the prosthesis 1010 can be deployed by axially advancing the inner tube 1016 relative to the inner core 1020 of the delivery catheter 1004 and, hence, the prosthesis 1010. Some embodiments of the prosthesis 1010 can be self-expanding such that removing the radial constraint provided by the distal sheath 1012 can cause the portion of the prosthesis 1010 constrained by the inner tube 1016 to expand toward the vessel wall. In some embodiments, the proximal portion 1010*b* of the prosthesis 1010 can be deployed in this manner before the distal portion 1010*a* of the prosthesis 1010 is deployed, or simultaneously with the deployment of the distal portion 1010*a* of the prosthesis 1010. In some embodiments, the proximal portion 1010*b* of the prosthesis 1010 can be deployed in this manner after the distal portion 1010*a* of the prosthesis 1010 is deployed.

Figure 53:
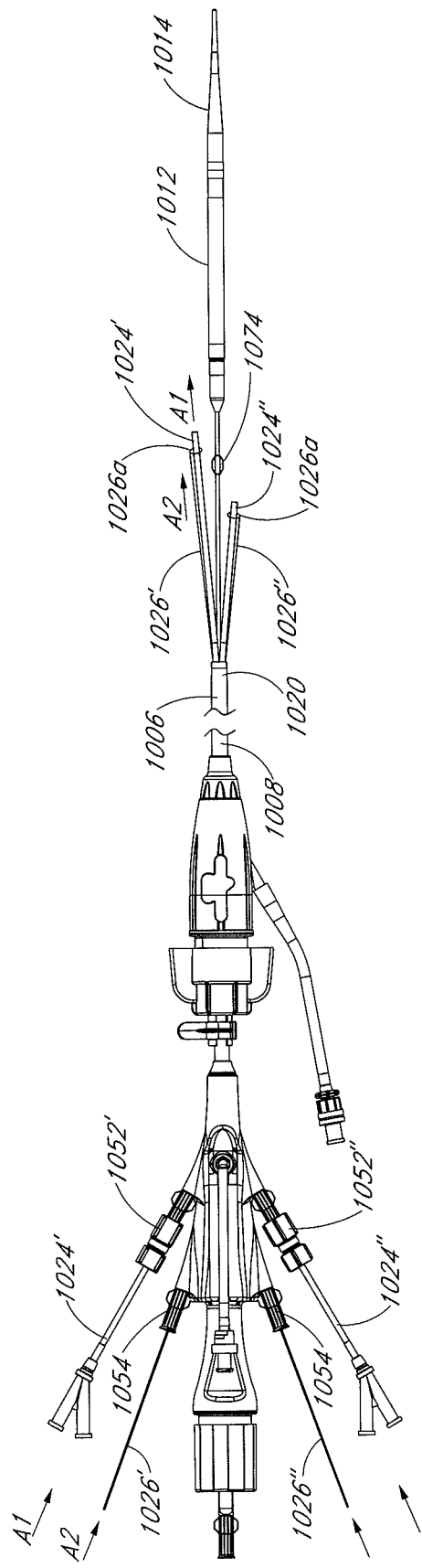
FIG. 53 is a side view of the embodiment of the catheter system shown in FIG. 43, showing the outer sheath in a partially retracted position and the embodiment of one branch sheath and one push catheter in a partially advanced position.

FIG. 53 is a side view of the embodiment of the catheter system 1000 shown in FIG. 43, showing the outer sheath 1006 in a partially retracted position and the embodiment of one branch sheath 1024' and one push catheter 1026' in a partially advanced position. The branch sheath 1024' can be advanced relative to the inner core 1020, the prosthesis, and the second branch sheath 1024" by advancing a proximal portion of the branch sheath 1024' in the direction of arrow A1 in FIG. 53 through the access port 1052' at the proximal end of the delivery catheter 1004. Similarly (not shown), the second branch sheath 1024" can be advanced relative to the inner core 1020, the prosthesis, and the first branch sheath 1024' by advancing a proximal portion of the branch sheath 1024" through the access port 1052" at the proximal end of the delivery catheter 1004. Additionally, either of the push catheters 1026', 1026" can be advanced relative to the branch sheaths 1024', 1024" by advancing the respective push catheter 1026 through the respective access port 1054. For example, the push catheter 1026' can be advanced by advancing the proximal portion of the push catheter 1026' in the direction of arrow A2 in FIG. 53.

Figure 54:
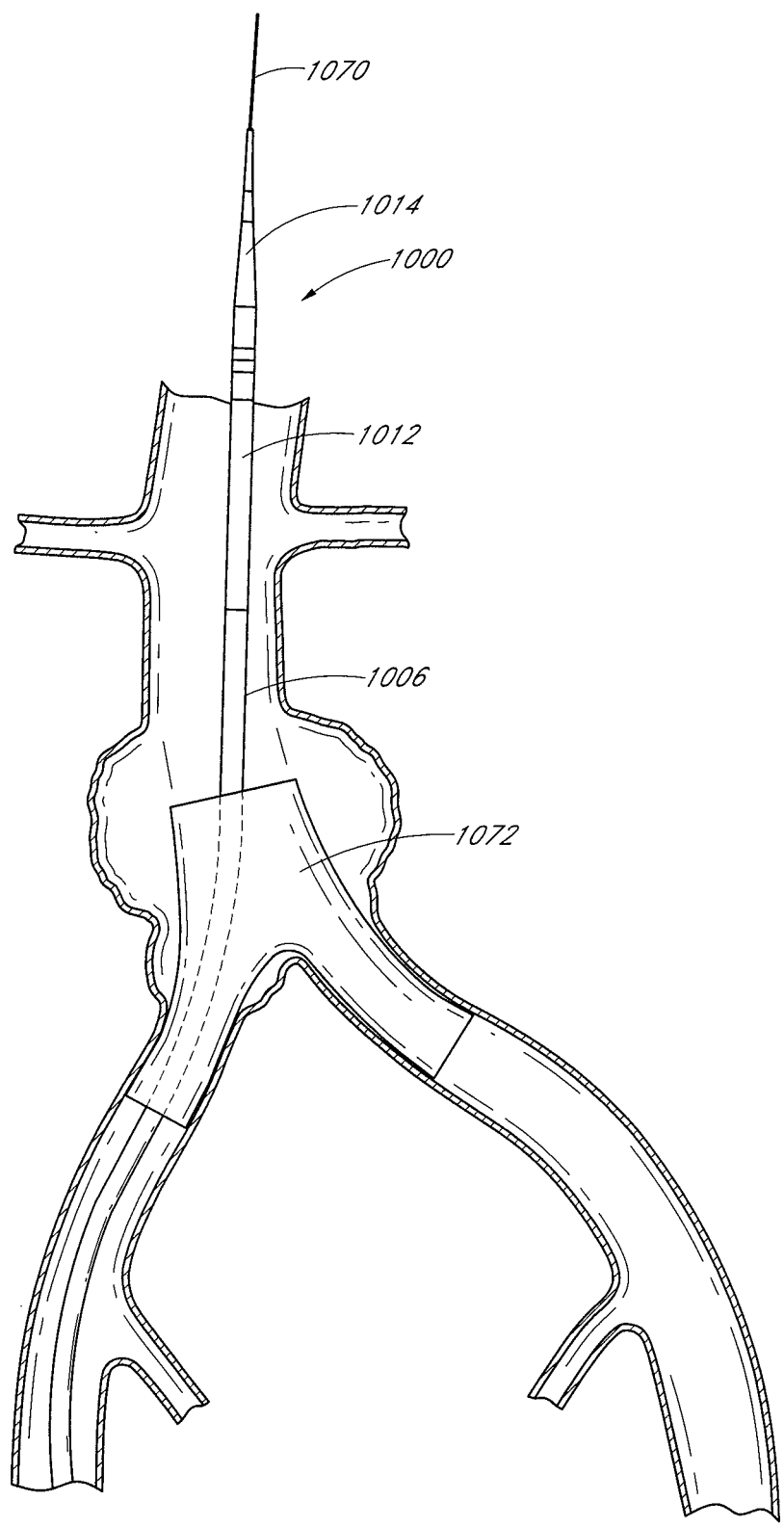
FIG. 54 is a section view of a portion of a patient's vasculature, showing the embodiment of the delivery catheter illustrated in FIG. 43A being advanced through a patient's abdominal aorta.

With the embodiments of the catheter system 1000 having been described, several configurations of deployment methods for an endoluminal prosthesis, including any suitable prosthesis or any endoluminal prosthesis disclosed herein, will now be described with reference to FIGS. 54-61. FIG. 54 is a section view of a portion of a patient's vasculature, showing the delivery catheter 1000 being advanced through a patient's abdominal aorta over a guidewire 1070 positioned within a patient's vasculature. In some embodiments, as in the illustrated embodiment, the delivery catheter 1000 can be advanced through a prosthesis 1080 (which can be a bifurcated prosthesis) deployed within the patient's vasculature.

Figure 55:
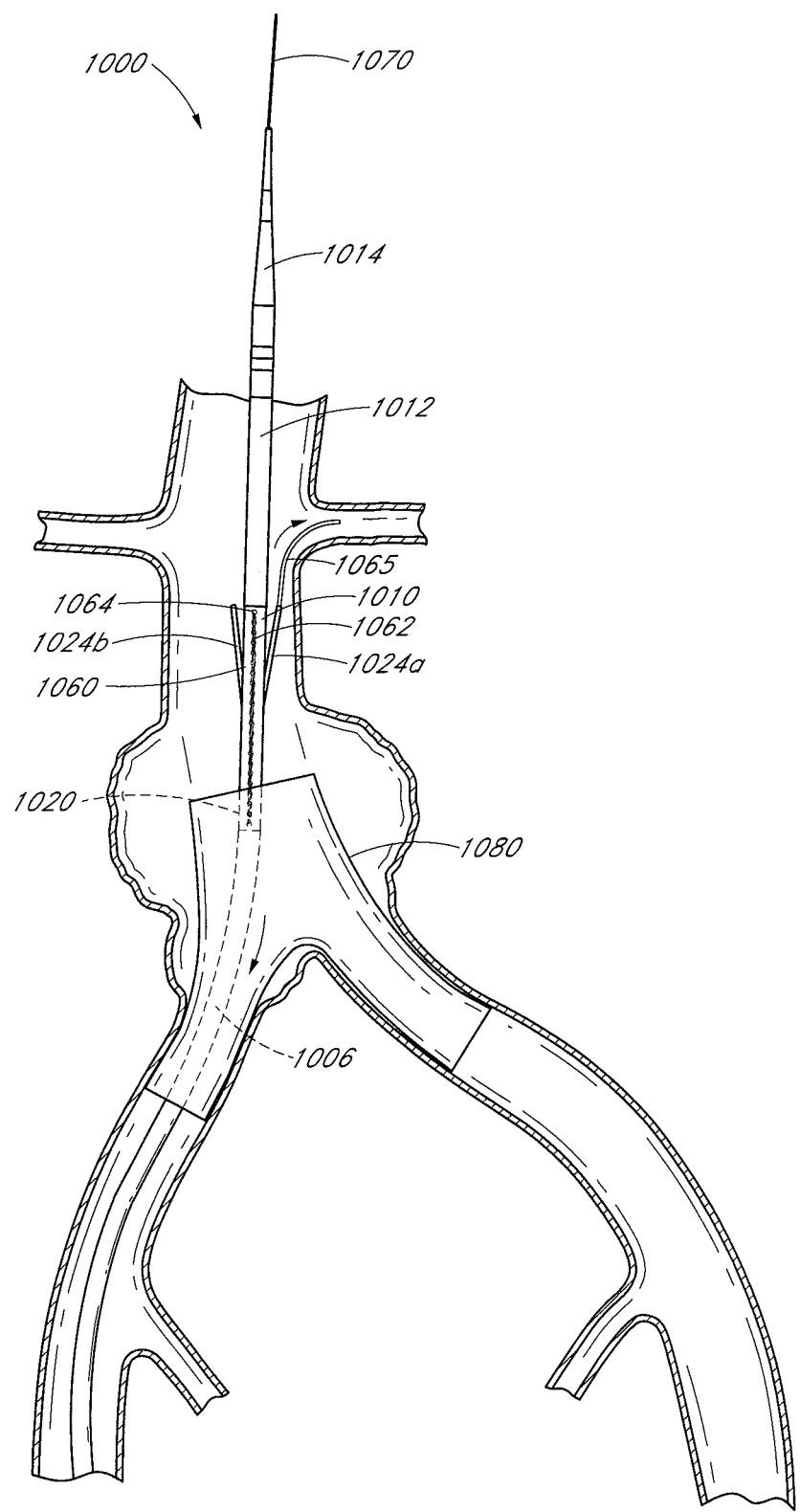
FIG. 55 is a section view of a portion of a patient's vasculature, showing the embodiment of the delivery catheter illustrated in FIG. 43A and an angiographic catheter being advanced through a branch sheath of the delivery catheter toward a branch vessel.

FIG. 55 is a section view of a portion of a patient's vasculature, showing the delivery catheter 1000 and an angiographic catheter 1065 being advanced through a branch sheath 1024 of the delivery catheter toward a target branch vessel. As illustrated, an outer sheath 1006 of the catheter system 1000 has been retracted relative to the inner core (not shown) and the prosthesis 1010, exposing a middle portion of the prosthesis 1010 (i.e., a portion of the prosthesis 1010 radially adjacent to the one or more fenestrations 1011) and the branch sheaths 1024*a*, 1024*b*. In some embodiments, after the branch sheaths 1024*a*, 1024*b* have been exposed, a suitable angiographic catheter 1065 can be advanced through the lumen of either or both of the branch sheaths 1024*a*, 1024*b* and directed into the target branch vessel or vessels. A user can rotate the inner core 1020 to approximately rotationally align the fenestrations 1011 of the prosthesis 1010 or the branch sheaths 1024 with the branch vessels.

In some embodiments, as discussed above, the optional sheath 1060 can constrain the mid and distal portions of the prosthesis 1010 such that, when the outer sheath 1006 is retracted, the mid and distal portions of the prosthesis 1010 do not self-expand. However, in some embodiments, the mid portion of the prosthesis 1010 radially adjacent to the one or more fenestrations 1011 can be unsupported by any stents, struts, connectors or can be minimally supported by stents or connectors 1254 (also referred to herein as connecting members). In some embodiments of this configuration, the prosthesis 1010 can be configured such that there is no radial force or support provided to the mid portion of the prosthesis 1010, or such that the mid portion of the prosthesis 1010 will not be biased to self-expand when the outer sheath 1006 is retracted. Accordingly, some embodiments can be configured such that no additional restraint in addition to, for example, the outer sheath 1006, is required. Therefore, in some embodiments, only the outer sheath 1006 and the distal sheath 1012 can be used to restrain the prosthesis 1010. In this configuration, the outer sheath 1006 can be partially retracted to release the sheaths 1024 so that one or more angiographic catheters 1065 can be advanced through the sheaths 1024 and into the target branch vessels before the proximal and distal portions of the prosthesis 1010 are released from the deployment catheter 1004.

Some embodiments of the angiographic catheter 1065 can be configured such that an end portion thereof is biased to have a curved disposition. In some embodiments, this can be accomplished by shortening the length of the wall of one side of the end portion of the angiographic catheter 1065 as compared to the length of the wall of the other side of the angiographic catheter 162. In some embodiments, an end portion of the sheaths 1024 can be also be formed so as to be biased to have a curved end portion. Some embodiments of the sheaths 1024 can be formed in this configuration by heat setting an end portion of the sheath in a curved disposition, or by otherwise shortening the wall of one side of the end portion of the catheter as compared to the other side of the end portion of the catheter. In some embodiments, the branch sheaths 1024 can have a curved end portion so that such sheaths 1024 can be directed into the branch arteries or vessels without the use of an angiographic catheter.

Figure 56:
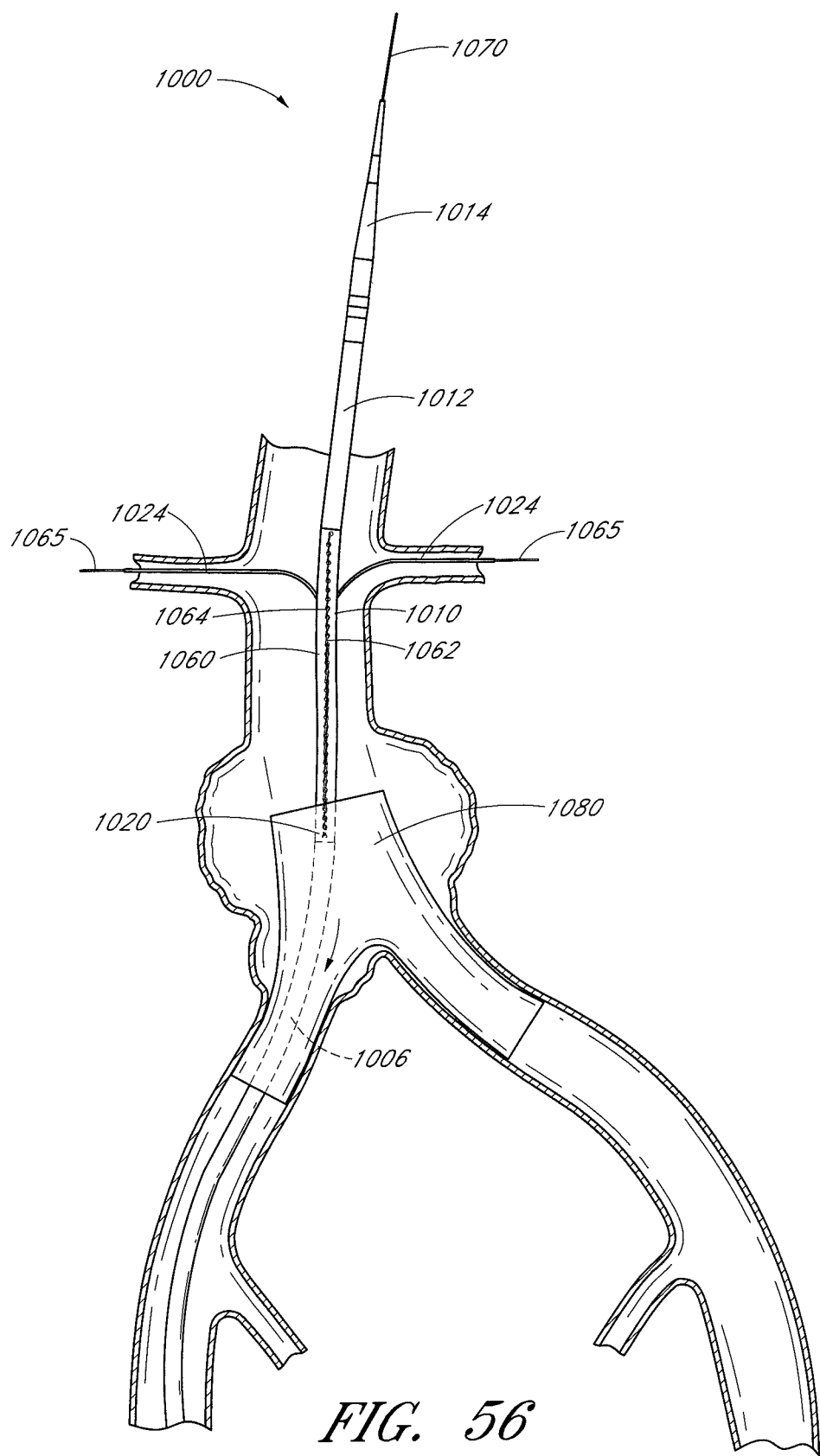
FIG. 56 is a section view of a portion of a patient's vasculature, showing the embodiment of the delivery catheter illustrated in FIG. 43A and the branch sheaths of the delivery catheter being advanced into a patient's branch arteries.

As shown, an angiographic catheter 1065 is being advanced relative to the branch sheath 1024*a* and into the target branch vessel, in this case a renal artery. Some embodiments of the delivery catheter 1000 can be configured such that an angiographic catheter can be advanced through the desired branch sheath 1024 and into the target vessel without retracting the outer sheath 1006. After the angiographic catheters 1065 have been directed into the target location, in this case the branch vessels, either or both of the branch sheaths 1024 can be independently or simultaneously advanced over the angiographic catheters 1065 into the target branch vessels, as is illustrated in FIG. 56. In some embodiments, the branch sheaths 1024, the fenestrations 1011, 1061 formed in either the prosthesis 1010 or the sheath 1060, respectively, and/or any other components or features of the delivery catheter 1000 can have radiopaque markers or other indicators to assist a medical practitioner in the deployment procedures described herein or other suitable deployment procedures.

Figure 57:
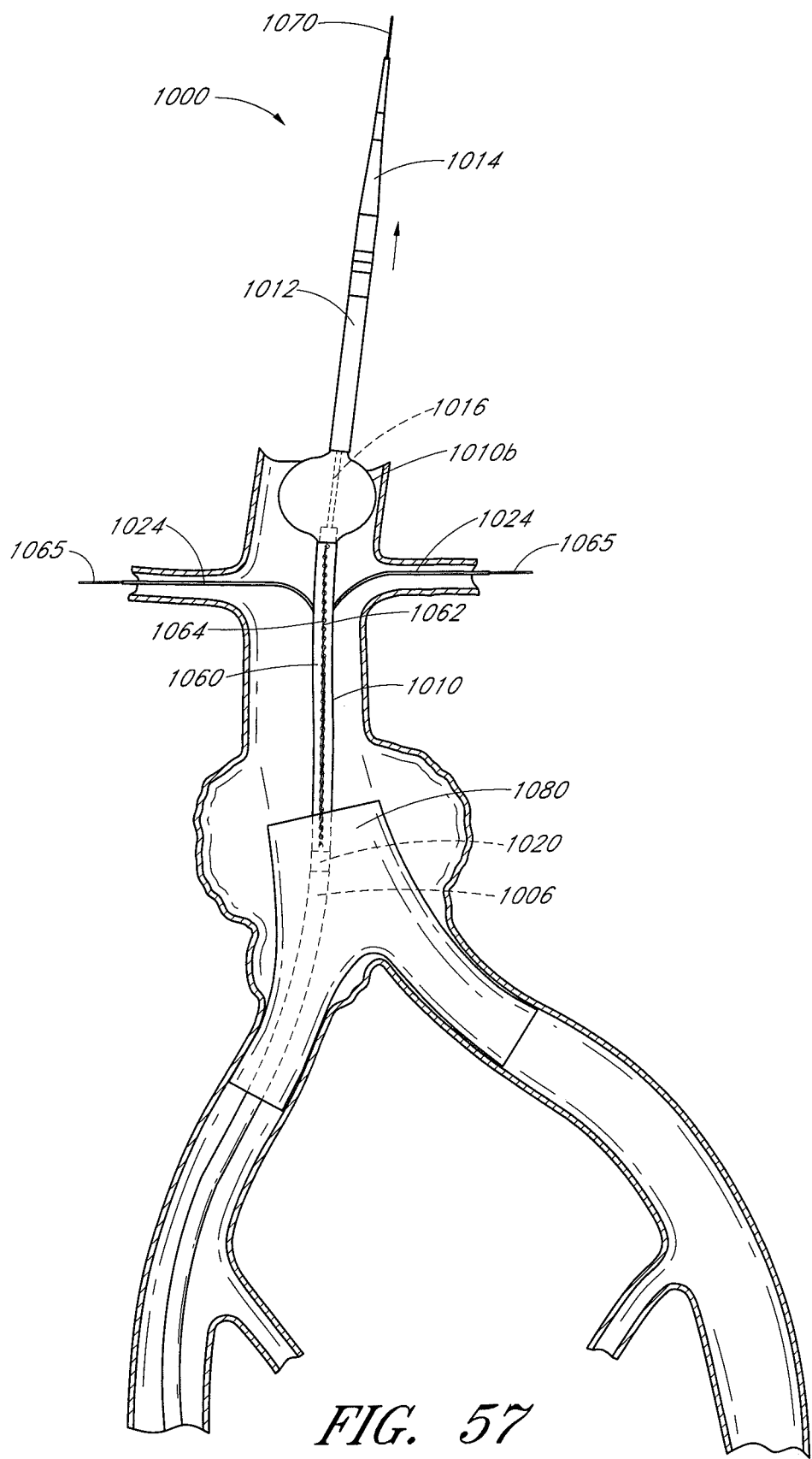
FIG. 57 is a section view of a portion of a patient's vasculature, showing an embodiment of a distal sheath of the embodiment of the delivery catheter illustrated in FIG. 43A being advanced to deploy a proximal portion of the prosthesis.

With the branch sheaths 1024 in the target vessels and the outer sheath 1006 axially retracted, as shown in FIG. 57, a proximal portion 1010*b* of the prosthesis 1010 can be deployed by axially advancing the distal sheath 1012 relative to the inner core 1020 and the prosthesis 1010. In some embodiments, the prosthesis 1010 can be axially and rotationally secured to the outer tube 1018, which can be axially and rotationally secured to the inner core 1020, such that advancing the distal sheath 1012 relative to the inner core 1020 will advance the distal sheath 1012 relative to the prosthesis 1010. As described above, the distal sheath 1012 can be advanced relative to the inner core 1020 and the prosthesis 1010 by advancing the inner tube 1016 relative to the inner core 1020, the inner tube 1016 being axially engaged with the distal tip 1014 which can support the distal sheath 1012.

Figure 58:
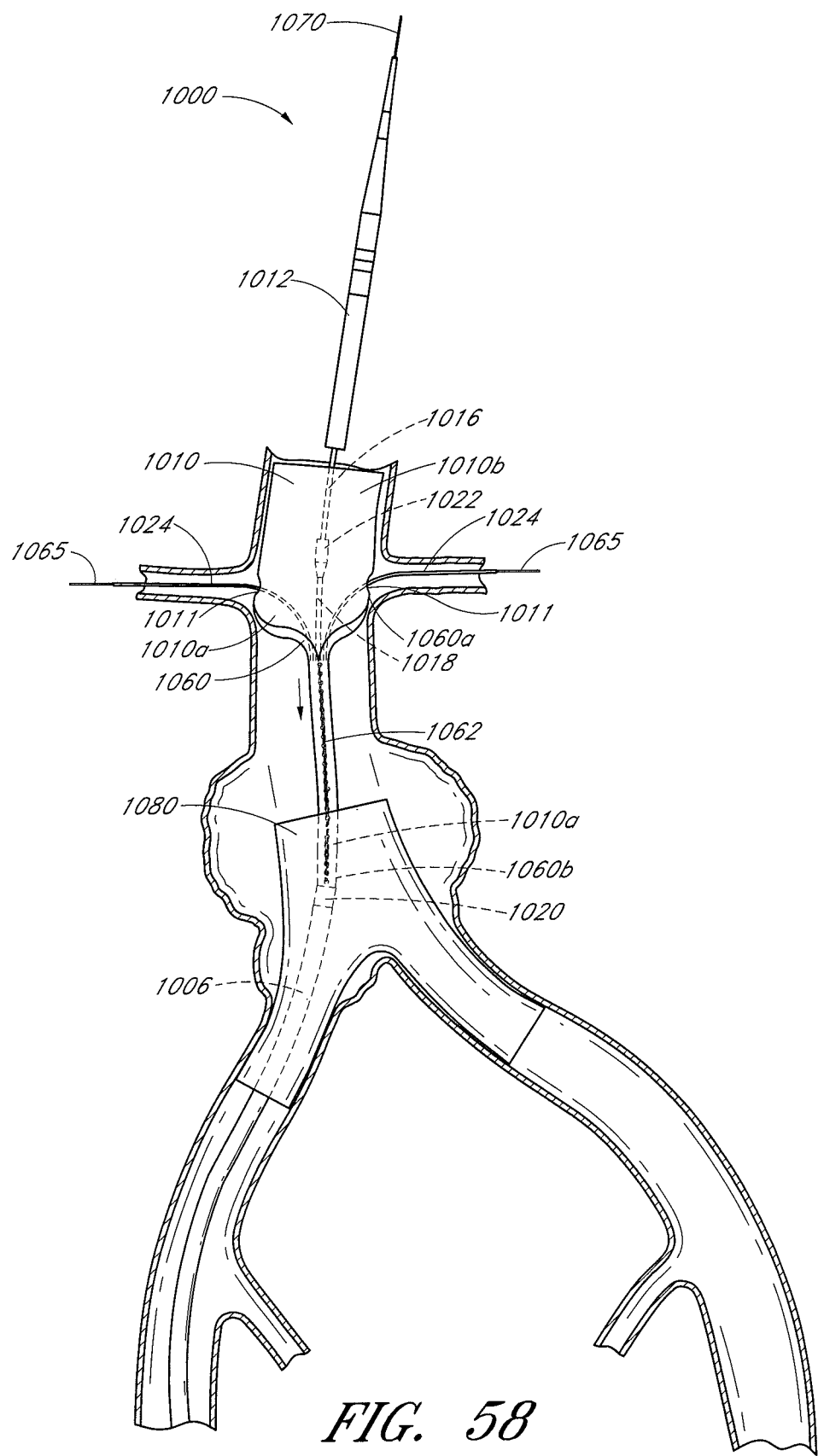
FIG. 58 is a section view of a portion of a patient's vasculature, showing an embodiment of a peelable sheath of the embodiment of the delivery catheter illustrated in FIG. 43A being removed to deploy a distal portion of the prosthesis.

FIG. 58 is a section view of a portion of a patient's vasculature, showing an embodiment of a peelable sheath 1060 being removed from the distal portion 1010*a* of the prosthesis 1010 so as to deploy a distal portion 1010*a* of the prosthesis 1010. Some embodiments of the sheath 1060 can be removed by axially retracting a release wire 1062, which can be looped or other otherwise threaded through openings or perforations 1064 formed in the sheath material. The release wire 1062 can be configured to tear through the sheath material between the perforations 1064, thereby permitting the self-expanding prosthesis 1010 to expand toward the vessel walls. As mentioned, some embodiments of the prosthesis 1010 can be configured to be restrained within the outer sheath 1006 and the distal sheath 1012 such that an additional restraint, such as the peelable sheath 1060, is not required.

In some embodiments, as illustrated, a distal portion 1060a of the sheath 1060 can be torn by the release wire 1062 before a proximal portion 1060b of the sheath 1060 is torn by the release wire so that a proximal portion 1010a of the prosthesis (i.e., adjacent to the proximal portion 1060a of the sheath 1060) can be deployed before a distal portion 1010b of the sheath 1010. In some embodiments (not illustrated), a proximal portion 1060b or a middle portion of the sheath 1060 can be torn by the release wire 1062 before a distal portion 1060a of the sheath 1060 is torn by the release wire. In some embodiments, the release wire 1062 can be secured to the proximal portion 1060b or other suitable portion of the sheath 1060 such that, after the sheath 1060 has been torn, the sheath 1060 can be removed through the delivery catheter 1000 by continuing to axially retract the release wire 1062 relative to the prosthesis 1010.

As illustrated, a distal portion 1010b of the prosthesis 1010 (i.e., the downstream portion of the prosthesis 1010) can be deployed within an opening of an adjacent prosthesis, such as without limitation the bifurcated prosthesis 1080 illustrated in FIG. 58. However, in some embodiments, the delivery catheter 1000 or any other delivery catheter described herein can be used to deploy any suitable prosthesis, including a bifurcated prosthesis or otherwise, in any portion of a patient's vasculature. As such, in some embodiments, the prosthesis 1000 can be a bifurcated prosthesis.

Figure 59:
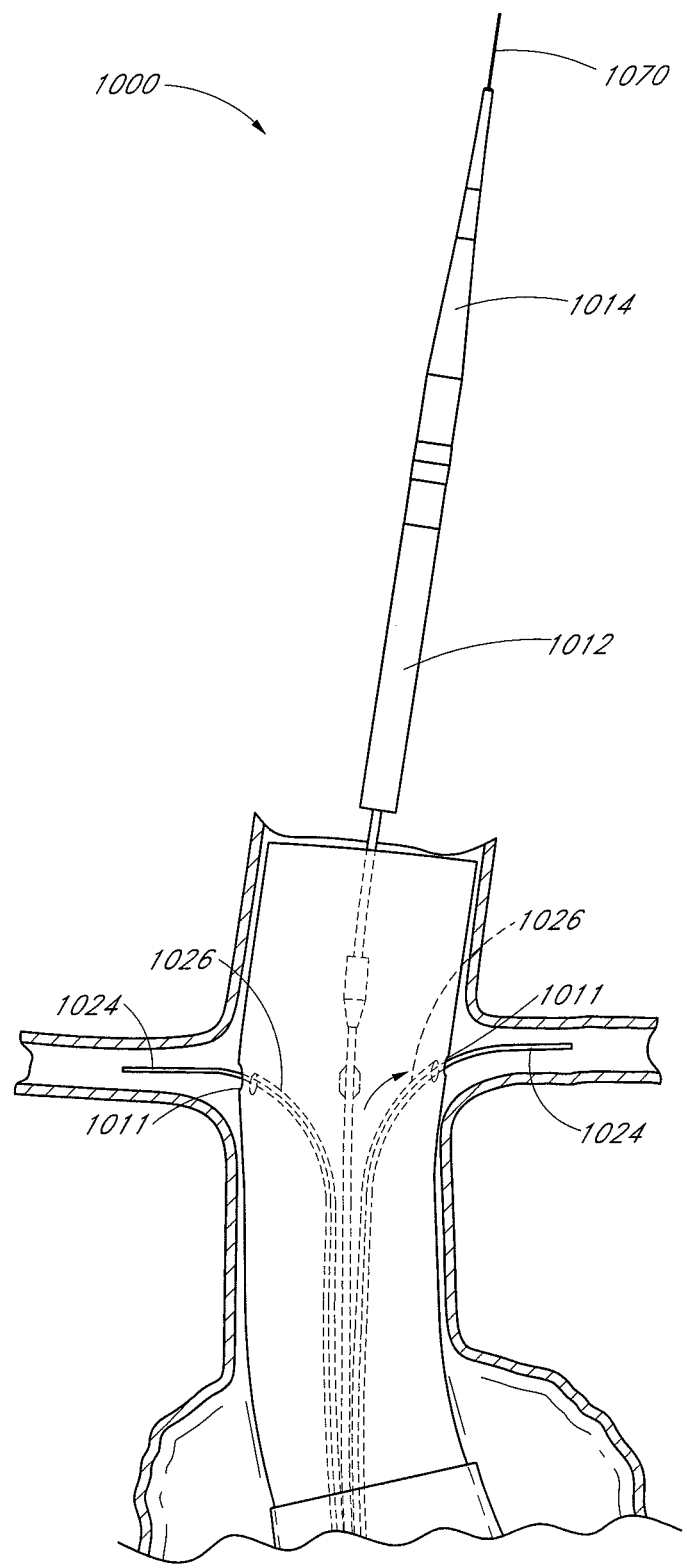
FIG. 59 is a section view of a portion of a patient's vasculature, showing an embodiment of a push catheter of the embodiment of the delivery catheter illustrated in FIG. 43A advancing an inner wall of the prosthesis adjacent to a fenestration toward an ostium of the target branch vessel.

FIG. 59 is a section view of a portion of a patient's vasculature, showing an embodiment of a push catheter 1026 advancing an inner wall of the prosthesis 1010 adjacent to a fenestration 1011 toward an ostium of the target branch vessel. As illustrated, the push catheter 1026 can be advanced through a lumen in the inner core 1020 to push the fenestration 1011 of the prosthesis 1010 over the branch sheath 1024 and into approximate alignment with the ostium of the branch vessel. In some embodiments, the catheter system 1000 can be configured to not have a push catheter 1026, and can accordingly be configured to deploy a fenestrated graft without the use of such a component. As will be described below, in some embodiments, snares, protrusions, tabs, or other features can be formed on the sheaths 1024 to push the fenestrations toward the branch vessel ostium.

Figure 60:
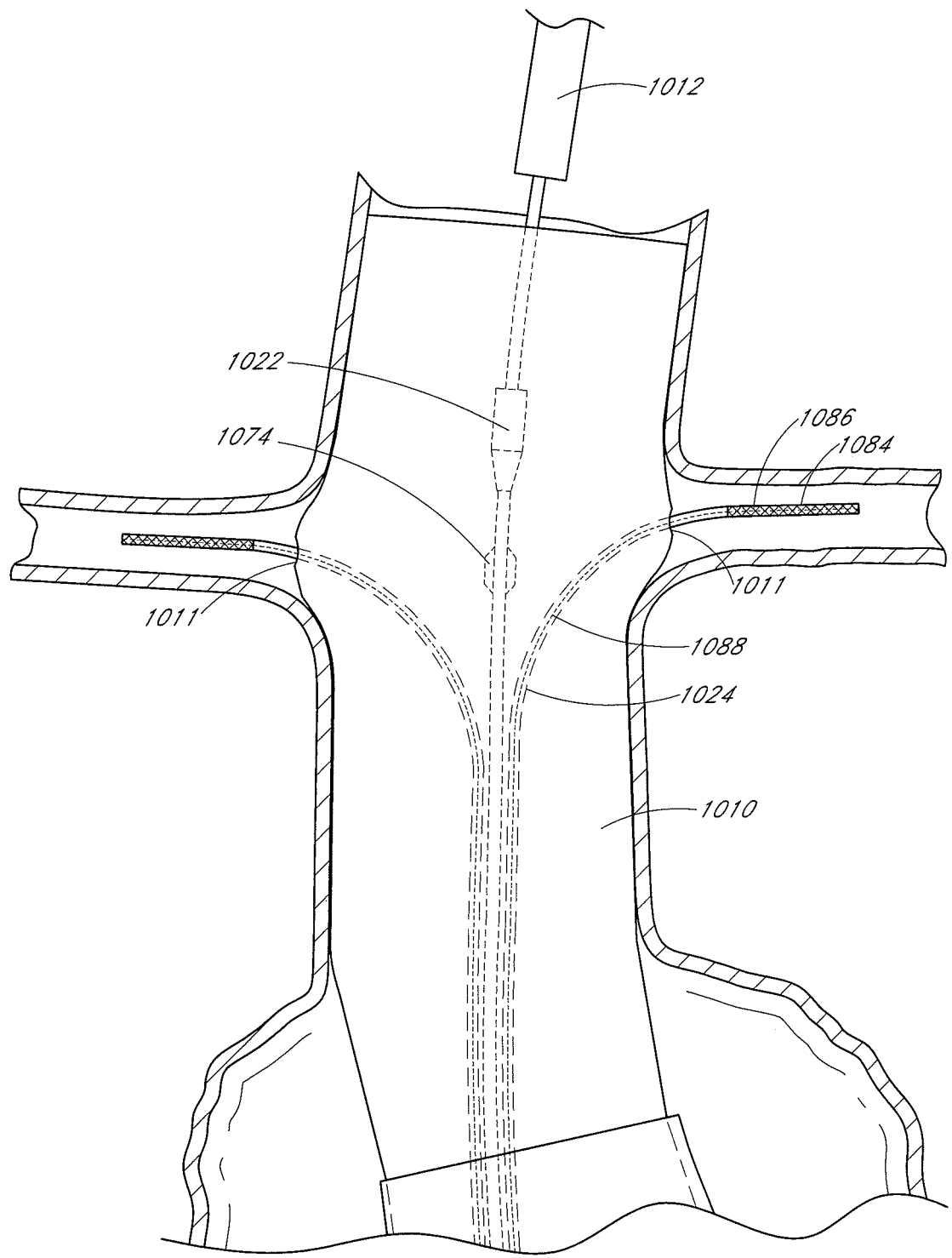
FIG. 60 is a section view of a portion of a patient's vasculature, showing an embodiment of a branch stent being advanced into the target branch vessel.
Figure 61:
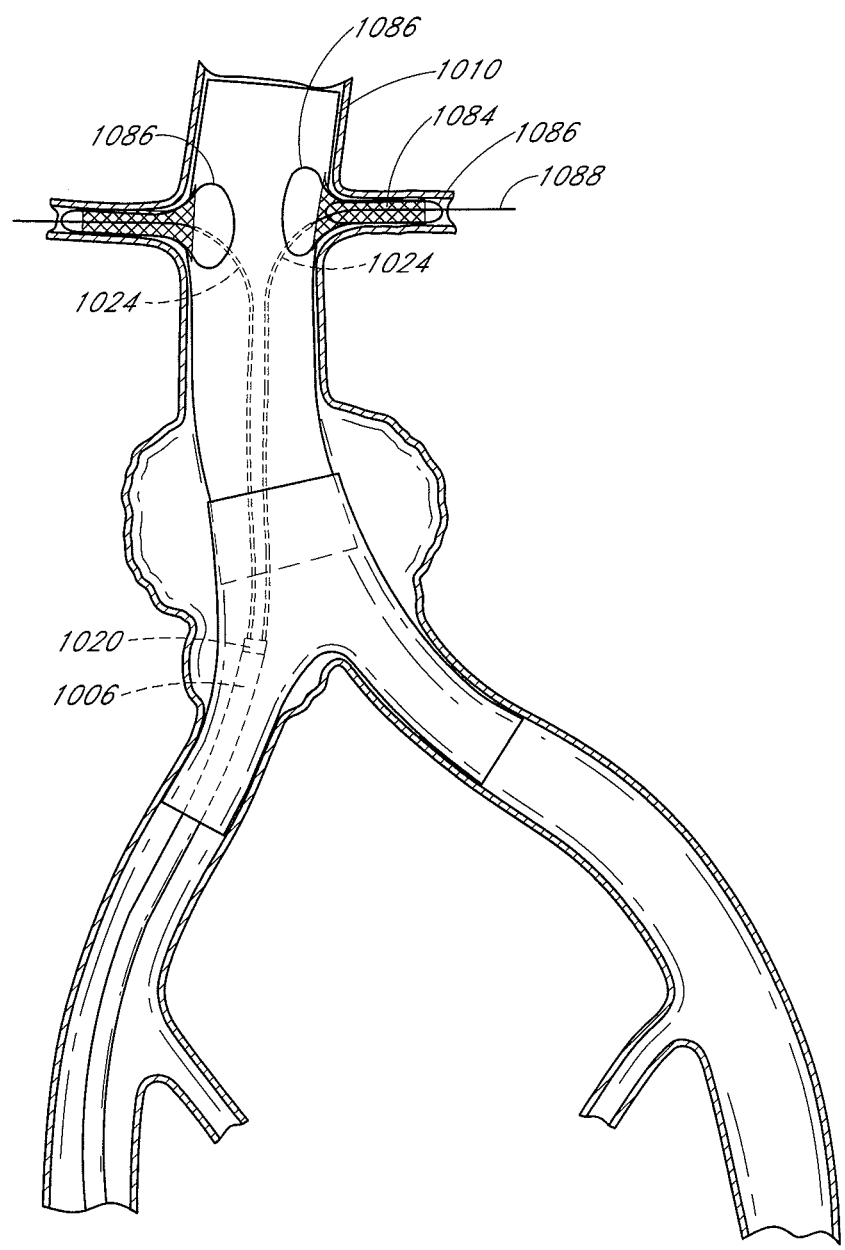
FIG. 61 is a section view of a portion of a patient's vasculature, showing the embodiment of the branch stent of FIG. 60 being expanded in the target branch vessel and flared.

In some embodiments, as illustrated in FIG. 60, a covered or uncovered branch stent 1084 can be deployed in the branch vessel by advancing the branch stent 1084 through the branch sheath 1024 using a suitable catheter, such as a renal stent catheter, into the target vessel, after the angiographic catheter has been removed from the branch sheath 1024. The stent 1084 can be supported on an inflation balloon 1086, which can be supported by a guidewire 1088. The guidewire 1088 can be configured to have an inflation lumen therein, to inflate the balloon 1086 and expand the branch stent 1084 in the target location after the branch sheath 1024 has been at least partially retracted so as to not interfere with the expansion of the branch stent 1084, as illustrated in FIG. 61. In some embodiments, the inflation balloon 1086 can be configured to expand and flare a portion of the stent 1084 within or to the inside of the fenestration 1011 formed in the prosthesis.

Some embodiments of the push catheter 1026 described above can be configured to be supported within a renal or branch stent delivery catheter. For example, without limitation, the push catheter 1026 can be configured to be supported within a modified embodiment of a renal stent catheter, such as the renal stent catheter illustrated in FIG. 60. In some embodiments, the push catheter 1026 can be configured to only partially surround the branch sheath 1024 or the branch stent delivery catheter. In this configuration, the push catheter 1026 can be configured to be entirely positioned within and advanceable through a lumen of the branch sheath 1024 or the branch stent delivery catheter. For example, the push catheter 1026 can have an expandable end portion that can automatically expand when the end portion is advanced past the end of the lumen, so as to enable the end portion to snare or engage the graft material surrounding the fenestration.

Additionally, in some embodiments, the branch stent delivery catheter can be configured to have a snare, protrusion, or other object tethered to the balloon or stent, or to be projecting from an outside surface thereof to snare or engage the graft material adjacent to the fenestration, so as to cause the fenestration to be advanced toward the ostium as the branch stent delivery catheter is advanced through the fenestrations. For example, without limitation, the branch stent delivery catheter can have a biased wire member supported on an outside surface of the branch stent delivery catheter that is biased to expand when the wire member is advanced past the end of the branch sheath 1024. The wire member can expand to a size that is larger than the size of the fenestration. The wire member can be supported at a position that is offset from an end of the branch stent delivery catheter.

In some embodiments, the fenestration 1011 in the prosthesis 1010 can be expanded as the branch stent 1084 is being expanded, to improve the seal between the fenestration 1011 and the branch stent 1084. In some embodiments, a second expansion balloon can be positioned in the portion of the stent 1084 within or to the inside of the fenestration 1011 to flare that portion of the stent 1084, either with or without removing the first balloon used to expand the main portion of the branch stent 1084.

Some arrangements are directed to methods of deploying an endoluminal prosthesis, such as without limitation the prosthesis 1010 described above, comprising inserting a delivery catheter such as catheter system 1000 into an artery, exposing one or more branch sheaths 1024, advancing one or more angiographic catheters with one or more guidewires into the one or more branch sheaths 1024 and cannulating the target branch vessels, advancing the one or more branch sheaths 1024 over the angiographic catheters and into the target branch vessels, deploying a proximal portion of the prosthesis, deploying a distal portion of the prosthesis, removing the one or more angiographic catheters and/or the guidewires, inserting one or more branch stents into the branch vessels, retracting the branch sheaths, expanding the branch stents, and flaring a portion of the branch stents. The steps of the foregoing procedure can be performed in the sequence described, or can be performed in any suitable sequence. In some arrangements, the target branch vessels are the renal arteries. The step of deploying a distal portion of the prosthesis can be performed in some arrangements by tearing and retracting a peelable sheath member, or by retracting a tubular sheath such as an outer sheath. Deploying a proximal portion of the prosthesis can be performed in some arrangements by distally advancing a tubular sheath.

Some arrangements are directed to methods of deploying an endoluminal prosthesis, such as without limitation the prosthesis 1010 described above, comprising inserting a delivery catheter such as catheter system 1000 into an artery, exposing one or more branch sheaths 1024, advancing one or more angiographic catheters having one or more guidewires into the one or more branch sheaths 1024 and cannulating the target branch vessels, advancing the one or more branch sheaths 1024 over the angiographic catheters and into the target branch vessels, removing the one or more angiographic catheters and/or guidewires, inserting one or more branch stents into the branch vessels, retracting the branch sheaths, expanding the branch stents, and flaring a portion of the branch stents. The target branch vessels can be the renal arteries. The steps of the foregoing procedure can be performed in the sequence described, or can be performed in any suitable sequence.

Some arrangements are directed to methods of deploying an endoluminal prosthesis, such as without limitation the prosthesis 1010 described above, comprising inserting a delivery catheter such as catheter system 1000 into an artery, exposing one or more branch sheaths 1024, advancing one or more angiographic catheters having one or more guidewires into the one or more branch sheaths 1024 and cannulating the target branch vessels, advancing the one or more branch sheaths 1024 over the angiographic catheters and into the target branch vessels, deploying a prosthesis, removing the one or more angiographic catheters and/or guidewires, inserting one or more branch stents into the branch vessels, retracting the branch sheaths, expanding the branch stents, and flaring a portion of the branch stents. In some arrangements, the target branch vessels are the renal arteries. The steps of the foregoing procedure can be performed in the sequence described, or can be performed in any suitable sequence.

Some arrangements are directed to methods of deploying an endoluminal prosthesis, such as without limitation the prosthesis 1010 described above, comprising inserting a delivery catheter such as catheter system 1000 into an artery, exposing one or more branch sheaths 1024, advancing one or more angiographic catheters having one or more guidewires into the one or more branch sheaths 1024 and cannulating the target branch vessels, advancing the one or more branch sheaths 1024 over the angiographic catheters and into the target branch vessels, advancing the wall of the prosthesis adjacent to each of one or more fenestrations in the prosthesis toward the ostium of the target branch vessels, removing the one or more angiographic catheters and/or guidewires, inserting one or more branch stents into the branch vessels, retracting the branch sheaths, expanding the branch stents, and flaring a portion of the branch stents. In some arrangements, the target branch vessels are the renal arteries. Some arrangements also comprise deploying a proximal and distal portion of the prosthesis. The steps of the foregoing procedure can be performed in the sequence described, or can be performed in any suitable sequence.

Some arrangements are directed to methods of deploying an endoluminal prosthesis, such as without limitation the prosthesis 1010 described above, comprising inserting a delivery catheter such as catheter system 1000 into an artery, exposing one or more branch sheaths 1024, advancing one or more angiographic catheters having one or more guidewires into the one or more branch sheaths 1024 and cannulating the target branch vessels, advancing the one or more branch sheaths 1024 over the angiographic catheters and into the target branch vessels, deploying a proximal portion of the prosthesis, advancing the wall of the prosthesis adjacent to each of one or more fenestrations in the prosthesis toward the ostium of the target branch vessels, removing the one or more angiographic catheters and/or guidewires, inserting one or more branch stents into the branch vessels, retracting the branch sheaths, expanding the branch stents, and flaring a portion of the branch stents. In some arrangements, the target branch vessels are the renal arteries. Some arrangements also comprise deploying a proximal and distal portion of the prosthesis. The steps of the foregoing procedure can be performed in the sequence described, or can be performed in any suitable sequence.

Some arrangements are directed to methods of deploying an endoluminal prosthesis, such as without limitation the prosthesis 1010 described above, comprising advancing a delivery catheter such as catheter system 1000 into a blood vessel or artery, exposing one or more branch sheaths 1024, advancing one or more angiographic catheters into the one or more branch sheaths 1024 and cannulating the target branch vessels, and advancing the one or more branch sheaths 1024 over the angiographic catheters and into the target branch vessels. The steps of the foregoing procedure can be performed in the sequence described, or can be performed in any suitable sequence. In some embodiments, the step of advancing the one or more angiographic catheters into the one or more branch sheaths 1024 and cannulating the target branch vessels can be completed before expanding a main body portion of the prosthesis. In some embodiments, the one or more angiographic catheters can have one or more guidewires therein.

Some arrangements are directed to methods of deploying a stent graft across at least one branch vessel, the stent graft having at least one lateral opening or fenestration formed therein and the stent graft being constrained within a delivery system having a distal and a proximal end, wherein a catheter extends from the proximal end of the delivery system through the fenestration formed in the stent graft. In some arrangements, a guidewire can be passed from the proximal end of the delivery system through the catheter and into the target branch vessel with the proximal and distal end of the stent graft remaining constrained in the delivery system.

Some embodiments are directed to apparatuses for placing a prosthesis across at least one branch vessel, the prosthesis having a distal end, a proximal end, a midsection, and at least one lateral opening in the midsection of the prosthesis. In some embodiments, the prosthesis can be constrained in a delivery system having a distal and a proximal end. The apparatus can comprise a catheter extending from the proximal end of the delivery system through the lateral opening in the prosthesis, wherein a guidewire can be passed from the proximal end of the delivery system through the catheter, into the branch vessel with at least the proximal and distal ends of the prosthesis remaining constrained in the delivery system. In some embodiments, the prosthesis can be a stent graft.

Figure 62A:
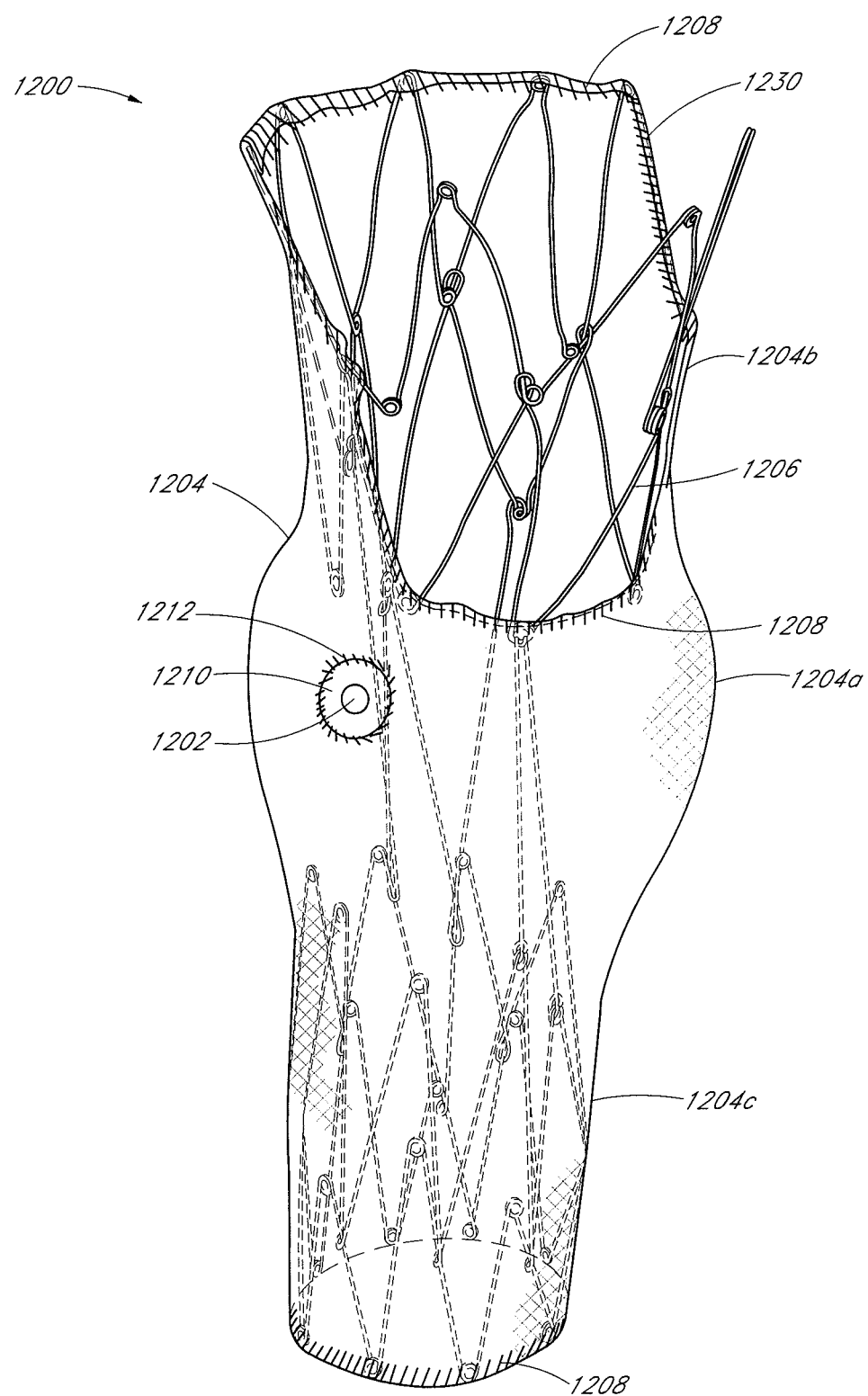
FIGS. 62A and 62B are perspective views of an embodiment of a prosthesis having one or more fenestrations therein, the graft being shown in dashed lines in FIG. 62B for clarity.
Figure 62B:
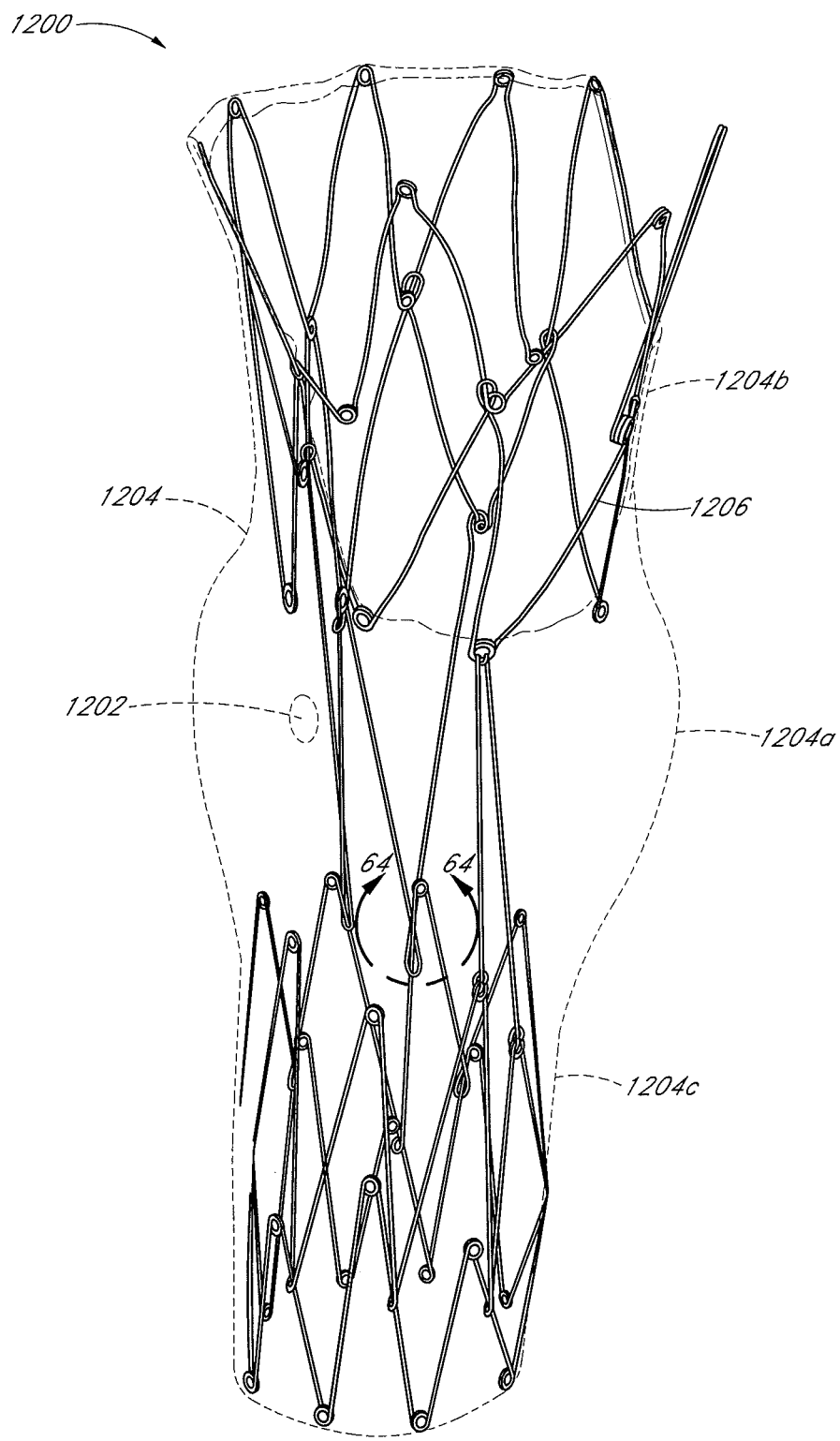

FIGS. 62A and 62B are perspective views of an embodiment of a prosthesis 1200 comprising one or more fenestrations 1202 formed in the graft 1204, and a stent or support member 1206. The embodiment of the graft 1204 is shown in dashed lines in FIG. 62B for clarity. In some embodiments, the prosthesis 1200 can have any of the features, components, or other details of any other prosthesis embodiments disclosed herein such as, without limitation, prosthesis 1010 described above. Further, any of the features of the embodiment of the prosthesis 1200 can be used in combination with any of the other prosthesis embodiments disclosed herein.

In some embodiments, the graft 1204 can be supported by the stent 1206 along at least a portion of the graft 1204. Further, the graft 1204 can be overlapped and can have stitching or sutures 1208 along one or more edges of the graft 1204, which can improve the tear resistance of the graft 1204 and can improve the connection between the graft 1204 and the stent 1206.

Similar to other graft embodiments described herein, some embodiments of the graft 1204 can be configured to have excess or slack graft material in at least a portion thereof relative to the stent which supports the graft. For example, without limitation, the excess graft material can form a bulge or other enlargement in the graft 1204 in the approximate location of one or more fenestrations 1202 formed through the graft material. The excess or slack material along the circumference of the graft 1204 (for example, without limitation, in the enlarged portion 1204a of the graft 1204) can allow for circumferential and/or axial movement of the graft material and, hence, the one or more fenestrations 1202, relative to the stent 1206 and the ostium of the patient's branch vessels. Therefore, in some embodiments, the diameter of the graft 1204 at and/or adjacent to the location of one or more fenestrations 1202 can be larger than the local diameter of the target vessel. Similarly, in some embodiments, the diameter of the graft 1204 at and/or adjacent to the location of one or more fenestrations 1202 can be larger than the diameter of the non-enlarged portion of the graft material. In some embodiments, without limitation, the outside surface of the graft 1204 in the enlarged portion 1204a or otherwise can be free from any corrugations or other preformed folds, overlaps, or other similar pre-formed features.

Further, similar to any of the other graft embodiments disclosed herein, the graft 1204 can have excess graft material in an axial direction, in addition to or in the alternative of the diametrically enlarged portion. The excess or slack material along the length of the graft 1204 can increase the circumferential and/or axial adjustability or movement of the graft material adjacent to the one or more fenestrations 1202 formed in the graft 1204. Accordingly, in some embodiments, the length of the graft material between the proximal and distal attachment points to the stent 1206 can be longer than that of the stent 1206 between the proximal and distal attachment points. Or, in some embodiments, the graft material in a mid portion of the graft 1204, including on either side of the enlarged portion 1204a, can have an increased length relative to the stent radially adjacent to such graft portion.

Further, in some embodiments, the enlarged portion and/or excess length of the graft 1204 or any other graft embodiment disclosed herein can be free from any attachment points to the stent or support member which supports the graft 1204. In these configurations, the positional adjustability of the fenestrations can be increased because the graft material is free to move in an axial and/or circumferential direction relative to the stent and relative to the ostium of the target branch vessels. In some embodiments, the enlarged portion and/or excess length of the graft 1204 or any other graft embodiment disclosed herein can be configured to have only a limited number of attachment points to the stent or support member which supports the graft 1204. The attachment points can be sufficiently away from the fenestration or opening so as to not substantially affect the adjustability of the fenestration. For example, without limitation, some embodiments of the prosthesis 1010 can be configured such that the enlarged or slack portion of the graft has only a limited number of attachments to a stent or connector (such as connector 1254) away from the fenestrations 1202 so that the adjustability of the enlarged or slack portion is not significantly affected. For example, in embodiments having only one fenestration in the enlarged portion, the attachment or attachments to the stent or other support member can be positioned on an opposite side of the graft as compared to the position of the fenestration. In these configurations, the positional adjustability of the fenestrations can be increased because the graft material is substantially free to move in an axial and/or circumferential direction relative to the stent and relative to the ostium of the target branch vessels.

Figure 63:
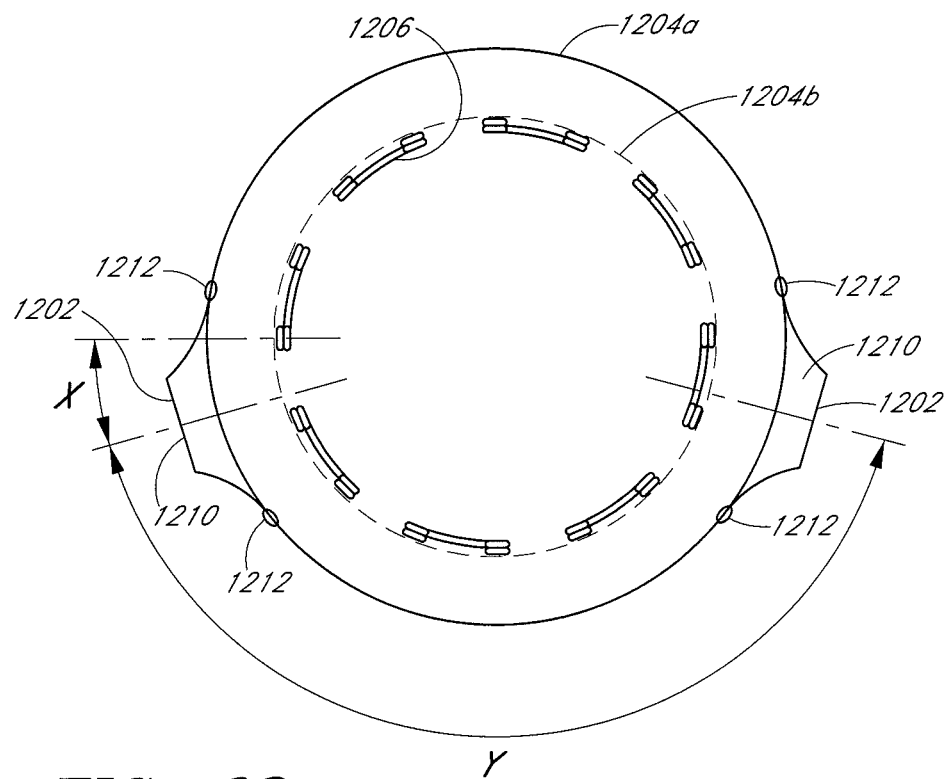
FIG. 63 is a top view of the embodiment of the prosthesis of FIG. 62.

With reference to FIGS. 62A-63, some embodiments of the graft 1204 can have one or more enlarged portions 1204a having an enlarged diameter relative to the target vessel or relative to one or more non-enlarged portions of the graft 1204, such as portions 1204b, 1204c that can improve the radial and/or axial adjustability of the fenestrations 1202 formed in the enlarged portions 1204a to better accommodate asymmetrically positioned branch vessel ostium. In some embodiments, with reference to FIGS. 62A and 62B, the graft 1204 can have an enlarged middle portion 1204a having one or more fenestrations 1202 formed therein, a non-enlarged proximal portion 1204b, and a non-enlarged distal portion 1204c.

As discussed above, in some embodiments of the prosthesis 1200, the enlarged portion 1204a of the graft 1204 can have a diameter that is approximately 30% larger than a diameter of the target vessel or the diameter of the non-enlarged portions 1204b, 1204c of the graft 1204. In some embodiments, the diameter of the enlarged portion 1204a of the graft 1204 can be from approximately 20% or less to approximately 50% or more, or from approximately 25% to approximately 40% larger than the target vessel or the diameter of the non-enlarged portions 1204b, 1204c of the graft 1204, or to or from any values within these ranges.

Additionally, in some embodiments, the enlarged portion 1204a or portion of the graft 1204 adjacent to the enlarged portion 1204a of the graft 1204 can be sized and configured to be substantially longer (i.e., in the axial direction) than the stent 1206, which can improve the radial and/or axial adjustability of the fenestrations 1202 formed in the enlarged portions 1204a to better accommodate the asymmetric and/or non-uniform positioning of branch vessel ostium. Some embodiments of the graft 1204 can be longer than the stent 1206 in both the enlarged portion 1204a of the graft 1204 and/or in the portion of the non-enlarged distal portion 1204c of the graft adjacent to the enlarged portion 1204a of the graft 1204. For example, without limitation, the enlarged portion 1204a or portion of the graft 1204 adjacent to the enlarged portion 1204a of the graft 1204 can be sized and configured to be approximately 20% longer in the axial direction than the stent 1206. In some embodiments, the enlarged portion 1204a or portion of the graft 1204 adjacent to the enlarged portion 1204a of the graft 1204 can be sized and configured to be from approximately 10% to approximately 40% or more longer in the axial direction than the stent 1206.

FIG. 63 is a top view of the embodiment of the prosthesis 1200 of FIG. 62. With reference to FIGS. 62-63, some embodiments of the prosthesis 1200 can have fenestrations 1202 formed in an enlarged portion 1204a of the graft 1204. In some embodiments, the fenestrations 1202 can be formed at non-diametrically opposed positions. This can improve the alignment of the fenestrations 1202 with the ostium of the target branch vessels, which in general can be located at non-diametrically opposed positions. In some embodiments, the fenestrations 1202 formed in either the enlarged portion or portions 1204a or non-enlarged portions 1204b, 1204c of the graft 1204, can be angled away from the diametrically opposed position (represented by angle X in FIG. 63) such that the fenestrations 1202 are separated by an angle (represented by angle Y in FIG. 63) that is less than 180 degrees.

For example, without limitation, some embodiments of the graft 1204 can have two fenestrations 1202 formed at an angle away from the diametrically opposed position (represented by angle X in FIG. 63) of approximately 15 degrees such that the fenestrations 1202 are separated by an angle (represented by angle Y in FIG. 63) that is approximately 150 degrees. Some embodiments of the graft 1204 can have two fenestrations 1202 formed at an angle away from the diametrically opposed position of between approximately 10 degrees or less and approximately 20 degrees or more, such that the fenestrations 1202 are separated by an angle (represented by angle Y in FIG. 63) that is between approximately 160 degrees and approximately 140 degrees.

Some embodiments of the graft 1204 can have two fenestrations 1202 formed in an enlarged portion 1204a of the graft and wherein the fenestrations 1202 are separated by an angle that is less than 180 degrees, for example approximately 150 degrees. In this configuration, positioning the fenestrations 1202 to be separated by an angle that is less than 180 degrees (such as, for example, approximately 150 degrees) can improve the alignment of the fenestrations 1202 with the ostium of the target branch vessels such that the enlarged portion 1204a of the graft 1204 can be from approximately 20% to approximately 60% greater than the non-enlarged portion 1204b, 1204c of the graft 1204. In some embodiments of this configuration, the enlarged portion 1204a of the graft 1204 can be from approximately 20% to approximately 40% greater than the non-enlarged portion 1204b, 1204c of the graft 1204.

Some embodiments of the graft 1204, which can be a bifurcated or other suitably configured graft, can have two fenestrations 1202 formed in an enlarged portion 1204a of the graft, wherein the fenestrations 1202 can be separated by an angle that is less than 180 degrees, and wherein the length of at least a portion of the graft 1204 can be substantially greater than the length of the stent 1206, for example approximately 10% greater than the length of the stent 1206. In this configuration, positioning the fenestrations 1202 to be separated by an angle that is less than 180 degrees (such as, for example, approximately 150 degrees) and increasing the length of the graft 1204 to be approximately 10% greater than the length of the stent 1206 can improve the alignment/alignability of the fenestrations 1202 with the ostium of the target branch vessels such that the enlarged portion 1204a of the graft 1204 can be from approximately 10% or less to approximately 20% greater than the non-enlarged portion 1204b, 1204c of the graft 1204.

With reference to FIGS. 62-63, though not required, some embodiments of the prosthesis 1200 can have reinforced fenestrations 1202 comprising a tubular member 1210 inserted through the fenestration 1202 and stitched to the graft 1204 with one or more sutures 1212. In this configuration, which will be described in greater detail below, the tubular member 1210 can improve the tear resistance of the fenestration 1202 and also improve the sealability between the fenestrations 1202 and the branch grafts and stents deployed within the fenestrations 1202 as well as the pull-out resistance of the branch grafts and stents within the fenestrations 1202. This configuration can reduce leakage between the fenestrations 1202 and the branch grafts and stents deployed within the fenestrations 1202. In some embodiments, this configuration can also increase the force required to pull the branch grafts and stents deployed within the fenestrations 1202 out of the fenestrations 1202, thereby reducing the inadvertent axial movement of the branch grafts and stents deployed within the fenestrations 1202.

Figure 66:
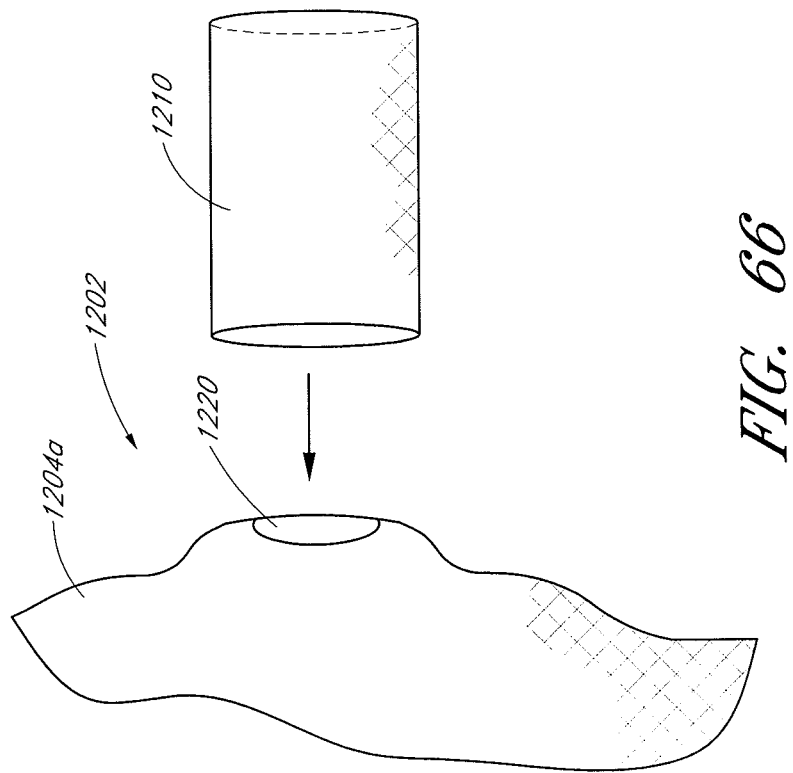
FIG. 66 is an enlarged side view of the embodiment of the fenestration shown in FIG. 65, defined by curve 66-66 of FIG. 65.
Figure 65:
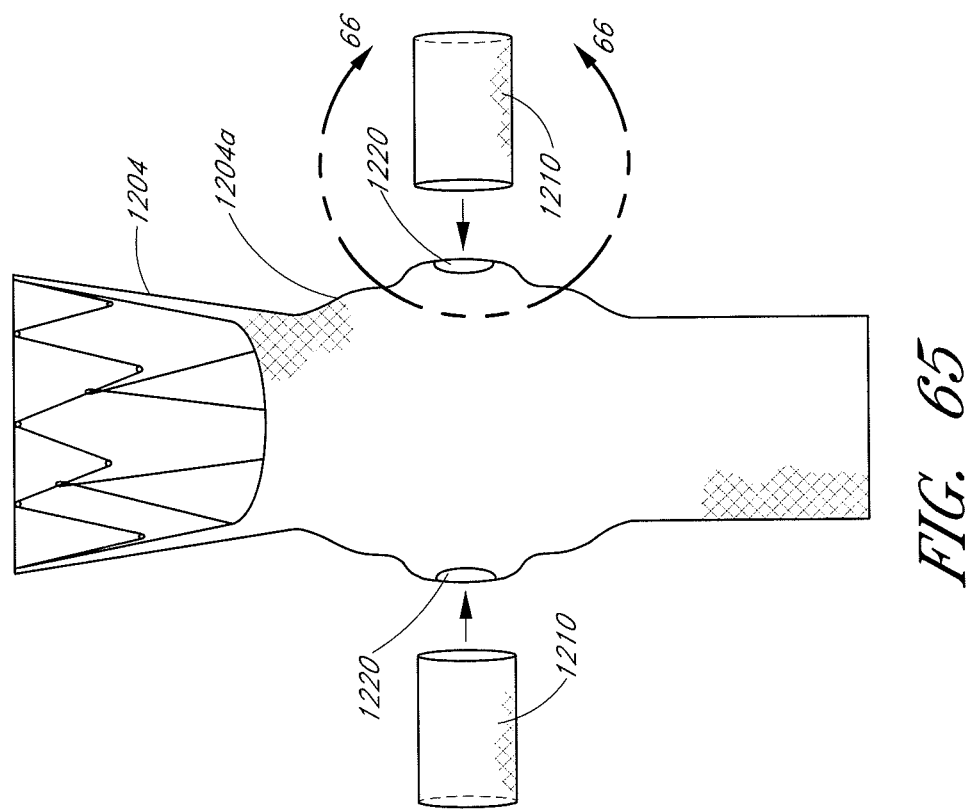
FIG. 65 is a partially exploded schematic representation of the prosthesis embodiment shown in FIG. 62.

With reference to FIGS. 65-68, some embodiments of the fenestration 1202 and some arrangements of methods for manufacturing the fenestrations 1202 will be described. FIG. 65 is a partially exploded schematic representation of the prosthesis 1200 shown in FIG. 62, and FIG. 66 is an enlargement of the fenestration 1202 shown in FIG. 65, defined by curve 66-66 of FIG. 65. As shown therein, in some embodiments, the tubular member 1210 can be contracted and advanced into the openings 1220 formed in the graft 1204. In some embodiments, the diameter of the tubular member 1210 can be significantly greater than the diameter of the opening 1220. For example, without limitation, the diameter of the tubular member 1210 can be approximately 500 percent of the diameter of the opening 1220, or from approximately 200 percent to approximately 800 percent of the diameter of the opening 1220, from approximately 400 percent to approximately 600 percent of the diameter of the opening 1220, or to or from any values within these ranges. In some embodiments, the diameter of the tubular member 1210 can be approximately 10 mm, and the diameter of the opening 1220 can be approximately 2 mm.

In some embodiments, the length of the tubular member 1210 can be greater than the diameter of the tubular member 1210 or the diameter of the fenestration 1202. In some embodiments, the length of the tubular member 1210 can be from approximately 5 mm or less to approximately 25 mm or more, or from approximately 10 mm to approximately 15 mm, or to or from any values within these ranges.

Figure 67:
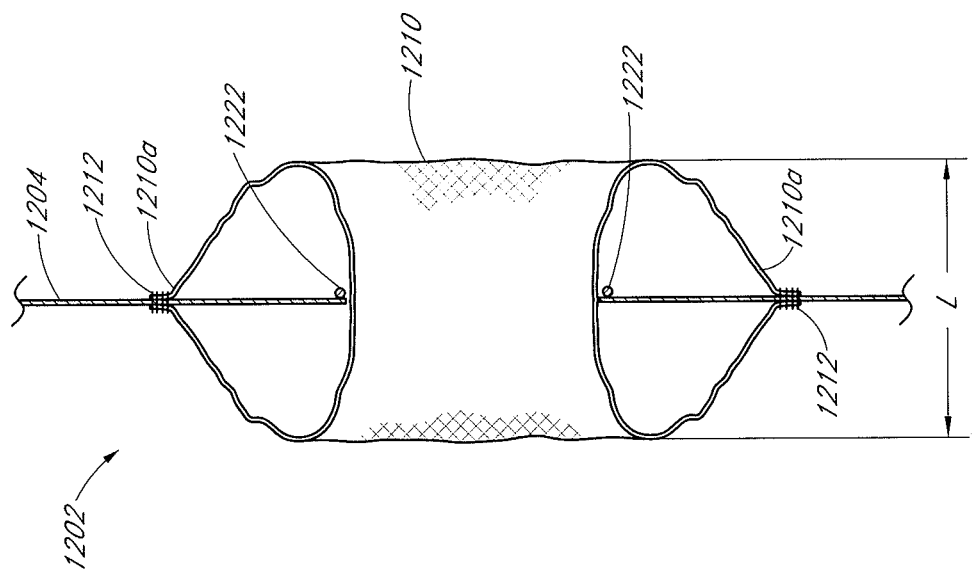
FIG. 67 is an enlarged section view of the embodiment of the fenestration illustrated in FIG. 65, showing the end portions of the embodiment of the tubular member being pulled back against the graft.
Figure 68:
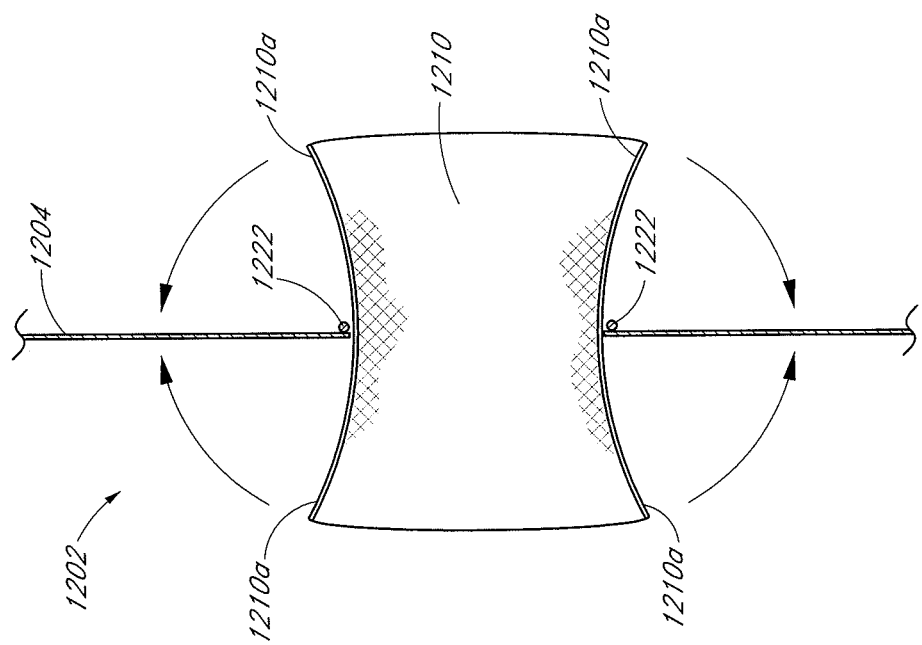
FIG. 68 is an enlarged section view of the embodiment of the fenestration shown in FIG. 65, showing the end portions of the embodiment of the tubular member stitched to the graft.

FIG. 67 is an enlarged section view of the fenestration 1202 illustrated in FIG. 65, showing the end portions 1210a of the tubular member 1210 being pulled back against the wall of the graft 1204 surrounding the opening 1220. As illustrated therein, an annular radiopaque marker 1222 can be positioned around the outside surface of the tubular member 1210, so that such marker 1222 is secured within the annular space created by folding or stretching the end portions 1210a of the tubular member 1210 against the wall of the graft 1204. As illustrated in FIG. 68, the end portions 1210a of the tubular member 1210 can thereafter be fixed to the wall of the graft 1204 using adhesive, sutures, or any other suitable fasteners, material, or technique.

In this configuration, in some embodiments, the length of the seal zone or contact length of the fenestration 1202 in the relaxed state (represented by length L in FIG. 68), before a branch stent or graft is deployed within the fenestration 1202, can be significantly greater than a contact length of a conventional fenestration not having a tubular member therein. In some embodiments, the contact length L of the fenestration 1202 in the relaxed state can be approximately the same as the diameter of the fenestration 1202 in the unstretched state. In some embodiments, the contact length L of the fenestration 1202 in the relaxed state can be from approximately 50 percent or less to approximately 150 percent of the diameter of the fenestration 1202 in the unstretched state, or from approximately 80 percent or less to approximately 120 percent of the diameter of the fenestration 1202 in the unstretched state.

With reference to FIGS. 62A and 62B, although not required, some embodiments of the graft 1204 can have a scallop or cut-away 1230 at a proximal end portion 1204b of the graft 1204. The cut-away 1230 can be sized and configured to permit unrestricted blood flow through a branch artery, such as the suprarenal and/or the celiac arteries. The size of the cut-away 1230 can be based on the anatomy of a patient, or can be sized to accommodate a wide range of vessel anatomies. In some embodiments, the cut-away 1230 can have a length approximately equal to the length of two stent struts, such as stent strut 1246 described below. The graft 1204 can be overlapped and have stitching 1208 along an edge of the cut-away 1230. In some embodiments, the prosthesis 1200 can have a flared proximal end portion to increase the sealability of such end portion of the prosthesis 1200.

In some embodiments, as described above, the prosthesis 1200 can have one or more radiopaque markers, such as but not limited to the annular radiopaque marker 1222 surrounding at least a portion of the fenestration 1202, for improved visibility under fluoroscopy during deployment. In some embodiments, any of the radiopaque markers can be formed from gold or platinum, or any suitable material. In some embodiments, any of the radiopaque markers can be formed from a suitable non-reinforcing metallic material.

Figure 70:
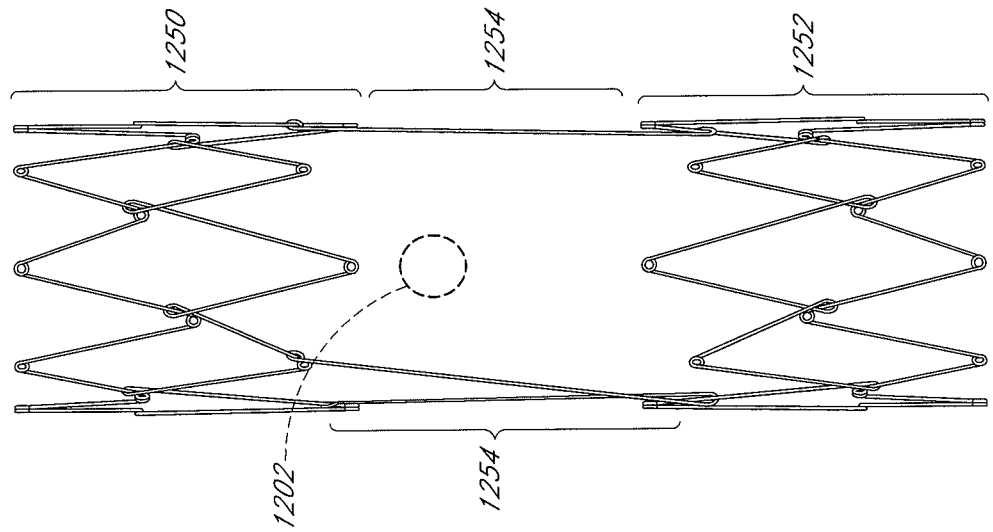
FIG. 70 is a side view of the embodiment of the stent shown in FIG. 62, along an axis projecting through the fenestration.
Figure 69:
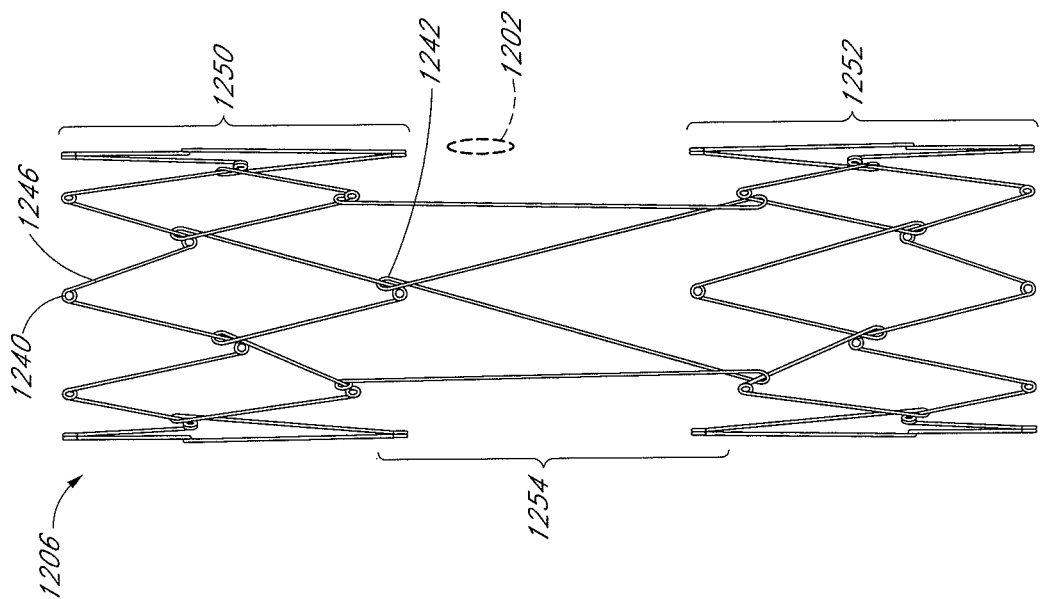
FIG. 69 is a side view of the embodiment of the stent shown in FIG. 62, perpendicular to an axis projecting through the fenestration.

FIG. 69 is a side view of the embodiment of the stent 1206 shown in FIG. 62, viewed along a line that is perpendicular to an axis projecting through a fenestration formed in the graft 1204 (not shown). For clarity, the location of a fenestration 1202 is shown dashed lines. FIG. 70 is a side view of the stent 1206, viewed along an axis projecting through a fenestration. Again, for clarity, the location of a fenestration 1202 is shown dashed lines.

Figure 64:
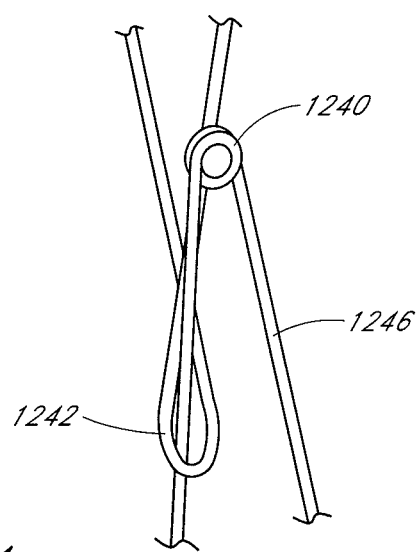
FIG. 64 is an enlarged view of a portion of the embodiment of the prosthesis of FIG. 62, defined by curve 64-64 of FIG. 62B.

With reference to FIGS. 64 and 69-70, in some embodiments, the stent 1206 can be formed from one or more wires forming a plurality of loops 1240, which can be closed loops or eyelets, bends 1242, and struts 1246. Some of the bends 1242 can be configured to slide along a portion of the length of a respective strut 1246, to improve the flexibility and bendability of the stent 1206. In some embodiments, the positioning of the plurality of loops 1240 and bends 1242 can be longitudinally offset or staggered to decrease the collapsed diameter of the prosthesis 1200.

In some embodiments, the stent 1206 can comprise a first stent segment 1250 formed from one or more lengths of wire, a second stent segment 1252 formed from one or more lengths of wire, and one or more connecting members 1254 formed from one or more lengths of wire. In some embodiments, the first and second stent segments 1250, 1252 can be positioned proximally and distally relative to the location of the fenestration (shown in dashed lines) that can be formed in the graft (not illustrated) that can be supported by the stent 1206. The length of the first stent segment 1250 can be sufficient to result in an increased seal zone in the suprarenal portion of the aorta, such as a length that extends to a position adjacent to or overlapping the superior mesenteric artery and/or the celiac artery.

In some embodiments, two connecting members 1254 can be positioned between the first and second stent segments 1250, 1252, and can be sized and offset from one another to provide a significant gap around the position of the fenestrations 1202 to increase the accessibility and adjustability of the fenestrations 1202 during deployment of the prosthesis 1200. As illustrated, some embodiments of the connecting members 1254 can have four struts. Some embodiments of the connecting members 1254 can have three or less struts, or can have five or more struts. Some embodiments of the connecting members 1254 can have a first connecting member 1254 having fewer struts than a second connecting member 1254.

FIGS. 71-83 are side views of additional embodiments of prostheses 1200 having one or more enlarged portions 1204b in the grafts 1204 thereof, and one or more fenestrations 1202 formed in the enlarged portions 1204b. In any of the embodiments shown in FIGS. 71-83, the graft 1204 can have one or more enlarged portions 1204b having any of the shapes or combination of shapes illustrated in FIGS. 71-83. Additionally, any of the graft embodiments shown in FIGS. 71-83 can also have excess length or slack relative to the stent 1206 along any suitable portion of the graft 1204, such as without limitation in, above, and/or below the enlarged portions 1204b.

With reference to FIG. 71, the embodiment of the graft 1204 can define a curved or arcuately shaped enlarged portion 1204b, having a pair of diametrically opposed fenestrations 1202 formed therein. The embodiment of the graft 1204 shown in FIG. 72 can define an enlarged portion 1204b having a generally flat outer surface 1204d between two generally horizontally oriented surfaces 1204e. One or more fenestrations 1202 can be formed through the wall of the graft 1204 in the enlarged portion 1204b. The embodiment of the graft 1204 shown in FIG. 73 can define an enlarged portion 1204b having a generally flat outer surface 1204d between two angled or tapered surfaces 1204e. One or more fenestrations 1202 can be formed through the wall of the graft 1204 in the enlarged portion 1204b.

The embodiment of the graft 1204 shown in FIG. 74 can define an enlarged portion 1204b having two angled or tapered surfaces 1204e and one or more fenestrations 1202 formed at the approximate juncture of the angled surfaces 1204e. The juncture of the angled surfaces 1204e can otherwise form a pointed or smoothly curved surface. Any of the embodiments of the prostheses 1200 illustrated in FIGS. 71-74 can, but are not required to, have a scallop or cut-away 1230 at a proximal end portion 1204b of the graft 1204.

Additionally, FIGS. 75-85 illustrate some non-limiting examples of stent configurations suitable for any of the embodiments of the prostheses disclosed herein. For example, with reference to FIG. 75, in some embodiments, a first stent 1206a can be supported within a proximal portion 1204b of the graft 1204, i.e., above the enlarged portion 1204b. Similarly, a second stent 1206b can be supported within a distal portion 1204c of some embodiments of the graft 1204, i.e., below the enlarged portion 1204b. In some embodiments, as in the embodiment illustrated in FIG. 75, the first and second stents 1206a, 1206b can be fixed to the graft 1204 without having any stents, connectors, struts, or other support structures therebetween. In this configuration, the enlarged portion 1204a can be free of any attachments points to the stent 1206.

As illustrated in FIG. 76, in some embodiments, a first stent 1206a and a second stent 1206b can be supported within a proximal portion 1204b of the graft 1204, i.e., above the enlarged portion 1204b. Similarly, a third stent 1206c and a fourth stent 1206d can be supported within a distal portion 1204c of some embodiments of the graft 1204, i.e., below the enlarged portion 1204b. In some embodiments, as in the embodiment illustrated in FIG. 76, the first and second stents 1206a, 1206b can be fixed to the graft 1204 without having any stents, connectors, struts, or other support structures therebetween. However, in some embodiments, as illustrated in FIG. 77, the first and second stents 1206a, 1206b can have one or more connectors 1254 therebetween. Similarly, in some embodiments, as illustrated in FIG. 76, the third and fourth stents 1206c, 1206d can be fixed to a distal portion 1204c of the graft 1204 without having any stents, connectors, struts, or other support structures therebetween. However, in some embodiments, as illustrated in FIG. 77, the third and fourth stents 1206c, 1206d can have one or more connectors 1254 therebetween. Similar to the prosthesis embodiment illustrated in FIG. 76, the enlarged portion 1204a of the graft 1204 can be free from any attachment points to the stent 1206.

The embodiment of the prosthesis 1200 illustrated in FIG. 78 can have one or more struts or connectors 1254 attached to one or more apices of the first and second struts 1206a, 1206b. In some embodiments, the connectors 1254 can be straight struts spanning the enlarged portion 1204a. For example, without limitation, the prosthesis 1200 illustrated in FIG. 78 can have four total struts 1254 interconnecting the first and second stents 1206a, 1206b, as illustrated. Some embodiments of the prosthesis 1200, such as the embodiment of the prosthesis 1200 illustrated in FIG. 79, can have eight total struts 1254 interconnecting the first and second stents 1206a, 1206b, as illustrated, or any suitable number of struts 1254. The prostheses 1200 illustrated in FIGS. 78 and 79 can be configured such that the graft material in the enlarged portion 1204a is free from any attachment to the stents 1206 or the connectors 1254.

In some embodiments, the connectors or struts 1254 can be generally straight, as illustrated in FIGS. 78-79. However, in some embodiments, the struts 1254 can have one or more bends 1256 therein. The bends 1256 can decrease the stiffness of the struts 1254 so that the struts 1254 are more flexible in both the axial direction and also when the prosthesis 1200 is bent.

In some arrangements, the end portions of the connectors 1254 can be fixed to the apices of adjacent stents 1206, or can be slidingly supported by the struts of the stents 1206. Further, in some embodiments, the end portions of the connectors 1254 can be supported at offset apex positions, as illustrated in FIG. 80. Additionally, as mentioned, any of the embodiments disclosed herein can be configured such that the enlarged portion 1204a can be free of any attachments points to the stent 1206, or such that the enlarged portion 1204a has a minimal number of attachments points to the stent 1206.

With reference to FIGS. 81-83, which are side views of several additional embodiments of prostheses 1200, one or more of the prostheses 1200 can have asymmetrically positioned enlarged portions 1204a' formed in the grafts 1204 thereof. Such configurations may be suitable for, for example and without limitation, the thoracic artery. With reference to FIG. 81, the embodiment of the prosthesis 1200 illustrated therein can have a first asymmetric enlarged portion 1204a' and a second asymmetric enlarged portion 1204a" formed therein. Some embodiments of the prostheses disclosed herein can have a third asymmetric enlarged portion 1204a''' formed therein (not illustrated), or any number or combination of symmetrical and asymmetric enlarged portions formed therein.

In some embodiments, the prosthesis 1200 illustrated in FIG. 81 can have a first stent 1206a positioned at a first end portion of the graft 1204, a second stent 1206b positioned at a second end portion of the graft 1204, and a third stent 1206c positioned between the asymmetric enlarged portions 1204a', 1204a". However, in some embodiments, as illustrated in FIG. 82, the graft material can be radially unsupported between the first and second asymmetric enlarged portions 1204a', 1204a", and also in the asymmetric enlarged portions 1204a', 1204a". As illustrated in FIG. 83, first and second asymmetric enlarged portions 1204a', 1204a" can be formed at any desired axial and/or circumferential position on the graft 1204. Any of the embodiments disclosed herein can have one or more connectors 1254 between any of the stents or stent segments.

With reference to FIGS. 84-85, some embodiments of the prostheses 1200 or any prostheses disclosed herein can have end portions configured for anastomotic connection with one or more blood vessels of a patient's body. As illustrated, the embodiments of the prostheses 1200 illustrated in FIGS. 84 and 85 can have any number and/or combination of symmetric or asymmetric enlarged regions 1204a, and any suitable number or configuration of stents 1206 within the grafts 1204. Further, the anastomotic end portions 1260 can be supported by the graft 1204 and can have any suitable size or shape for the desired anastomosis.

In some embodiments, the anastomotic end portion 1260 can be made from ePTFE graft material or woven or knitted graft material. The length of the anastomtoic end portions 1260 can be more than 2 cm long and as long as 20 cm to allow trimming of the end portions by the physician to accommodate the specific anatomy of the patient. In this configuration, the prostheses 1200 can be suitable for hybrid procedures in which one end of the prosthesis (for example, the anastomotic end portion 1260) is sewn surgically to the blood vessel and the other end is secured by a stent inside the lumen of the blood vessel.

Some embodiments of the graft 1204 and/or the tubular members 1210, or any other graft embodiments disclosed herein, can be formed from a bi-directionally expanded, layered PTFE material that can have improved tear resistance. In some embodiments, the graft 1204 can be formed from at least two layers of a bi-directionally expanded PTFE material, wherein the preferred or likely tear direction in a first layer of the material is different than the preferred or likely tear direction in a second layer of the material. Some embodiments of the graft 1204 and/or the tubular members 1210, or any other graft embodiments disclosed herein, can be formed from polyurethane or any other suitable material, polymeric or otherwise.

Additionally, any of the stent embodiments disclosed herein, including but not limited to the embodiments of the stent 1206 and/or any branch stent embodiments, can be self-expanding, balloon expandable, or otherwise, and can be formed by any suitable process. For example, without limitation, some embodiments of the stents disclosed herein can be laser cut from a tube of suitable material, such as Nitinol, stainless steel, or otherwise. Additionally, any of the stent embodiments disclosed herein can be formed as described in U.S. Pat. No. 6,077,296 or 7,520,895, which patents are hereby incorporated by reference in their entireties as if fully set forth herein.

FIG. 86 illustrates calculations regarding the theoretical axial adjustability of at least some embodiments of the grafts disclosed herein. FIG. 87 illustrates calculations regarding the theoretical angular or radial adjustability of at least some embodiments of the grafts disclosed herein.

While the above detailed description has shown, described, and pointed out novel features as applied to various embodiments, it will be understood that various omissions, substitutions, and changes in the form and details of the device or process illustrated can be made without departing from the spirit of the disclosure. Additionally, the various features and processes described above can be used independently of one another, or can be combined in various ways. All possible combinations and subcombinations are intended to fall within the scope of this disclosure.

As will be recognized, certain embodiments described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

For example, while some embodiments of the delivery and graft systems are described herein with respect to the abdominal aortic artery, the delivery and graft systems can be used for repairing vasculature in other portions of the body, including but not limited to the SMA, the thoracic artery, the inferior mesenteric artery, or any other arteries or blood vessels in the body suitable for such procedures or apparatuses.

What is claimed is:

1. An endoluminal prosthesis system comprising:
a delivery catheter having a flexible catheter body and a proximal and a distal end;
an endoluminal prosthesis comprising a main graft body having a lumen axially therethrough and a plurality of fenestrations in a wall portion of the main graft body and without integral branch grafts, the plurality of fenestrations being in communication with the lumen, the plurality of fenestrations being offset from each other along a longitudinal length of the main graft body; and
a plurality of guidewire sheaths, each of the plurality of guidewire sheaths being positioned through at least a portion of the lumen of the main graft body, and through a corresponding fenestration in the wall portion of the main graft body when the endoluminal prosthesis is in a collapsed, pre-delivery state within the catheter body,
a push catheter extending through at least a portion of the delivery catheter, the push catheter comprising a radially enlarged end portion relative to a remaining portion of the push catheter, the end portion configured to slide relative to one of the guidewire sheaths to contact and advance an inner wall of the endoluminal prosthesis adjacent one of the fenestrations toward an ostium of a target branch vessel, wherein the delivery catheter comprises a distal tip comprising a plurality of channels, each of the plurality of channels configured to receive a corresponding guidewire sheath.

2. The system of claim 1, wherein the plurality of fenestrations are longitudinally aligned.

3. The system of claim 1, wherein the plurality of fenestrations comprises a first fenestration, a second fenestration, and a third fenestration.

4. The system of claim 1, wherein the endoluminal prosthesis further comprises one or more stents supporting the main graft body.

5. The system of claim 1, wherein the main graft body comprises an enlarged portion with an enlarged diameter relative to a remaining portion of the main graft body.

6. The system of claim 1, wherein the delivery catheter further comprises a plurality of openings in a wall portion of the flexible catheter body.

7. The system of claim 6, wherein each of the plurality of guidewire sheaths is positioned through one of the plurality of openings in the wall portion of the flexible catheter body.

8. The system of claim 1, wherein the push catheter is prepositioned within the delivery catheter when the delivery catheter is in a predeployment state.

9. The system of claim 1, further comprising a second push catheter extending through at least a portion of the delivery catheter.

10. An endoluminal prosthesis system comprising:
a delivery catheter having a flexible catheter body and a proximal and a distal end;
an endoluminal prosthesis comprising a main graft body having a lumen axially therethrough and a plurality of fenestrations in a wall portion of the main graft body and without integral branch grafts, the plurality of fenestrations being in communication with the lumen, the plurality of fenestrations being offset from each other along a longitudinal length of the main graft body;
a plurality of pre-loaded guidewires, each of the plurality of guidewires being positioned through at least a portion of the lumen of the main graft body, and through a corresponding fenestration in the wall portion of the main graft body when the endoluminal prosthesis is in a collapsed, pre-delivery state within the catheter body; and
a plurality of push catheters, each push catheter configured to be advanced over a corresponding pre-loaded guidewire, an end portion of each push catheter being radially enlarged relative to a remaining portion of each respective push catheter to engage a corresponding one of the fenestrations,
wherein each of the push catheters are located within the lumen of the main body graft in the collapsed, pre-delivery state.

11. The system of claim 10, wherein the plurality of fenestrations are longitudinally aligned.

12. The system of claim 10, wherein the plurality of fenestrations comprises a first fenestration, a second fenestration, and a third fenestration.

13. The system of claim 10, wherein the endoluminal prosthesis further comprises one or more stents supporting the main graft body.

14. The system of claim 10, wherein the delivery catheter further comprises a plurality of openings in a wall portion of the flexible catheter body.

15. The system of claim 14, wherein each of the plurality of guidewires is positioned through one of the plurality of openings in the wall portion of the flexible catheter body.

16. The system of claim 10, wherein when fully expanded, the main body graft comprises an enlarged portion with an enlarged diameter relative to a remaining portion of the main graft body.

* * * * *